US012033423B2

(12) United States Patent
Khuri-Yakub et al.

(10) Patent No.: US 12,033,423 B2
(45) Date of Patent: *Jul. 9, 2024

(54) INTERACTIVE BIOMETRIC TOUCH SCANNER

(71) Applicants: The Board of Trustees of the Leland Stanford Junior University, Stanford, CA (US); Orchid Sound Technologies LLC, Stamford, CT (US)

(72) Inventors: Butrus T. Khuri-Yakub, Palo Alto, CA (US); Morten Fischer Rasmussen, San Francisco, CA (US); Gerard Touma, Stanford, CA (US); John N. Irwin, III, Greenwich, CT (US)

(73) Assignees: The Board of Trustees of the Leland Stanford Junior University, Stanford, CA (US); Orchid Sound Technologies LLC, Stamford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/188,127

(22) Filed: Mar. 22, 2023

(65) Prior Publication Data

US 2024/0005693 A1    Jan. 4, 2024

Related U.S. Application Data

(63) Continuation of application No. 17/318,833, filed on May 12, 2021, now Pat. No. 11,645,862, which is a
(Continued)

(51) Int. Cl.
G06V 30/142    (2022.01)
A61B 5/024    (2006.01)
(Continued)

(52) U.S. Cl.
CPC ...... *G06V 40/1306* (2022.01); *A61B 5/02416* (2013.01); *A61B 5/02438* (2013.01);
(Continued)

(58) Field of Classification Search
CPC .......... G06V 40/1306; G06V 40/1382; G06V 40/1394; G06V 40/45; G06V 30/142;
(Continued)

(56) References Cited

U.S. PATENT DOCUMENTS 4,358,677 A   11/1982   Ruell et al.
4,429,413 A   1/1984   Edwards
(Continued)

FOREIGN PATENT DOCUMENTS

CN    106068515    11/2016
CN    106169074    11/2016
(Continued)

OTHER PUBLICATIONS

"Fingerprint vs. Vascular Biometrics—Are they Different?" downloaded from http://www.m2sys.com/blog/important-biometric-terms-to-know/fingerprint-vs-vascular-biometrics-what-are-the-differences/ on Sep. 14, 2018.
(Continued)

*Primary Examiner* — Stephen P Coleman
(74) *Attorney, Agent, or Firm* — Knobbe, Martens, Olson & Bear, LLP

(57) ABSTRACT

Aspects of this disclosure relate to a biometric sensing device that combines sensing with an actuator for two way communication between a finger on a surface and the device. The sensor can also function as an actuator. A finger can be authenticated based on an image of the finger generated by the sensor and also based on a response to energy delivered
(Continued)

to the finger by the actuator. Two way communication can provide more robust authentication than fingerprint sensing alone.

20 Claims, 98 Drawing Sheets

Related U.S. Application Data continuation of application No. 16/811,547, filed on Mar. 6, 2020, now Pat. No. 11,023,704, which is a continuation of application No. 16/057,666, filed on Aug. 7, 2018, now Pat. No. 10,592,718.

(60) Provisional application No. 62/543,280, filed on Aug. 9, 2017, provisional application No. 62/543,278, filed on Aug. 9, 2017.

(51) Int. Cl.
| | | |
|---|---|---|
| *A61B 5/026* | (2006.01) | |
| *A61B 5/08* | (2006.01) | |
| *A61B 5/1172* | (2016.01) | |
| *A61B 5/1455* | (2006.01) | |
| *G06F 3/043* | (2006.01) | |
| *G06V 40/12* | (2022.01) | |
| *G06V 40/13* | (2022.01) | |
| *G06V 40/40* | (2022.01) | |
| *H04M 1/03* | (2006.01) | |
| *A61B 5/00* | (2006.01) | |
| *G06V 40/10* | (2022.01) | |

(52) U.S. Cl.
CPC .......... *A61B 5/0261* (2013.01); *A61B 5/0816* (2013.01); *A61B 5/1172* (2013.01); *A61B 5/14552* (2013.01); *G06F 3/0436* (2013.01); *G06V 40/1382* (2022.01); *G06V 40/1394* (2022.01); *G06V 40/45* (2022.01); *H04M 1/03* (2013.01); *A61B 5/14551* (2013.01); *A61B 5/489* (2013.01); *G06F 2203/04103* (2013.01); *G06V 30/142* (2022.01); *G06V 40/15* (2022.01)

(58) Field of Classification Search
CPC ................ G06V 40/15; A61B 5/02416; A61B 5/02438; A61B 5/0261; A61B 5/0816; A61B 5/1172; A61B 5/14552; A61B 5/14551; A61B 5/489; G06F 3/0436; G06F 2203/04103; H04M 1/03
USPC .......................................................... 382/124
See application file for complete search history.

(56) References Cited

U.S. PATENT DOCUMENTS

| | | | |
|---|---|---|---|
| 4,977,601 A | 12/1990 | Wieslaw | |
| 5,456,256 A | 10/1995 | Schneider et al. | |
| 5,935,071 A | 8/1999 | Schneider et al. | |
| 6,292,576 B1 | 9/2001 | Brownlee | |
| 6,314,195 B1 | 11/2001 | Fukuzumi | |
| 6,327,376 B1 | 12/2001 | Harkin | |
| 7,400,750 B2 | 7/2008 | Nam | |
| 8,201,739 B2 | 6/2012 | Schneider et al. | |
| 8,310,372 B2 | 11/2012 | Kukula et al. | |
| 8,509,882 B2 | 8/2013 | Albert et al. | |
| 8,724,859 B2 | 5/2014 | Schneider et al. | |
| 8,801,274 B2 | 8/2014 | Mainguet et al. | |
| 8,977,013 B2 | 3/2015 | Maev et al. | |
| 9,323,393 B2 | 4/2016 | Djordjev et al. | |
| 9,424,456 B1 | 8/2016 | Karnath Koteshwara | |
| 9,453,822 B2 | 9/2016 | Schneider et al. | |
| 9,572,499 B2 | 2/2017 | Gopalakrishnan et al. | |
| 9,678,591 B2 | 6/2017 | Nikoozadeh et al. | |
| 9,839,363 B2 | 12/2017 | Albert | |
| 9,898,901 B1 | 2/2018 | Kurian | |
| 9,953,205 B1 | 4/2018 | Rasmussen et al. | |
| 9,984,270 B2 | 5/2018 | Yousefpor et al. | |
| 9,984,271 B1 | 5/2018 | King et al. | |
| 10,047,459 B1 | 8/2018 | Starner et al. | |
| 10,061,964 B2 | 8/2018 | Huang | |
| 10,135,822 B2 | 11/2018 | Adams, Jr. | |
| 10,489,627 B2 | 11/2019 | Rasmussen et al. | |
| 10,592,718 B2 | 3/2020 | Khuri-Yakub et al. | |
| 10,691,912 B2 | 6/2020 | Khuri-Yakub et al. | |
| 11,023,704 B2 | 6/2021 | Khuri-Yakub et al. | |
| 11,645,862 B2 | 5/2023 | Khuri-Yakub et al. | |
| 2003/0001459 A1 | 1/2003 | Scott | |
| 2004/0064708 A1 | 4/2004 | Angelo et al. | |
| 2004/0140735 A1 | 7/2004 | Scott et al. | |
| 2004/0240712 A1 | 12/2004 | Rowe | |
| 2005/0069182 A1 | 3/2005 | Schneider et al. | |
| 2005/0157912 A1 | 7/2005 | Schneider et al. | |
| 2005/0163353 A1 | 7/2005 | Schneider et al. | |
| 2005/0240778 A1 | 10/2005 | Saito | |
| 2006/0173316 A1 | 8/2006 | Schneider et al. | |
| 2006/0293575 A1 | 12/2006 | Norris | |
| 2008/0273768 A1 | 11/2008 | Dennis et al. | |
| 2009/0219154 A1 | 9/2009 | Kukula et al. | |
| 2010/0113952 A1 | 5/2010 | Raguin et al. | |
| 2012/0177257 A1 | 7/2012 | Maev et al. | |
| 2012/0279865 A1 | 11/2012 | Regniere et al. | |
| 2013/0131515 A1 | 5/2013 | Lee | |
| 2013/0255741 A1 | 10/2013 | Edwards et al. | |
| 2014/0051955 A1 | 2/2014 | Tiao | |
| 2014/0090473 A1 | 4/2014 | Schneider et al. | |
| 2014/0194760 A1 | 7/2014 | Albert | |
| 2014/0219521 A1 | 8/2014 | Schmitt et al. | |
| 2014/0228665 A1 | 8/2014 | Albert | |
| 2014/0341447 A1 | 11/2014 | Cho et al. | |
| 2014/0354596 A1 | 12/2014 | Djordjev et al. | |
| 2014/0355387 A1 | 12/2014 | Kitchens, II et al. | |
| 2015/0016223 A1 | 1/2015 | Dickinson et al. | |
| 2015/0018702 A1 | 1/2015 | Galloway et al. | |
| 2015/0036065 A1 | 2/2015 | Yousefpor et al. | |
| 2015/0051501 A1 | 2/2015 | Dugan | |
| 2015/0100001 A1 | 4/2015 | Bujak | |
| 2015/0169136 A1 | 6/2015 | Ganti et al. | |
| 2015/0198699 A1 | 7/2015 | Kuo et al. | |
| 2015/0241393 A1 | 8/2015 | Ganti et al. | |
| 2015/0324627 A1 | 11/2015 | Cho et al. | |
| 2016/0070404 A1 | 3/2016 | Kerr et al. | |
| 2016/0070967 A1 | 3/2016 | Du et al. | |
| 2016/0070968 A1 | 3/2016 | Gu et al. | |
| 2016/0078268 A1 | 3/2016 | Mankowski et al. | |
| 2016/0117541 A1 | 4/2016 | Lu et al. | |
| 2016/0143532 A1 | 5/2016 | Lee et al. | |
| 2016/0171521 A1 | 6/2016 | Ramirez et al. | |
| 2016/0246396 A1* | 8/2016 | Dickinson | G06F 3/043 |
| 2016/0350573 A1 | 12/2016 | Kitchens, II | |
| 2016/0367138 A1 | 12/2016 | Kim | |
| 2017/0060315 A1 | 3/2017 | Park et al. | |
| 2017/0075700 A1 | 3/2017 | Abudi et al. | |
| 2017/0080255 A1 | 3/2017 | Law | |
| 2017/0090024 A1 | 3/2017 | Kitchens, II et al. | |
| 2017/0090028 A1 | 3/2017 | Djordjev et al. | |
| 2017/0124370 A1 | 5/2017 | He et al. | |
| 2017/0147865 A1 | 5/2017 | Jensen | |
| 2017/0177917 A1 | 6/2017 | Pant | |
| 2017/0200054 A1 | 6/2017 | Du et al. | |
| 2017/0230734 A1 | 8/2017 | Oleson et al. | |
| 2017/0231534 A1 | 8/2017 | Agassy et al. | |
| 2017/0285877 A1 | 10/2017 | Hinger | |
| 2017/0326593 A1 | 11/2017 | Garlepp | |
| 2017/0330012 A1 | 11/2017 | Salvia et al. | |
| 2018/0181786 A1 | 6/2018 | Gao | |

(56) References Cited

U.S. PATENT DOCUMENTS

| | | | |
|---|---|---|---|
| 2018/0268642 | A1 | 9/2018 | Pan et al. |
| 2019/0087621 | A1 | 3/2019 | Khuri-Yakub et al. |

FOREIGN PATENT DOCUMENTS

| | | | |
|---|---|---|---|
| CN | 106473751 | | 3/2017 |
| CN | 106897715 | | 6/2017 |
| CN | 106991387 | | 7/2017 |
| CN | 206322195 | | 7/2017 |
| DE | 102016101609 | A1 | 8/2017 |
| EP | 1988489 | | 11/2008 |
| JP | 2010535594 | | 11/2010 |
| JP | 2011138090 | | 7/2011 |
| JP | 2012238186 | | 12/2012 |
| JP | 2014166215 | | 9/2014 |
| JP | 2016522507 | | 6/2016 |
| JP | 2016526947 | | 9/2016 |
| JP | 2016533234 | | 10/2016 |
| JP | 2017503255 | | 1/2017 |
| JP | 2017056029 | | 3/2017 |
| JP | 2017514108 | | 6/2017 |
| KR | 10-2013-0075533 | | 7/2013 |
| KR | 10-2014-0134459 | | 11/2014 |
| KR | 10-2016-0083032 | | 7/2016 |
| KR | 2016-0089816 | | 7/2016 |
| KR | 20160111447 | | 9/2016 |
| KR | 10-2017-0048390 | | 5/2017 |
| KR | 20170053019 | | 5/2017 |
| KR | 101850378 | | 10/2018 |
| TW | M497691 | | 3/2015 |
| TW | 201610756 | | 2/2016 |
| TW | 201616393 | A | 5/2016 |
| TW | 201727526 | A | 8/2017 |
| WO | WO 2005/070297 | | 8/2005 |
| WO | WO 2006/042144 | | 4/2006 |
| WO | WO 2009/021130 | | 2/2009 |
| WO | WO 2014/172451 | | 10/2014 |
| WO | WO 2015/134816 | | 9/2015 |
| WO | WO 2016/037078 | | 3/2016 |
| WO | WO 2017/053877 | | 3/2017 |
| WO | WO 2018/026163 | | 2/2018 |

OTHER PUBLICATIONS

"IARPA Awards SRI International Multi-Year $12.5 Million Contract to Address Vulnerabilities in Current Biometric Security Systems," Jun. 27, 2017, downloaded from https://www.sri.com/newsroom/press-releases/iarpa-awards-sri-international-multi-year-125-million-contract-address, downloaded on Sep. 14, 2018.
Aboalsamh, Hatim A., "Vein and Fingerprint Biometrics Authentication-Future Trends," International Journal of Computers and Communications, Issue 4, vol. 3, Jan. 2009.
Al-Angari, Haitham, et al., "Use of Sample Entropy Approach to Study Heart Rate Variability in Obstructive Sleep Apnea Syndrome," IEEE Transactions on Biomedical Engineering, vol. 54, No. 10, Oct. 2007.
AliveCor, "Bridging the Gap between Wearables and Healthcare," Sep. 14, 2018 downloaded from https://www.alivecor.com/technology/.
An, Byeong Wan, "Transparent and Flexible Fingerprint Sensor Array with Multiplexed Detection of Tactile Pressure and Skin Temperature," Nature Communications, (2018)9: 2458, Jul. 3, 2018.
Bamber, Lee, "Pulse Detection with Intel® ReaslSense™ Technology," updated Jul. 31, 2015, available at https://software.intel.com/en-us/articles/pulse-detection-with-intel-realsense-technology.
Bhogal, Amar S., et al., "Pattern Analysis of Oxygen Saturation Variability in Healthy Individuals: Entropy of Pulse Oximetry Signals Carries Information about Mean Oxygen Saturation," Frontiers in Physiology, Aug. 2017, Bolume B, Article 555, Aug. 2, 2017.
Biobeat Watch downloaded from http://www.bio-beat.com/index.html#biowatch on Sep. 14, 2018.
Biocatch White Paper, "Invisible Challenges. Biocatch's Game-Changing Technology for Online Fraud Prevention," Apr. 2017.
Biometrics, "Ultrasonic fingerprint sensing Capture," http://biometrics.mainguet.org/types/fingerprint/fingerprint_sensors_physics_ultrasound.htm (accessed Jan. 16, 2019), copyright 2004-2016.
Brandom, Russell, "Two-Factor Authentication is a Mess," The Verge, Jul. 10, 2017, downloaded from https://www.theverge.com/2017/7/10/15946642/two-factor-authentication-online-security-mess.
Brown, Mark, "MIT algorithm measures your pulse by looking at your face," Wired, Jul. 25, 2012, available at http://www.wired.co.uk/article/mit-algorithm.
Burt, Chris, "Fingerprint Cards Publishes ebook on Biometric Payment Cards," May 10, 2018 downloaded from https://www.biometricupdate.com/201805/fingerprint-cards-publishes-ebook-on-biometric-payment-cards on Sep. 19, 2018.
Burt, Chris, "Researchers develop transparent, flexible fingerprint sensor that detects tactile pressure and skin temperature," Jul. 8, 2018, downloaded from https://www.biometricupdate.com/201807/researchers-develop-transparent-flexible-fingerprint-sensor-that-detects-tactile-pressure-and-skin-temperature on Sep. 19, 2018.
Cbinsights, "Google Patent Envisions Devices Controlled & Authenticated Via Touch Pattern," Aug. 22, 2018, downloaded from https://www.cbinsights.com/research/google-interactive-cord-patent/ on Sep. 21, 2018.
Chong, A.Von et al., "Towards a Novel Single-LED Pulse Oximeter based on a Multispectral Sensor for IoT Applications," Microelectronics Journal xxx (2017) 1-9, Mar. 31, 2018.
Collinson, Patrick, "Forget fingerprints—banks are starting to use vein patterns for ATMs," The Guardian, May 14, 2014, available at: https://www.theguardian.com/money/2014/may/14/fingerprints-vein-pattern-scan-atm.
Conner-Simons, Adam, et al., "Detecting emotions with wireless signals," MIT News, Sep. 20, 2016, available at http://news.mit.edu/2016/detecting-emotions-with-wireless-signals-0920.
Dantu, et al., "Non-Invasive Blood Glucose Monitor Based on Spectroscopy Using a Smartphone", Conf. Proc IEEE Eng. Med. Biol. Soc. 2014, pp. 3695-3698.
Demirci, U., et al., "Forward-Viewing CMUT Arrays for Medical Imaging," IEEE Transactions on Ultrasonics, Ferroelectrics, and Frequency Control, vol. 51, Jul. 2014, pp. 887-895, 2004.
Dolcourt, Jessica, "Qualcomm announces first ultrasonic fingerprint reader: Headed to the Galaxy S10?," Dec. 4, 2018, available at: https://www.cnet.com/news/qualcomm-announces-first-ultrasonic-fingerprint-reader-headed-to-the-galaxy-s10/ (accessed Jan. 16, 2019).
Drahansky, Martin (2011). Liveness Detection in Biometrics, Advanced Biometric Technologies, Dr. Girija Chetty (Ed.), ISBN: 978-953-307-487-0, InTech, Available from: http://www.intechopen.com/books/advancedbiometric-technologies/liveness-detection-in-biometrics.
Duo Mobile, App Store Preview downloaded from https://itunes.apple.com/us/app/duo-mobile/id422663827 on Sep. 19, 2018.
Fesenko, Pavlo, "Capacitive micromachined ultrasonic transducer (cMUT) for biometric applications," Thesis for the Degree of Erasmus Mundus Master of Nanoscience and Nanotechnology, Chalmers University of Technology, 2012.
Fingerprints, "Biometrics—The Missing Piece of the Payment Card Puzzle?" May 2018.
Freitas, Ubiratan S., "Remote Camera-based Pulse Oximetry," eTELEMED 2014: The Sixth International Conference on eHealth, Telemedicine, and Social Medicine. 2014, available at https://www.thinkmind.org/download.php?articleid=etelemed_2014_3_40_40198.
Garde, Ainara et al., "Correntropy-Based Spectral Characterization of Respiratory Patternsin Patients with Chronic Heart Failure," IEEE transactions on bio-medical engineering, Mar. 2010.
Garde, Ainara,et al., "Estimating Respiratory and Heart Rates from the Correntropy Spectral Density of the Photoplethysmogram," PLOS one Jan. 2014, vol. 9, Issue 1, e86427.

(56) References Cited

OTHER PUBLICATIONS

Handy, Alex "Intel hopes RealSense inspires developers," SD Times, Apr. 6, 2015, available at http://sdtimes.com/intel-hopes-realsense-inspires-developers/#sthash.GgInssdS.dpuf.
Happich, Julien, "Fingerprint sensors under price pressure, says Yole," eeNews Europe, Jan. 20, 2017, available at: http://www.eenewseurope.com/news/fingerprint-sensors-under-price-pressure-says-yole.
HID White Paper, "Best Practices for Integrating Mobile into the Access Control Architecture," Oct. 16, 2014.
HID White Paper, "Data Intelligence Advances Authentication Technologies for Financial Institutions," Feb. 15, 2018.
HID White Paper, "Mobile Authentication," Sep. 25, 2013.
Hitachi Ltd., "Finger Vein Authentication: White Paper," 2006.
Holly, Russell "Fujitsu smartphone camera tech can monitor your pulse," Geek.com, Mar. 18, 2013, available at https://www.geek.com/geek-pick/fujitsu-smartphone-camera-tech-can-monitor-your-pulse-1543239/.
Honan, Matt, "How Apple and Amazon Security Flaws Led to My Epic Hacking," Aug. 6, 2012 downloaded from https://www.wired.com/2012/08/apple-amazon-mat-honan-hacking/ on Sep. 19, 2018.
Integrity Applications, "Integrity Applications is devoted to breakthrough innovations that bring positive change and provide real solutions," copyright 2017, available at http://www.integrity-app.com/the-glucotrack/the-products/.
International Search Report for PCT/US2018/045619 dated Nov. 27, 2018 in 4 pages.
International Search Report dated Aug. 10, 2018 for International Patent Application No. PCT/US2018/029309, 4 pages.
International Search Report dated Nov. 30, 2018 for International Patent Application No. PCT/US2018/045614, 3 pages.
Communication pursuant to Article 94(3) EPC dated Mar. 27, 2023 in EP 18843494.8.
Lamberti, N., et al., "A high frequency cMUT probe for ultrasound imaging of fingerprints," Sensor Actuat. A-Phys., vol. 172, pp. 561-569, Dec. 2011.
Larson, Selena, "Beyond Passwords: Companies use Fingerprints and Digital Behavior to ID Employees," Mar. 18, 2018, downloaded from https://money.cnn.com/2018/03/18/technology/biometrics-workplace/indec.html on Sep. 14, 2018.
Laude, D., et al., "Effect of breathing pattern on blood pressure and heart rate oscillations in humans," Clinical and Experimental Phamacology and Physiology, 1993, vol. 20, pp. 619-626.
Leonard, P., et al., "Standard pulse oximeters can be used to monitor respiratory rate," BMJ Journals, vol. 20, Iss. 6, 2003, available at http://emj.bmj.com/content/20/6/524.
Liu, Yaojie, et al., "Learning Deep Models for Face Anti-Spoofing: Binary of Auxilliary Supervision," Michigan State University, Mar. 29, 2018.
Looney, David, et al., "A Novel Multivariate Sample Entropy Algorithm for Modeling Time Series Synchronization," Entropy, Jan. 24, 2018.
Lu, Y., et al., "Ultrasonic fingerprint sensor using a piezoelectric micromachined ultrasonic transducer array integrated with complementary metal oxide semiconductor electronics," Applied Physics Letter 106, Jun. 29, 2015.
Pappas, Stephanie, "The Best Heart Rate Monitor Apps," Live Science, Jan. 30, 2015, available at https://www.livescience.com/49653-best-heart-rate-monitor-apps.html.
Photonics Media, "Photoacoustic spectroscopy takes sting out of glucose testing," Photonics.com., Jan. 2014,available at https://www.photonics.com/Article.aspx?PID=1&VID=118&IID=740&AID=55779.
Pleitez, Miguel A., et al., "Windowless ultrasound photoacoustic cell for in vivo mid-IR spectroscopy of human epidermis: Low interference by changes of air pressure, temperature, and humidity caused by skin contact opens the possibility for a non-invasive monitoring of glucose in the interstitial fluid," Review of Scientific Instruments, vol. 84, Iss. 8. Aug. 2013.

Purcher, Jack, "Samsung's Ultrasonic based Fingerprint Scanner for under a Smartphone Display was confirmed in a Patent this Week," Jul. 29, 2018, downloaded from http://www.patentlymobile.com/2018/07/samsungs-ultrasonic-based-fingerprint-scanner-for-under-a-smartphone-display-was-confirmed-in-a-patent-this-week.html on Sep. 19, 2018.
Purchur, Jack, "Apple Granted Patents for iDevices with Ultrasonic Face & Backside Biometrics, a very Mysterious MacBook Design and More," May 29, 2018, downloaded from http://www.patentlyapple.com/patently-apple/2018/05/apple-granted-patents-for-idevices-with-ultrasonic-face-backside-biometrics-a-very-mysterious-macbook-design-and-more.html on Sep. 19, 2018.
Qualcomm, "Qualcomm Announces Advanced Fingerprint Scanning and Authentication Technology," Jun. 28, 2017, available at: https://www.qualcomm.com/news/releases/2017/06/28/qualcomm-announces-advanced-fingerprint-scanning-and-authentication (accessed Jan. 16, 2019).
Raja, et al., "Robust Verification With Subsurface Fingerprint Recognition Using Full Field Optical Coherence Tomography," Jul. 2017, provided by Computer Vision Foundation, pp. 144-152.
Rasmussen, et al., "3D ultrasound imaging performance of a row-column addressed 2D array transducer: a simulation study," in Proc. of SPIE vol. 8675, Medical Imaging 2013: Ultrasonic Imaging, Tomography, and Therapy, pp. 86750C-1-86750C-11.
Savoia, A., et al., "Design and Fabrication of a cMUT Probe for Ultrasound Imaging of Fingerprints," 2010 IEEE International Ultrasonics Symposium Proceedings, pp. 1877-1880, 2010.
Scherhag, Ulrich Johannes, "Presentation Attack Detection for State-of-the-Art Speaker Recognition Systems," Hochschule Darmstadt, University of Applied Science—Bio metrics and Internet-Security Research Group , Faculty of Computer Science, Mar. 30, 2016, available at https://dasec.h-da.de/wp-content/uploads/2016/05/Masterthesis_Scherhag.pdf.
Schneider, J. K., et al., "Ultrasonic imaging systems for personal identification," IEEE Ultrasonics Symposium Proceedings, pp. 595-601, 2001.
Schneier on Security, "NIST is no Longer Recommending Two-Factor Authentication using SMS," posted Aug. 3, 2016. Downloaded from https://www.schneier.com/blog/archives/2016/08/nist_is_no_long.html on Sep. 19, 2018.
Schuckers, Sac, "Spoofing and Anti-Spoofing Measures," Information Security Technical Report, vol. 7, No. 4, pp. 56-62, Dec. 2002.
Scott, V.A., et al., "Retinal pulse oximetry: towards a method for measuring cerebral oxygen saturation," Engineering in Medicine and Biology Society, 1995, IEEE 17th Annual Conference. Sep. 1995.
Sepasian, Mojtaba et al. "Vitality Detection in Fingerprint Identification." WSEAS Transactions on Information Science and Applications, Issue 4, vol. 7, pp. 498-507, Apr. 30, 2010.
Spector, Rosanne, "New method developed for measuring oxygen in blood," Stanford News, Stanford Report, Jan. 19, 2005, available at http://news.stanford.edu/news/2005/january19/med-oximeter-0119.html.
Spectros, "First Clinical Experiences with Non-Pulsatile Optical Diffusion Tissue Oximetry during Cardiopulmonary Bypass," 2003 ASA Annual Meeting, San Francisco, CA, Oct. 11-15, 2003, available at http://www.spectros.com/uploads/tx_rtgfiles/Van_der_Starre_-_Optical_Tissue_Oximetry_During_CPB_04.pdf/.
Spectros, "The contribution of capillary, venous and arterial blood in the oxygen saturation reported by the T-Stat VLS Tissue Oximeter," available at http://www.spectros.com/uploads/tx_rtgfiles/Contribution_of_Capillary_-_Venous_Arterial_Blood_in_O2_Sat_by_T-Stat.pdf.
TDK InvenSense, "InvenSense@ Announces UltraPrint™ Mass-Manufacturable Ultrasound Fingerprint Touch Sensor Solution," Oct. 28, 2015, available at: https://www.invensense.com/news-media/invensense-announces-ultraprint-mass-manufacturable-ultrasound-fingerprint-touch-sensor-solution/ (accessed Jan. 16, 2019).
Thakkar, Danny, "Fingerprint vs Finger-Vein: The Quest for Ideal Biometric Authentication," downloaded from https://www.bayometric.com/fingerprint-vs-finger-vein-biometric-authentication/ on Sep. 14, 2018.
Van Gastel, Mark, "New principle for measuring arterial blood oxygenation, enabling motion-robust remote monitoring," Scientific

(56) References Cited

OTHER PUBLICATIONS

Reports 6, Article No. 38609, Dec. 7, 2016, available at https://www.nature.com/articles/srep38609.
Written Opinion dated Aug. 10, 2018 for International Patent Application No. PCT/US2018/029309, 9 pages.
Written Opinion of International Searching Authority for PCT/US2018/045619 dated Nov. 27, 2018 in 6 pages.
Written Opinion dated Nov. 30, 2018 for International Patent Application No. PCT/US2018/045614, 7 pages.
Yu, Yipeng, "Piezoelectric Micromachined Ultrasonic Transducers for Fingerprint Sensing," Dissertation, University of California Davis, May 2015.
Yubico, YubiKey for Mobile product page copyrighted 2018, downloaded from https://www.yubico.com/products/yubikey-for-mobile/ on Sep. 19, 2018.
Yury, Carrie, "Your Heartbeat May Soon Be Your Only Password," Wired, Jun. 2014, available at https://www.wired.com/insights/2014/06/heartbeat-may-soon-password/.
Zesch, et al., "Deposition of highly oriented low-stress ZnO films," IEEE, 1991 Ultrasonics Symposium, Dec. 8-11, 1991, pp. 445-448.
Zhang, Congcong, et al. "Reflection-type Finger Vein Recognition for Mobile Applications," Journal of the Optical Society of Korea vol. 19, No. 5, Oct. 2015, pp. 467-476.
ZKTeco College, "Fundamental of Finger Vein Recognition," 2017 downloaded from www.zkteco.eu.

\* cited by examiner

Integration of Optical and Ultrasound Systems
Optical System Below Ultrasound Transducer Array -
Transparent Metal Lines and Transducer Material Integration of Optical and Ultrasound Systems
Optical System Below Ultrasound Transducer Array -
Transparent Metal Lines and Transducer Material Integration of Optical and Ultrasound Systems
Optical System Below Ultrasound Transducer Array -
Transparent Metal Lines and Transducer Material Integration of Optical and Ultrasound Systems
Optical System Below Ultrasound Transducer Array -
Opaque Metal Lines and Transparent Transducer Material Integration of Optical and Ultrasound Systems
Optical System Next To The Ultrasound Transducer Array -
Opaque Metal Lines and Transparent Transducer Material

Two-way Communication - Actuation: Light Source

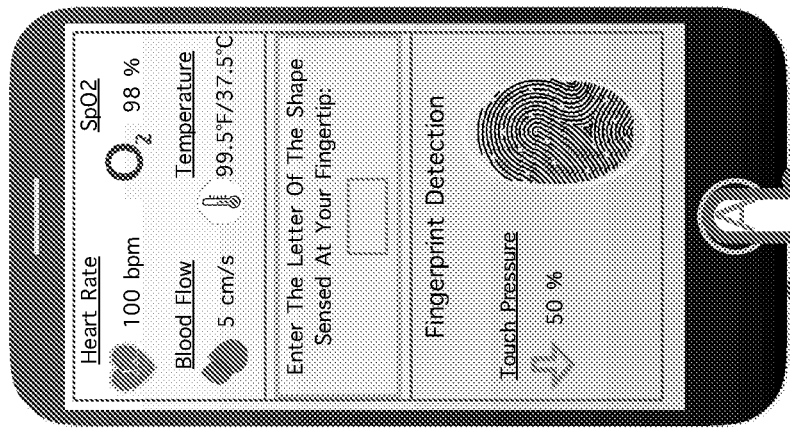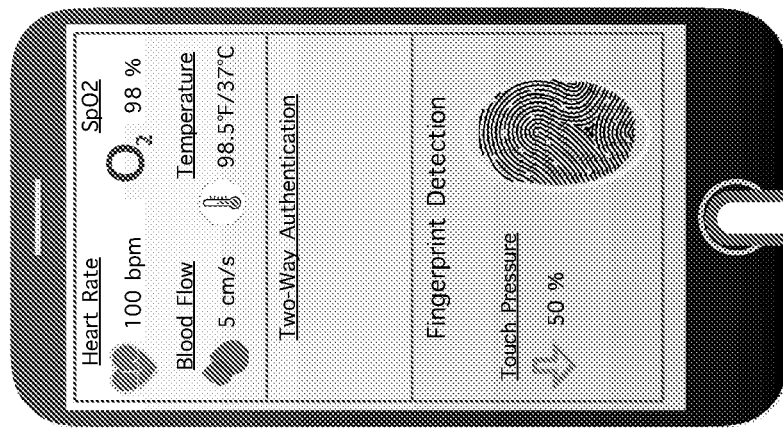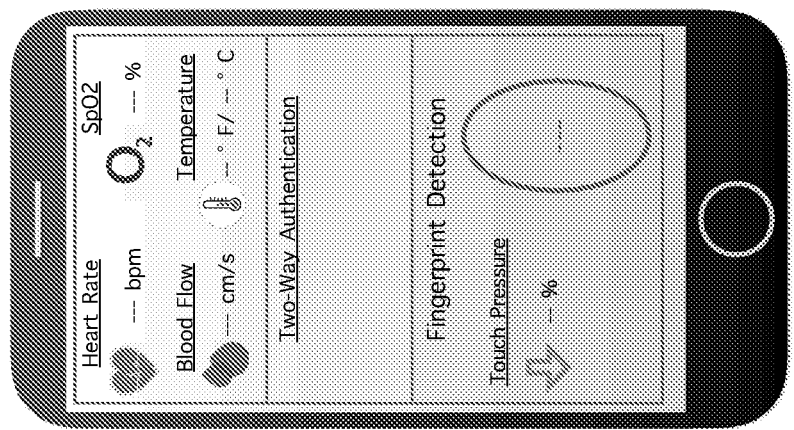
FIG. 78

Two-way Communication - Scenario
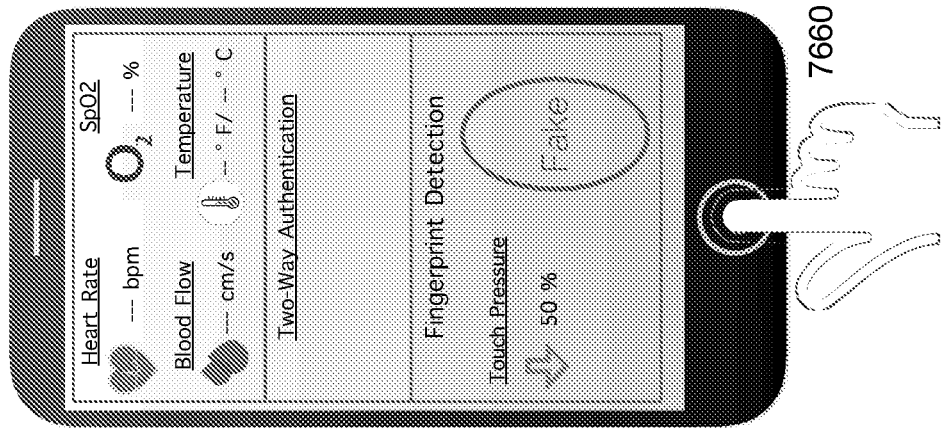
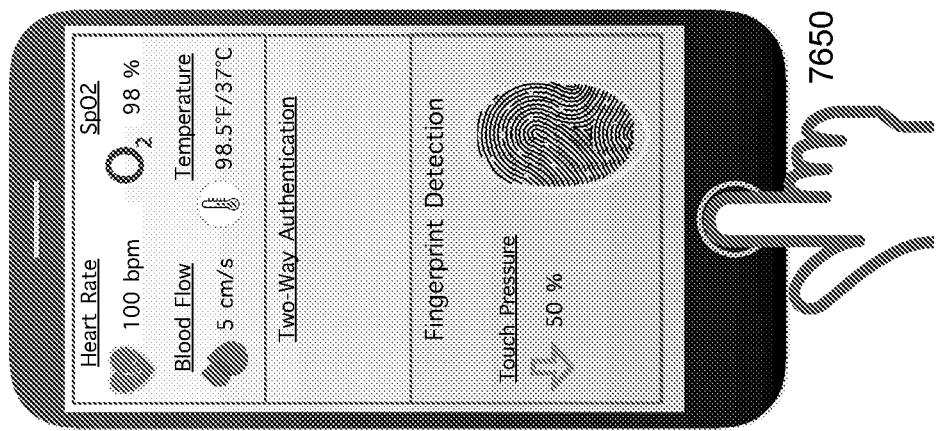
FIG. 82

INTERACTIVE BIOMETRIC TOUCH SCANNER

CROSS REFERENCE TO PRIORITY APPLICATIONS

This application is a continuation of U.S. patent application Ser. No. 17/318,833, filed May 12, 2021, "INTERACTIVE BIOMETRIC TOUCH SCANNER," which is a continuation of U.S. patent application Ser. No. 16/811,547, filed Mar. 6, 2020, entitled "INTERACTIVE BIOMETRIC TOUCH SCANNER," which is a continuation of U.S. patent application Ser. No. 16/057,666, filed Aug. 7, 2018, entitled "INTERACTIVE BIOMETRIC TOUCH SCANNER," which claims the benefit of priority of U.S. Provisional Patent Application No. 62/543,280, filed Aug. 9, 2017, entitled "BIOMETRIC TOUCH SCANNER INTEGRATED WITH OPTICS," and also claims the benefit of priority of U.S. Provisional Patent Application No. 62/543,278, filed Aug. 9, 2017, entitled "INTERACTIVE BIOMETRIC TOUCH SCANNER." The technical disclosures of each of the above-mentioned priority applications are hereby incorporated by reference herein in their entireties and for all purposes.

BACKGROUND

Technological Field

The disclosed technology relates to biometric scanning, including applications to fingerprint recognition and live finger detection.

Description of the Related Technology

Fingerprints have been associated with a wide variety of applications and uses including criminal identification, banking, ID recognition for personal devices, official forms, and others. Automated optical fingerprint scanners have been used to acquire fingerprint images. Ultrasound-based fingerprint scanners and capacitive fingerprint scanners are other fingerprint detection technologies. There is a need for robust and cost-effective fingerprint scanning systems with robust authentication.

SUMMARY OF CERTAIN INVENTIVE ASPECTS

The innovations described in the claims each have several aspects, no single one of which is solely responsible for its desirable attributes. Without limiting the scope of the claims, some prominent features of this disclosure will now be briefly described.

One aspect of the disclosed technology is a biometric sensing device. The device includes a surface configured to receive a finger. The device further includes an ultrasonic fingerprint sensor comprising ultrasonic transducers configured to transmit an ultrasound signal to the surface. The ultrasonic fingerprint sensor is configured to generate data indicative of an image of at least a portion of a fingerprint of the finger on the surface. The device further includes an optical system integrated with the fingerprint sensor. The optical system is configured to transmit light to the receiving surface through the ultrasonic fingerprint sensor.

In an embodiment, the ultrasonic transducers are transparent to the light transmitted by the optical system. In an embodiment, the ultrasonic fingerprint sensor includes electrodes for addressing the ultrasonic transducers in which the electrodes are transparent to the light transmitted by the optical system.

In an embodiment, the ultrasonic transducers are positioned under the receiving surface and the optical system is positioned under the ultrasonic transducers.

In an embodiment, the ultrasonic transducers are positioned under the receiving surface and the optical system includes a light source and an optical sensor that are positioned laterally relative to the ultrasonic transducers.

In an embodiment, the ultrasonic transducers are positioned between the receiving surface and the optical system.

In an embodiment, the ultrasound signal has a frequency in a range from 50 megahertz to 500 megahertz. In an embodiment, the optical system includes a reflective pulse oximeter. In an embodiment, the optical system is configured to transmit light at two or more different wavelengths.

In an embodiment, the device further includes a processor. In an embodiment, the processor is configured to generate a liveness parameter based on a comparison of the light at the two or more different wavelengths reflected by the finger. In an embodiment, the processor is configured to generate a liveness parameter based on light reflected by the finger that is received by the optical system. In an embodiment, the liveness parameter is indicative of at least one of a heart rate, a blood oxygenation level, or a temperature. In an embodiment, the processor is configured to output an indication of whether the finger is alive.

In an embodiment, the device further includes a layer of transparent material, such as a glass or plastic layer, positioned between the fingerprint sensor and the surface configured to receive a finger. In an embodiment, the surface configured to receive a finger is a surface of the layer of transparent material.

Another aspect is a biometric sensing device. The device includes ultrasonic transducers configured to transmit an ultrasound signal to an object. The device further includes an optical system integrated with the ultrasonic transducers. The optical system is configured to transmit light to the object and receive light reflected from the object. The device further includes one or more processors. The one or more processors are configured to generate an image of at least a portion of the object based on a reflection of the ultrasound signal from the object. The one or more processors are further configured to generate a liveness parameter based on the received light reflected from the object.

In an embodiment, the optical system is configured to transmit the light through the ultrasonic transducers to the object.

In an embodiment, the device further includes electrodes for addressing the ultrasonic transducers, and the electrodes are transparent to the light transmitted by the optical system. In an embodiment, the electrodes and the ultrasonic transducers are both transparent to the light transmitted by the optical system.

In an embodiment, the device further includes electrodes for addressing the ultrasonic transducers. In an embodiment, the electrodes are opaque to the light transmitted by the optical system.

In an embodiment, the ultrasonic transducers are positioned under the receiving surface and the optical system is positioned under the ultrasonic transducers. In an embodiment, the ultrasonic transducers are positioned under the receiving surface and the optical system includes a light source and an optical sensor that are positioned laterally relative to the ultrasonic transducers.

In an embodiment, the ultrasonic transducers are transparent to the light transmitted by the optical system. In an embodiment, the ultrasonic transducers are arranged as an array. In an embodiment, the optical system comprises a light source and a light sensor that are integrated within the array.

In an embodiment, the ultrasound signal has a frequency in a range from 50 megahertz to 500 megahertz. In an embodiment, the device further includes a surface configured to receive the object and a glass layer positioned between the ultrasonic transducers and the surface.

Another aspect is biometric sensing device. The device includes a sensor configured to generate data indicative of an image of at least a portion of an object. The device further includes an optical system integrated with the sensor, the optical system configured to transmit light to the object through the sensor. In certain embodiments, the object includes a finger, a palm, a sole of a foot, a toe, etc.

Another aspect is a biometric sensing device. The device includes ultrasonic transducers configured to transmit an ultrasound signal to an object. The device further includes an optical system integrated with the ultrasonic transducers. The optical system is configured to transmit light to the object and receive light reflected from the object. The device further includes one or more processors. The one or more processors are configured to generate an image of at least a portion of the object based on a reflection of the ultrasound signal from the object and to generate a liveness parameter based on the received light. In an embodiment, the object includes a finger.

Another aspect is a method of biometric authentication. The method includes transmitting, by a fingerprint sensor comprising a piezoelectric layer, an ultrasound signal to a finger. The method further includes generating an image of at least a portion of the finger based on a reflection of the ultrasound signal from the finger. The method further includes transmitting light through the piezoelectric layer of the fingerprint sensor to the finger. The method further includes generating a liveness parameter based on a reflection of the light from the finger. The method further includes authenticating a user based on the image and the liveness parameter.

In an embodiment, the signal is an ultrasound signal and the received signal is a reflection of the ultrasound signal from the finger. In an embodiment, the signal is a light signal and the received signal is a reflection of the light signal from the finger. The ultrasonic signal can be transmitted through glass. The method can be performed by a mobile phone that comprises the fingerprint sensor and an optical system configured to transmit the light. The method can be performed using a smart card that includes the fingerprint sensor.

Another aspect is an interactive biometric sensing system. The system includes a sensor configured to generate a biometric image associated with an object. The system further includes an actuator configured to deliver energy to the object. The system further includes a processor configured to authenticate the object based on the biometric image and a response to the energy delivered by the actuator.

In an embodiment, the sensor is configured to implement the actuator. In an embodiment, the actuator is configured to detect the response and provide an indication of the response to the processor.

In an embodiment, the actuator is part of a computing device that includes the fingerprint sensor. For example, the actuator can include MEMS devices of a mobile phone that includes the interactive biometric system. In this example, the MEMS devices can also be arranged to make the mobile phone vibrate.

In an embodiment, the interactive biometric sensing system is configured to detect a real-time response to the energy delivered to the object.

In an embodiment, the object is a finger. In an embodiment, the biometric image is an image of a fingerprint.

In an embodiment, the system further includes a surface configured to receive the object. In an embodiment, the actuator is configured to deliver the energy to the object while the object is on the surface.

In an embodiment, the system further includes a surface configured to receive the object, and the response to the energy delivered to the object is associated with the object being on the receiving surface.

In an embodiment, the response is involuntary. In an embodiment, the response is voluntary.

In an embodiment, the actuator is configured to cause a change in a temperature of the object, and the response is a change in the temperature of the object. In an embodiment, the actuator is configured to apply pressure to the object.

In an embodiment, the sensor includes ultrasound transducers. In an embodiment, the actuator includes the ultrasound transducers.

In an embodiment, the ultrasound transducers are configured to apply pressure to the object and the response is to the pressure applied to the object.

In an embodiment, the ultrasound transducers are configured to cause a change in a temperature of the object, and the response is detected using the ultrasound transducers.

In an embodiment, the actuator includes a light source configured to transmit light to the object.

In an embodiment, the actuator includes a temperature sensor configured to cause a change in a temperature of the object. In an embodiment, the sensor includes a capacitive sensor. In an embodiment, the sensor comprises an optical system.

Another aspect of this disclosure is an interactive biometric authentication system comprising: a sensor and a processor. The sensor is configured to generate biometric image data associated with an object. The sensor is further configured to deliver energy to the object. The processor is in communication with the sensor. The processor is configured to authenticate the object based on the biometric image data and an indication of a response to the energy delivered to the object by the sensor.

The sensor can include ultrasound transducers. The ultrasound transducers can be configured to apply pressure to the object, and the response is to the pressure applied to the object. The ultrasound transducers can be configured to cause a change in a temperature. The response can be detected using the ultrasound transducers.

The sensor can be configured to detect the response and provide the indication of the response to the processor. The sensor can be configured to deliver the energy to the object as a prompt in a manner that exhibits statistical randomness.

The interactive biometric authentication system can be configured to detect a real-time response to the energy delivered to the object. The processor can be configured to authenticate the object on a millisecond timescale after the energy is delivered to the object.

The interactive biometric authentication system can further include a surface configured to receive the object, wherein the sensor is configured to deliver energy to the object while the object is positioned on the surface. The interactive biometric authentication system can further include engineered glass disposed between the sensor and the surface, wherein the sensor is configured to deliver the energy to the object through the engineered glass.

The response can be involuntary. Alternatively, the response can be voluntary.

The interactive biometric authentication system can further include a user interface configured to receive the response.

Another aspect of this disclosure is method of interactively authenticating a person. The method comprises: transmitting, by a fingerprint sensor, a signal to a finger of the person positioned on a surface; generating an image of at least a portion of the finger based on a received signal associated with the signal transmitted to the finger; delivering energy to the finger while the finger is positioned on the surface; detecting a response to the energy delivered to the finger; and authenticating the person based on the image and the detecting.

The fingerprint sensor can include ultrasound transducers, and the delivering is performed using the ultrasound transducers. The detecting can include detecting the response via a user interface. The method can be performed by a mobile phone.

Another aspect of this disclosure is a mobile phone with interactive biometric authentication. The mobile phone comprises: an antenna configured to a transmit a wireless communication signal; a surface configured to receive a finger; a sensor configured to generate biometric image data associated with the finger being positioned on the surface, the sensor being further configured to deliver energy to the finger positioned on the surface; and a processor in communication with the sensor, the processor configured to authenticate the finger based on the biometric image data and an indication of a response to the energy delivered to the finger by the sensor.

The sensor can include ultrasound transducers. The mobile phone can further include engineered glass disposed between the sensor and the surface.

Another aspect is an interactive biometric sensing device. The device includes a surface configured to receive an object. The device further includes a sensor configured to generate biometric information associated with the object, deliver energy to the object while the object is on the surface, and detect a response to the delivered energy.

Another aspect is a method of authenticating a user. The method includes transmitting, by a fingerprint sensor, a signal to a receiving surface. The method further includes generating an image of at least a portion of a finger on the receiving surface based on a received signal associated with the signal transmitted to the finger. The method further includes delivering energy to the finger. The method further includes generating a liveness parameter based on a detected response to the energy delivered to the finger. The method further includes authenticating a user based on the image and the liveness parameter.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 26 illustrates a simulation of the one-way insertion loss.

FIG. 27 illustrates a circuit for IQ demodulation of an RF signal into I and Q channels.

FIG. 28 illustrates an example of the simulated demodulated in-phase and quadrature signals.

FIG. 29 illustrates the response of the low pass filter used for IQ demodulation for the process of FIG. 27.

FIG. 30 illustrates an IQ demodulated envelope for a signal demodulated by the circuit of FIG. 27.

FIG. 31 illustrates 100 MHz samples taken of the IQ demodulated envelope of FIG. 30.

FIG. 32 illustrates a circuit for IQ sampling of an IQ demodulated signal.

FIG. 33 illustrates sampled in-phase and quadrature signals of an IQ demodulated signal.

FIG. 34 illustrates graphs of the envelope of an IQ demodulated signal for IQ sampling rates of 200 MHz, 150 MHz, 100 MHz and 50 MHz.

FIG. 35 illustrates an ultrasound transducer array with transparent top and bottom metal electrodes.

FIG. 36 illustrates an exploded view of the ultrasound transducer array of FIG. 35 above an optical system and below glass, with the glass, ultrasound transducer array and optical system.

FIG. 37 illustrates the integration of the optical system, ultrasound transducer array, and glass of FIG. 36. Unlike FIG. 36, the components are illustrated in close proximity to each other. They can adjoin and not be spatially separated.

FIG. 38 illustrates a cross sectional view of the integrated optical and ultrasound system of FIG. 37 during transmission of light at a first wavelength from a light emitter of the optical system through the transparent transducer array and glass to a finger on the receiving surface of the glass.

FIG. 39 illustrates a cross sectional view of the integrated optical and ultrasound system of FIG. 37 during reception of reflected light at the first wavelength off of the finger through the glass and the transparent transducer array to an optical sensor in the optical system.

FIG. 40 illustrates a cross sectional view of the integrated optical and ultrasound system of FIG. 37 during transmission of light at a second wavelength from a light emitter of the optical system through the transparent transducer array and glass to a finger on the receiving surface of the glass.

FIG. 41 illustrates a cross sectional view of the integrated optical and ultrasound system of FIG. 37 during reception of reflected light at the second wavelength off of the finger through the glass and the transparent transducer array to an optical sensor in the optical system.

FIG. 42 illustrates the light transmission and reception at the first and second wavelengths, as illustrated in FIGS. 38-41. Comparisons in received light at different wavelengths may be used to, for example, take a reflected pulse oximetry or any other suitable reading of a finger on the receiving surface.

FIG. 43 is a perspective view of the example embodiment with an optical system below an ultrasound transducer array with transparent metal electrodes during a transmit phase without a finger on the receiving surface.

FIG. 44 is a perspective view of the example embodiment with an optical system below an ultrasound transducer array with transparent metal electrodes during a transmit phase with a finger on the receiving surface.

FIG. 45 is a perspective view of the example embodiment with an optical system below an ultrasound transducer array with transparent metal electrodes during a receive phase with a finger on the receiving surface.

FIG. 46 illustrates an ultrasound transducer array with opaque top and bottom metal electrodes.

FIG. 47 illustrates an exploded view of the ultrasound transducer array of FIG. 46 above an optical system and below glass, with the glass, ultrasound transducer array and optical system. As shown in FIGS. 48-55, the glass, ultrasound transducer array, and optical system can be in close proximity to each other. They can adjoin and not be spatially separated.

FIG. 48 illustrates a cross sectional view of the integrated optical and ultrasound system of FIG. 47 during transmission of light at a first wavelength from a light emitter of the optical system through the transparent transducer array and glass to a finger with on the receiving surface of the glass. FIG. 48 illustrates that the transparent transducer array is transparent between the opaque metal electrodes.

FIG. 49 illustrates a cross sectional view of the integrated optical and ultrasound system of FIG. 48 during reception of reflected light at the first wavelength off of the finger through the glass and the transparent transducer array to an optical sensor in the optical system. The transparent transducer array is transparent between the opaque metal electrodes.

FIG. 50 illustrates a cross sectional view of the integrated optical and ultrasound system of FIG. 47 during transmission of light at a second wavelength from a light emitter of the optical system through the transparent transducer array and glass to a finger on the receiving surface of the glass. FIG. 48 illustrates that the transparent transducer array is transparent between the opaque metal electrodes.

FIG. 51 illustrates a cross sectional view of the integrated optical and ultrasound system of FIG. 48 during reception of reflected light at the second wavelength off of the finger through the glass and the transparent transducer array to an optical sensor in the optical system. The transparent transducer array is transparent between the opaque metal electrodes.

FIG. 52 illustrates the light transmission and reception at the first and second wavelengths, as illustrated in FIGS. 48-51. Comparisons in received light at different wavelengths may be used to, for example, take a reflected pulse oximetry reading of a finger on the receiving surface.

FIG. 53 is a perspective view of the example embodiment with an optical system below an ultrasound transducer array with opaque metal electrodes during a transmit phase without a finger on the receiving surface.

FIG. 54 is a perspective view of the example embodiment with an optical system below an ultrasound transducer array with opaque metal electrodes during a transmit phase with a finger on the receiving surface.

FIG. 55 is a perspective view of the example embodiment with an optical system below an ultrasound transducer array with opaque metal electrodes during a receive phase with a finger on the receiving surface.

FIG. 56 illustrates an ultrasound transducer array with opaque top and bottom metal electrodes, with integrated light sources and light sensors.

FIG. 57 illustrates an exploded view of the ultrasound transducer array with integrated light sources and light sensors of FIG. 56 below glass, with the glass, and ultrasound transducer array with integrated light sources and sensors. As shown in FIGS. 58-66, the glass and ultrasound transducer array with integrated light sources and sensors can be in close proximity to each other. They can be adjoined and not spatially separated.

FIG. 58 illustrates a cross sectional view of the integrated optical and ultrasound system of FIG. 57 during transmission of light at a first wavelength from a light emitter through the glass to a finger on the receiving surface of the glass.

FIG. 59 illustrates a cross sectional view of the integrated optical and ultrasound system of FIG. 48 during reception of reflected light at the first wavelength off of the finger through the glass to an optical sensor.

FIG. 60 illustrates a cross sectional view of the integrated optical and ultrasound system of FIG. 57 during transmission of light at a second wavelength from a light emitter through the glass to a finger on the receiving surface of the glass.

FIG. 61 illustrates a cross sectional view of the integrated optical and ultrasound system of FIG. 48 during reception of reflected light at the first wavelength off of the finger through the glass to an optical sensor.

FIG. 62 illustrates the light transmission and reception at the first and second wavelengths, as illustrated in FIGS. 58-61. Comparisons in received light at different wavelengths may be used to, for example, take a reflected pulse oximetry reading of a finger on the receiving surface.

FIG. 63 is a perspective view of the example embodiment with an optical system integrated inside the ultrasound transducer array with opaque metal electrodes during a transmit phase without a finger on the receiving surface.

FIG. 64 is a perspective view of the example embodiment with an optical system integrated inside the ultrasound transducer array with opaque metal electrodes with opaque metal electrodes during a transmit phase with a finger on the receiving surface.

FIG. 65 is a perspective view of the example embodiment with an optical system integrated inside the ultrasound transducer array with opaque metal electrodes with opaque metal electrodes during a receive phase with a finger on the receiving surface.

FIG. 66 illustrates an example embodiment with an optical system next to/adjoining an ultrasound transducer array with opaque metal electrodes. FIG. 66 illustrates a transmit phase of this embodiment.

FIGS. 76-81 illustrate representative steps of two-way communication scenarios. The first scenario is illustrated in FIGS. 76-79. The second scenario is illustrated in FIGS. 76, 77, 80 and 81.

FIG. 76 illustrates the user interface of a representative portable communications device including an acoustic biometric touch scanner and a display for measurement or indications of heart rate, pulse oxidation levels, blood flow, temperature, two way authentication, and fingerprint detection.

FIG. 77 illustrates an intermediate step of the two-way communication scenarios of FIGS. 76-81, in which the user's fingerprint is scanned and biometric information acquired.

FIG. 78 illustrates an intermediate step of the two-way communication scenario of FIGS. 76-79. After scanning the biometric measures, the device generates a sensation at the user's fingertip with an actuator. The user is then prompted to input what sensation is felt. In FIG. 78, a sensation corresponding to shape A is drawn on the user's fingertip.

FIG. 79 illustrates an intermediate step of the two way communication scenario of FIGS. 76-79. The user is prompted to enter the letter of the shape sensed at the fingertip. If the user enters the shape that was drawn, the user is authenticated.

FIG. 80 illustrates an intermediate step of the two way communication scenario of FIGS. 76, 77, 80 and 81. After scanning the biometric measures, the device generates a sensation at the user's fingertip. The user is then prompted to input what sensation is felt. In FIG. 80, a sensation corresponding to three pulses is applied to the user's fingertip.

FIG. 81 illustrates an intermediate step of the two way communication scenario of FIGS. 76, 77, 80 and 81. The user is prompted to enter the number of pulses felt by the user at his fingertip. If the user enters the correct number of pulses, the user is authenticated.

FIG. 82 illustrates two way communication scenarios to determine whether a finger exhibits properties of being attached to a live person.

DETAILED DESCRIPTION OF CERTAIN EMBODIMENTS

Figure 1:
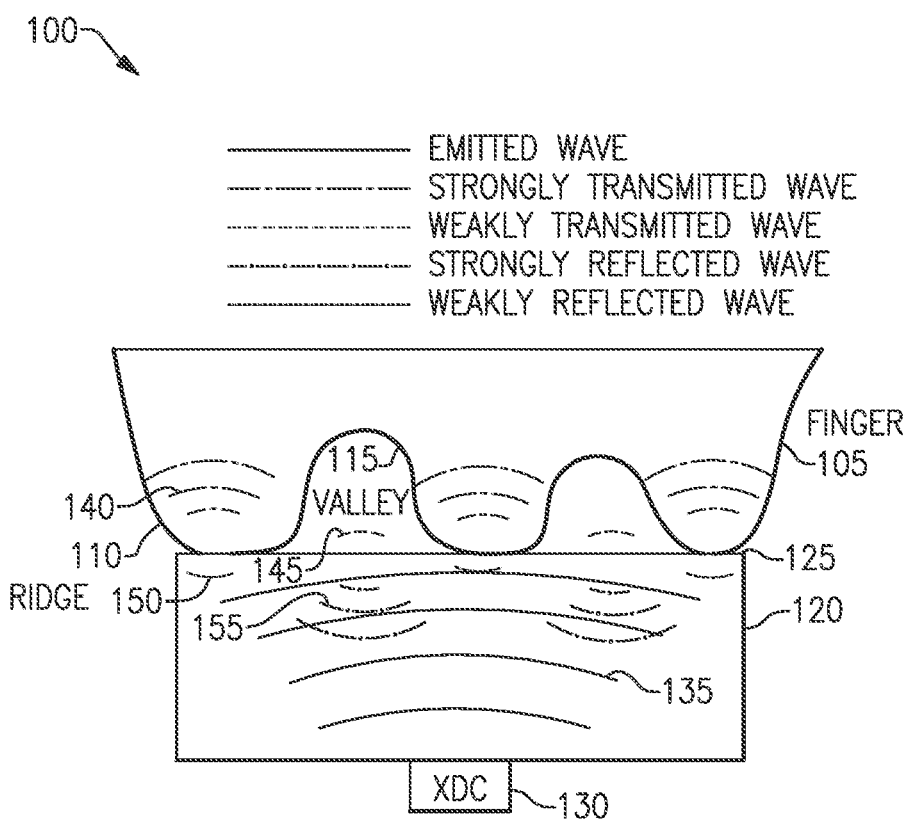
FIG. 1 illustrates acoustic fingerprint scanning, in which an ultrasound transducer emits an ultrasound wave which can be strongly reflected and weekly transmitted at the surface-finger interface and also from within the finger as shown.

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. The headings provided herein are for convenience and do not necessarily affect the scope or meaning of the claims.

This disclosure provides acoustic biometric touch scanners and methods. Ultrasound fingerprint sensing devices are disclosed. Such devices can include an array of ultrasound transducers configured to transmit an ultrasound signal having a frequency in a range from 50 MHz to 500 MHz. The ultrasound transducers include a piezoelectric layer and a receiving surface configured to receive a finger. The fingerprint sensing device can perform transmit focusing. A processor can generate an image of at least a portion of a fingerprint of the finger based on a reflection of the ultrasound signal from the finger. The ultrasound transducers can also generate a liveness parameter that can be used to authenticate the finger. The liveness parameter can be based on a force at which a finger contacts the surface and/or a temperature associated with the sound speed of the reflection. In some instances, a pattern associated with the liveness parameter can be used for authentication. Any suitable principles and advantages of the ultrasound fingerprint sensors disclosed herein can be implemented in combination with any suitable features related to an integrated optical system and/or interactive biometric sensing disclosed herein.

Ultrasonic biometric sensing devices integrated with an optical system are described herein. The ultrasonic biometric sensing device can be at least partially transparent such that the optical system can emit and/or receive light through the ultrasonic biometric sensing device. For instance, the ultrasonic biometric sensing device can be positioned between the optical system and a surface configured to receive a finger. Light can be transmitted from a light source of the optical system through ultrasound transducers and/or electrodes to the finger. Reflected light can propagate from the finger through ultrasound transducers and/or electrodes to an optical detector of the optical system. The optical system can be used to generate one or more liveness parameters that can be used to authenticate the finger. In some instances, a liveness parameter can be tracked over time and this can be used to authenticate the finger. Information generated by the optical system together with the ultrasonic biometric sensing device can be used to provide robust authentication. One or more processors can be used to authenticate a finger based on outputs from the optical system and the ultrasonic biometric sensing device.

Interactive biometric authentication is disclosed herein. Two-way communication can be established between an authentication device and an object, such as a finger, being authenticated. Biometric sensing devices disclosed herein can detect a fingerprint and also function as an actuator that can deliver energy to the finger. Two-way communication can involve a real-time interactive authentication process. This can enable multi-factor authentication and provide robust authentication. Interactions with a finger for authenticating during authentication can prevent scammers or other bad actors from authenticating with prior data. In some instances, interactive biometric authentication can be performed using an ultrasonic biometric sensing device integrated with an optical system.

Biometric Touch Scanner

Ultrasound-based fingerprint scanners can visualize not only the epidermal (superficial) layer of the fingerprint, but also the inner (dermis) layers, which makes them robust when dealing with wet hands, oil, grease, or dirt. This provides additional levels of security, and makes them harder to spoof, which is desirable for various applications. Ultrasound-based fingerprint scanner systems can acquire 2D maps of the epidermis layers and/or 3D volumetric images of finger dermis layers. Scanning methods include impediography, acoustic microscopy, echo and Doppler imaging. The fingerprint sensing systems discussed herein can achieve a scan resolution of 500 pixels per inch (PPI) to meet Federal Bureau of Investigation (FBI) and/or other standards. Such a resolution can translate to a lateral resolution of 50 micrometers at the focal depth, which typically depends on the center frequency, the acoustic aperture size, and the focal distance.

Other fingerprint sensing technologies can encounter challenges that may not be present with ultrasound-based finger print scanners. For instance, optical fingerprint scanners can encounter challenges with resolving fingerprints with contamination. As another example, capacitive fingerprint scanners which can be forged relatively easily via fake fingerprint molds.

Another type of sensors is based on the concept of impediography in which the fingerprint surface touches the transducer elements and alters their acoustic impedance depending whether the surface is tissue (ridge) or air (valley). Although this technique can be convenient as it does not involve generating and processing ultrasound pulses and echoes, it can be limited to acquiring the image of the fingerprint surface. Further, the impedance of a piezoceramic ultrasound transducer in some previous approaches can be relatively highly sensitive to frequency. For example, the impedance of an element loaded by a fingerprint valley can be approximately 800 Ohms at a frequency of 19.8 MHz and approximately 80,000 Ohms at a frequency of 20.2 MHz. Similarly, the impedance of an element loaded by a fingerprint ridge can be approximately 2,000 Ohms at a frequency of 19.8 MHz and approximately 20,000 Ohms at a frequency of 20.2 MHz. This can involve multiple impedance measurements at different frequencies to obtain reliable measurements, which could affect the frame acquisition time. Another inconvenience with such approaches is that the contact between the finger and the transducers can contaminate or even permanently damage the transducer surface and can affect its performance.

Some other approaches involve ultrasonic transducers with acoustic waveguides made from material with acoustic impedance similar to the human tissue to couple the ultrasound waves from the transducer array to the finger, and using beamforming techniques to achieve the required resolution. Although using waveguides relaxes the frequency constraint, fabrication of waveguides typically involves additional lithography steps, which increase the complexity and cost of the transducer design. Such approaches have achieved results that have been undesirable in certain applications. In some instances, such approaches have encountered relatively high insertion loss that impacted the capability of this design even when beamforming is implemented and has increased the complexity of the electronics. Relatively high voltage bias and pulses, which are unsuitable for consumer electronics, have also been used in such approaches.

The disclosed technology includes acoustic biometric touch devices that when touched by naked skin scans both the outer skin layers (epidermis) and the underlying tissue (dermis and subcutis). Such sensors can be used to identify a person. The commonly used area to scan is the fingers, but any other area of the body could be scanned, for instance, soles of feet, toes, or palms. For brevity, the fingers are henceforth referred to as the area of interest to scan. As used herein, the term "finger" encompasses a thumb. Any suitable principles and advantages discussed herein can be applied to scanning any suitable area of interest of a human or other animal.

Biometric sensing systems discussed herein include a thin film piezoelectric device configured to transmit acoustic signals having a frequency in a range from 50 MHz to 500 MHz. With this frequency, an image with a desired resolution, such as 50 micrometers, can be generated even when using an acoustic coupling layer such as glass where the speed of sound is relatively high (e.g., 5760 m/s). A thin film transducer array can be fabricated using the sputtering processes. Piezoelectric material of the transducers can be zinc oxide, aluminum nitride, or lead zirconium titanate, for example. Simulations for a ZnO transducer device with 16 microns thickness, 0.2 $mm^2$ area, 50 Ohms source and receiver impedance, and 1 nH inductive tuning give less than 3 dB insertion loss. This can change depending on the number of elements in the array that are used to transmit and receive. The biometric sensing device can obtain 3D ultrasound images of fingerprint layers. The biometric sensing device can implement row column addressing and beamforming to increase the image quality and/or to reduce the complexity of integration and electronics design.

In combination with imaging a fingerprint, several other features are discussed herein such as (1) finger touch force detection by measuring the ridge widening and the fingerprint surface area, and (2) generating a temperature of a finger and detecting the ambient temperature by measuring the variation in the speed of the sound which is temperature dependent. Measuring the blood flow, heart beat/rate, and other structural features of biometric sensing devices are discussed herein.

The disclosed devices have the ability to scan through an intermediate medium between the finger and the scanner.

The medium could for instance be a glass, a metal, plastic, or any suitable material that allows ultrasound propagation in a frequency range of interest. This could, for instance, be used to make any part or the entire part of the front glass on a cell phone into a fingerprint scanner.

Since the ultrasound also enters the finger and passes through the skin layers, a three-dimensional (3D) scan can be made of the finger surface and also of the internal finger tissue. Among other things, the blood veins and/or arteries could be scanned and their blood flow could be estimated. The measurement of the blood flow can be periodic with the heart rate. Hence, the sensor can also measure the heart rate of the individual touching the glass.

The finger print scanners discussed herein can detect one or more liveness parameters associated with an object, such as a finger, that is in contact with a surface of the fingerprint scanner. Detecting one or more liveness parameters can be done using an ultrasound-based sensing device that also generates an image of at least a portion of a fingerprint. The image can have an accuracy of 500 PPI. Based on a liveness parameter, the fingerprint scanner can provide an indication of whether the finger is part of a live human based on the liveness parameter. This can be used to prevent molds, prosthetic fingers, or other objects from being identified as matching a fingerprint associated with a particular finger. The liveness parameter can be determined based on a reflection of an acoustic wave transmitted by one or more transducers of the fingerprint scanner. The liveness parameter can be a temperature and/or tissue stiffness, for example.

If the finger is at body temperature and the sensor is at room temperature, once touched, the temperature of the glass or other intermediate layer should typically get warmer. This can generally decrease the speed of sound in the glass. In some instances, the device can be warmed to a temperature greater than body temperature (e.g., by sunlight), and heat can transfer from the device to the finger to cool the device. Hence, another objective of this disclosure is to determine the temperature of the finger. This can be done to ascertain that it is a live finger and not a prosthetic finger that is touching the glass. When the finger is not touching the glass, the ambient temperature can be determined by the device.

When a finger pushes harder on the glass, the contact area between the finger and a surface, such as glass, should increase from widening of the ridge and/or flattening of the finger surface. This can be used to detect a force at which the finger contacts a surface. Hence, another objective of this application is to measure pressure and/or force that is applied through a calculation of the contact density with the surface.

Pressure of the finger on the glass should increase with each heartbeat when the heart muscle contracts and arterial pressure increases. Between contractions, the heart fills with blood and pressure decreases. A time series of fingertip force measurements can follow a periodic, rhythmic pattern with a frequency corresponding to the person's pulse rate. Therefore, in addition to measuring temperature, the disclosed acoustic scanner can estimate a pulse rate and use it to confirm that the fingertip is not a prosthetic, and is attached to a live person with a measured pulse rate.

Further, the disclosed devices allow for tissue stiffness estimation by comparing the above-mentioned pressure estimation with that of a direct force or pressure measurement. This can increase the certainty that the object touching the sensor is a true finger and not a prosthetic.

The disclosed devices may also use machine learning techniques to identify users and/or ensure the liveness of a finger or other body part being scanned. As an example, the devices may monitor individual characteristics of how a particular user interacts with and/or responds to the device during an authentication session, in order to increase the accuracy of the authentication. In particular, the devices may check for consistent patterns in the user's interaction with and/or response to the device and any stimulus provided by the response and, when such interaction patterns are consistent, be able to further authenticate the user. As one particular example, the devices may monitor a user's pulse and may at least partially authenticate the user based on patterns in their pulse (such as a resting pulse rate or other pulse attributes).

The disclosed devices can be used to identify or authenticate a person for applications including logging in to a communications or computing device, logging into a software app, unlocking a door or antitheft device, authorizing an electronic payment, or unlocking a safety device, among other applications.

FIG. 1 illustrates an acoustic fingerprint scanning device 100, in which an ultrasound transducer 130 (XDC) emits an ultrasound wave 135 that is reflected at the surface-finger interface 125 and also from within the finger 105. The transducer 130 can transmit an ultrasound signal having a frequency in a range from 50 megahertz (MHz) to 500 MHz. An acoustic fingerprint scanner scans the interface between the finger 105 and the medium 120 it touches. The medium 120 can be rigid. Where the ridges 110 of the finger 105 touch the surface 125, part of the acoustic wave 140 will enter the finger 105 and less energy will be reflected via reflection 150. At locations where there is a valley 115 of the finger 105, relatively more (for example, practically all of) the acoustic energy is reflected back to the ultrasound transducer 130 as reflection 155. This contrast of reflection coefficients associated with ridges 110 and valleys 115 can be used by the device to scan the finger 105 surface. For instance, medical ultrasound imaging techniques can be implemented to scan the surface of the finger 105.

Since the ultrasound wave is entering the finger 105 via the ridges 110, the scanner can also image the internal features of the finger 105. This could be used for identification via pulse recognition and/or other biometric features such as tissue structure, ligaments, veins, and arteries. As an example, an acoustic scanning device can detect a pattern of blood vessels in a finger and/or a palm of hand and identify a person based on the pattern of blood vessels. This three-dimensional scan of the finger 105 can be used to generate two and/or three dimensional images of the finger 105. The two and/or three dimensional images can be processed using image processing and pattern recognition techniques.

In order to identify fingerprints, a finger print recognition device can resolve ridges in a finger with a resolution that is better than 50 µm. Ultrasound approaches can measure the impedance mismatch between a plate (e.g., a glass plate) and tissue, which can represent ridges, and the plate and air, which can represent valleys between ridges.

Some ultrasound scanners that use waveguides in a glass plate can guide ultrasound signals with a lower frequency than the frequency of the ultrasound signal from the transducer 130 (i.e., lower than 50 MHz) to allow the measurement of the impedance mismatch between a finger and the glass plate. Some ultrasound sensors can include posts of piezoelectric material that are narrower than 50 µm and such scanners can measure the impedance change due to surface contact between each post and the finger. In ultrasound scanners with waveguides and/or narrow posts of piezoelectric material, relatively complex construction can be involved to measure on a scale of 50 µm with ultrasound signals whose wavelength is much larger than 50 µm. Such a complex assembly can result in a relatively expensive and difficult to construct system for ultrasound fingerprint scanning. Other disadvantages of such an example can include opacity and difficulty engineering a receiving surface incorporating waveguides in certain metal and/or glass surfaces.

Some ultrasound scanners can generate ultrasound signals with a frequency of over 1 GHz (e.g., around 5 GHz) to avoid issues associated with diffraction. However, at such frequencies, the ultrasound signals may not penetrate tissue. Moreover, scanners with ultrasound signals at such frequencies can be constructed of materials that allow signals with such frequencies to propagate without significant attenuation. Furthermore, a two-dimensional (2D) array of 50 µm transducer elements could be prohibitively complex for addressing, and is further complicated by the electrical crosstalk while operating at frequencies over 1 GHz.

Figure 2:
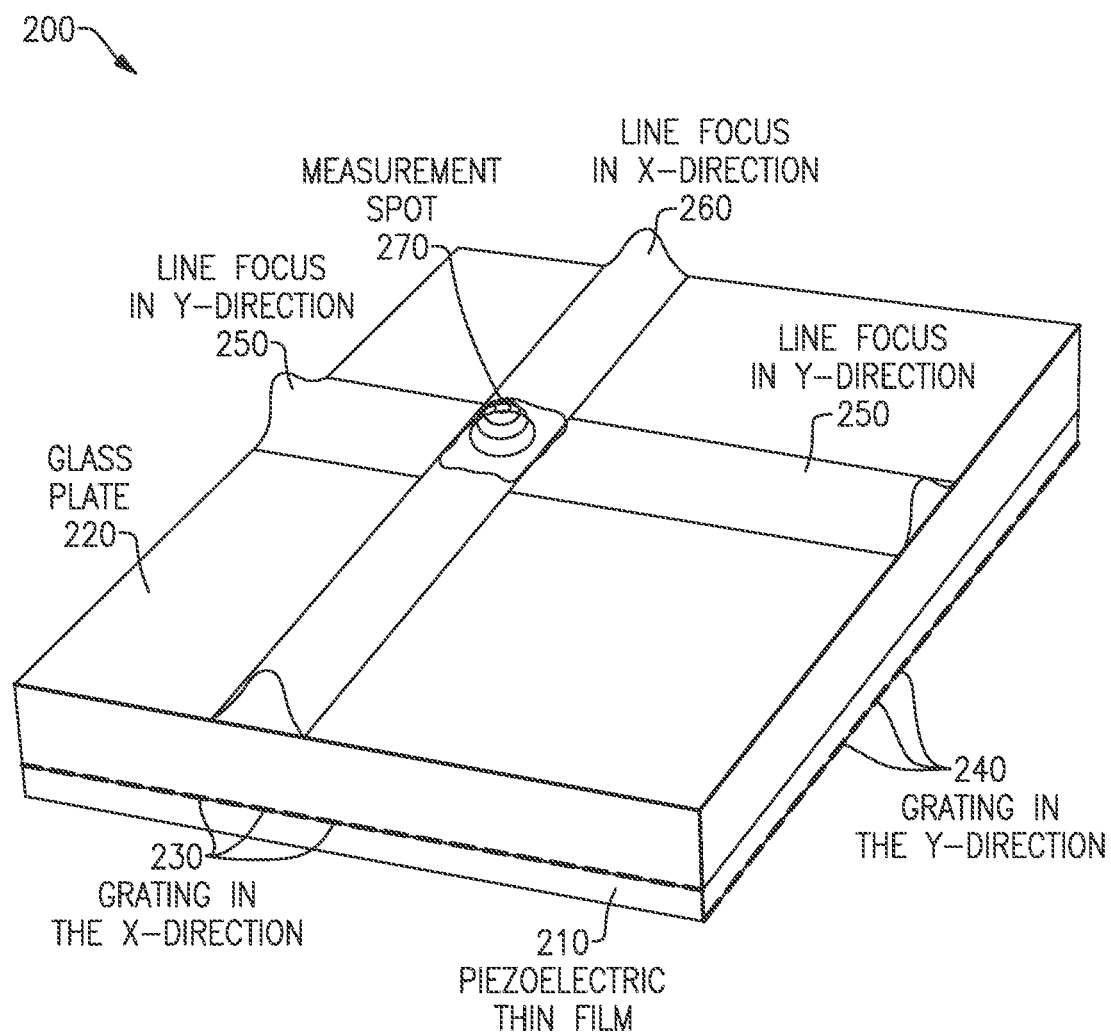
FIG. 2 illustrates a device for focusing sound waves with a row-column addressed two-dimensional (2D) array. Only one transmit focal line can be active at a time. One or more receive focus lines can be active at a time. The transmit and receive focus lines are perpendicular to each other and intersect at a measurement spot with a compact focal spot size.

The disclosed technology, as exemplified in the device in FIG. 2, can overcome the above-mentioned deficiencies, among others, of ultrasound scanners that operate at lower and higher frequencies.

FIG. 2 illustrates a device 200 for focusing sound waves with a row-column addressed 2D array of ultrasound transducers. The device 200 includes piezoelectric thin film 210, glass plate 220, a grating in the x-direction 230, and a grating in the y-direction 240. As shown in FIG. 2, the device 200 can operate so as to have a line of focus in the x-direction 250, a line of focus in the y-direction 260, and a measurement spot 270 where the line of focus in the x-direction 250 intersects with the line of focus in the y-direction 260. Only one transmit focal line can be active at a time. One or more receive focus lines can be active at a time. The transmit and receive focus lines are perpendicular to each other and intersect at a measurement spot with a compact focal spot size.

The device 200 uses ultrasound imaging at a sufficiently high frequency (e.g., in a range from 50 MHz to 500 MHz, such as approximately 150 MHz) in order to achieve a 50 µm resolution using beamforming. Thus, the device 200 can achieve a desired 50 µm resolution without waveguides. Accordingly, the device 200 can have a simpler construction relative to ultrasonic scanner devices that include waveguides. Additionally, there can be less constraint on the type of touch material and/or thickness of this material.

The piezoelectric layer 210 can generate an acoustic signal having a frequency in range from 50 MHz to 500 MHz. A transducer array arranged to transmit such acoustic signals can be implemented efficiently and achieve a desired image resolution without waveguides between the transducers and a receiving surface of the device 200, in which the receiving surface is configured to receive and make physical contact with the finger. In some applications, the piezoelectric layer 210 can generate an acoustic signal having a frequency in range from 125 MHz to 250 MHz. According to certain implementations, the piezoelectric layer 210 can generate an acoustic signal having a frequency in range from 50 MHz to 100 MHz. For example, an acoustic signal in the range of 50 MHz to 100 MHz may be used for a device implemented in a credit card.

The piezoelectric layer 210 can include any suitable piezoelectric material. For example, the piezoelectric layer 210 can be a zinc oxide layer, an aluminum nitride layer, a lithium niobate layer, a lithium tantalate layer, bismuth germanium oxide, lead zirconium titanate, or even a polymer piezoelectric such as a polyvinyl difluoride layer. The thickness of the piezoelectric layer 210 can be suitable for generating an acoustic signal having a frequency in a range from 50 MHz to 500 MHz. The piezoelectric layer can have a thickness in a range from 3 micrometers to 75 micrometers. In some applications, a zinc oxide piezoelectric layer can have a thickness of in a range from about 10 to 20 micrometers. A zinc oxide piezoelectric layer is an example of a piezoelectric layer that can be sputtered onto a substrate, such as a glass substrate. According to certain applications, a lithium niobate piezoelectric layer can have a thickness in a range from about 5 to 10 micrometers. Such a lithium niobate piezoelectric layer can be bonded to a substrate, such as a glass substrate, by an epoxy.

As illustrated, the device 200 includes a glass plate 220. The glass plate 220 is an example substrate on which a piezoelectric layer can be disposed. Any of the acoustic sensing devices discussed herein can include other substrates as suitable. For example, a metal layer or a plastic substrate can be a suitable substrate in certain applications.

In an embodiment, the glass plate 220 can be about 500 µm thick. This thickness can be any suitable thickness based on the piezoelectric material used, ultrasound frequency, and application. Such a thickness can be nominal for portable communication and computing device. In other instances, the glass plate 220 can be thinner and attached to thicker plates of any suitable material. Accordingly, the finger print device could be on the metal housing of a phone or any such system. The arrangement can be any suitable size. Accordingly, the device 200 can cover most or all of a whole plate to make a touch screen and finger print recognition at the same time.

In operation, the device 200 can measure the reflection coefficient at the location of the focus, that is at the measurement spot 270 at the intersection of the lines of focus 250 and 260 in x and y directions. The size of the measurement spot 270 can be determined by the diffraction resolution of the device. For instance, for ultrasonic transducers providing 150 MHz acoustic signals in glass, this spot size 270 can be about 40 micrometers. The change in reflection coefficient at the glass finger interface would be either 1 or about 0.85 depending on the type of glass used in the finger print device. By adding a matching layer on the glass, between the glass and the finger, it is possible to enhance the coupling into the tissue and end up with a contrast in the reflection coefficient of approximately 1 to 0. The thickness of the matching layer can be chosen to be a quarter of a wavelength of the ultrasound signal in the matching layer material. As an example, a matching layer can include epoxy with a thickness of about 5 µm for a device 200 that transmits acoustic signals in of around 150 MHz.

The device 200 can include electronics for linear array imaging. Such linear imaging can be similar to linear imaging in medical ultrasound imaging systems. In such operation, a number of elements in the array are grouped together and excited with different phased signals such that the arrival times at the plate-finger interface occur at the same time from all the array elements. The receiver array elements, similar in number to the transmit array elements, would then receive the reflected signals, and electronic phase delays are added to each element to make their arrival times be the same for dynamic active focusing of tissue. Once a measurement is made at one spot, the receiving array elements can be shifted by one element to enable a measurement of the next adjacent resolution spot. The process can be repeated to image a whole line by scanning the receive array. Next, the transmit array can be moved by one element, and the process can be repeated for receiving on another line. Overall, this process can be repeated to image the whole area or any desired portion of the finger.

In the above description, the imaging is done at the plane of the plate finger interface 125. However, at the locations where the finger is in touch with the plate, ultrasound energy can penetrate into the finger and reflections would occur from tissue inside the finger. Hence, information can be gathered from within the finger, such as information on blood flow in capillary blood vessels in the finger. From such information, the device 200 can derive information such as heart rate, indicating the subject is alive, or even some measure of capillary vessel health based on pulse wave velocity in the vessel.

The fingerprint scanner can scan the surface and possibly the volume of a finger. The device 200 can perform such imaging with a two-dimensional (2D) array of ultrasound transducers and no moving parts. Addressing a full 2D transducer array quickly can be a challenge due to a relatively large number of interconnects.

Figure 3:
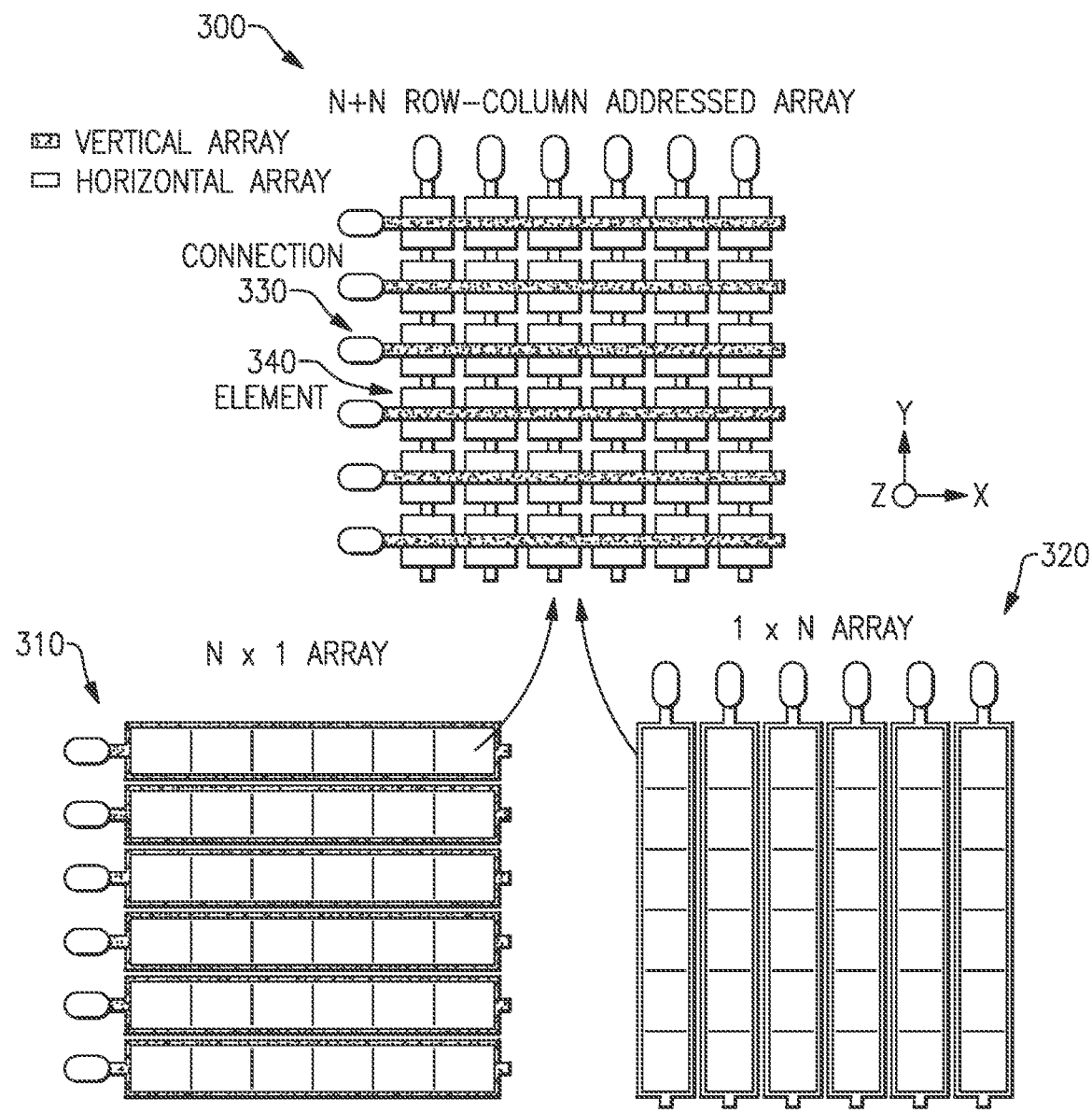
FIG. 3 illustrates a two-dimensional row-column addressed array of transducer elements addressed by a vertical array of row electrodes and a horizontal array of column electrodes, the vertical and horizontal arrays orthogonal to each other and on different sides of the array.

An alternative to full addressing is row-column addressing where an entire row of elements or an entire column of elements are addressed at a time. This can be achieved by having elements in the same row share the top (or bottom) electrode and elements in the same column share the bottom (or top) electrode. Accordingly, the transmit and receive electrodes can be on different sides of the array (top or bottom), and the transmit and receive apertures can be in two different directions (row or column). This can reduce the number of interconnections that fan out from the transducer array. FIG. 3 illustrates a two-dimensional N×N row-column addressed array 300 of transducer elements 340 addressed by a horizontal array of row electrodes 310 and a vertical array of column electrodes 320, the horizontal and vertical arrays 310 and 320, respectively, orthogonal to each other. While FIG. 3 illustrates a square N×N array, any suitable M×N rectangular array with M rows and N columns can alternatively be implemented in which N and M are different positive integers. FIG. 3 includes connections 330 at the ends of each horizontal array 310 of N×1 row arrays and each vertical array 320 of 1×N column arrays.

One way of using the row-column addressed array 300 has already been discussed with reference to FIG. 2. One receive focus is generated per transmit-receive event. A 512×512 2D array that uses 13 active elements in both the transmit and receive aperture can use about 500×500=250,000 transmit-receive events to make one scan. That would take approximately 43 ms to complete one scan, when the coupling medium is glass with a speed of sound of 5760 m/s and a thickness of 0.5 mm. If the receive electronics are expanded to record all receive elements in parallel, the scan can be completed in 500 transmit-receive events. This would about take about 87 µs for a full scan.

To further increase the scanning speed, parallelization can also be introduced in the transmit stage such that multiple transmit waves are emitted at a time. To parallelize the transmit beams for row-column addressed arrays, the transmit beams can be separated in the frequency domain and then received by different filters to separate them. The different filters can then pass the data to the receive beamformers. Any combination of transmit and receive parallelization can be utilized. The ultrasound beams can also be angle steered instead of translating the active aperture, or a combination of the two can be used. The scan can also be synthetically focused by using synthetic transmit focusing, synthetic receive focusing, or both.

This can effectively utilize the 2D transducer array as two 1D transducer arrays, which are orthogonal to each other. When one array is used for transmission and the other for reception, then full 3D imaging is achievable. One interconnect and beamformer-channel can be used per row and per column.

As an example, a fully addressed 256×256 element array can involve 65536 interconnections, whereas if it is row-column addressed 512 interconnections 330 can be implemented.

In operation, one set of electrodes, e.g., x-axis electrodes, can be used to transmit a line-focused beam of ultrasound. The focus can be at the location of the surface-finger interface. Once a pulse is transmitted by the x-axis aligned electrodes, the y-axis aligned electrodes can be used to detect a line focus in the x-direction as also shown schematically in the FIG. 2. The total response of the system is the intersection of the two focal lines and results in a resolution spot commensurate with diffraction limited resolution.

Transmit beamforming can be used for both fully addressed arrays and row-column addressed arrays to focus the emitted ultrasound beam at a chosen focal depth in the medium. This maximizes the acoustic pressure at the area of interest, which improves the SNR and image quality at that focal area. The pulse characteristics, such as length, amplitude level, and center frequency can also be varied to obtain the required imaging performance.

Figure 4:
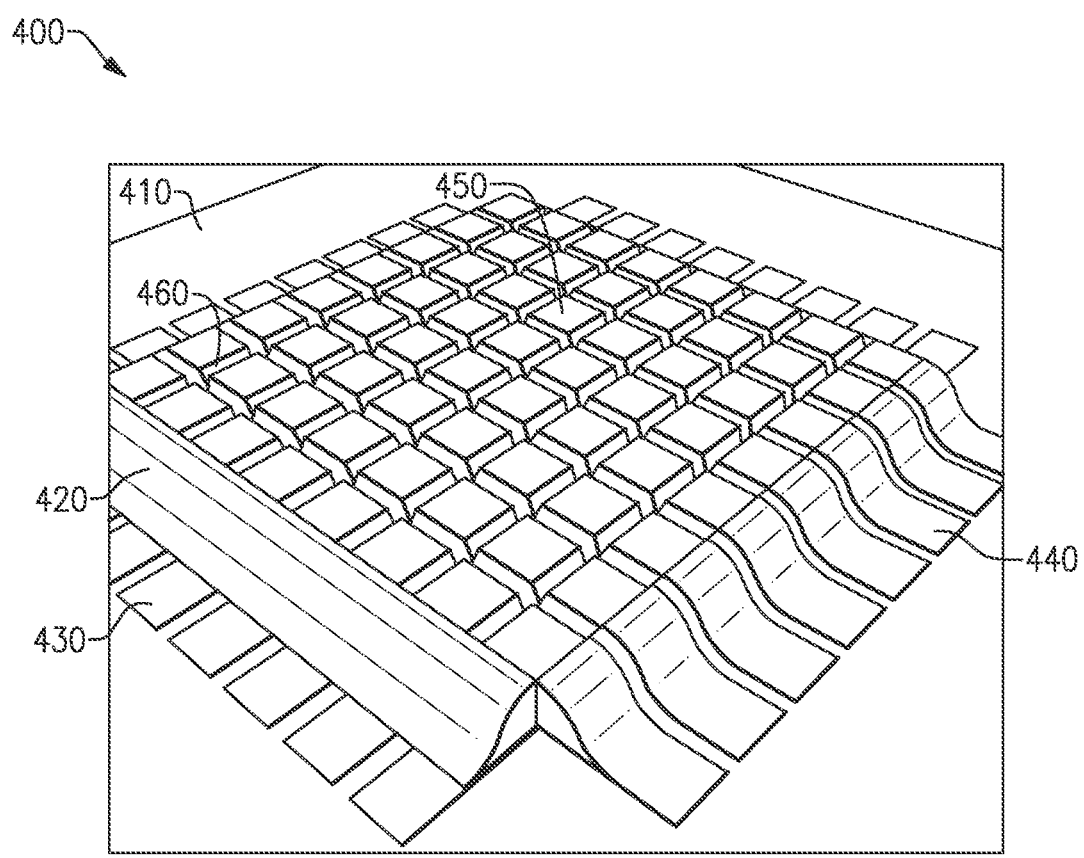
FIG. 4 illustrates a perspective view of an example ultrasound transducer array mounted on a substrate.

FIG. 4 illustrates a perspective view of a schematic of an example ultrasound transducer array 400 on glass 410. The ultrasound transducer array 400 includes bottom electrodes 430 on top of the glass substrate 410. The bottom electrodes 430 form a vertical array of lines in a horizontal direction. A piezoelectric thin film 420, such as zinc oxide, is on top of the bottom electrodes 430 and glass substrate 410. The piezoelectric thin film 420 can be square or rectangular in shape. The piezoelectric thin film 420 overlaps the array of bottom electrodes, but end portions of each bottom electrode 430 are not overlapped by the piezoelectric thin film 420 as illustrated to allow for creating metallic contacts. The piezoelectric thin film 420 is etched with trenches or grooves, such as v-shaped etchings 460 in both vertical and horizontal direction to reduce crosstalk for both receiving and transmitting in the array of transducer elements 450. The v-shaped etchings 460 are one example of trenches or grooves. Other embodiments can include trenches or grooves that are not v-shaped and have another suitable shape. In certain embodiments, any other suitable transparent layer, such as a transparent layer of plastic, can replace the transparent layer of glass 410.

The top of each transducer element 450 is substantially square as illustrated. The top of one or more transducer elements 450 can have a different shape, such as a rectangular shape, in some other instances. Top electrodes 440 form a horizontal array of lines in a vertical direction. The top electrodes 440 are orthogonal to the bottom electrodes 430. The top electrodes 440 conform to the shape of the transducer elements 450, including the tops of and sides of transducer elements 450 formed by v-shaped etches 460. The width of each of the bottom electrodes 430 and the top electrodes 440 substantially corresponds to the length of the corresponding edges of the transducer elements 450. For example, the bottom electrodes 430 each have a width substantially the same as the width of the top electrodes 440, which is substantially equal in length to each side of the square tops of each transducer element 450 of the two-dimensional ultrasound transducer array 400.

The ultrasound transducer array 400 can be fabricated using a piezoelectric thin film 420 that is deposited on the surface by one of many thin film deposition techniques such as and not limited to: evaporation, DC or AC sputtering, sol-gel deposition, chemical vapor deposition, etc. Any suitable deposition method can provide a properly oriented thin film that would provide a reasonable electro-mechanical coupling coefficient to enable the excitation and detection of ultrasound signals. In order to reach a frequency in the mid-high range frequencies above 50 MHz and below 500 MHz piezoelectric transducers (e.g., zinc oxide based transducers) can be fabricated using sputtering technology or with a relatively thin piezoelectric plate (e.g., of lithium niobate or lithium tantalate). Assuming a speed of sound of a 360 rotated Y-cut lithium niobate piezoelectric layer, the plate can have a thickness in a range from about 7.4 micrometers to 74 micrometers. With a lithium niobate or lithium tantalate piezoelectric layer, a thin bonding layer can be included between the piezoelectric and the substrate.

The frequency of operation of an ultrasonic sensor device can depend on the material of the sensor plate or substrate to generate an image with a desired resolution. If the sensor plate is made of sapphire, the speed of sound in sapphire is relatively high at 11,100 m/sec. so a wavelength (resolution) of 50 µm involves a frequency of operation of 222 MHz. And, because sapphire has a higher mechanical impedance than most piezoelectric materials, the piezoelectric would operate in the so-called quarter-wavelength mode thus involving a thinner piezoelectric film. For instance if zinc oxide (ZnO) is being used, the thickness can be about 7.1 µm. A similar exercise shows that for operation in quartz with a speed of sound of 6,320 m/sec, a wavelength of 50 µm is obtained by operating at 126.4 MHz, and a ZnO film that is about 25 µm thick. For operation in polypropylene with a speed of sound of 2,740 m/sec, a wavelength of 50 µm is obtained by operation at 55 MHz, and ZnO film thickness of about 57 µm. In the situations where the thickness of the particular piezoelectric film is too large for simple deposition, other alternative manufacturing methods such as epoxy bonding can be utilized.

The wavelength in the plate can be roughly equal to the resolution which for finger print recognition is 50 µm. Hence once a material is chosen, the frequency of operation is given by f=speed of sound/50 µm. The thickness of the piezoelectric is about half a wavelength for the cases where the plate has a lower impedance than the piezoelectric material. Hence, the thickness of the piezoelectric is given by t=speed of sound/twice the frequency of operation.

In an embodiment, the piezoelectric film is a ZnO thin film with a thickness of about 16 µm, a transducer size of 20 µm×20 µm to 30 µm×30 µm for a single sub-element, a line spacing (kerf) of 10-20 µm, a line width of 10-20 µm, and a pitch of 40-50 µm. The line width, line spacing, pitch, or any combination thereof can be within these ranges when the piezoelectric film includes a different material.

The device 400 can be made by first depositing a pattern of lines in one direction along the glass substrate. For example, the lines and spaces can be of the order of 25 µm and can be followed by the deposition of a piezoelectric thin film about 15 µm in thickness. Another set of lines and spaces can be formed along an orthogonal direction to the previous lines and spaces between the lines. Manufacturing such a device can be relatively simple compared to other ultrasound finger print solutions. The lithography of the lines and spaces is well within the capabilities of current semiconductor manufacturing capabilities, and the deposition of the piezoelectric thin film (15 µm) can be done by either physical vapor deposition (sputtering) or sol-gel manufacturing methods. Either way, a number of choices of piezoelectric materials are available for this purpose. These three manufacturing steps can be used to manufacture the device. Next, the x- and y-electrodes can be connected to electronic circuitry for the operation of the finger print recognition.

Figure 5:
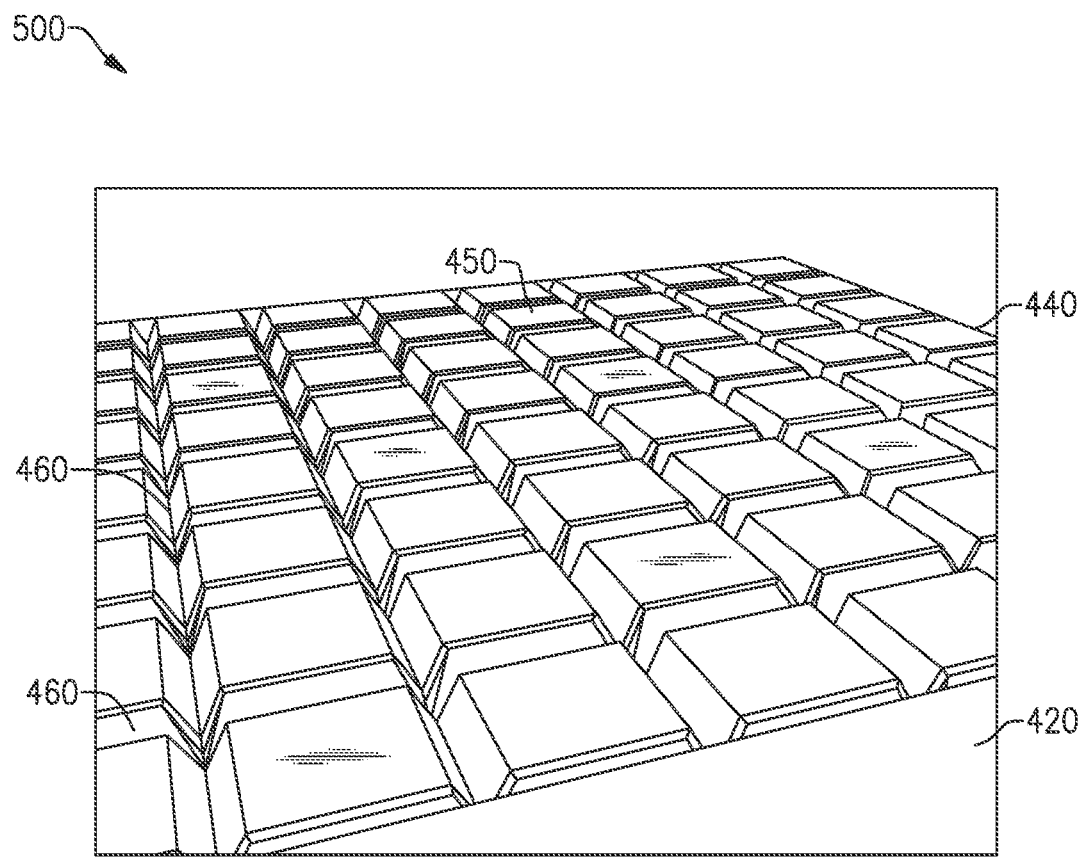
FIG. 5 illustrates a perspective view of a portion of an ultrasound transducer array mounted on a substrate.

FIG. 5 illustrates a perspective view of a portion of an ultrasound transducer array on a substrate. FIG. 5 illustrates a portion of the acoustic biometric touch scanner of FIG. 4, including piezoelectric thin film 420, top electrodes 440, transducer elements 450, and v-shaped etchings 460. FIG. 5 illustrates the v-shaped etchings 460 between transducer elements 450, in both horizontal and vertical directions. The top electrodes 440 conform to the v-shaped etchings 460 in the direction of the top electrodes 440, but do not cover or conform to the v-shaped etchings 460 in the direction orthogonal to the top electrodes 440. As noted above, an embodiment may include etched trenches or grooves that are not v-shaped.

Figure 6:
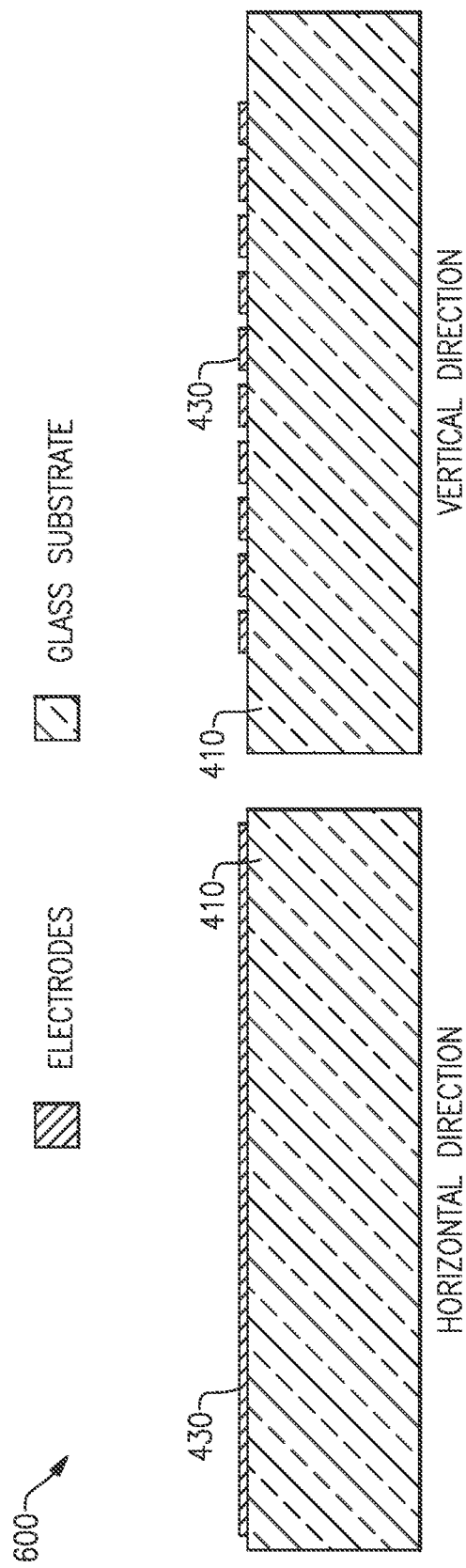
FIG. 6 illustrates an intermediate step of manufacturing an ultrasound transducer array by depositing bottom electrodes on top of a glass substrate.

FIG. 6 illustrates an intermediate step 600 of manufacturing an ultrasound transducer array, such as the scanner of FIGS. 4 and 5, by depositing bottom electrodes on top of a glass substrate. FIG. 6 includes horizontal and vertical direction views of bottom metal electrodes 430 deposited on glass substrate 410. The bottom electrodes 430 form a vertical array of horizontal elements.

Figure 7:
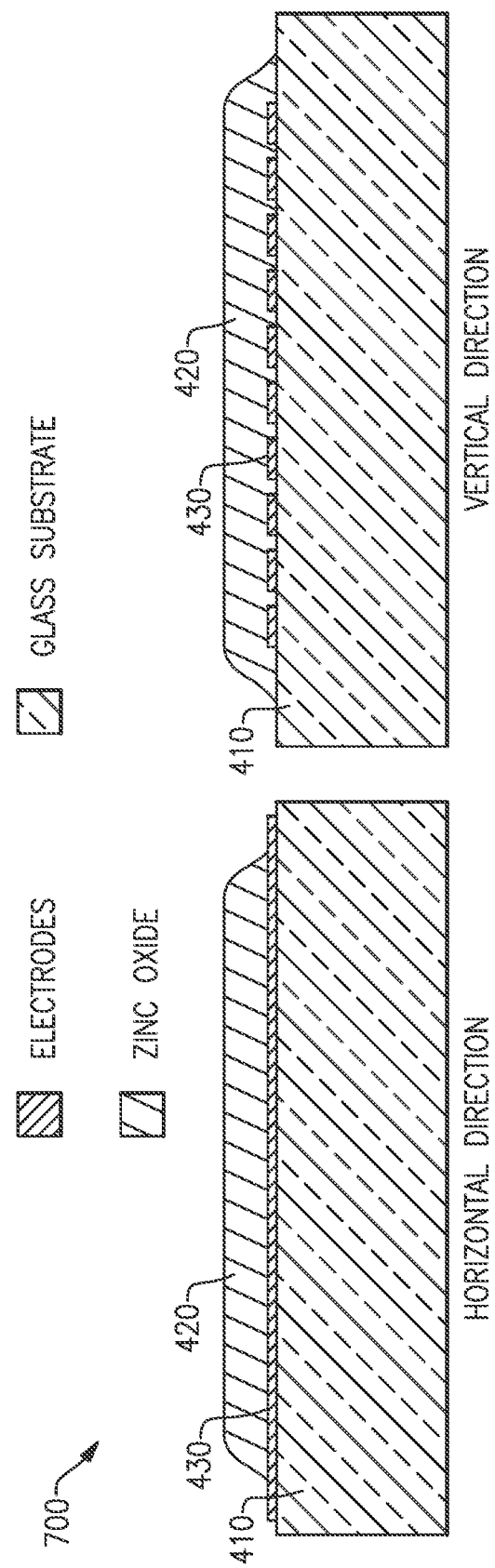
FIG. 7 illustrates an intermediate step of manufacturing an ultrasound transducer array by depositing piezoelectric film over the bottom electrodes.

FIG. 7 illustrates an intermediate step 700 of manufacturing an ultrasound transducer array, such as the array of FIGS. 4 and 5, by depositing a piezoelectric thin film 420, such as zinc oxide, over the bottom electrodes 430. The piezoelectric thin film 420 is adjacent to the bottom electrodes 430 in areas where the bottom electrodes 430 are present, and is adjacent to the glass substrate 410 in areas where the bottom electrodes 430 are absent, such as between the bottom electrodes 430. The piezoelectric thin film 420 may be deposited through magnetron sputtering. Parts of the bottom electrodes 430 are left uncovered at the edges on both sides to allow creation of contacts in a subsequent step.

Figure 8:
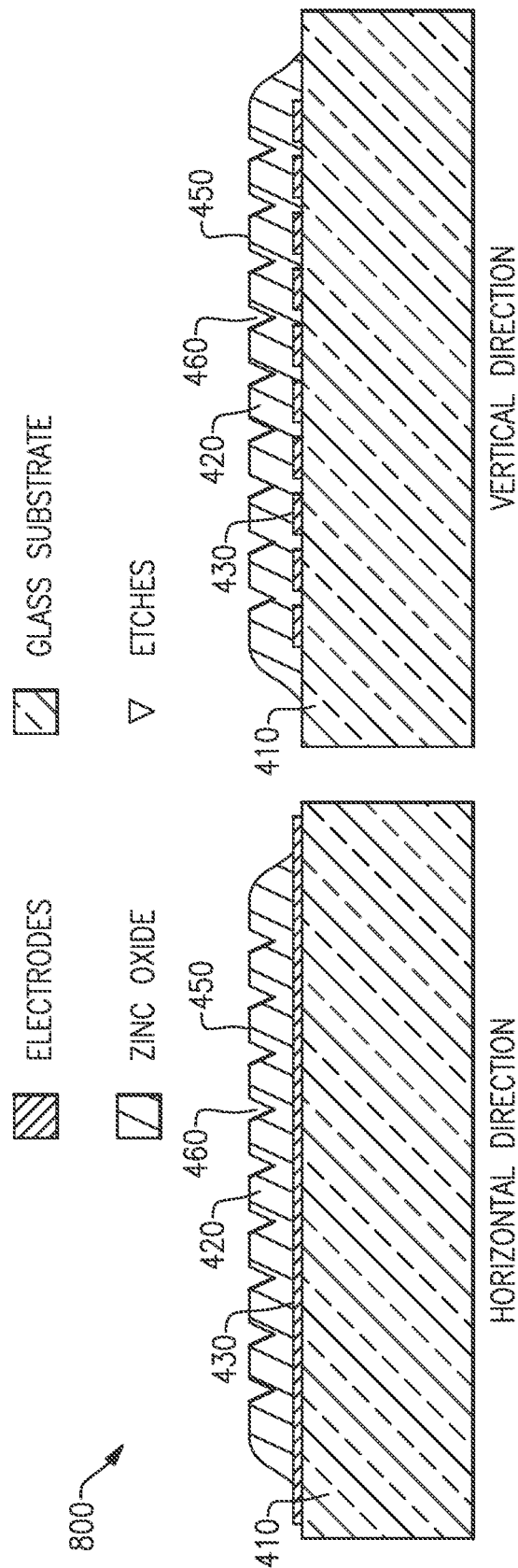
FIG. 8 illustrates an intermediate step of manufacturing an ultrasound transducer array by etching trenches or grooves in two directions on the top side of the film to reduce crosstalk between elements.

FIG. 8 illustrates an intermediate step of manufacturing an ultrasound transducer array, such as the array of FIGS. 4 and 5, by etching v-shaped etches 460 in horizontal and vertical directions on the top side of the film 420 to reduce crosstalk between elements 450. While v-shaped etches 460 are illustrated, any other suitably shaped etch can be implemented. The v-shaped etches 460 form top boundaries of a two-dimensional array of transducer elements 450 in horizontal and vertical directions. The tops of the transducer elements 450 are substantially square in the example of FIG. 8. The v-shaped etches 460 can reduce crosstalk between different transducer elements 450 of the array.

Figure 9:
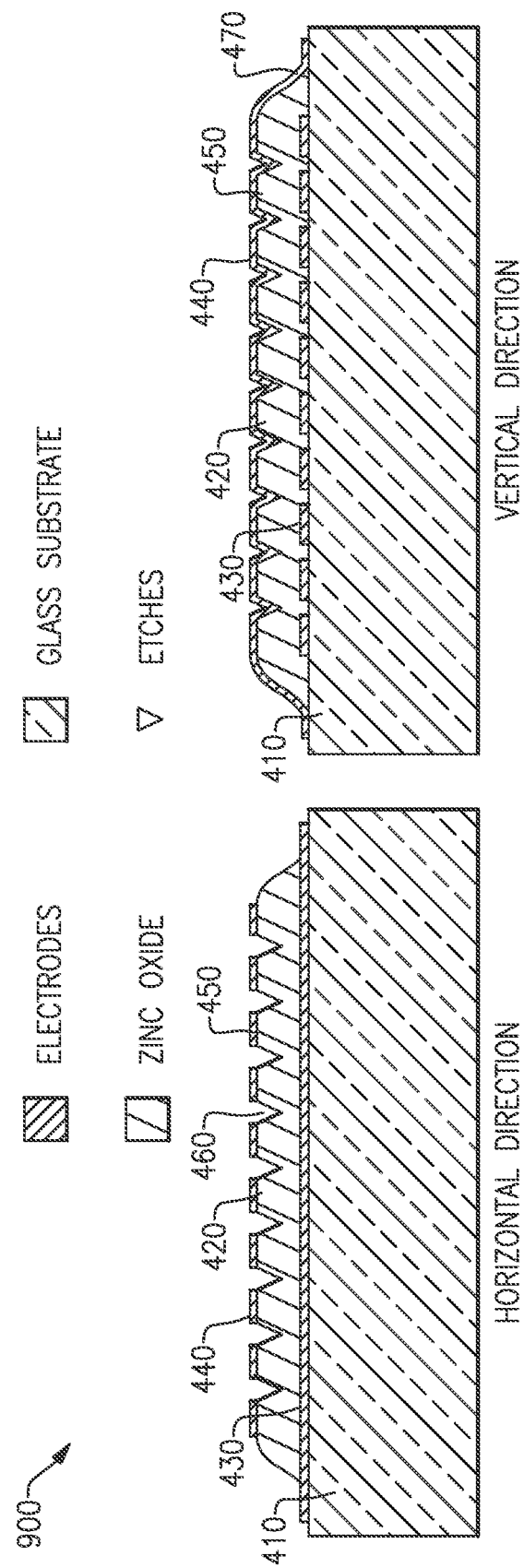
FIG. 9 illustrates an intermediate step of manufacturing an ultrasound transducer array by depositing top electrodes in a perpendicular direction relative to the bottom electrodes.

FIG. 9 illustrates an intermediate step of manufacturing an ultrasound transducer array, such as the array of FIGS. 4 and 5, by depositing top electrodes 440 in a perpendicular direction relative to the bottom electrodes 430. At the edges 470, the top electrodes 440 drop to the same plane as the bottom electrodes 430 from both sides to allow making contacts.

In an embodiment (not shown), absorbing layers, such as rubber or epoxy loaded with particles of tungsten or silicon carbide or any such material, are placed at the edge of the plate to reduce reflections from the edges of the plate that may come back an interfere with the signals of interest. Such edge reflections could also have the effect of reducing the repetition rate at which the finger is interrogated and hence the image frame rate.

Figure 10:
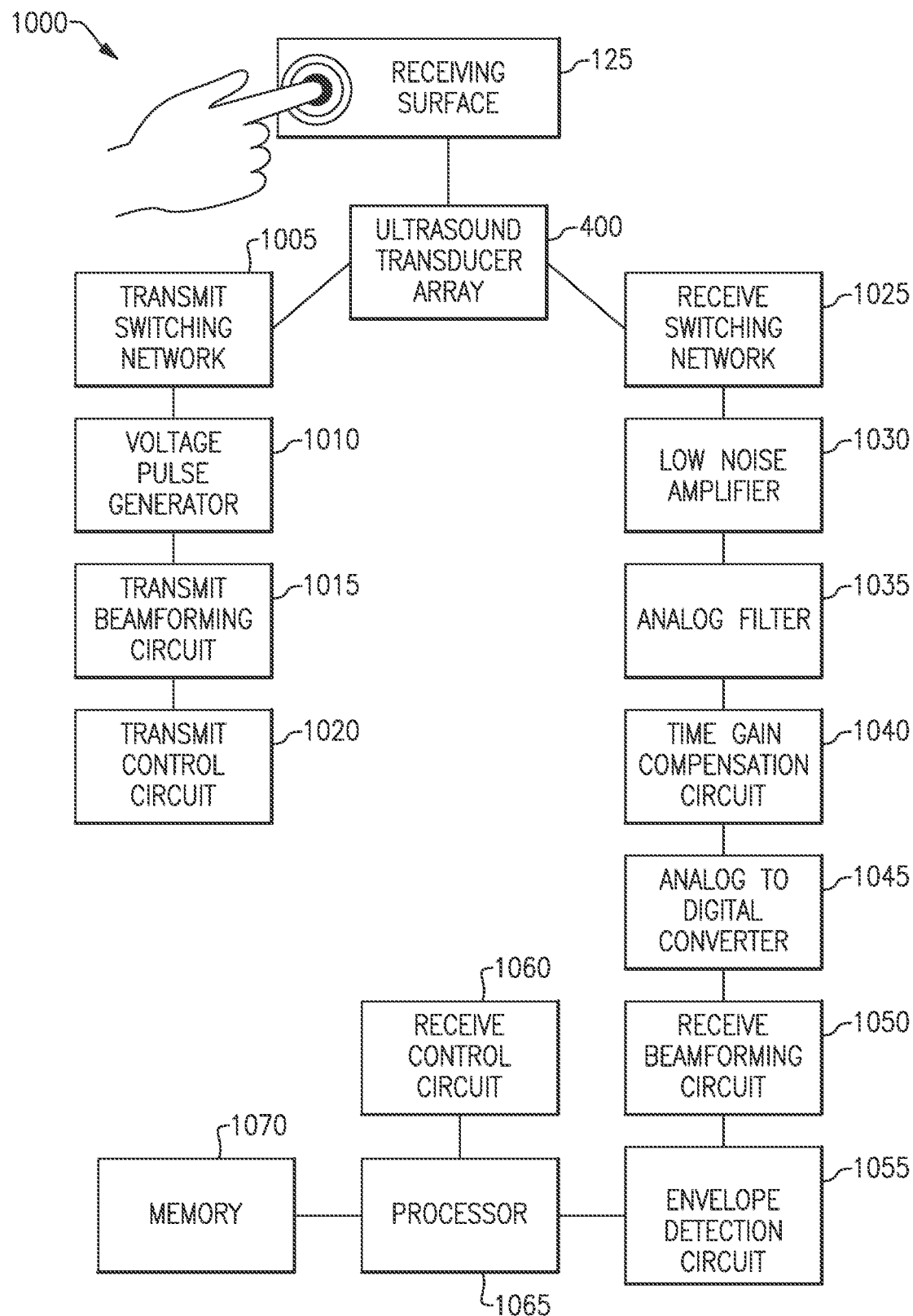
FIG. 10 illustrates an example acoustic biometric touch scanner, including an ultrasound transducer array, transmit electronics, and receive electronics.

FIG. 10 illustrates an example acoustic biometric touch scanner 1000 that includes an ultrasound transducer array 400 as described above with reference to FIGS. 2-9. The acoustic biometric touch scanner 100 includes a receiving surface 125 to receive the touch of a person. The illustrated ultrasound transducer array 400 is interfaced with electronics that control its operation. These electronics include transmit and receive circuits.

The transmit circuits excite the ultrasound transducer array 400 to emit an ultrasound beam toward the imaging area of interest. The excitation can be created by applying an electric voltage pulse across the electrodes of a set of transducer elements within the transducer array. The bottom electrodes can be grounded when the pulse is applied to the top electrodes, and the top electrodes can be grounded when the pulse is applied to the bottom electrodes. The size and shape of a transmit aperture can be varied depending on the imaging area of interest. The illustrated transmit electronics include a transmit switching network 1005, a voltage pulse generator 1010, a transmit beamforming circuit 1015, and a transmit control circuit 1020.

The ultrasound transducer array includes multiple transmit channels, each associated with at least one electrode and ultrasound transducer elements. Each transmit channel can include at least a voltage pulse generator 1010 that generates the pulses, and a transmit control circuit 1020 to provide the inter-channel phase delays when used when triggering the pulses. Each transmit electrode may be connected to a dedicated transmit channel, or multiple electrodes can be grouped together and assigned to one transmit channel. The transmit beamforming is omitted in certain implementations.

A transmit switching network 1005 can be a multiplexer that reduces the number of transmit channels by directing the pulses to the required active elements. During row-column addressing operation, when one side of the electrodes can operate in the transmit or receive mode, the other side is connected to ground. This can be achieved using switches that connect the electrodes to ground/transmit channels, or resistors that provide a relatively low impedance path to connect to ground.

The transmit beamforming circuit 1015 can implement beamforming to focus the emitted ultrasound beam at a chosen acoustic focal depth in the medium. This can produce the smallest spot size (diffraction limited resolution) and maximum acoustic pressure at the focal line, thus providing optimum performance at that focal area. In order to focus on a particular focal area, beamforming circuit 1015 can include delay elements to delay channels relative to each other. For example, the ultrasound transducer array 400 may transmit on multiple bottom electrodes, for example 14 electrodes, at a time. Ultrasound transducer array 400 may transmit over an aperture of, for example, 20 electrodes, and then shift by one or more electrodes, and transmit again. By transmitting over, for example, 20 electrodes at a time is a stronger signal with better signal to noise ratio than would result from transmitting over one electrode at a time. Beamforming circuit 1015 can adjust delays between electrodes. The voltage pulse generator 1010 (pulser) can generate the pulses with a shape, length, level, frequency and bandwidth to obtain a desired imaging performance.

Figure 11:
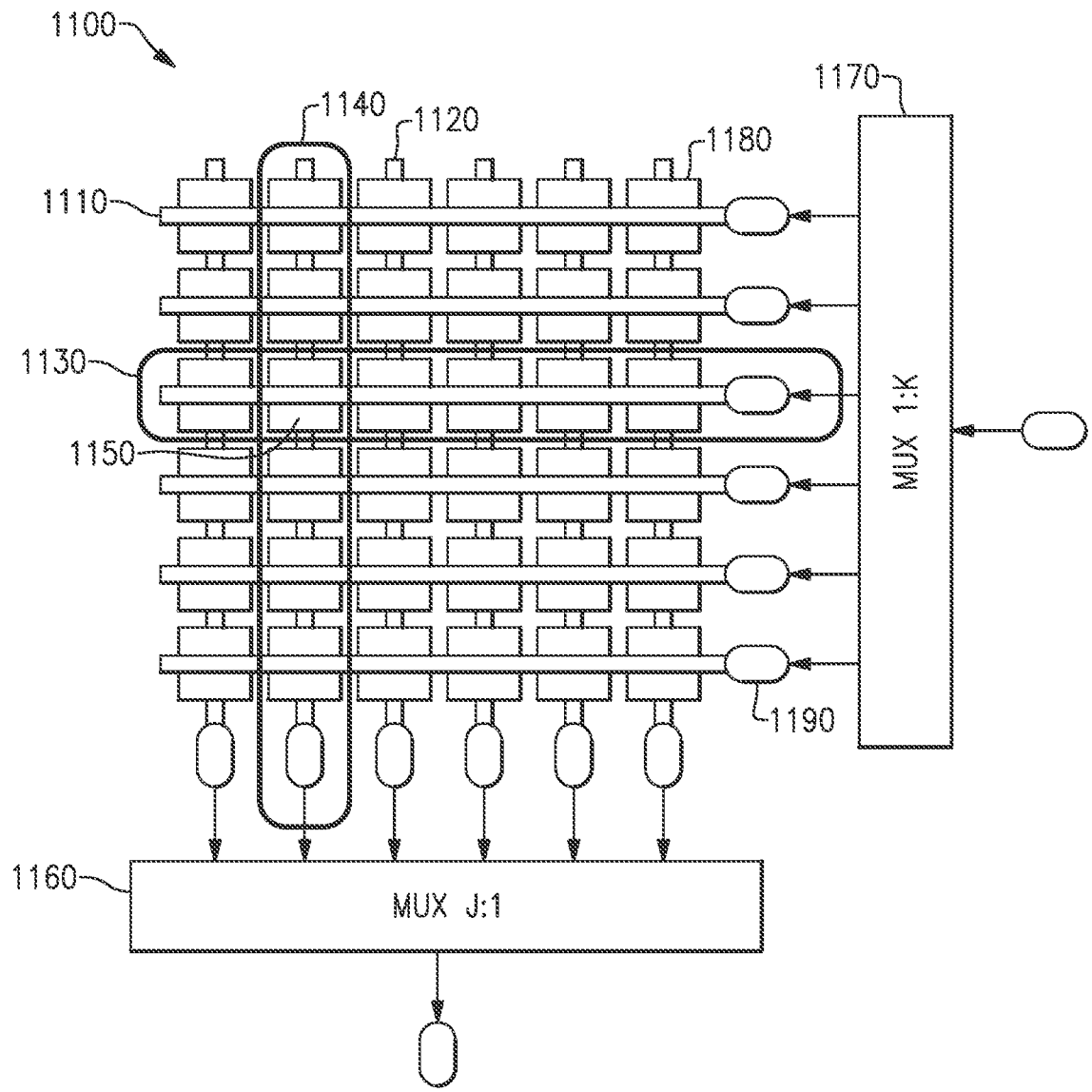
FIG. 11 illustrates a multiplexed single channel row-column addressed transducer array with an intersection of a single active row and a single active column.

As noted above, the size and shape of the transmit aperture can be varied depending on the imaging area of interest. For example, FIG. 11 illustrates a multiplexed single channel row-column addressed array 1100 with an intersection 1150 of a single active row and a single active column. The array 1100 includes rows 1110 and columns 1120 of transducer elements 1180, and contacts 1190. Switching network 1160 is selecting active column 1140, and switching network 1170 is selecting active row 1130. The active column 1140 and active row 1130 intersect at intersection 1150. The active aperture is the full length of line elements. As illustrated in FIG. 11, there are two active apertures, one for transmit and one for receive. This array can focus on a point—the intersection of the two line foci. In FIG. 11 there may be no focusing at all. Instead, the focusing can be performed as a post-processing step of synthetic aperture focusing.

Figure 12:
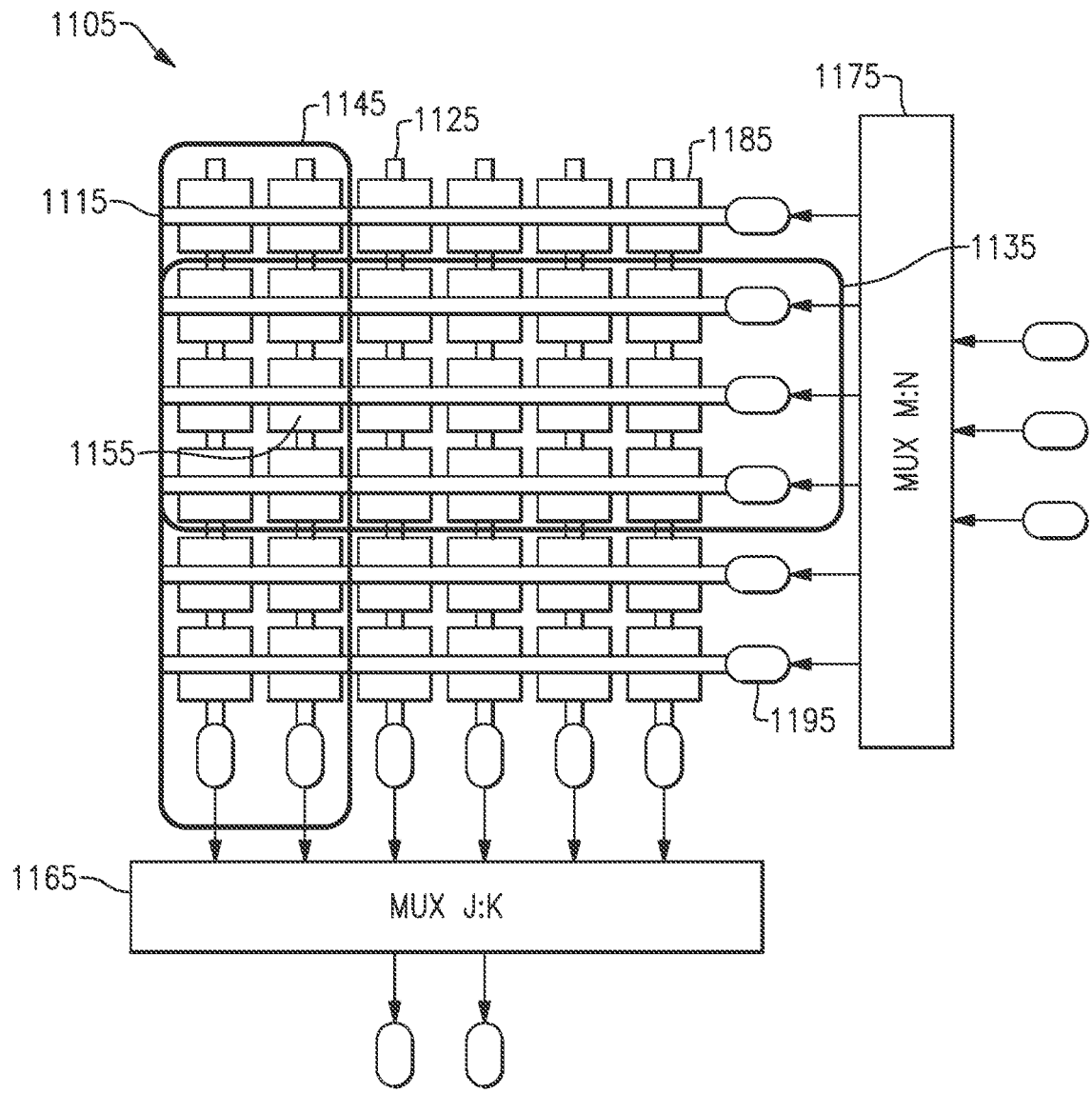
FIG. 12 illustrates a multiplexed single channel row-column addressed transducer array with an intersection of three rows and two columns.

In FIG. 12, the device can include uses hardware beamformers without implementing a post processing step of synthetic aperture focusing. The array 1105 includes rows 1115 and columns 1125 of transducer elements 1185, and contacts 1195. Switching network 1165 is selecting two active columns 1145, and switching network 1175 is selecting three active rows 1135. The active columns 1145 and active rows 1135 intersect at intersection 1155. Any suitable combination of one or more rows and one or more columns of the transducer array can be controlled so as to be concurrently active.

Referring back to FIG. 10, the receive circuits can process the electric radio frequency (RF) signals that are generated by the transducers in response to receiving the ultrasound echo signals from the medium. The receive circuits can then sample the signals, and digital data can be provided to a processor 1065 that is configured to generate an ultrasound image.

The illustrated receive circuits include a receive switching network 1025, a low noise amplifier 1030, an analog filter 1035, a time gain compensation circuit 1040, an analog to digital converter 1045, a receive beamforming circuit 1050, an envelope detection circuit 1055, and a receive control circuit 1060.

The receive switching network 1025 can be a multiplexer that reduces the number of receive channels by switching to the required receive electrodes. During row-column addressing operation, when one side of the electrodes can operate in the transmit or receive mode, the other side can be connected to ground. This can be achieved using switches that connect the electrodes to ground/transmit channels, or receive channels/ground.

The received ultrasound signals can be particularly noise sensitive and at low power. The low noise amplifier 1030 can amplify the received ultrasound signals. This first stage can influence the noise levels in the signal, which should be sufficiently low to allow for the scan to achieve the required signal-to-noise level. The subsequent stages can vary in functionality depending on the implementation. These functions include sampling and receive-beamforming. It should be noted that the subsequent stage is the ultrasound image reconstruction processor, and the receive circuitry can provide the processor with the sampled data representing the received ultrasound echoes.

The analog filter 1035 can remove unwanted frequency components (e.g., the analog filter 1035 can be a bandpass filter to remove unwanted frequency components outside of a pass band). In some other instances, the analog filter 1035 can be coupled between the time gain compensation circuit 1040 and the analog-to-digital converter 1045 and/or an additional filter can be included between the time gain compensation circuit 1040 and the analog-to-digital converter 1045. The time gain compensation circuit 1040 can compensate for the increased attenuation of ultrasound signals that traveled longer distances. For example, reflections from a farther structure within a finger will attenuate more than reflections from a surface structure of a finger. The time gain compensation circuit 1040 can compensate by increasing the gain of the reflection from the farther structure relative to the gain of the reflection from the near structure, traveled for a shorter period of time.

After time gain compensation, the resultant signal can be digitized by analog to digital converter (ADC) 1045, to for subsequent digital processing of the signal. In an embodiment, the analog to digital conversion may occur at a different stage of the processing. For example, in an embodiment with beamforming in the analog domain, analog to digital conversion may be deferred until after receive beamforming.

The receive beamforming circuit 1050 can combine the received signals from multiple receive electrodes that were amplified, filtered, and compensated for by the low noise amplifier 103, analog filter 1035, and time gain compensation circuit 1040, respectively. The receive beamforming circuit 1050, which can be either an analog beamformer or a digital beamformer, can apply delays to combine the reflections received by the active receive electrodes, using delays for focus.

The receive control circuit 1060 can switch off the ADC 1045 or put it in standby mode so that the receive side circuits are inactive, in order to make the ADC 1045 idle when waiting for reflections to subside between consecutive measurements. This can make the acoustic biometric touch scanner 1000 more efficient from a power consumption standpoint.

The receive control circuit 1060 can also control the timing and operation of the receive beamforming circuit 1050. For example, receive control circuit 1020 can provide the inter-channel phase delays when required for received reflections of pulses by different electrodes. In the analog domain, beamforming could be achieved by using analog delay lines and an analog summing circuitry. The analog delay lines can provide a desired relative phase delay between the channels, and the analog summing circuitry will sum all analog signals to generate the beamformed signal. That single beamformed signal can then be sampled, digitized, and sent to the processing unit for reconstruction of the ultrasound image.

In some instances, the single beamformed signal can be envelope detected in the analog domain to reduce the sampling rate requirement. The envelope detected, single beamformed signal can then be sampled, digitized and sent to the processor 1065 for reconstruction of the ultrasound image.

Beamforming can alternatively or additionally be implemented in the digital domain, where the individual signals of the receive channels are sampled and digitized before they are delayed and summed. The digital data can be relatively delayed using digital delay circuitry and summed using a digital summing circuitry. Another approach is to acquire and store only the samples at glass-finger interface, instead of gathering temporal samples along the axial direction. This can reduce the complexity of the hardware and could be done using similar circuitry to the analog beamforming implementation, but instead of using a sampling circuitry to sample all the signal at full speed, a peak detection and a single-sample sampling circuitry can be used to detect the signal level only at the interface, and then use the digital data from different active apertures locations to generate the image of the full scan.

Envelope detection circuits 1055 can detect the envelope of the beamformed signal to reduce the required sampling rate, and then sample the beamformed signal.

Figure 13:
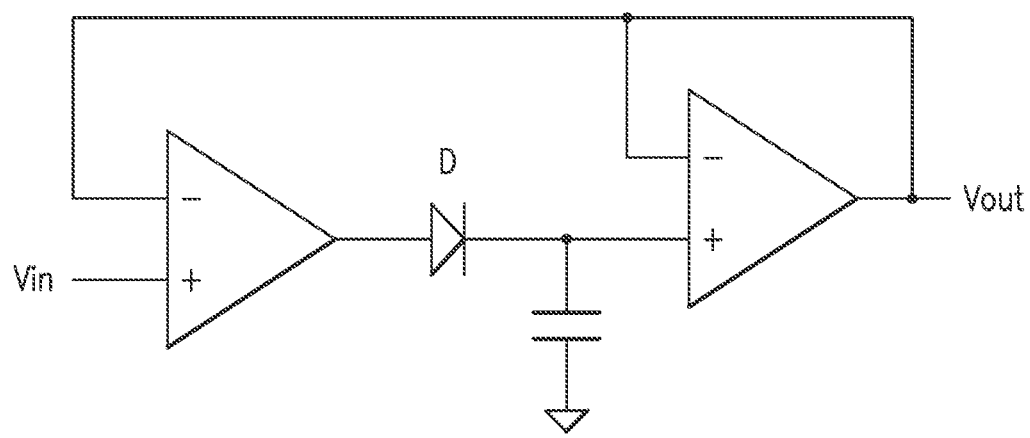
FIG. 13 illustrates peak detection circuitry using op-amps to detect a peak in an ultrasound signal.

There are multiple options for how to implement envelope detection, including peak detection using op-amps. One option is shown in FIG. 13, which illustrates peak detection circuitry 1300 using op-amps to detect a peak in an ultrasound signal. This analog-hardware peak detector can be implemented with reduced hardware complexity and cost compared to some other options. The peak detector is a relatively inexpensive version of an envelope detector and the resulting signal is therefore similar to the baseband signal, which can be sampled at a reduced sampling frequency.

Figure 14:
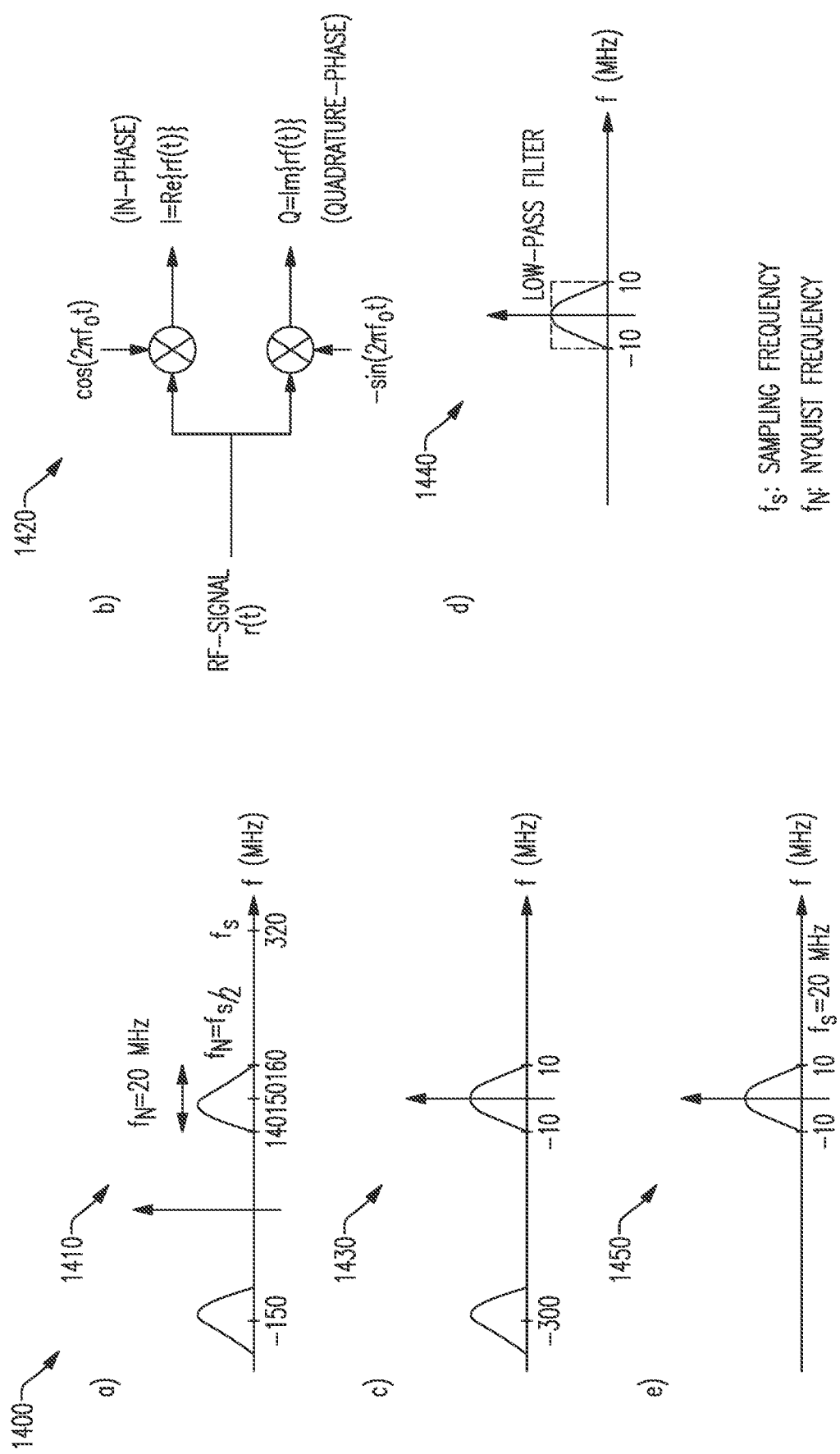
FIG. 14 illustrates frequency domain plots associated with signals in receive circuitry in communication with an ultrasound transducer array.

A second option is shown in FIG. 14, in which an IQ demodulator is used to down mix the RF signal down to base band where it can be sampled with a lower sampling frequency. FIG. 14 illustrates frequency domain plots and signal mixing for in-phase and quadrature demodulation of a signal. Graph 1410 illustrates a signal in the frequency domain centered at 150 MHz with a bandwidth of 20 MHz, sampled at 320 MHz. Block diagram 1420 illustrates mixers to down mix the signal of graph 1410. Graph 1430 illustrates the downmixed signal in the frequency domain, with the baseband signal centered at 0 Hz and an image at higher (negative) frequencies. In graph 1440, the downmixed signal of 1430 is low passed filtered, leaving the baseband signal. Graph 1450 illustrates that the baseband signal can now be sampled at a reduced frequency.

Figure 15:
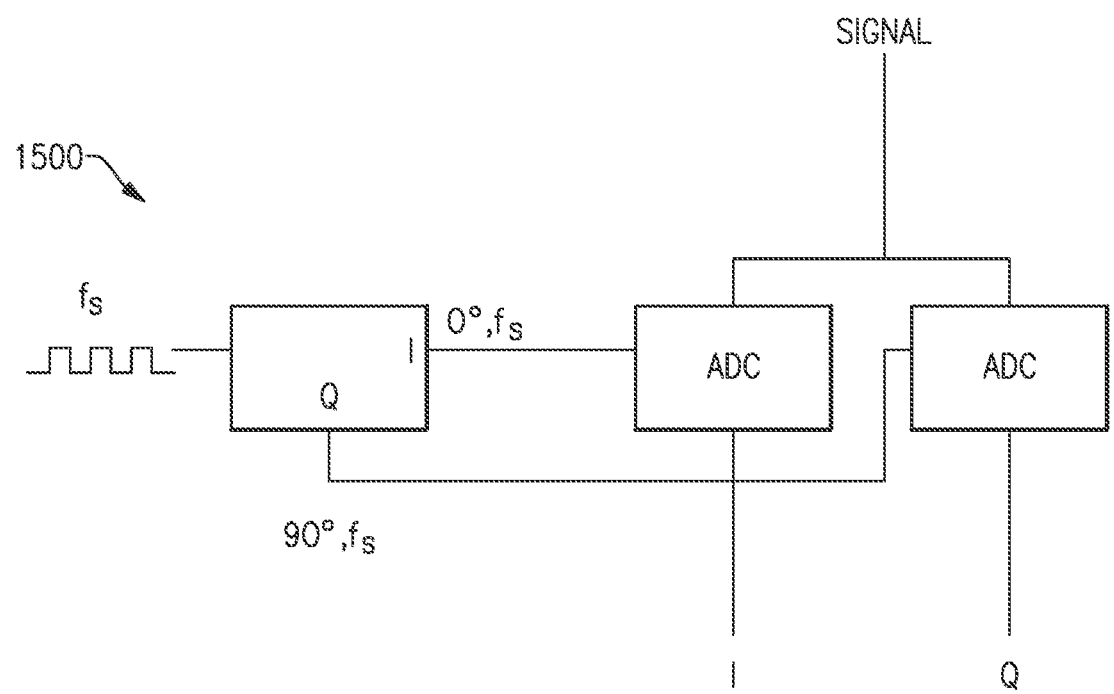
FIG. 15 illustrates a functional block diagram for direct in-phase and quadrature (IQ) sampling in receive circuitry in communication with an ultrasound transducer array.

A third option is shown in FIG. 15, which illustrates a functional block diagram 1500 for direct in-phase and quadrature (IQ) sub-sampling. This approach can be useful if the received signal is narrow band. IQ sub-sampling circuitry combines the functionality of a demodulator followed by a sampling circuitry. The more narrow band the signal is, the lower the sampling rate can be while preserving the image quality. The quadrature signal is only at 900 phase shift for one single frequency, hence it can perform better for narrow band signals than for wide band signals.

Figure 16:
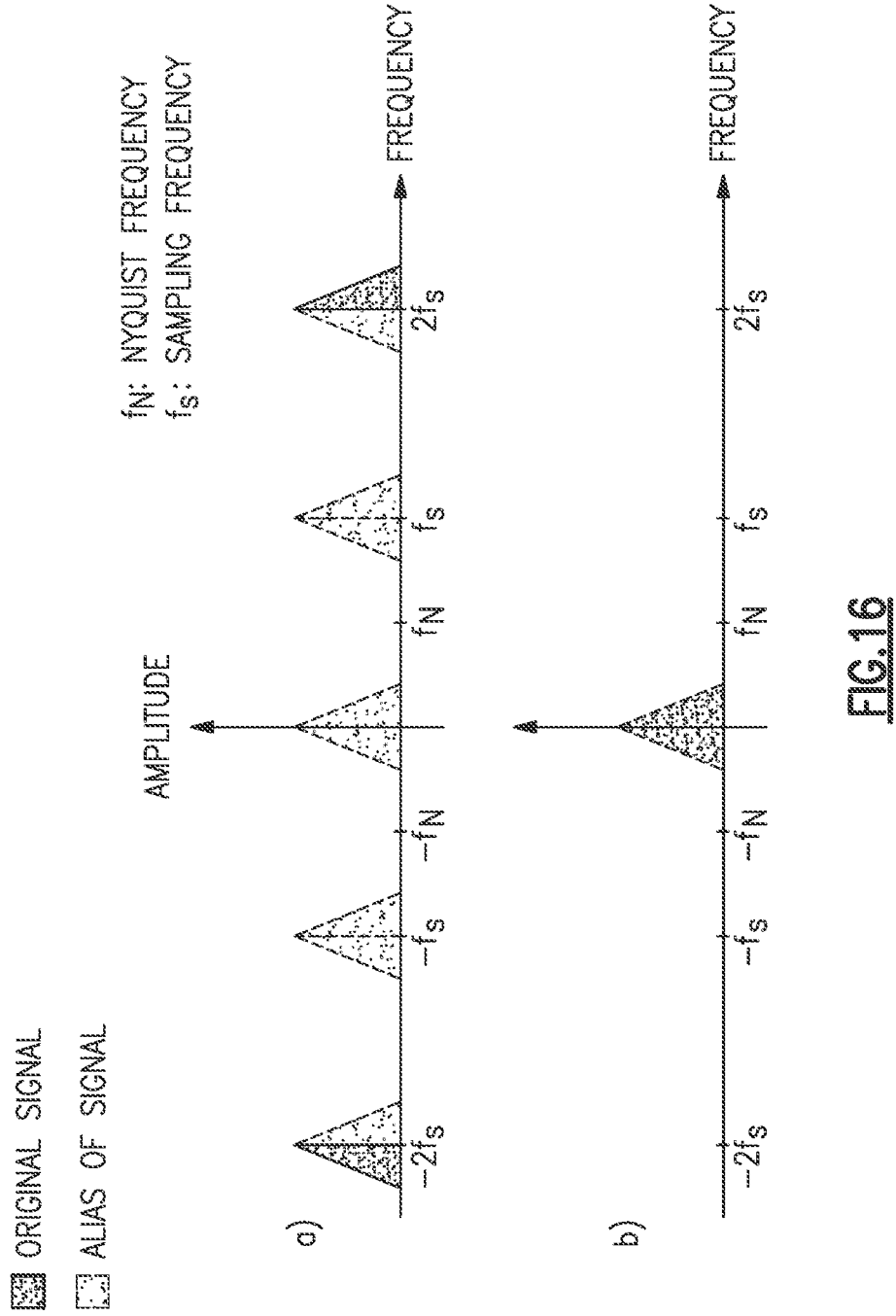
FIG. 16 illustrates an original high frequency signal and its spectral aliases when undersampled, and the baseband alias after undersampling.

A fourth option to reduce the data rate but still keep signal information is under-sampling of a band-limited signal. When sampling a continuous time signal, its frequency content is determined by the discrete time Fourier transform, which has images of the original signal at multiples of the sampling frequency, fs. FIG. 16. illustrates an original high frequency signal and its spectral aliases when it is under-sampled, as well as the baseband alias of the signal after undersampling.

A fifth option is to sample the radio frequency signals at twice the frequency of the highest frequency content in the signal. This option involves a relatively high sampling rate.

Referring back to FIG. 10, the acoustic biometric touch scanner 1000 includes a processor 1065 and memory 1070. The processor 1065 reconstructs images from the reflected ultrasound signals that were amplified, filtered, compensated, digitized, beamformed, sampled and envelope detected, as discussed above. The images reconstructed by processor 1065 may be three dimensional images, or in two dimensions. Images may be reconstructed at different times, or in a time series, to enable change detection or video processing of the finger in two or three dimensions.

The processor 1065 can apply image processing techniques to the reconstructed images to, for example, reduce speckle, highlight blood vessels, measure pulse rate, estimate temperature. Memory 1070 stores reconstructed images, processing results, transmit and receive control instructions, beamforming parameters, and software instructions. Memory 1070 can also store an image, such as a fingerprint image, that the biometric touch scanner 1000 uses to determine if a scanned image is a match.

Accordingly, the processor 1065 can generate an image of at least a portion of a fingerprint based on a reflection of an ultrasound signal from the ultrasound transducer array 400 that is reflected from a finger at the receiving surface 125. The reflection can be received by the ultrasound transducer array 400 and processed by the receive circuit. The processor 1065 can also generate additional information based on a reflection of an ultrasound signal from the ultrasound transducer array 400. Such additional information can include one or more liveness parameters, such a temperature associated with a finger and/or a force at which the finger contacts the device. Based on one or more liveness parameters, the processor 1065 can provide an indication of whether the detected image is associated with a live finger. The liveness parameter together with the fingerprint image can be used for any suitable identification and/or authentication applications. The processor 1065 can cause this indication to be output in any suitable visual, aural, or other manner.

Figure 17:
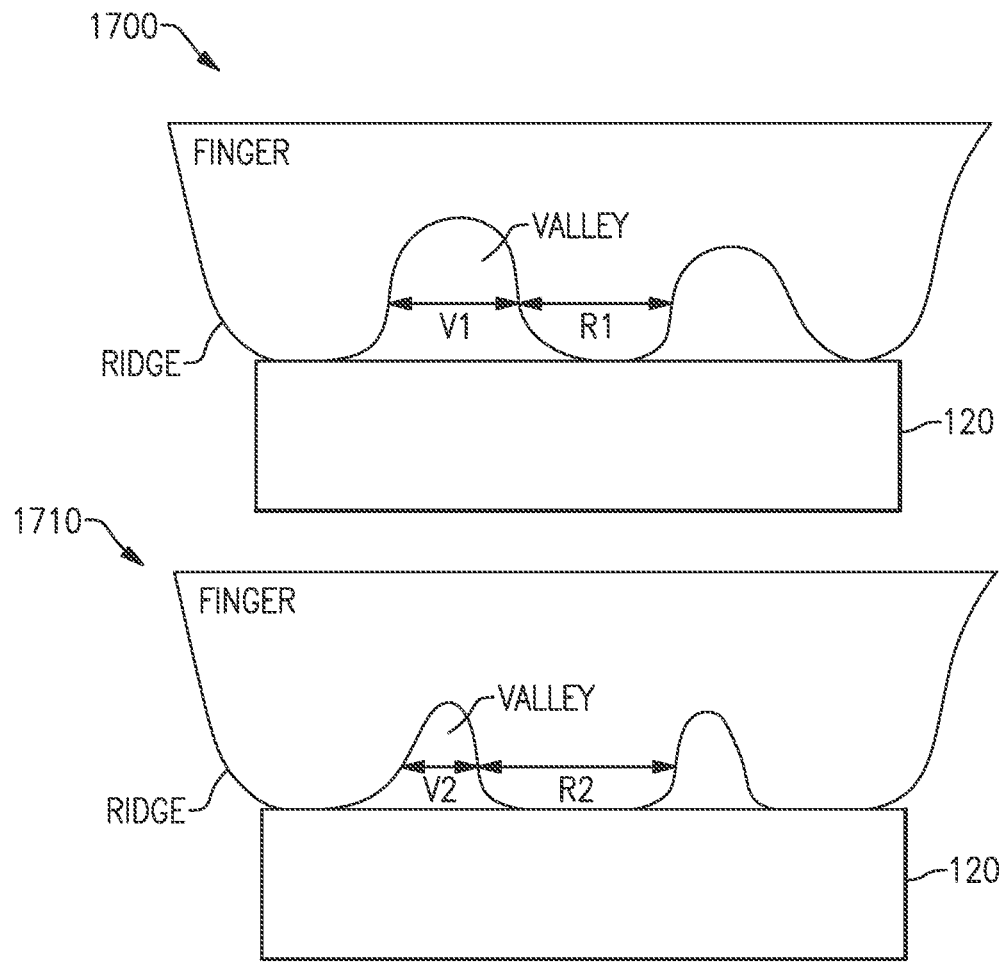
FIG. 17 illustrates that as the force with which a finger is pushed against a receive surface increases, fingerprint ridges widen and the total finger surface in contact with the receiving surface increases.

FIG. 17 illustrates that as the force with which a finger is pushed against a scanner increases, fingerprint ridges widen and the total finger surface in contact with the scanner increases. At lower force 1700, the width of a ridge and a valley in contact with the receiving surface is R1 and V1, respectively. At higher force, the width of the ridge and valley in contact with the receiving surface is R2 and V2, respectively. The width of the ridges can be dependent on the force with which the finger is pushed against the scanner. At higher forces the ridges widen (R2>R1) and the valleys narrow (V2<V1). For example, the width of the valley at lower force and the total surface in contact with the scanner increases. In the example of FIG. 17, as force increases, the surface area of the ridge in contact with the receiving surface increases. This total area, or contact density, can be measured and from this the applied force estimated by assuming a tissue stiffness. The stiffer the tissue is the less it should deform under pressure.

The tissue stiffness itself can also be estimated by measuring the applied force from the finger and comparing it with the estimated force based on the assumed tissue stiffness. The estimated tissue stiffness, α, is value which renders the following equation true:

$$F_{meas} = F_{est}(\alpha)$$

where $F_{meas}$ is the measured force and $F_{est}$ is the estimated force.

Any of the biometric sensing devices discussed herein can implement force detection. A biometric sensing device with force detection can include a processor and transducers configured to transmit an acoustic signal through a receiving surface to a finger. The processor can generate an image of at least a portion of a fingerprint of the finger based on a reflection of the acoustic signal from the finger, detect a surface area of ridges of the finger in contact with the receiving surface based on the reflection, and estimate a force at which the finger contacts the receiving surface based on the detected surface area. The processor can generate an indication of whether the finger is part of a live human based on the estimated force. The image of at least a portion of the fingerprint can have a resolution of 500 pixels per inch or greater.

Sound speed though a medium can change with temperature. In some materials, the speed of sound can increase with temperature. For various materials (e.g., solids such as glass, sapphire, metal, and the like), we expect the speed of sound to decrease with temperature. Accordingly, the dependence of the speed of sound in a material based on temperature can be used to evaluate temperature from a measurement of the speed of sound propagating through the material.

Figure 18:
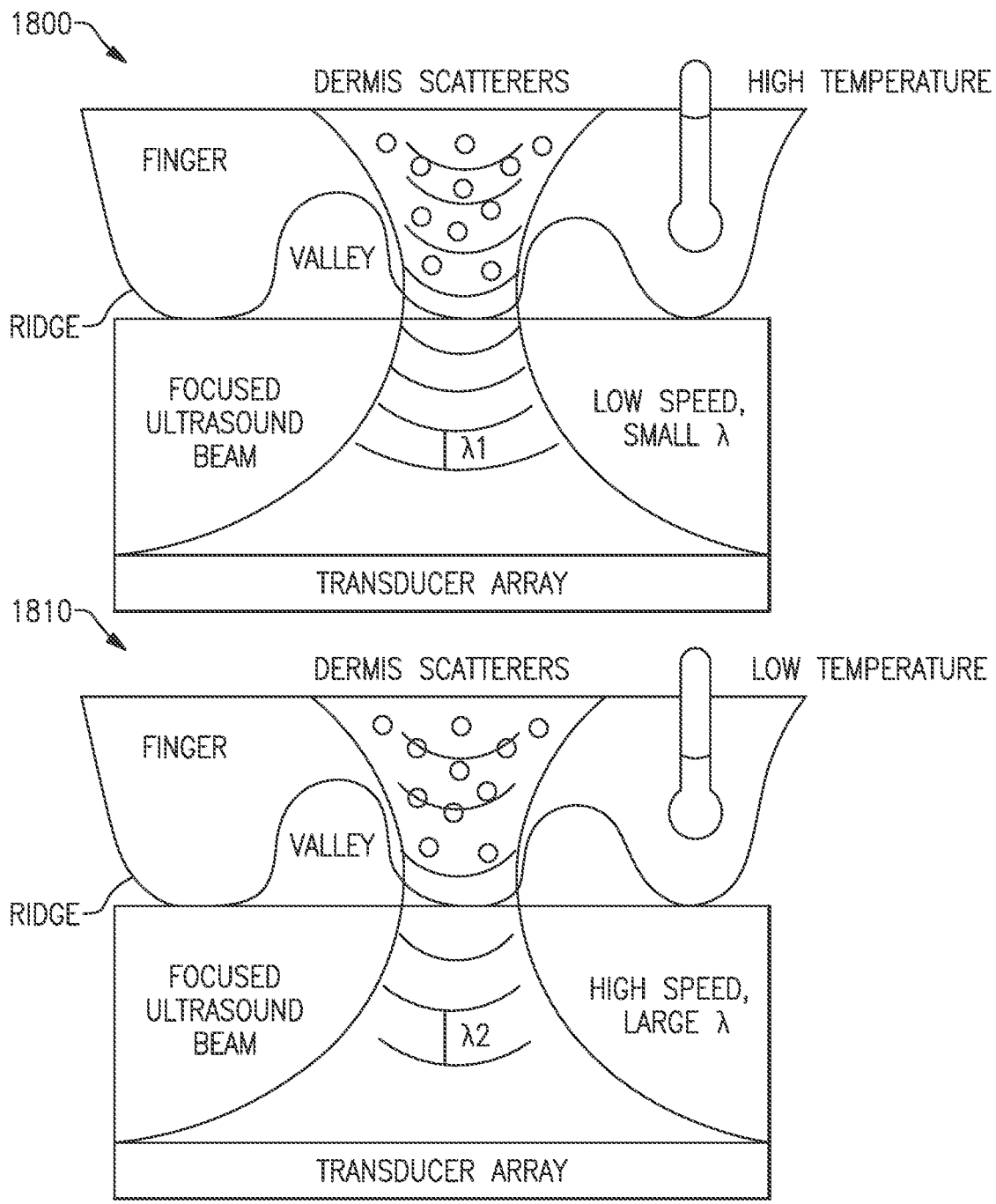
FIG. 18 illustrates the speed of a sound wave through a medium can change with a change in temperature in the medium.

FIG. 18 illustrates that the speed of a sound wave through a medium can decrease with an increase in temperature. The speed of sound propagating through a material is typically dependent on the material temperature. The speed of sound in solids typically decreases with higher temperatures. Within the normal operating range of temperatures of a biometric sensing device, there is an approximate linear relationship between the temperature and the speed of sound:

$$c(T) \propto T \times \phi,$$

where c(T) is a temperature dependent sound speed through a material, T is temperature, and φ is a sound speed slope that is based on the material. The sign of φ can be negative or positive, but is negative in various materials of the mediums discussed herein (e.g., glass, sapphire, and metal).

The distance between the ultrasound transducer and an acoustically reflecting object, like the opposite glass-air interface on a smart phone, can also increases with temperature due to thermal expansion. However, the elastic constant change which results in lowering the speed of sound is typically about an order of magnitude larger than the thermal expansion coefficient and should dominate the effect of increasing the delay of the pulse. The speed of sound can be estimated by the time it takes for the ultrasound signal to travel from the transducer to the acoustically reflecting object and back again. The shorter the time it takes, the faster the speed of sound and the warmer the material should be. In the example of FIG. 18, spacing between wavefronts corresponds to wavelength. The wavelength of the reflected ultrasound beam at high temperature 1800 and low temperature 1810 is λ1 and λ2, respectively, with λ2 being greater than λ1. From the speed of sound, the material temperature can be determined based on the equation above, analytically and/or numerically. The material temperature can be a temperature associated with the finger that can be used to generate an indication of whether the finger is part of a live human.

Any of the biometric sensing devices discussed herein can implement temperature detection. A biometric sensing device with temperature detection can include a processor and transducers configured to transmit an acoustic signal through a receiving surface to a finger. The processor can detect a temperature of the finger based on a sound speed associated with the acoustic signal and generate an image of at least a portion of a fingerprint of the finger based on a reflection of the acoustic signal from the finger. The processor can generate an indication of whether the finger is part of a live human based on the detected temperature. The processor can detect an ambient temperature based on a second sound speed associated with the acoustic signal when the finger is not in contact with the receiving surface. The processor can detect the temperature of the finger based on a difference in sound speed associated with the acoustic signal between when the finger is in contact with the receiving surface and when the receiving surface is uncontacted by the finger.

Figure 19:
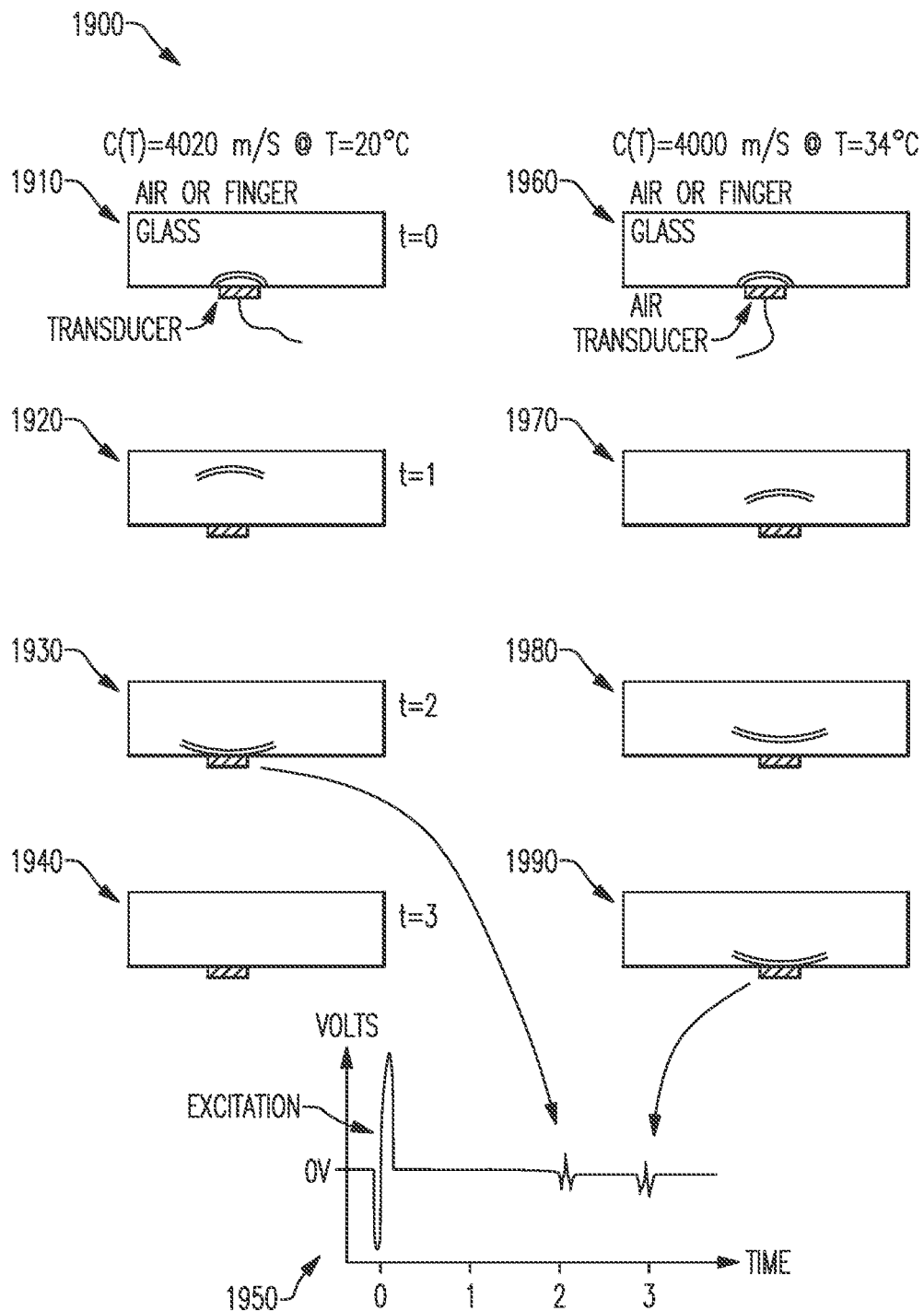
FIG. 19 illustrates that the time of flight from excitation until the reflected wavefront is recorded can change with temperature.

FIG. 19 illustrates that the time of flight from excitation until the reflected wavefront is shorter for higher temperatures. In particular, FIG. 19 shows that the time of flight from excitation until the reflected wavefront is recorded is shorter at 34° C. than at 20° C., because the speed of a sound wave increases with an increase in temperature. Since the finger is at body temperature and the sensor at room temperature, once touched, the temperature of the glass or other intermediate layer would get warm and generally increase the speed of sound in the glass. Therefore, biometric devices discussed herein can determine the temperature of the finger based on sound speed. This can ascertain that it is not a prosthetic finger that is touching the glass. When the finger is not touching the glass, the ambient temperature can be determined by the device.

FIG. 19 compares the time of travel of ultrasound at a higher temperature of 34° C. with the travel of ultrasound at a lower temperature of 20° C. As illustrated, the speed of sound is 4020 m/s at the lower temperature and 4000 m/s at the higher temperature. The time intervals are not drawn to scale to emphasize the difference in time of travel.

At time t=0, in graphic 1910, at the lower temperature, the pulse is transmitted by the transducer towards the air/glass interface. At time t=1, in graphic 1920, the pulse nears the air/glass interface. At time t=2, in graphic 1930, a reflection of the pulse reaches the transducer. There is not activity at time t=4, in graphic 1940, since the reflected pulse previously reached the transducer. Therefore, the time of flight from excitation to recording of the reflected wavefront is approximately two time intervals, as illustrated in the graph 1950, at the higher temperature.

At time t=0, in graphic 1960, at the higher temperature, the pulse is transmitted by the transducer towards the air/glass interface. At time t=1, in graphic 1970, the pulse approaches the air/glass interface, but is not yet near it. At time t=2, in graphic 1970, the reflection of the pulse approaches, but has not yet reached, the transducer. At time t=3, in graphic 1970, the reflection has reached the transducer. For the higher temperature, the time of flight from excitation to recording of the reflected wavefront is approximately three time intervals, as illustrated in the graph 1950. Therefore, the time of flight is shorter at the lower temperature. As time of flight varies with temperature, the time of flight can be used to estimate relative temperatures, and once calibrated, can be used to estimate absolute temperature.

Figure 20:
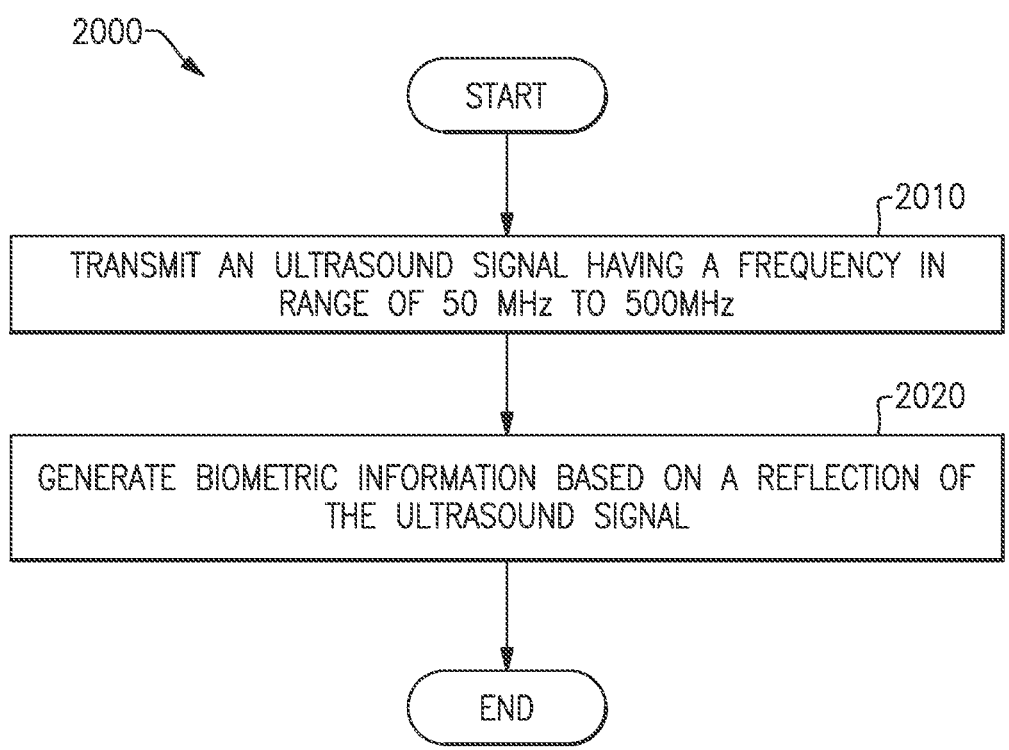
FIG. 20 is a flowchart of a method of generating biometric information according to an embodiment of the disclosed technology.

FIG. 20 is a flowchart of method 2000 of generating biometric information according to an embodiment of the disclosed technology. In block 2010, method 2000 transmits an ultrasound signal having a frequency in a range from 50 MHz to 500 MHz. In block 2020, method 2000 generates biometric information based on a reflection of the ultrasound system.

Figure 21:
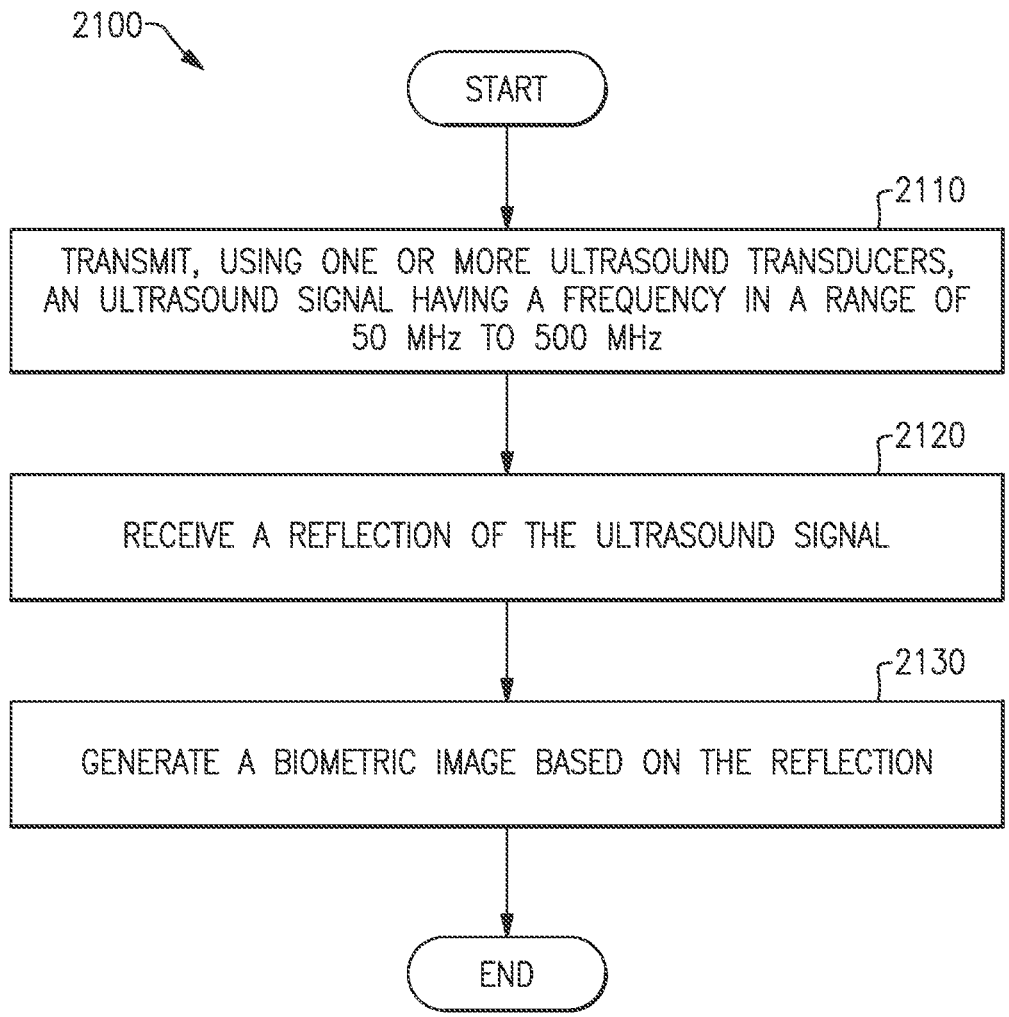
FIG. 21 is a flowchart of a method of generating a biometric image according to an embodiment of the disclosed technology.

FIG. 21 is a flowchart of method 2100 of generating a biometric image. In block 2110, method 2000 transmits, using one or more ultrasound transducers, an ultrasound signal having a frequency in a range of 50 MHz to 500 MHz. In block 2120, method 2100 receives a reflection of the ultrasound signal. In block 2130, method 2000 generates a biometric image based on the reflection.

Figure 22:
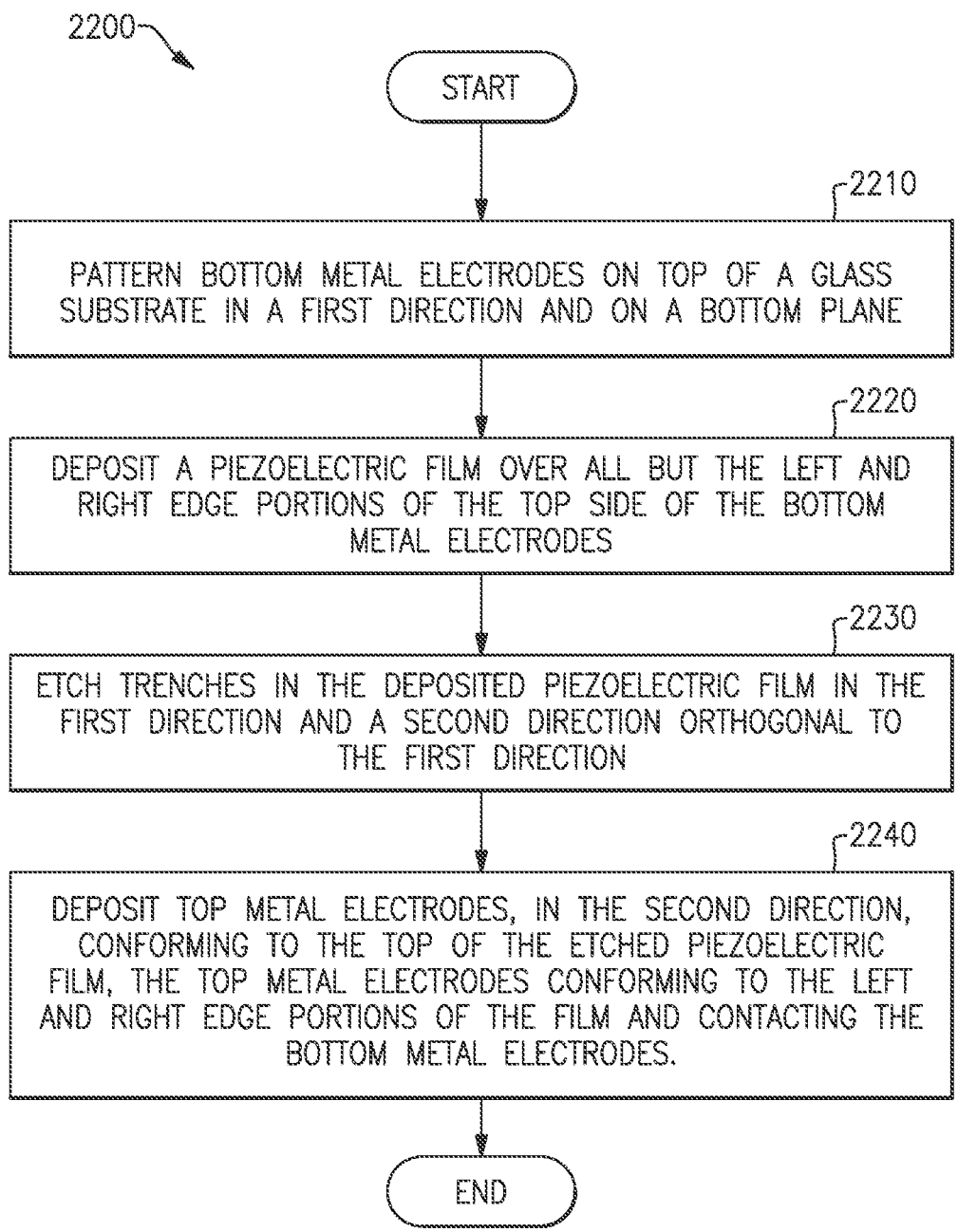
FIG. 22 is a flowchart of a method of manufacturing an acoustic biometric touch scanner according to an embodiment of the disclosed technology.

FIG. 22 is a flowchart of a method 2200 of manufacturing an acoustic biometric touch scanner according to an embodiment of the disclosed technology. In block 2210, method 2200 patterns bottom metal electrodes on top of a glass substrate in a first direction and on a bottom plane. In block 2220, method 2200 deposits a piezoelectric film over all but the left and right edge portions of the top side of the bottom metal electrodes. In block 2230, method 2200 etches trenches or grooves in the deposited piezoelectric film in the first direction and a second direction orthogonal to the first direction. In block 2240, method 2200 deposits top metal electrodes, in the second direction, conforming to the top of the etched piezoelectric film, the top metal electrodes conforming to the left and right edge portions of the film and contacting the bottom metal electrodes.

Figure 23:
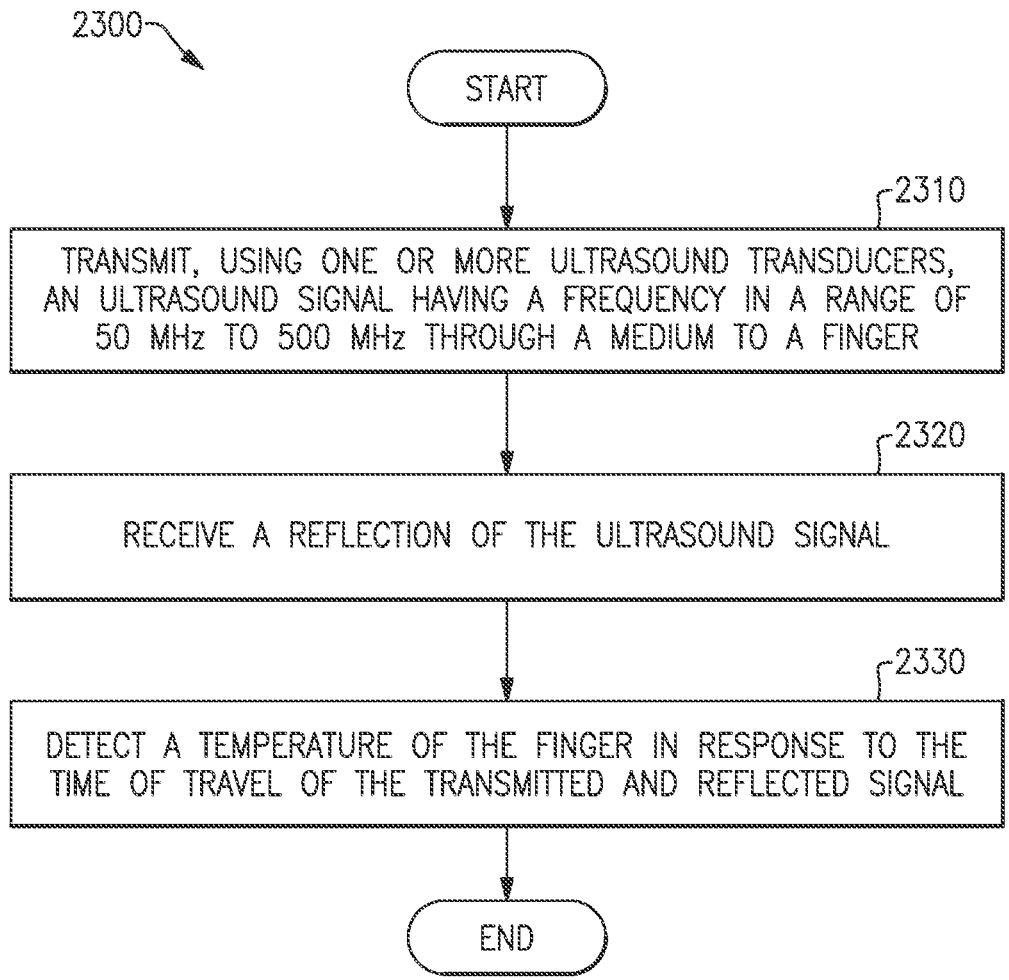
FIG. 23 is a flowchart of a method of detecting a temperature of a finger according to an embodiment of the disclosed technology.

FIG. 23 is a flowchart of a method 2300 of detecting a temperature of a finger according to an embodiment of the disclosed technology. In block 2310, method 2300 transmits, using one or more ultrasound transducers, an ultrasound signal having a frequency in a range of 50 MHz to 500 MHz through a medium to a finger. In block 2320, method 2300 receives a reflection of the ultrasound signal. In block 2330, method 2300 detects a temperature of the finger in response to the time of travel of the transmitted and reflected signal.

Figure 24:
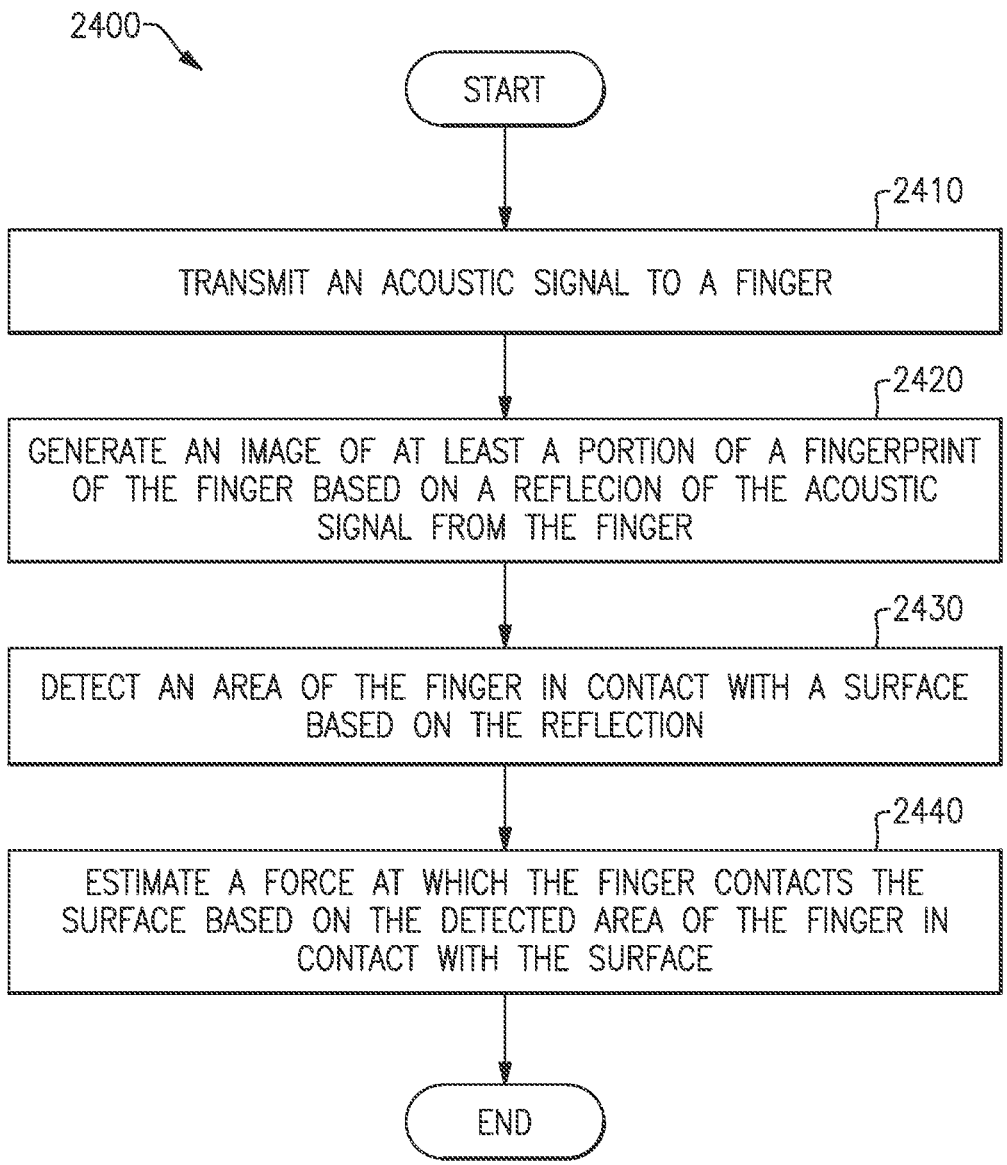
FIG. 24 is a flowchart of a method of estimating a force at which a finger contacts a surface according to an embodiment of the disclosed technology.

FIG. 24 is a flowchart of a method 2400 of estimating a force at which a finger contacts a surface according to an embodiment of the disclosed technology. In block 2410, method 2400 transmits an acoustic signal to a finger. In block 2420, method 2400 generates an image of at least a portion of a fingerprint of the finger based on a reflection of the acoustic signal from the finger. In block 2430, method 2400 detects an area of the finger in contact with a surface based on the reflection. In block 2440, method 2400 estimates a force at which the finger contacts the surface based on the detected area of the finger in contact with the surface.

Figure 25:
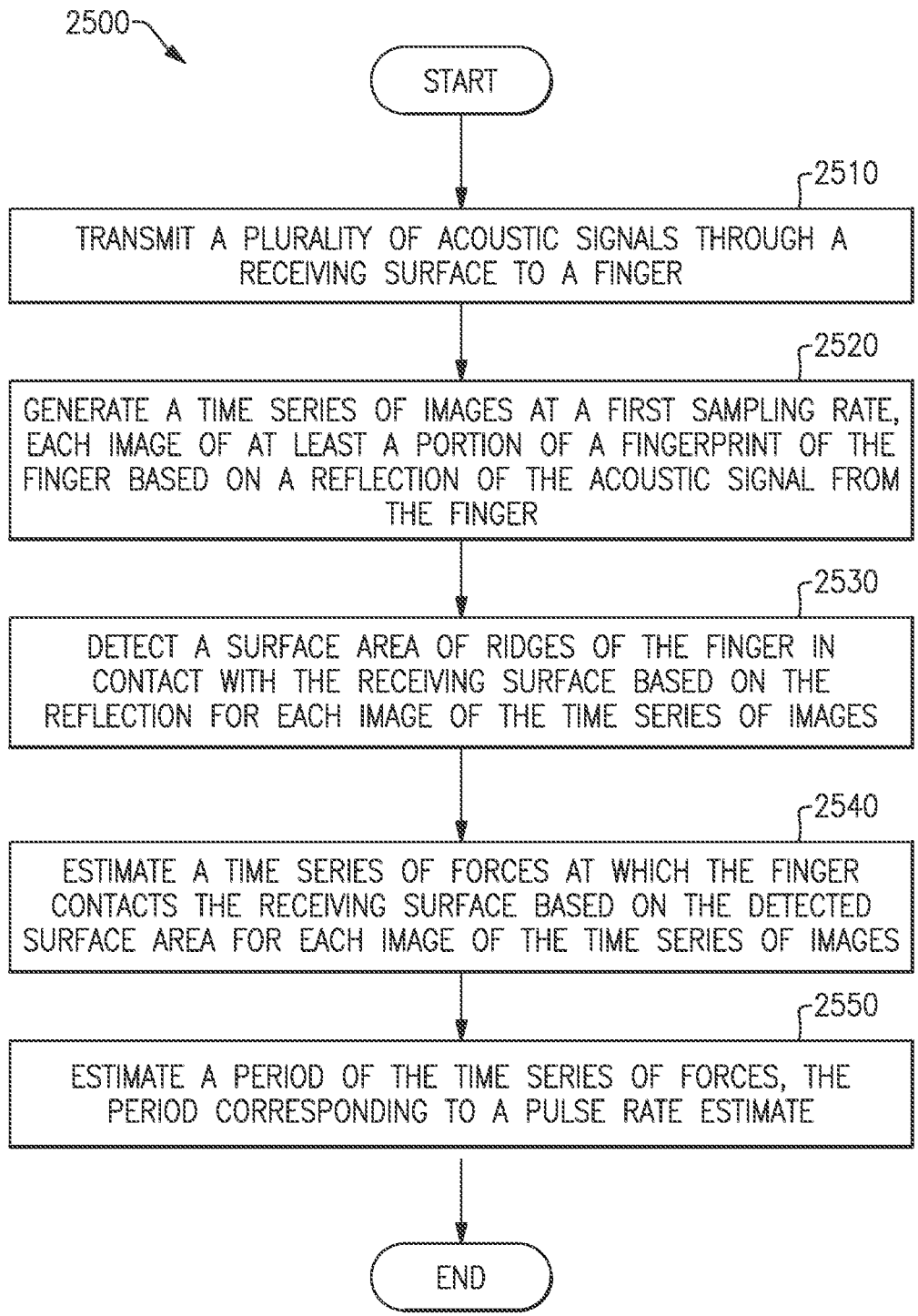
FIG. 25 is a flowchart of a method of estimating period of a time series of force measurements, the period corresponding to a pulse rate estimate, according to an embodiment of the disclosed technology.

FIG. 25 is a flowchart of a method 2500 of estimating period of a time series of force measurements, the period corresponding to a pulse rate estimate, according to an embodiment of the disclosed technology. In block 2510, method 2500 transmits a plurality of acoustic signals through a receiving surface to a finger. In block 2520, method 2500 generates a time series of images at a first sampling rate, each image of at least a portion of a fingerprint of the finger based on a reflection of the acoustic signal from the finger. In block 2520, method 2500 detects a surface area of ridges of the finger in contact with the receiving surface based on the reflection for each image of the time series of images. In block 2530, method 2500 estimates a time series of forces at which the finger contacts the receiving surface based on the detected surface area for each image of the time series of images. In block 2540, method 2500 estimates a period of the time series of forces, the period corresponding to a pulse rate estimate.

FIGS. 26-34 illustrate circuits and results of simulations of envelope detection methods for ultrasound fingerprint scanning. The simulation assumes an element width of 20 μm, a line spacing (kerf) of 20 μm, an element height of 10 mm, and an ultrasound bandwidth of 43:8%. Excitation is a 5 cycle sinusoid at 150 MHz. Fourteen active elements are used with an effective f #=0:893, where f # is the f-number or numerical aperture and is defined as the focal distance divided by the diameter of the active aperture.

Figure 26:
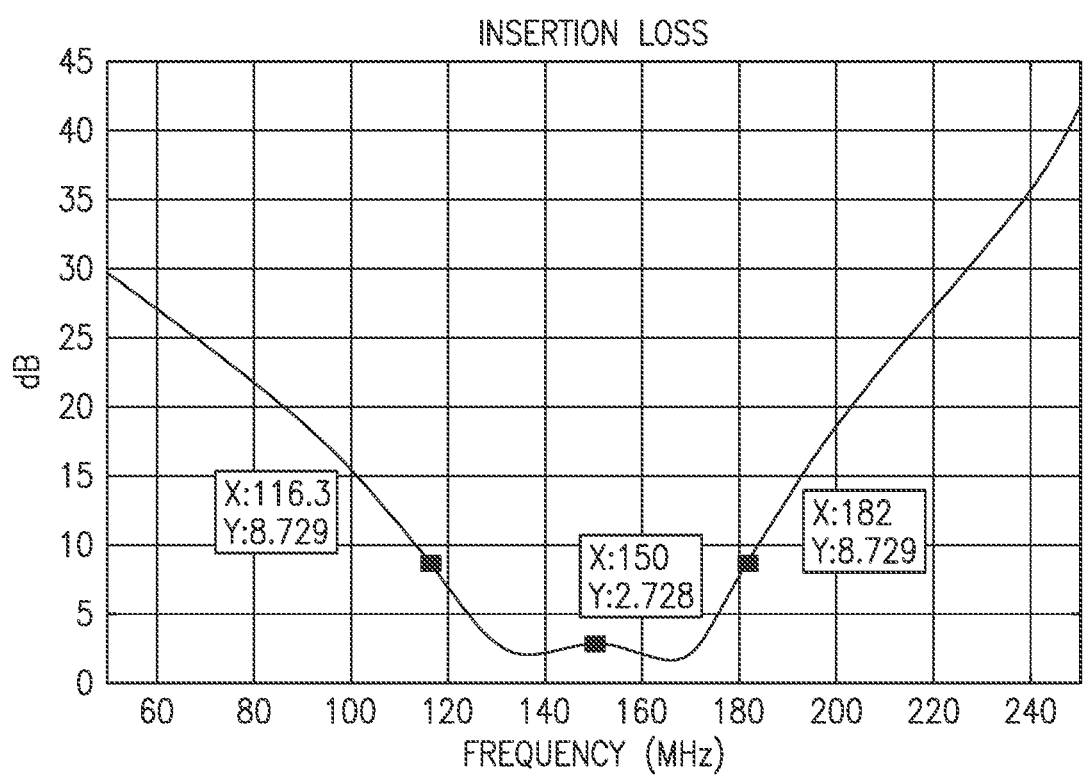
FIGS. 26-34 illustrates circuits and results of simulations of sampling and envelope detection methods for ultrasound finger print scanning.

FIG. 26 illustrates a simulation of the one-way insertion loss.

Figure 27:
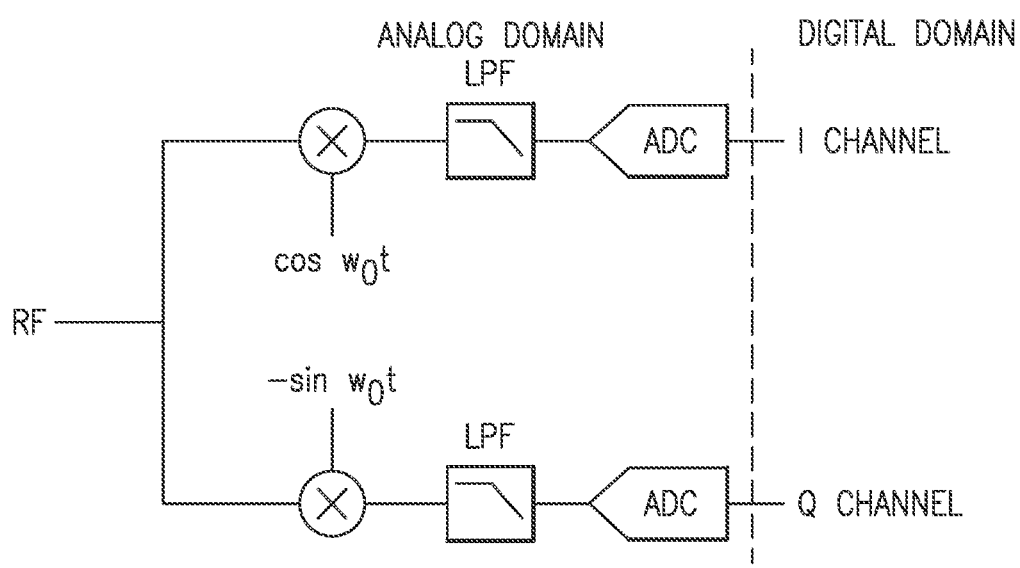

FIG. 27 illustrates a circuit for IQ demodulation of an RF signal into I and Q channels.

Figure 28:
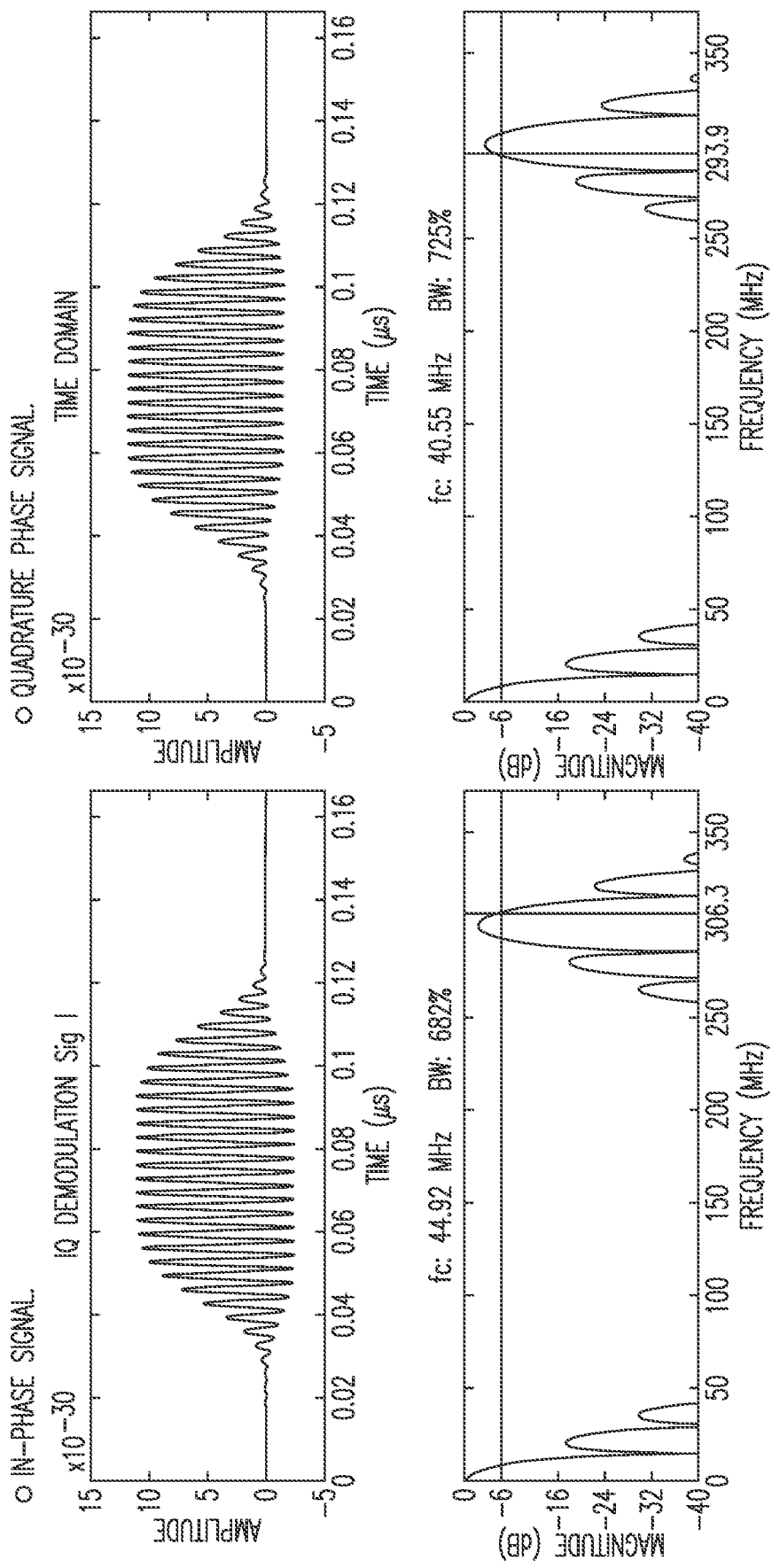

FIG. 28 illustrates an example of the simulated demodulated in-phase and quadrature signals.

Figure 29:
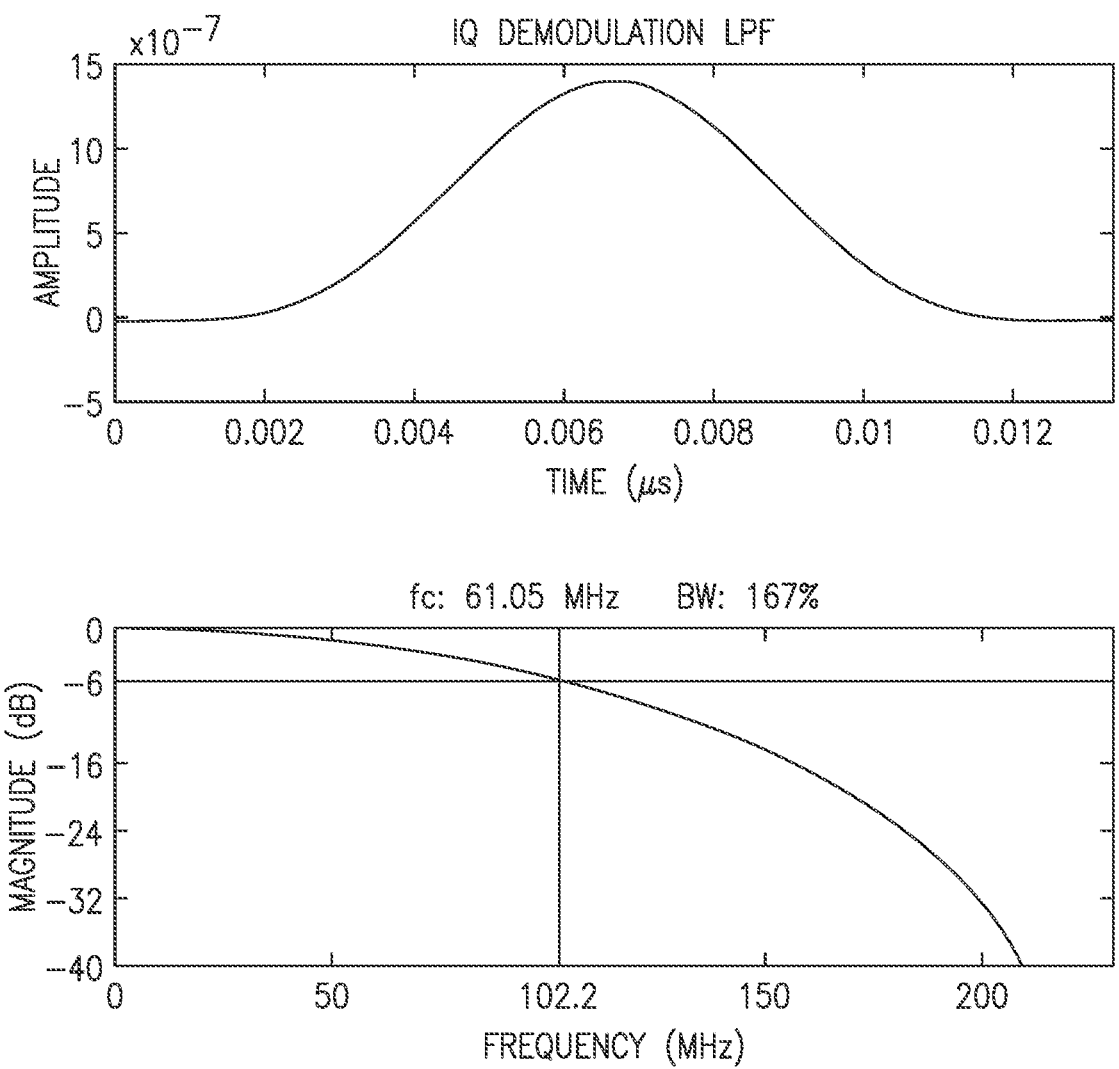

FIG. 29 illustrates the response of the low pass filter used for IQ demodulation for the process of FIG. 27.

Figure 30:
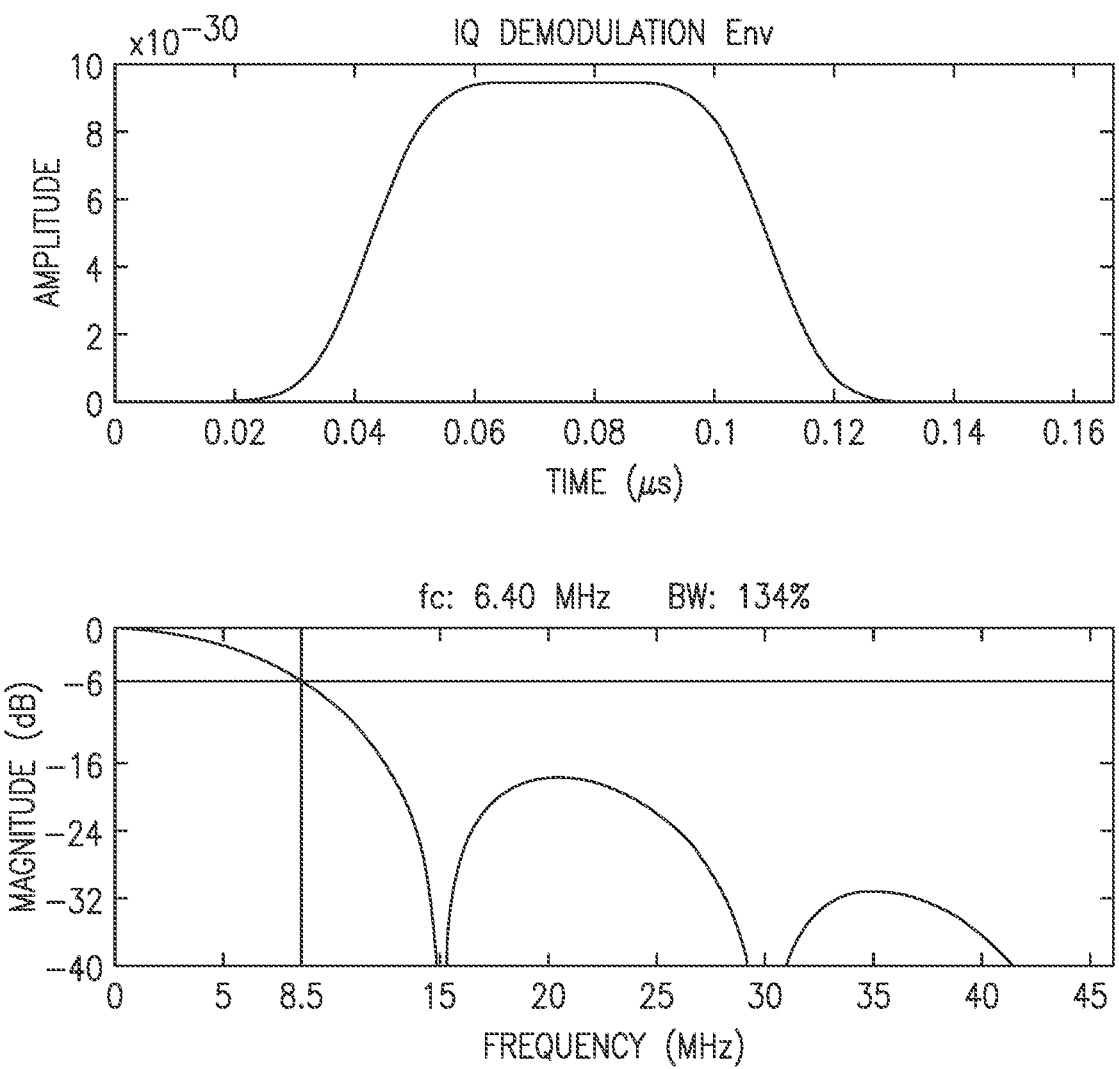

FIG. 30 illustrates an IQ demodulated envelope for a signal demodulated by the circuit of FIG. 27.

Figure 31:
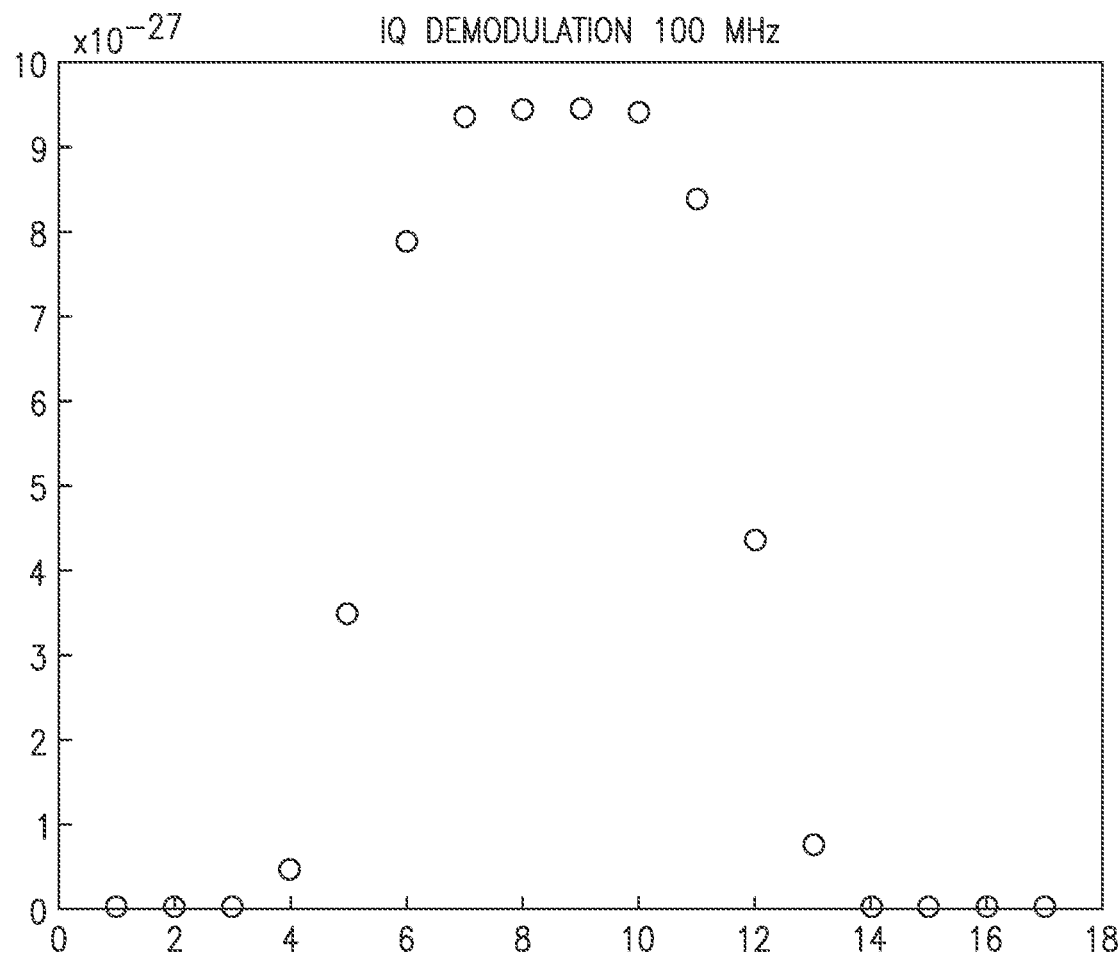

FIG. 31 illustrates 100 MHz samples taken of the IQ demodulated envelope of FIG. 30.

Figure 32:
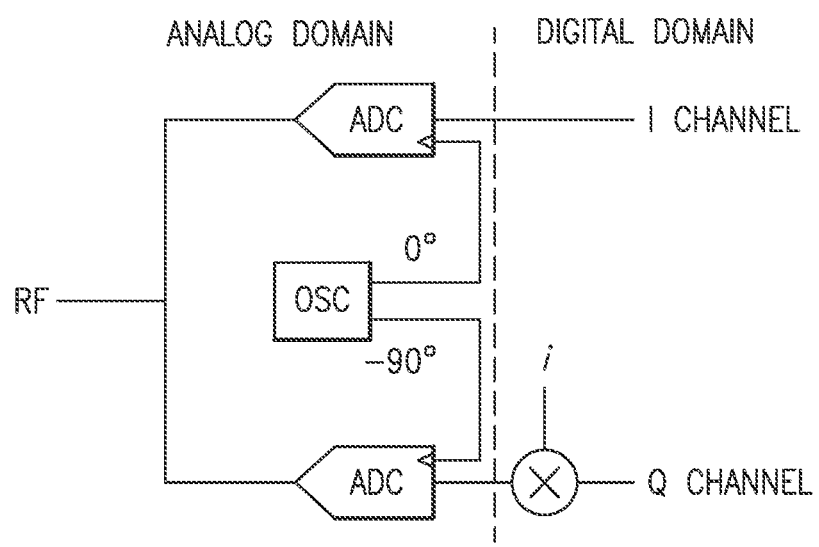

FIG. 32 illustrates a circuit for IQ sampling of an IQ demodulated signal.

Figure 33:
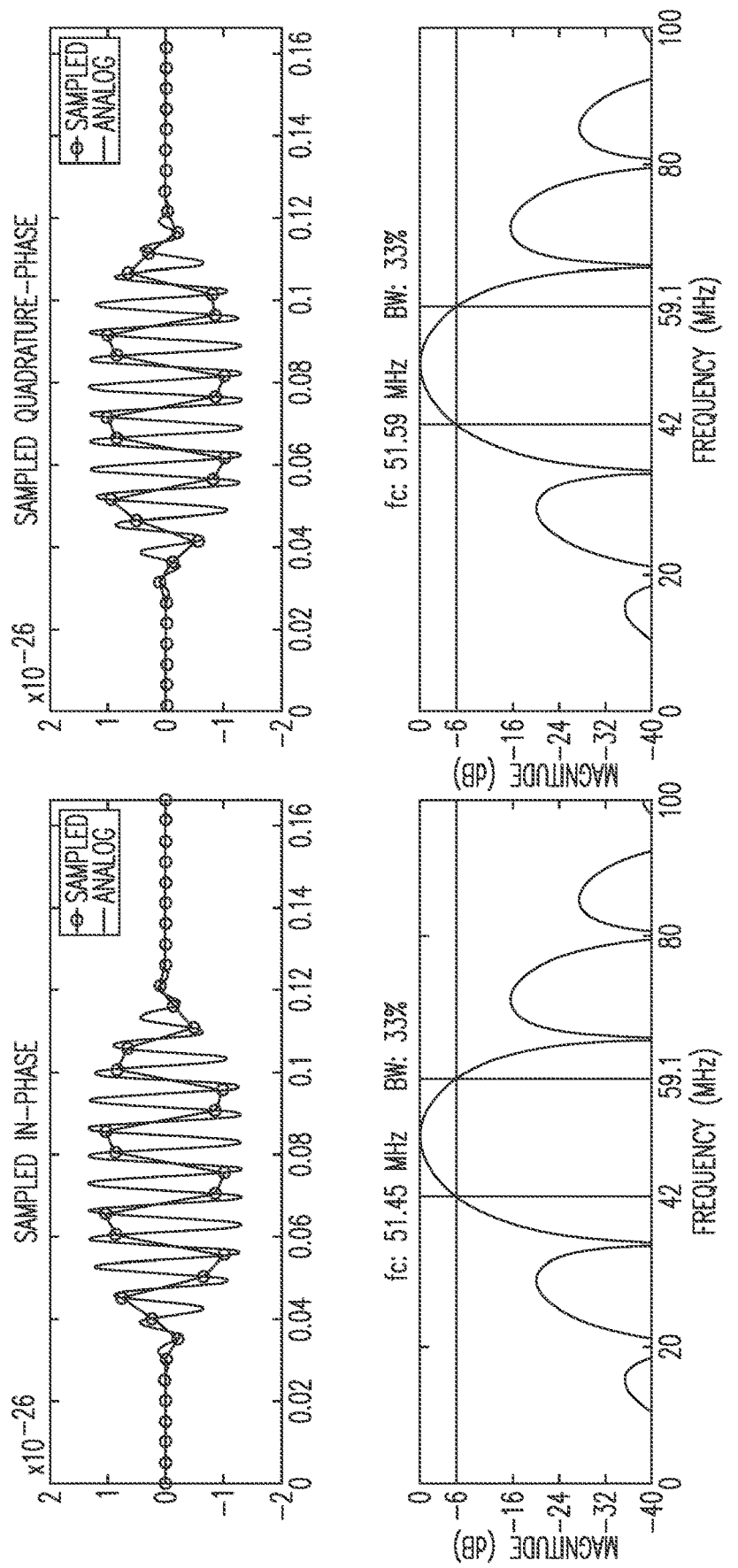

FIG. 33 illustrates sampled in-phase and quadrature signals of an IQ demodulated signal.

Figure 34:
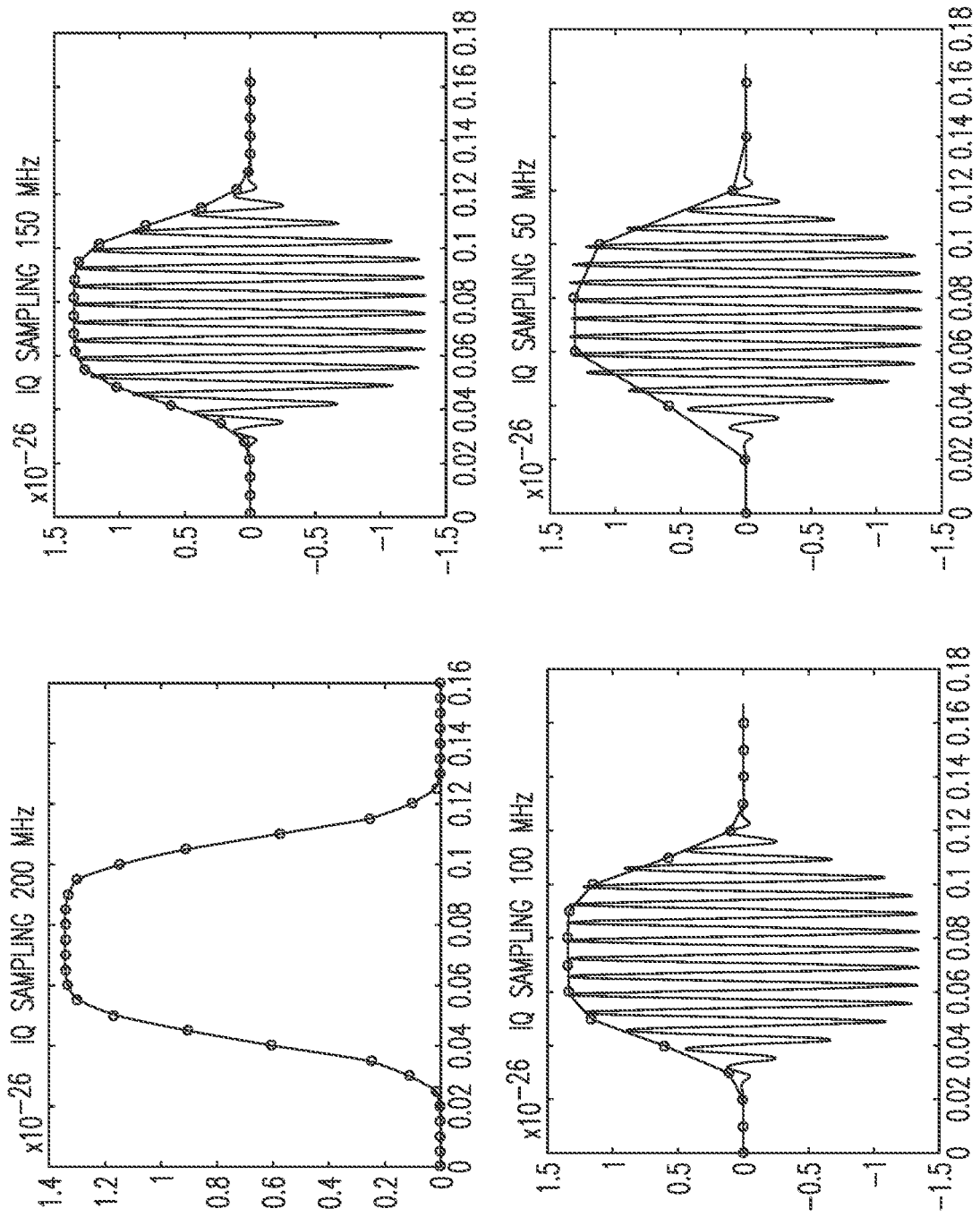

FIG. 34 illustrates graphs of the envelope of an IQ demodulated signal for IQ sampling rates of 200 MHz, 150 MHz, 100 MHz and 50 MHz.

Biometric Scanner Integrated with an Optical System

Aspects of this disclosure relate to a biometric scanner with an integrated optical system. The biometric scanner can be at least partially transparent such that the optical system can emit light through the biometric scanner to an object, such as a finger. The biometric scanner and the optical system can be used together for authentication. The biometric scanner can be a fingerprint scanner. The optical system can detect a liveness parameter associated with the finger print scanned by the fingerprint scanner. A processor can authenticate the finger based on an image of the finger generated by the fingerprint scanner and the liveness parameter generated by the optical system.

An integrated optical system can advantageously measure attributes that are not as easily and/or reliably measured by a fingerprint scanner, such as an ultrasound finger print sensor. For instance, an optical system can measure an oxygen level (e.g., $SbO_2$) and/or respiration. Furthermore, at certain frequencies of light transmitted by an optical system, measurements can be made deeper into a finger and/or illuminate different attributes of a finger than various ultrasound systems.

A fingerprint scanner, such as an ultrasound fingerprint scanner, can be optically transparent to enable multi-modality sensing using an optical system. For instance, the optical system, such as a photo plethysmography device, can transmit and receive light through the optically transparent fingerprint scanner. As an example, an ultrasound scanner in accordance with any of the principles and advantages discussed herein can include a transparent piezoelectric thin film, such as a thin film of zinc oxide, aluminum nitride, poly-di-vinyl fluoride, or the like. In some instances, such an ultrasound sensor can include metal electrodes that are transparent, such as indium tin oxide electrodes or the like. In certain embodiments, a biometric sensing device includes an ultrasound fingerprint sensor with a flexible piezoelectric film and an optical system arranged to transmit and/or receive light that propagates through the ultrasound fingerprint sensor.

A biometric scanning system that includes fingerprint scanner that is at least partially transparent integrated with an optical system configured to transmit and receive light through the fingerprint scanner can authenticate a finger by detecting a fingerprint and another biological property associated with the finger to enhance strength of authentication. Such a system can implement a multi-modality sensor (or actuator). As an example, the optical system can generate a liveness parameter, such as a heart rate or blood oxygenation level to aid in robustness of authentication. Multi-level authentication using a fingerprint scanner and an integrated optical system provide robust approach that can make authentication without a live finger difficult. Moreover, the integration of the fingerprint scanner and the optical device in accordance with the principles and advantages discussed herein can provide robust authentication with a relatively compact device.

A biometric scanning system that includes fingerprint scanner that is at least partially transparent integrated with an optical system can be implemented in any devices and/or system that use biometric authentication, such as a finger print authentication system, a palm print authentication system, or the like.

While example embodiments discussed below may include ultrasound fingerprint scanners integrated with optical systems, other suitable fingerprint scanners that are at least partially transparent can be integrated with optical systems in accordance with the principles and advantages discussed herein. For instance, an optical system can be integrated with a variety of fingerprint scanners, such as capacitive fingerprint scanners. Moreover, a fingerprint scanner can be transparent to any suitable energy modality that can be used to detect a liveness parameter.

FIGS. 35-45 illustrate an example embodiment of a biometric sensing device with an optical system 550 below an ultrasound transducer array 400 with transparent electrodes 430' and 440'. The ultrasound transducer array 400 is below glass 410 and a receiving surface for a finger or other object to be examined. In some instances, such as in mobile phones, the glass 410 can be an engineered glass. The engineered glass can be damage and scratch resistant. An example of engineered glass is CORNING® GORILLA® glass. While glass 410 is described with reference to these example embodiments, any other suitable transparent material, such as transparent plastic, can alternatively or additionally be used in certain applications. The electrodes 430' and 440' can be metal electrodes used to address transducers of the ultrasound transducer array. Other suitable metal electrodes for ultrasound transducers of the ultrasound transducer array 400 can alternatively be implemented.

The optical system 550 and any other optical systems disclosed herein can include any suitable number and/or type of light sources and/or any suitable optical detector. For instance, the optical system 550 can include a reflective oximeter that includes a red LED and an infrared LED plus a photoreceptor. As another example, the optical system 550 can include three or more LEDs. Alternatively or additionally, the optical system 550 can include one or more multispectral sensors, such as a buried quad junction photodetector. The optical system 550 can include one or more laser light sources in certain embodiments. According to some embodiments, the optical system 550 can include a LED and a laser light source.

Figure 35:
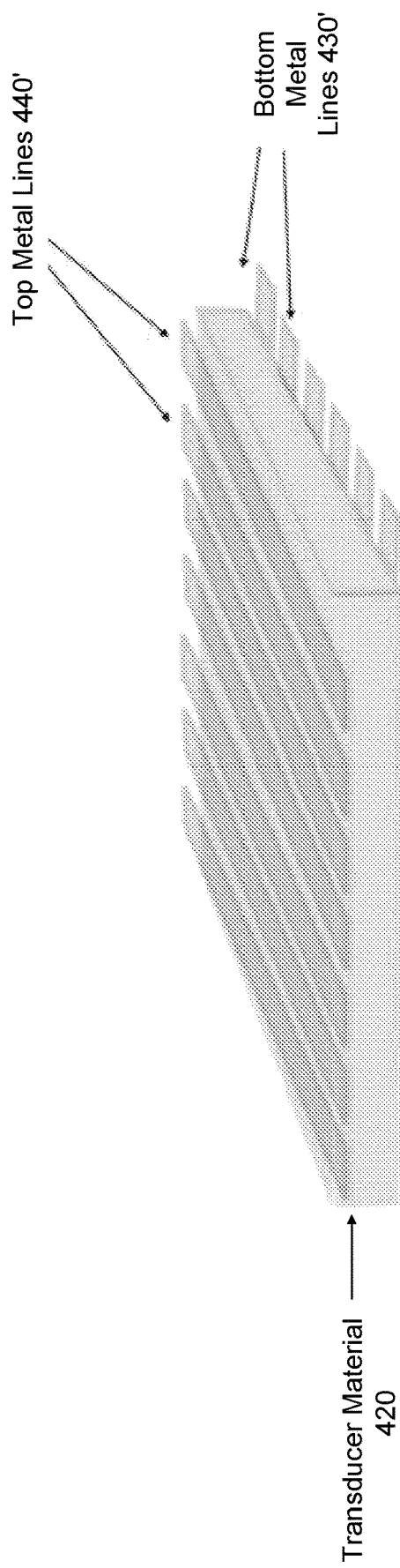
FIGS. 35-45 illustrate an example embodiment with an optical system below an ultrasound transducer array with transparent metal electrodes. The ultrasound transducer array is below the glass and a receiving surface for a finger or other object to be examined.

FIG. 35 illustrates an ultrasound transducer array 400 with transparent top and bottom metal electrodes. The ultrasound transducer array 400 can be implemented in accordance with any suitable principles and advantages described above with respect to FIGS. 2-10. The ultrasound transducer array 400 can be transparent to light. For instance, the ultrasonic transducer array 400 can include a piezoelectric layer that is transparent, such as zinc oxide, aluminum nitride, or poly-di-vinyl fluoride. The top electrodes 440 and bottom electrodes 430' are at least partially transparent in the embodiment of FIGS. 35-45. Transparency enables light to pass through the ultrasound transducer array 400 components of the bottom metal electrodes 430', the transducer material 420, and the top metal electrodes 440'. The bottom metal electrodes 430' and the top metal electrodes 440' can be implemented from any suitable transparent metal. For instance, these metal electrodes can be implemented by indium tin oxide.

Figure 36:
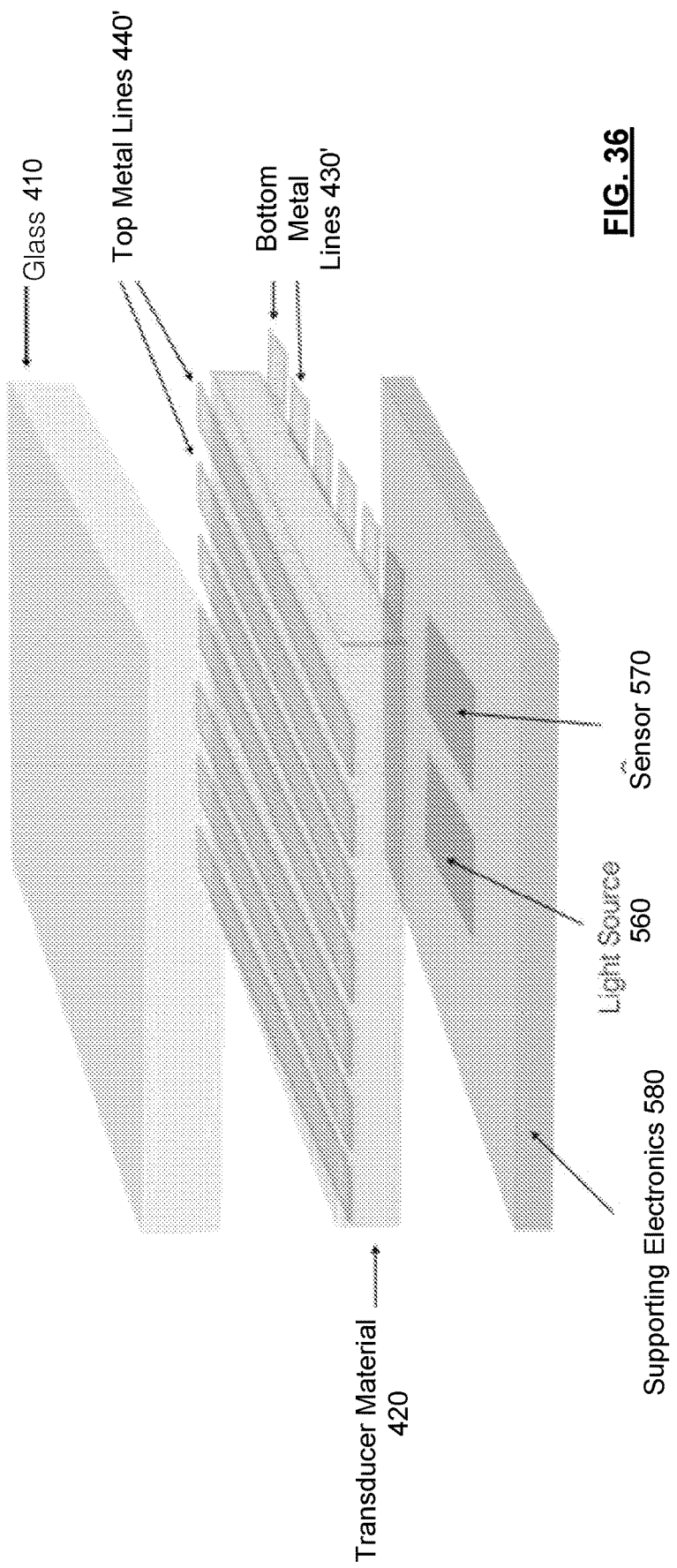

FIG. 36 illustrates an exploded view of the transparent ultrasound transducer array of FIG. 35 above an optical system 550 and below glass 410. Glass 410 is also transparent to light. Accordingly, light transmitted from the optical system 550 is transmitted through both the ultrasound transducer array 400 and glass 410, which has a top receiving surface upon which an object to be detected or scanned can be placed. Light that is reflected from the object to be detected or scanned can then pass through the glass 410 and the ultrasound transducer array 400 and to optical system 550.

Optical system 550 includes a light source 560, an optical sensor 570, and supporting electronics 580. The optical system 550 can be included in a camera and/or a video camera in certain applications. In such applications, the ultrasound transducer array 400 can be disposed between the surface configured to receive the finger and a camera and/or a video camera. The light source 560 transmits light at one or more wavelengths or frequency bands. In some instances, the light source 560 is arranged to transmit visible light. The light source 560 can transmit infrared light in certain applications. The light source 560 can transmit laser light in some applications. The supporting electronics 580 can control the wavelength, duration, and timing of light emitted by the light source 560. Transmitted light from light source 560 is transmitted through the transparent ultrasound transducer array 400. An optical sensor 570 receives light that had been transmitted by the light source 560. Light received by the sensor may correspond to reflections of light transmitted by light source 560.

Figure 67:
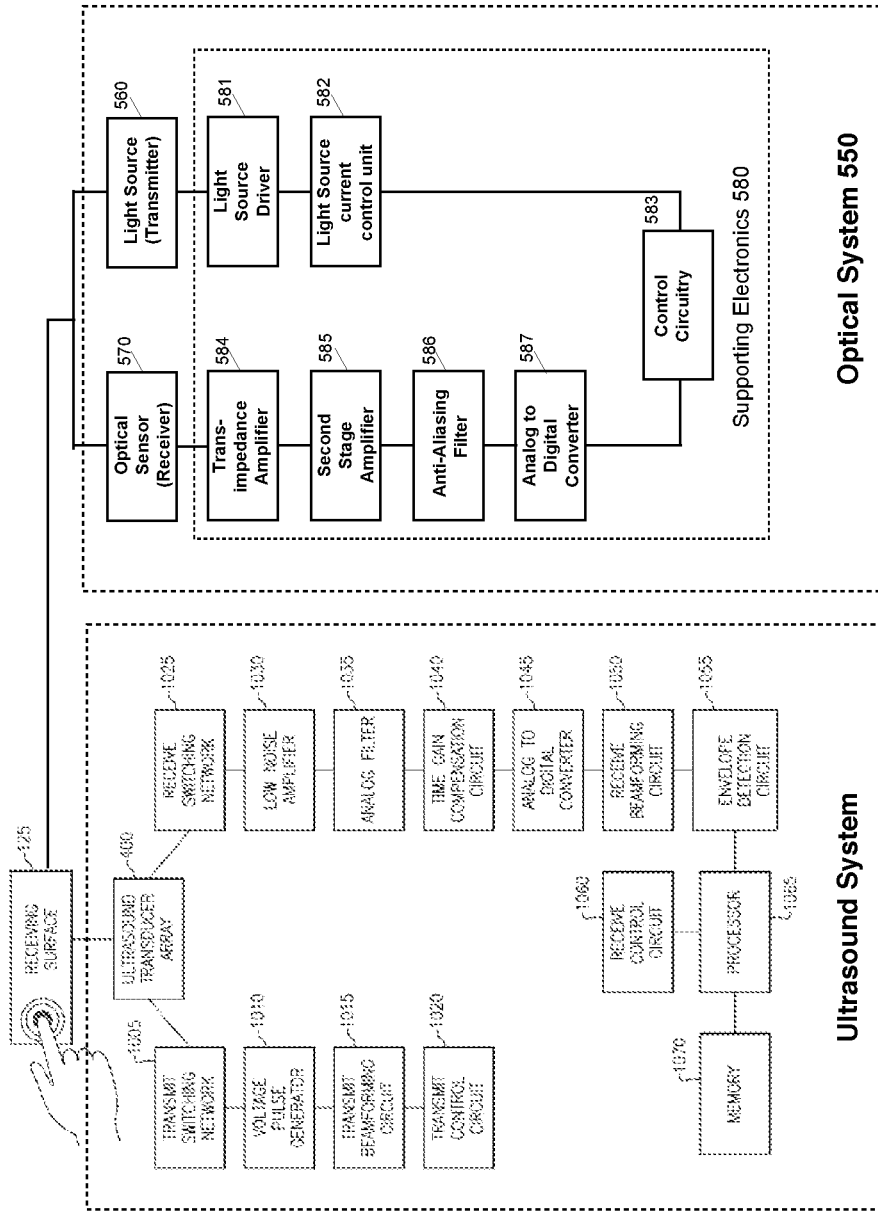
FIG. 67 illustrates an example acoustic biometric touch scanner, including an ultrasound system and an optical system. The ultrasound system includes an ultrasound transducer array, transmit electronics, and receive electronics. The optical system includes a light source, an optical sensor, and supporting electronics.

Supporting electronics 580 for the optical system 550 support the light source 560 transmission with a light source driver, a light source control unit, and control circuitry. The supporting electronics 580 support the optical sensor 570 with a trans-impedance amplifier, a second stage amplifier, an anti-aliasing filter, an analog to digital converter, and control circuitry. These supporting electronics 580 components are depicted in FIG. 67, and described below in the description of FIG. 67.

The glass 410, ultrasound transducer array 400, and optical system 550 are depicted in FIG. 36 with spatial separation so that the individual components are visible. These components are integrated with each other in a biometric sensing device.

Figure 37:
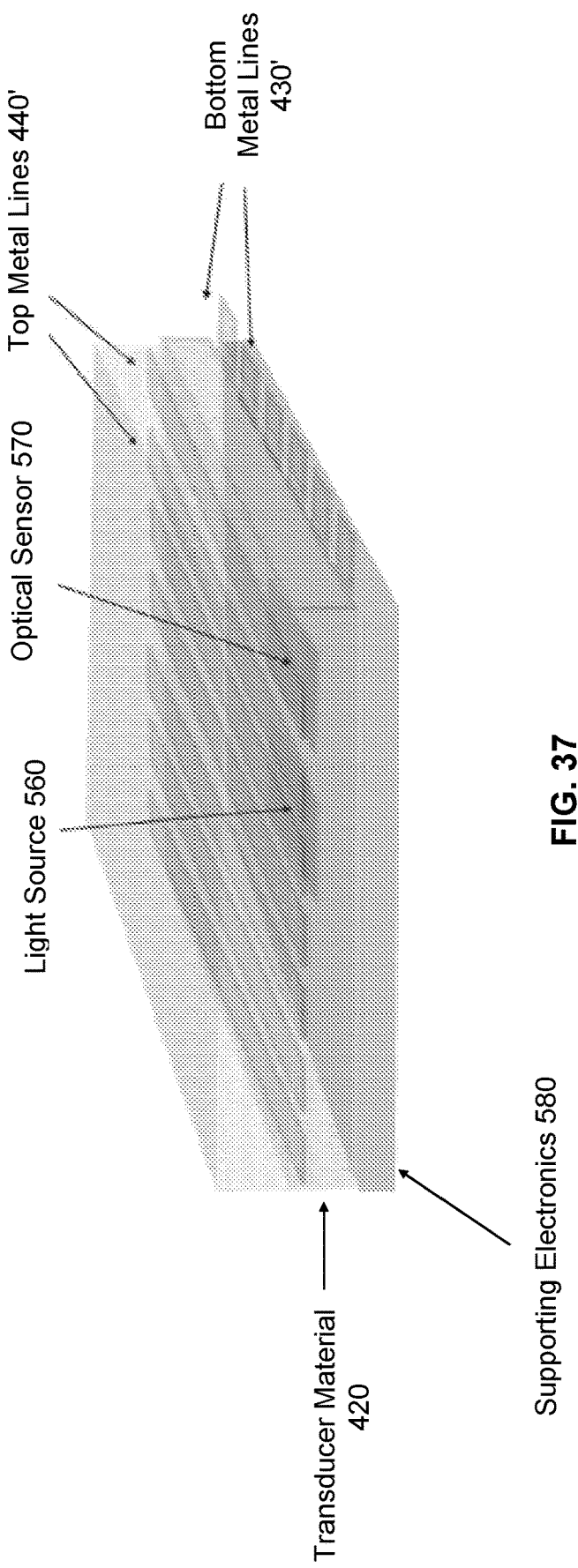

FIG. 37 illustrates the integration of the optical system 550, ultrasound transducer array 400, and glass 410 of FIG. 36. Unlike FIG. 36, the components are shown in close proximity to each other. The components are illustrated as adjoining and are not spatially separated from each other.

Figure 38:
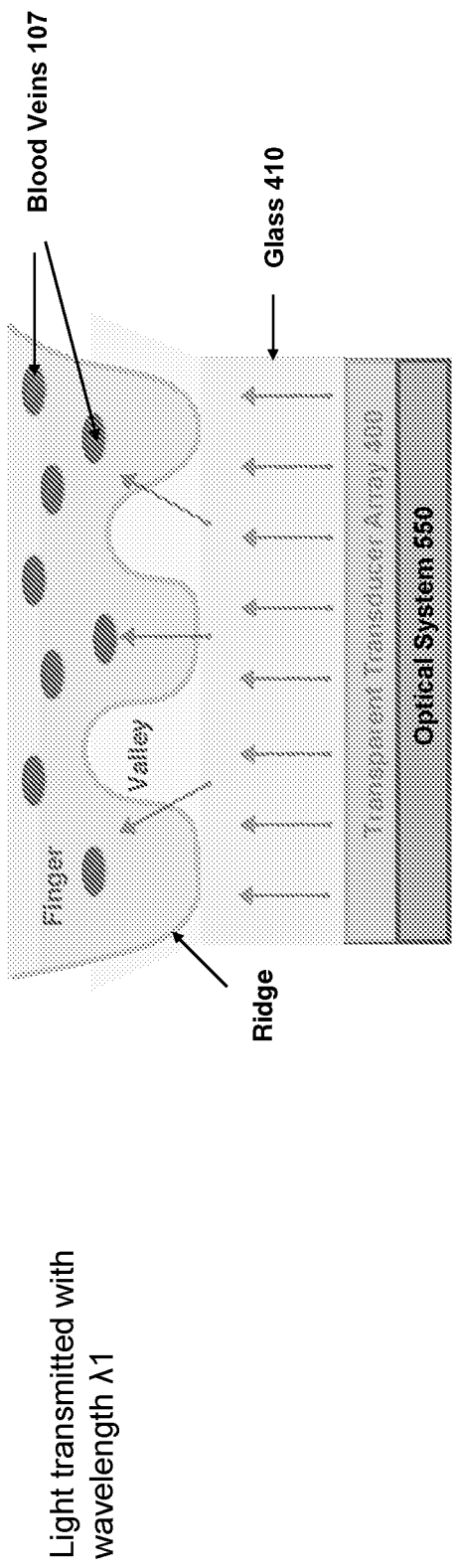

FIG. 38 illustrates a cross sectional view of the integrated optical and ultrasound system of FIG. 37 during transmission of light at a first wavelength λ1 from a light source 560 of the optical system 550 through the transparent transducer array 400 and glass 410 to a finger on the receiving surface of the glass 410. The finger has ridges and valleys and internal structures such as veins 107. The transmitted light of the first wavelength λ1 may reach the receiving surface of the glass, enter finger, and be transmitted to internal structures of the finger such as veins 107 that are relatively close to the surface of the finger. Light may be reflected from, for example, the internal structures of finger, such as veins 107 and from the surface of finger ridges.

Figure 39:
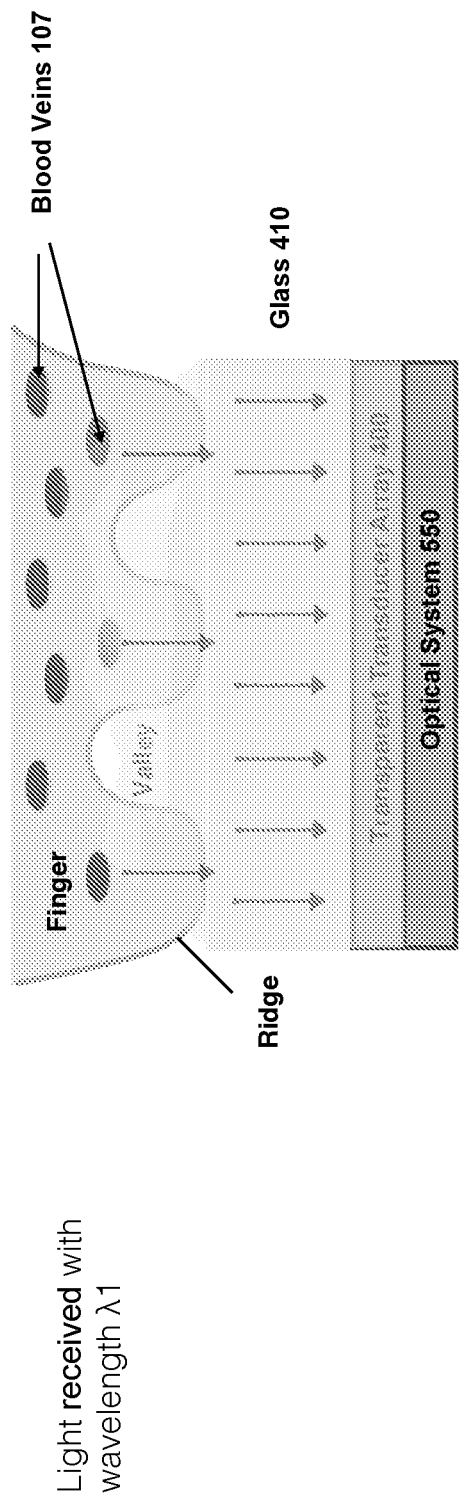

FIG. 39 illustrates a cross sectional view of the integrated optical and ultrasound system of FIG. 37 during reception of reflected light at the first wavelength λ1 off of the finger, back through the glass 410 and the transparent transducer array 400, to an optical sensor in the optical system 550. The sensed reflected light can be associated with recently transmitted light based on the wavelength of the received light or the duration of time since light was transmitted by the light source, or any suitable combination thereof. The received light can be evaluated based on the amount of reflected or absorbed light in the tissue.

Figure 40:
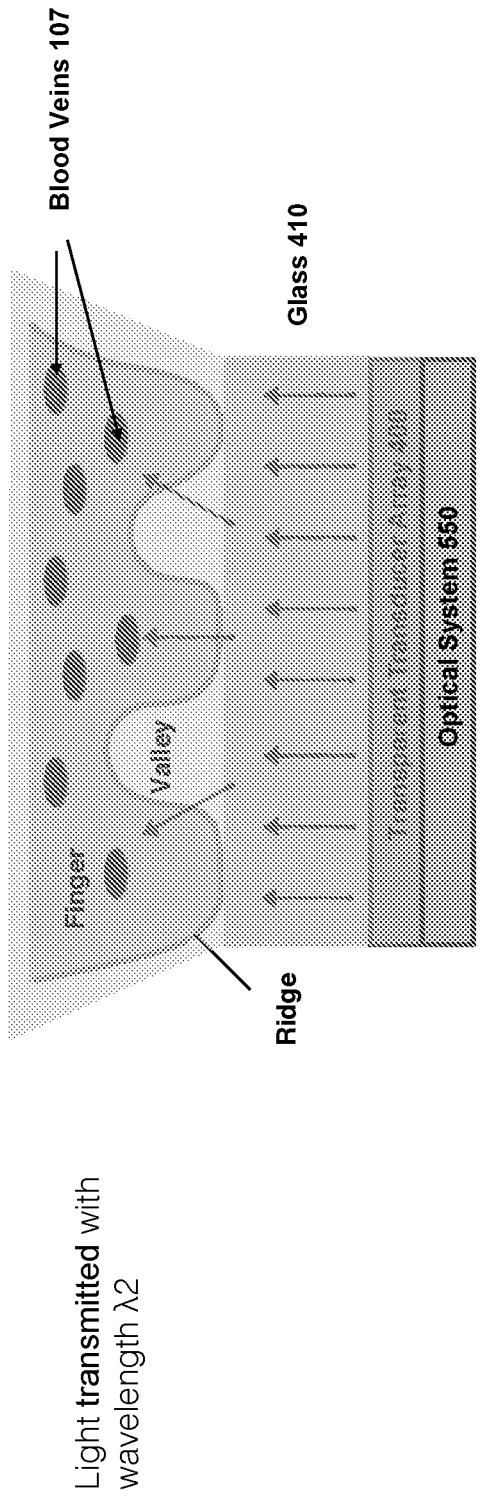

FIG. 40 illustrates a cross sectional view of the integrated optical and ultrasound system of FIG. 37 during transmission of light at a second wavelength λ2 from a light source of the optical system 550 through the transparent transducer array 400 and glass 410 to a finger on the receiving surface of the glass 410. The transmitted light of the second wavelength λ2 may reach the receiving surface of the glass, enter finger, and be transmitted to internal structures of the finger such as veins 107 that are relatively close to the surface of the finger. Light may be reflected from, for example, the internal structures of finger, such as veins 107, and from the surface of finger ridges.

Figure 41:
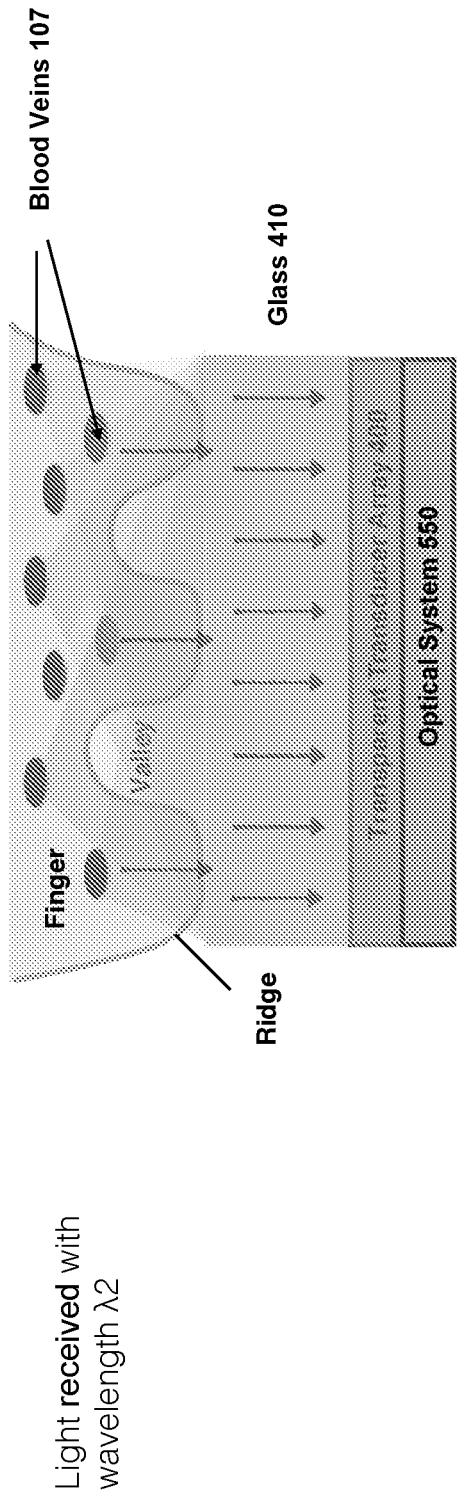

FIG. 41 illustrates a cross sectional view of the integrated optical and ultrasound system of FIG. 37 during reception of reflected light at the second wavelength λ2 off of the finger, back through the glass 410 and the transparent transducer array 400, to an optical sensor in the optical system 550. The sensed reflected light can be associated with recently transmitted light based on the wavelength of the received light, the duration of time since light was transmitted by the light source, the distance of the path taken by the transmitted and then received reflected light, or any suitable combination thereof.

Figure 42:
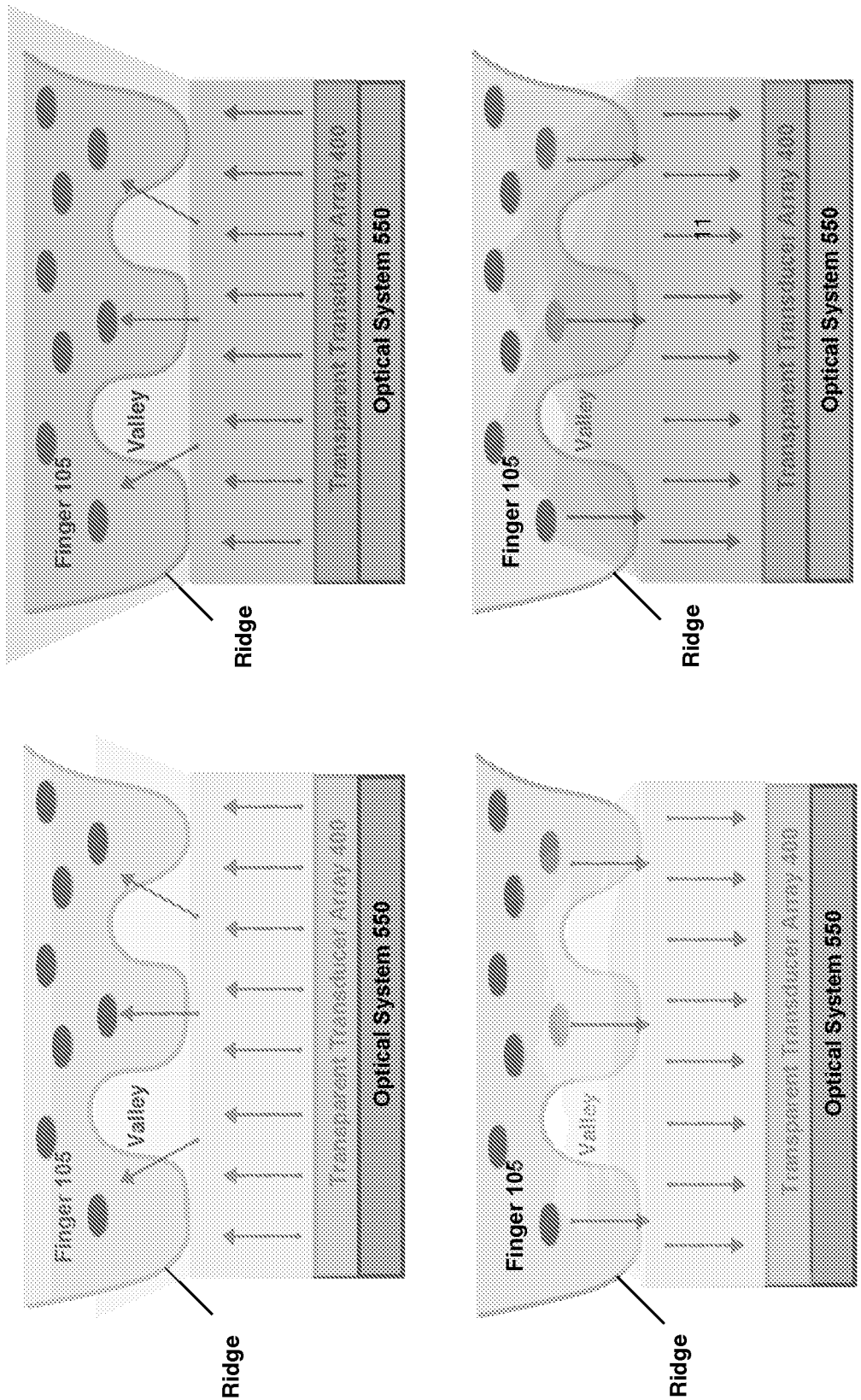

FIG. 42 illustrates the light transmission and reception, respectively, at the first and second wavelengths, respectively, as illustrated in FIGS. 38-41. Comparisons in received light at different wavelengths may be used to, for example, take a reflected pulse oximetry reading of a finger on the receiving surface. Such comparisons can be performed by any suitable processor in communication with the optical system 550. Bright red oxygenated blood absorbs more light at infrared wavelengths than at red wavelengths. In contrast, darker de-oxygenated blood absorbs more light at red wavelengths than infrared wavelengths. Reflective oximeters can quantify this difference in absorption by measuring absorption at red (for example, 660 nm) and infrared (for example, 940 nm) wavelengths, and converting a ratio of red light measurements to infrared light measurements to an estimate of saturation of peripheral oxygen (SpO2). Reflective oximeters can perform functions of pulse oximeters. In some instances, a pulse oximeter can be implemented in association with an integrated finger print sensor, such as an integrated ultrasonic fingerprint sensor. The embodiment of FIG. 42 captures measurements at two different wavelengths, such as for a pulse oximetry reading. Other applications of this embodiment may transmit and receive light at more than two frequencies (or frequency ranges) to characterize differences in absorption spectra at these frequencies.

Figure 43:
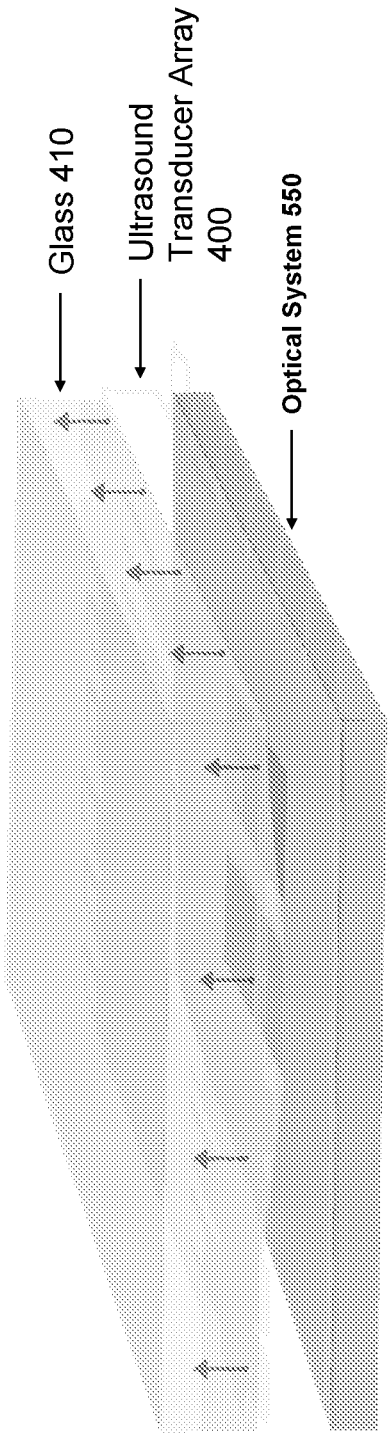

FIG. 43 is a perspective view of the example embodiment of FIG. 37 with an optical system 550 below an ultrasound transducer array 400 with transparent metal electrodes during a transmit phase without a finger on the receiving surface. Light emanates from a light source of the optical system 550 through the transparent transducer array 400 and glass 410. There is no finger illustrated on the receiving surface of the glass 410.

Figure 44:
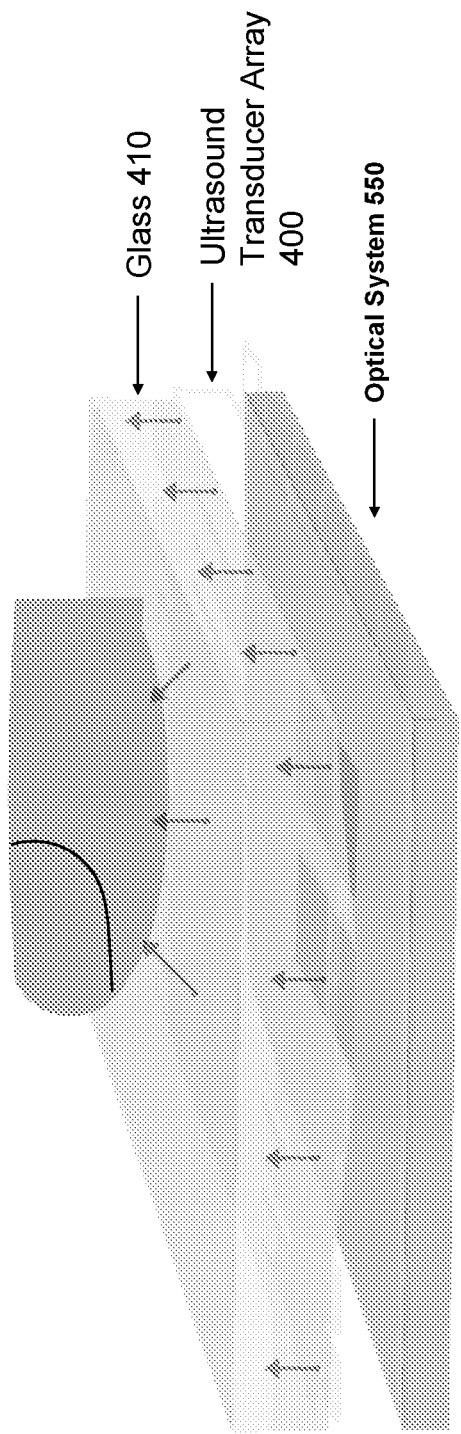

FIG. 44 is a perspective view of the example embodiment of FIG. 37 with an optical system 550 below an ultrasound transducer array 400 with transparent metal electrodes during a transmit phase with a finger on the receiving surface. Light emanates from a light source of the optical system 550 through the transparent transducer array 400 and glass 410 to a finger on the receiving surface of the glass 410. The transmitted light can reach the receiving surface of the glass 140, enter the finger, and be transmitted to internal structures of the finger such as veins that are relatively close to the surface of the finger. Light may be reflected from, for example, the internal structures of finger, such as veins, and from the surface of finger ridges.

Figure 45:
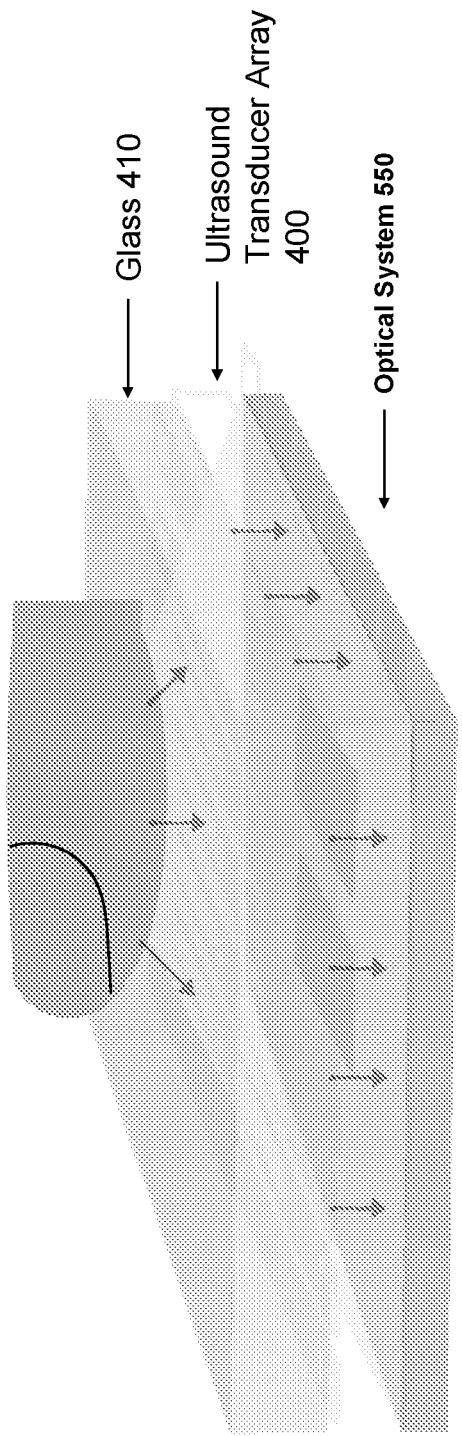

FIG. 45 is a perspective view of the example embodiment of FIG. 37 with an optical system 550 below an ultrasound transducer array 400 with transparent metal electrodes during a receive phase with a finger on the receiving surface. Light can be reflected off of the finger, back through the glass 410 and the transparent transducer array 400, to an optical sensor in the optical system 550. The sensed reflected light can be associated with recently transmitted light based on the wavelength of the received light, the duration of time since light was transmitted by the light source, the distance of the path taken by the transmitted and then received reflected light, or any suitable combination thereof.

FIGS. 46-55 illustrate an example embodiment with an optical system below an ultrasound transducer array with opaque metal electrodes. The ultrasound transducer array is below glass and a receiving surface for a finger or other object to be examined. Transparency enables light to pass through the transducer material 420, even though the bottom metal electrodes 430 and the top metal electrodes 440 are opaque.

Figure 46:
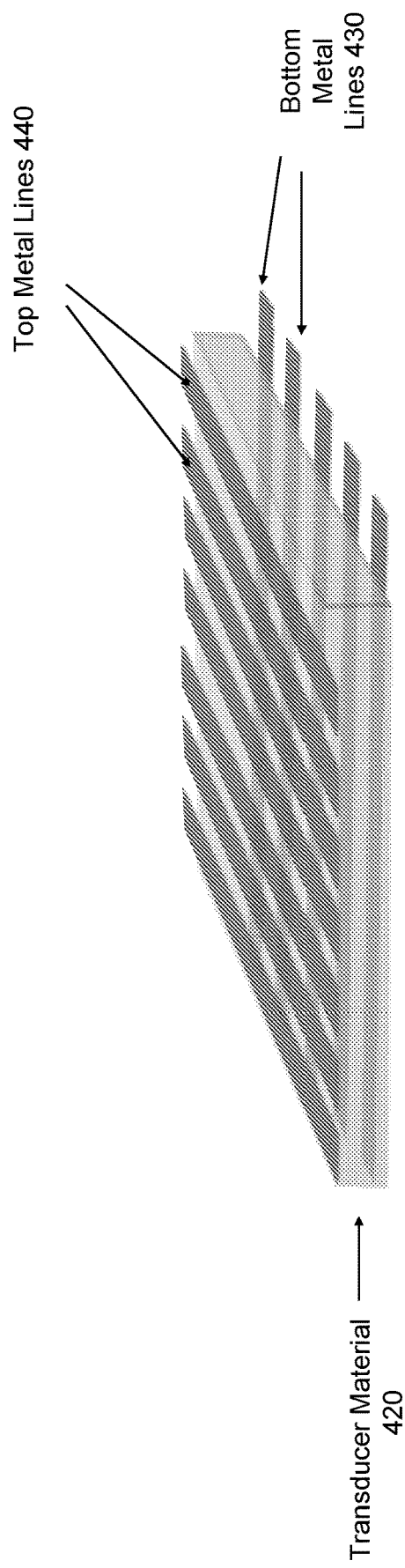
FIGS. 46-55 illustrate an example embodiment with an optical system below an ultrasound transducer array with opaque metal electrodes. The ultrasound transducer is below glass and a receiving surface for a finger or other object to be examined.

FIG. 46 illustrates an ultrasound transducer array with opaque top and bottom metal electrodes 440 and 430, respectively. The ultrasound transducer array 400 can be implemented in accordance with any suitable principles and advantages described above with respect to FIGS. 2-10. The top metal electrodes 440 and bottom metal electrodes 430 are opaque in the embodiment of FIGS. 35-45. Transparency enables light to pass through the transducer material 420, but light does not pass through the opaque bottom metal electrodes 430 or the top metal electrodes 440.

Figure 47:
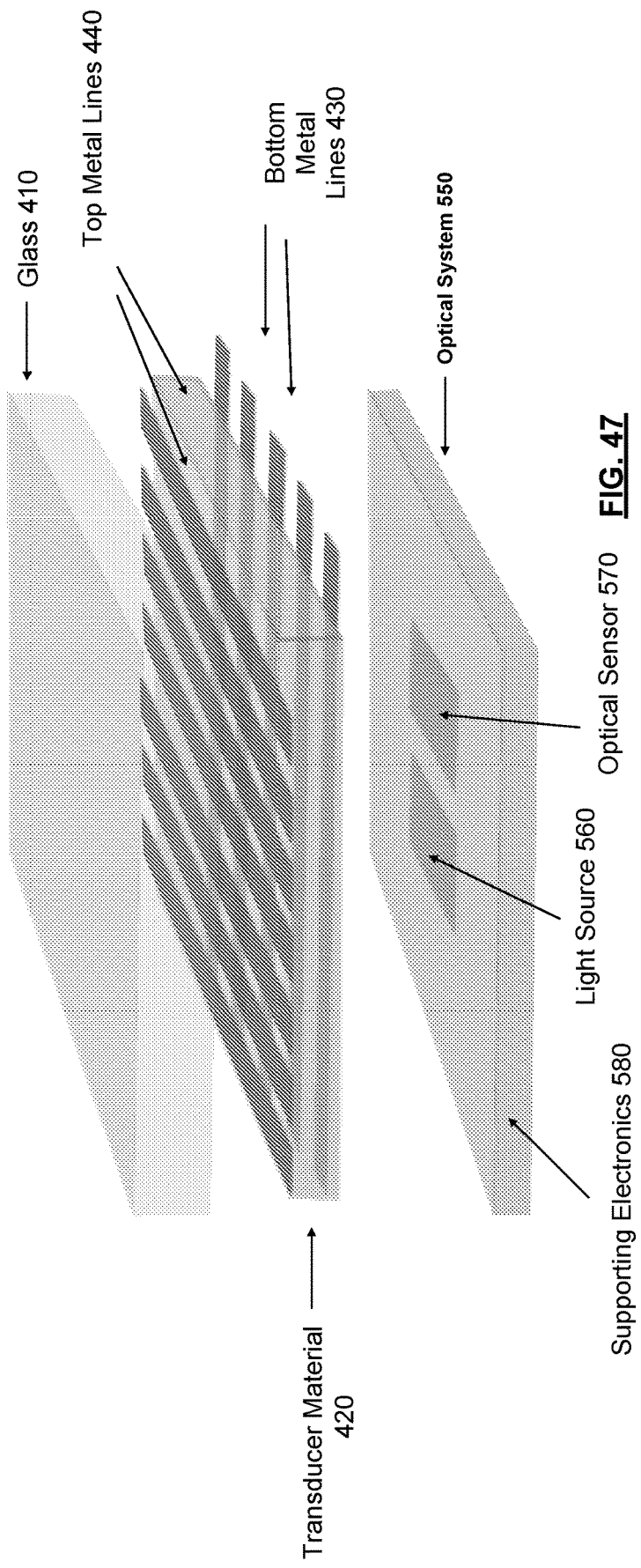

FIG. 47 illustrates an exploded view of the ultrasound transducer array 400 of FIG. 46 above an optical system 550 and below glass 410, with the glass 410, ultrasound transducer array 400 and optical system 550. As shown in FIGS. 48-55, the glass 410, ultrasound transducer array 400, and optical system 550 can be in close proximity to each other. These components can adjoin and not be spatially separated from each other. Glass 410 is also transparent to light, so that light transmitted from the optical system 550 is transmitted through both the ultrasound transducer array 400 and glass 410, which has a top receiving surface upon which an object to be detected or scanned can be placed. Light that is reflected from the object to be detected or scanned can then pass through the glass 410 and the ultrasound transducer array 400, but light does not pass through the opaque bottom metal electrodes 430 or the top metal electrodes 440 to the optical system 550.

Optical system 550 includes a light source 560, an optical sensor 570, and supporting electronics 580. The light source 560 can transmit light at one or more wavelengths or frequency band. The supporting electronics 580 can cause the light source 560 to adjust one or more of wavelength, duration, or timing of transmitting light. Light transmitted from light source 560 is transmitted through the portions of the transducer array 400 that are transparent, in the rectangular (or square) sections between opaque bottom metal electrodes 430 and top metal electrodes 440. An optical sensor 570 is arranged to receive light that had been previously transmitted. Light received by the optical sensor 570 can correspond to reflections of light transmitted by light source 560.

Supporting electronics 580 for the optical system 550 support the light source 560 transmission with a light source driver, a light source control unit, and control circuitry. The supporting electronics 580 can support the optical sensor 570 with a trans-impedance amplifier, a second stage amplifier, an anti-aliasing filter, an analog to digital converter, and control circuitry. These supporting electronics 580 components are depicted in FIG. 67, and described below in the description of FIG. 67.

The glass 410, ultrasound transducer array 400, and optical system 550 are depicted in FIG. 47 with spatial separation so that the individual components are visible.

Figure 48:
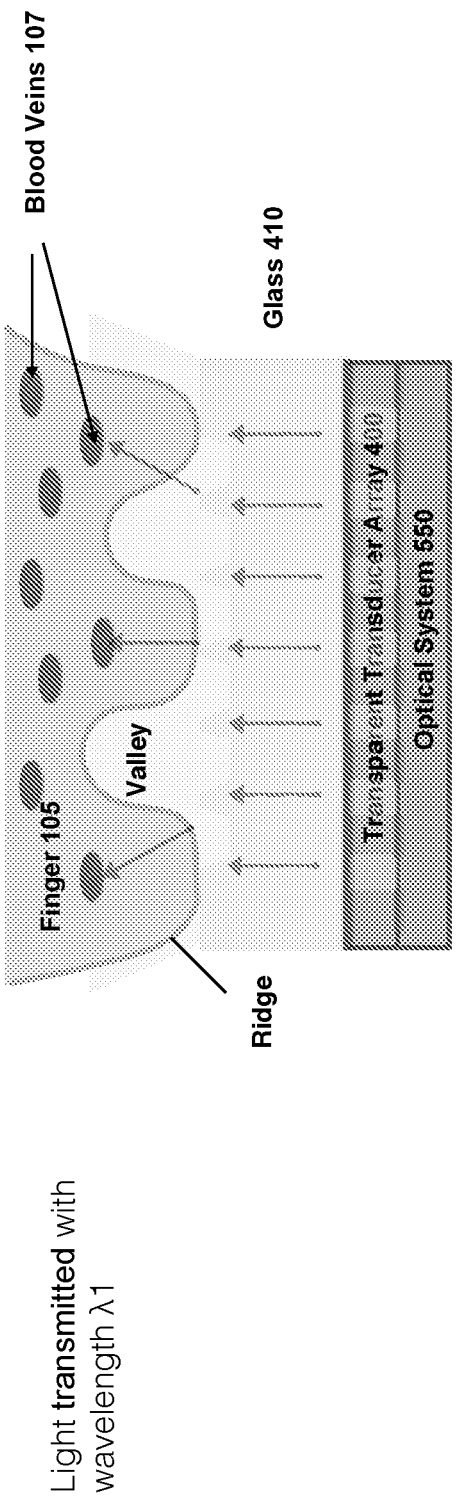

FIG. 48 illustrates a cross sectional view of the integrated optical and ultrasound system of FIG. 47 during transmission of light at a first wavelength $\lambda 1$ from a light source 560 of the optical system 550 through the portions of the transducer array 400 that are transparent, in sections between opaque bottom metal electrodes 430 and top metal electrodes 440, and glass 410, to a finger on the receiving surface of the glass 410. The transmitted light of the first wavelength $\lambda 1$ can reach the receiving surface of the glass, enter the finger, and be transmitted to internal structures of the finger, such as veins 107, that are relatively close to the surface of the finger. Light may be reflected from, for example, the internal structures of finger and from the surface of finger ridges.

Figure 49:
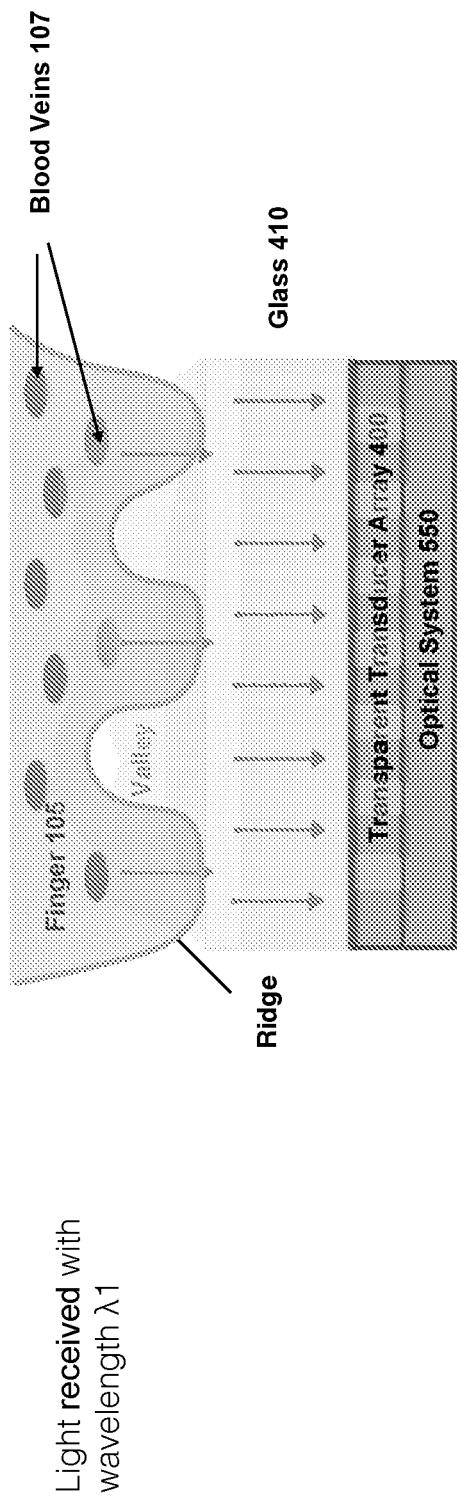

FIG. 49 illustrates a cross sectional view of the integrated optical and ultrasound system of FIG. 48 during reception of reflected light at the first wavelength $\lambda 1$ off of the finger, back through the glass 410 and through the portions of the transducer array 400 that are transparent to an optical sensor 570 in the optical system. The sensed reflected light can be associated with recently transmitted light based on the wavelength of the received light, the duration of time since light was transmitted by the light source, the distance of the path taken by the transmitted and then received reflected light, or any suitable combination thereof.

Figure 50:
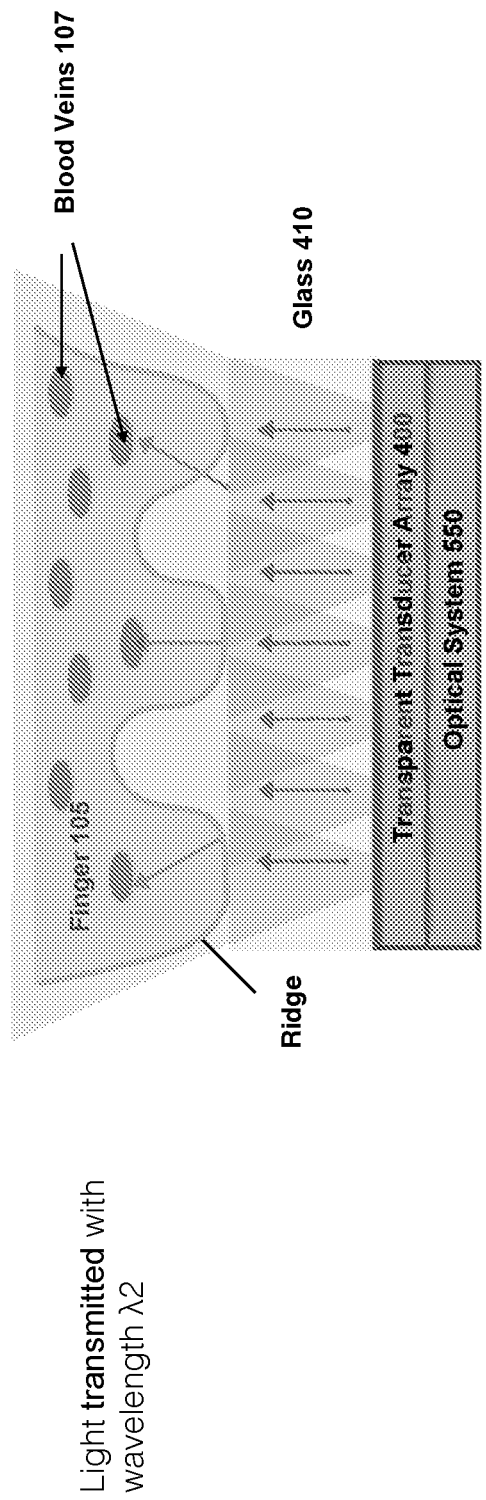

FIG. 50 illustrates a cross sectional view of the integrated optical and ultrasound system of FIG. 47 during transmission of light at a second wavelength $\lambda 2$ from a light source of the optical system 550 through the portions of the transducer array 400 that are transparent, in the sections between opaque bottom metal electrodes 430 and top metal electrodes 440, and glass 410 to a finger 105 on the receiving surface of the glass 410. The transmitted light of the second wavelength $\lambda 2$ can reach the receiving surface of the glass, enter the finger, and be transmitted to internal structures of the finger, such as veins 107 that are relatively close to the surface of the finger. Light may be reflected from, for example, the internal structures of finger and from the surface of finger ridges.

Figure 51:
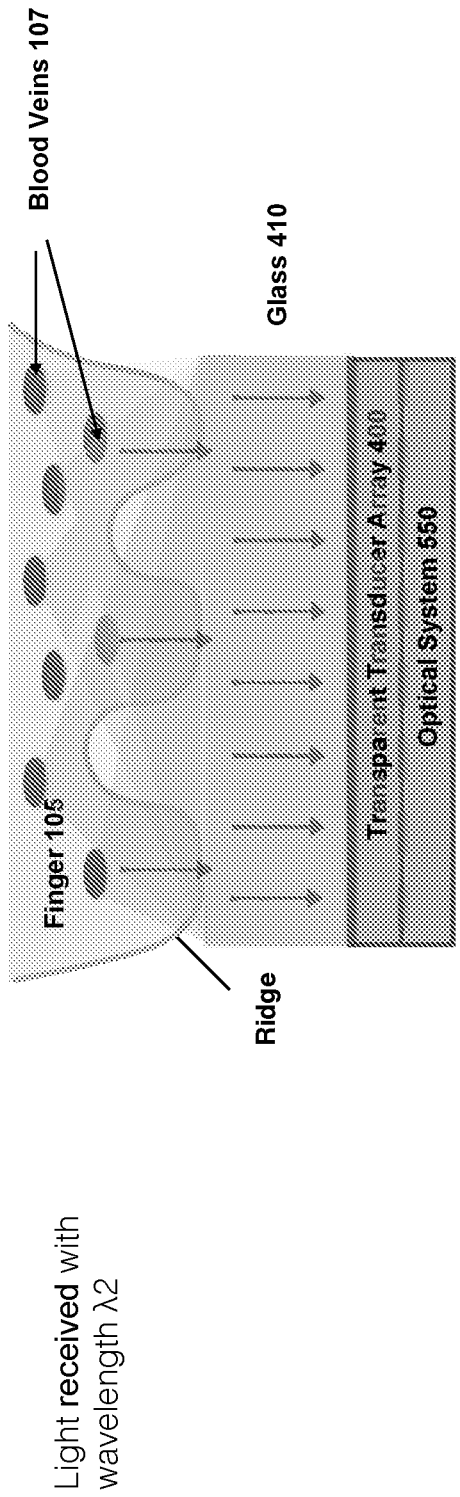

FIG. 51 illustrates a cross sectional view of the integrated optical and ultrasound system of FIG. 48 during reception of reflected light at the second wavelength $\lambda 2$ off of the finger back through the glass 410 and through the portions of the transducer array 400 that are transparent to an optical sensor in the optical system 550. The sensed reflected light can be associated with recently transmitted light based on the wavelength of the received light, the duration of time since light was transmitted by the light source, and/or the distance of the path taken by the transmitted and then received reflected light, or any suitable combination thereof.

Figure 52:
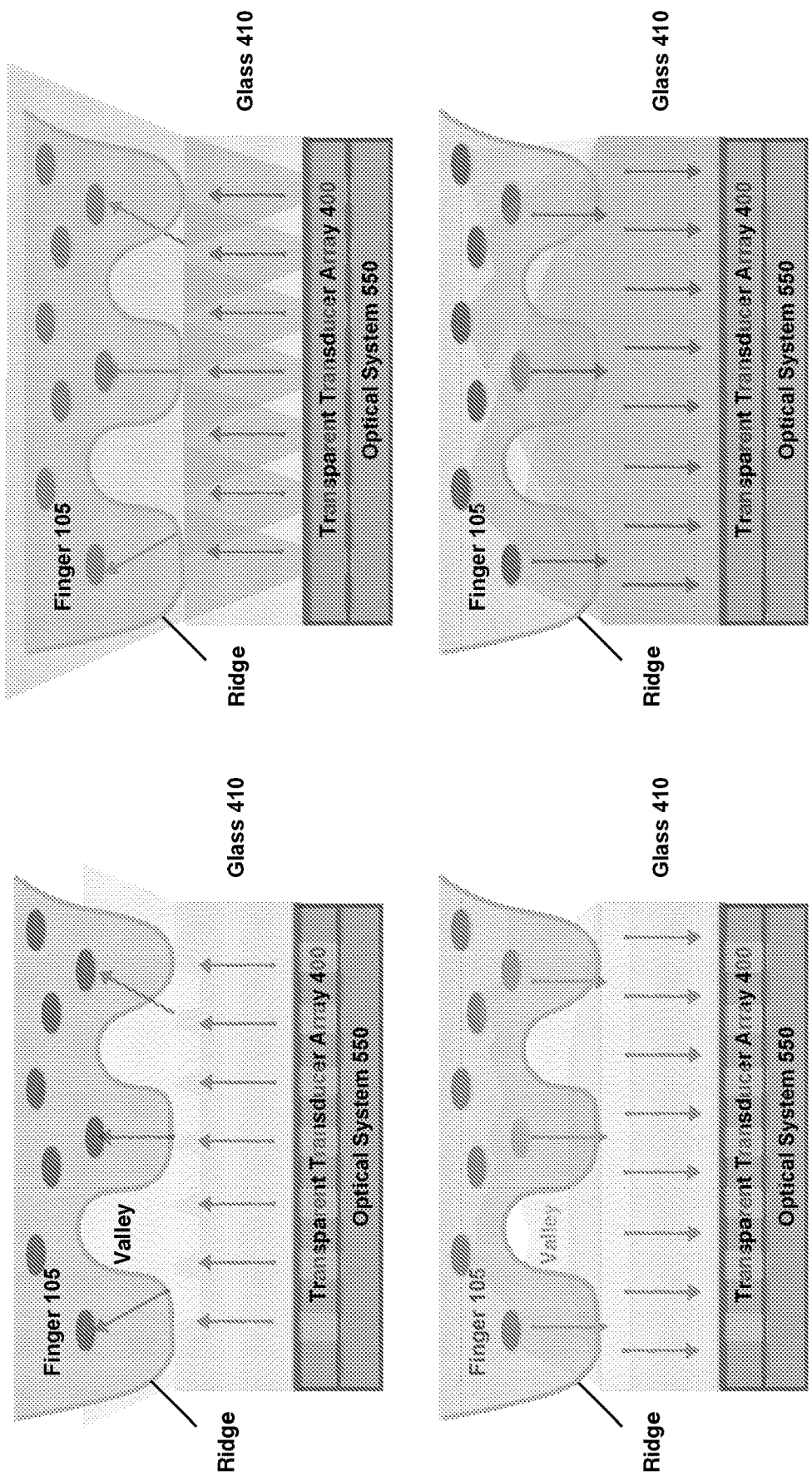

FIG. 52 illustrates the light transmission and reception at the first and second wavelengths, as illustrated in FIGS. 48-51. Comparisons in received light at different wavelengths may be used to, for example, take a reflected pulse oximetry reading of a finger on the receiving surface, as described above with respect to FIG. 42.

Figure 53:
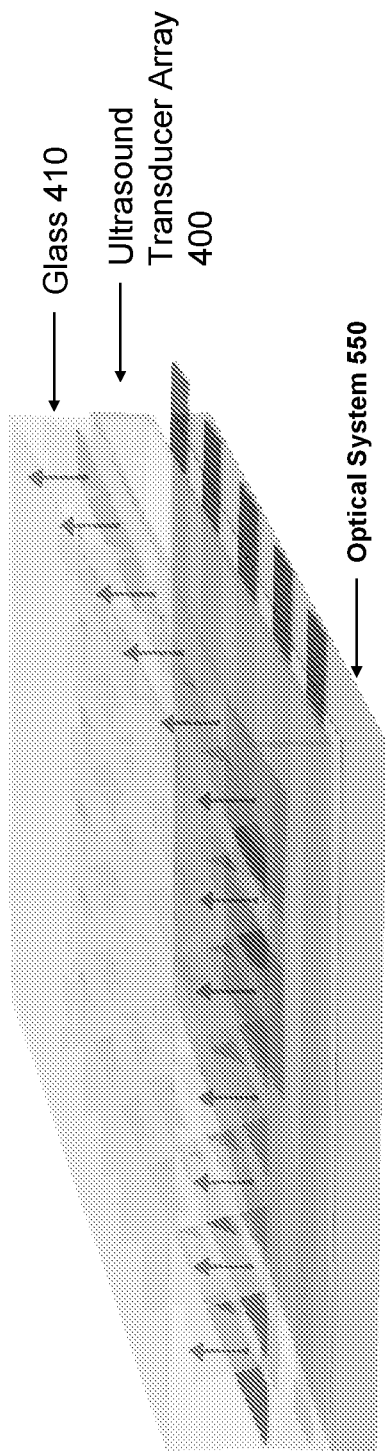

FIG. 53 is a perspective view of the example embodiment of FIG. 47 with an optical system 550 below an ultrasound transducer array 400 with opaque metal electrodes during a transmit phase without a finger on the receiving surface. Light emanates from a light source of the optical system 550 through the portions of the transducer array 400 that are transparent and the glass 410. There is no finger on the receiving surface of the glass 410 in FIG. 53.

Figure 54:
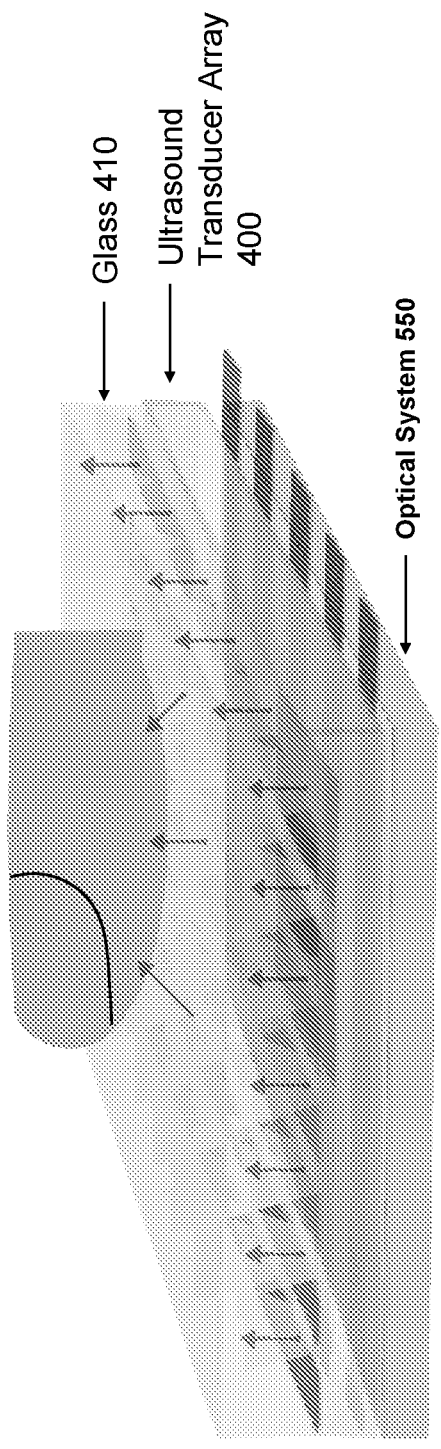

FIG. 54 is a perspective view of the example embodiment of FIG. 47 with an optical system 550 below an ultrasound transducer array 400 with opaque metal electrodes during a transmit phase with a finger on the receiving surface. Light emanates from a light source of the optical system 550 through the portions of the transducer array 400 that are transparent and the glass 410 to a finger 105 on the receiving surface of the glass 410. The transmitted light can reach the receiving surface of the glass 410, enter the finger, and be transmitted to internal structures of the finger, such as veins 107, that are relatively close to the surface of the finger. Light may be reflected from, for example, the internal structures of finger and from the surface of finger ridges to an optical system below an ultrasound transducer array with opaque metal electrodes.

Figure 55:
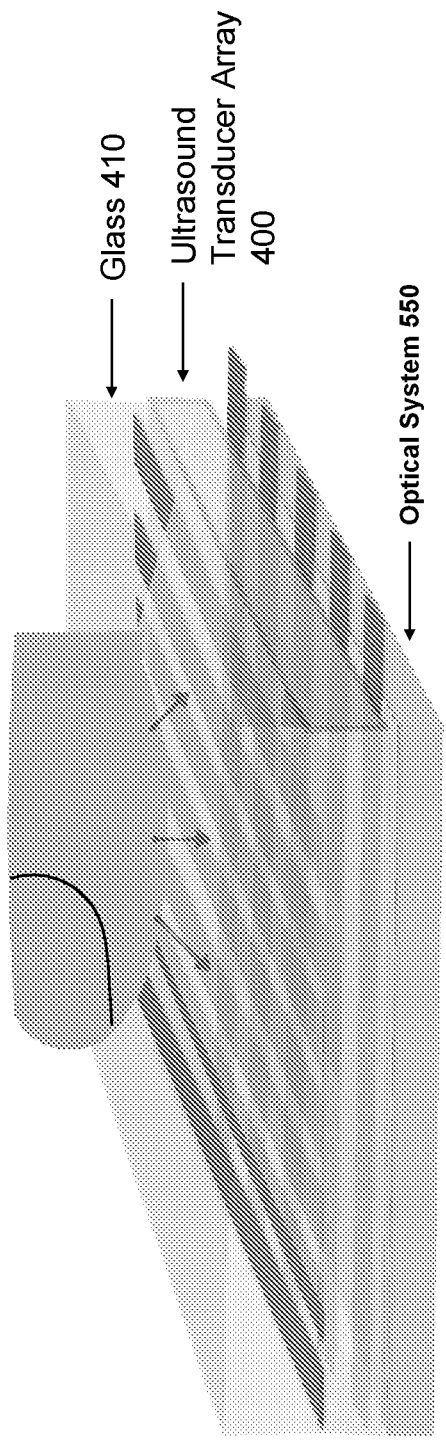

FIG. 55 is a perspective view of the example embodiment of FIG. 47 with an optical system 550 below an ultrasound transducer array 400 with opaque metal electrodes during a receive phase with a finger on the receiving surface during reception of reflected light off of the finger back through the glass 410 and the portions of the transducer array 400 that are transparent to an optical sensor of the optical system 550. The sensed reflected light can be associated with recently transmitted light based on, for example, the wavelength of the received light, the duration of time since light was transmitted by the light source, and the distance of the path taken by the transmitted and then received reflected light.

FIGS. 56-65 illustrate an example embodiment with an optical system embedded within a ultrasound transducer array with opaque metal electrodes. The ultrasound transducer array 400 with an embedded optical system is below glass and a receiving surface for a finger or other object to be examined. The bottom metal electrodes 430 and the top metal electrodes 440 are opaque as illustrated. In some other embodiments, the bottom metal electrodes 430 and/or the top metal electrodes 440 are transparent or at least partially transparent. The embedded optical system 550 includes embedded light sources 560 and light sensors 570. The supporting electronics 580 (not shown) can be embedded within the ultrasound transducer array, to the side of the ultrasound transducer array 400, and/or below the ultrasound transducer array 400.

Figure 56:
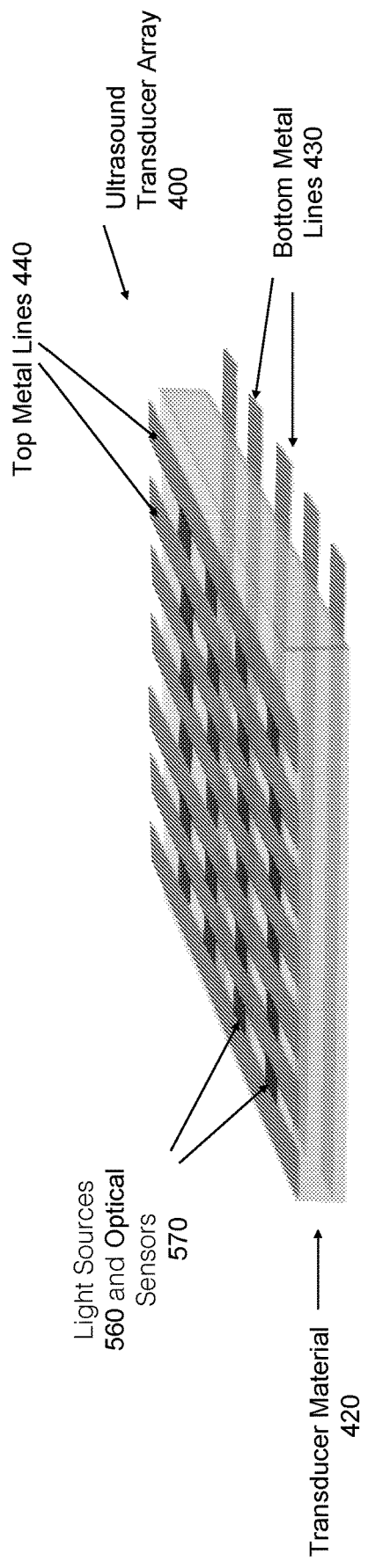
FIGS. 56-65 illustrate an example embodiment with an optical system integrated inside an array of ultrasound transducers.

FIG. 56 illustrates an ultrasound transducer array 400 with opaque top metal electrodes 430 and bottom metal electrodes 440 with embedded light sources 560 and light sensors 570. The ultrasound transducer array 400 can be implemented in accordance with any suitable principles and advantages described above with respect to FIGS. 2-10. Light sources 560 and sensors 570 are embedded within the ultrasound transducer array, for example, within the rectangular (or square) sections between opaque bottom metal electrodes 430 and top metal electrodes 440. Light from the light source 560 and light to the sensors 570 no longer needs to pass through the entire ultrasound transducer array 400, since the optical system 550 including the light sources 560 and sensors 570 are embedded within the ultrasound transducer array 400. In an embodiment where the light source 560 and/or the optical sensor 570 is at the top surface of the transducer material 420 and between the top metal electrodes 440, light need not travel through the transducer material 420, bottom metal electrodes 430, or top metal electrodes 440.

Figure 57:
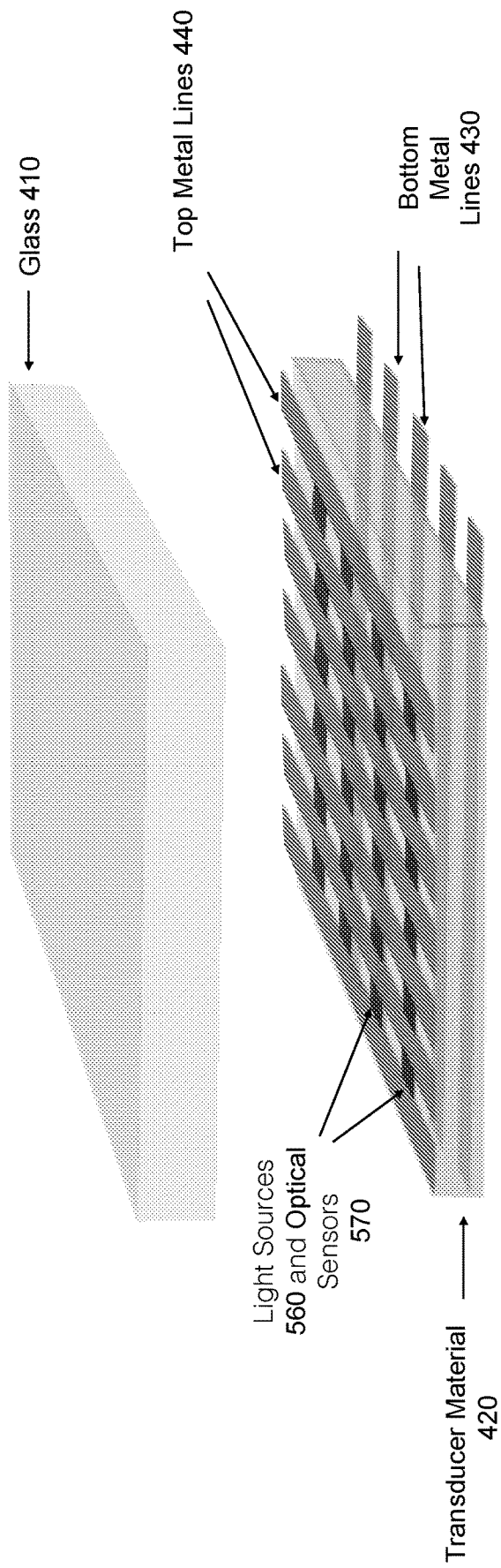

FIG. 57 illustrates an exploded view of the ultrasound transducer array 400 with embedded light sources 560 and light sensors 570 and the glass 410 of FIG. 56. As shown in FIGS. 58-66, the glass 410 and ultrasound transducer array 400 with embedded light sources 560 and sensors 570 are integrated with each other.

Figure 58:
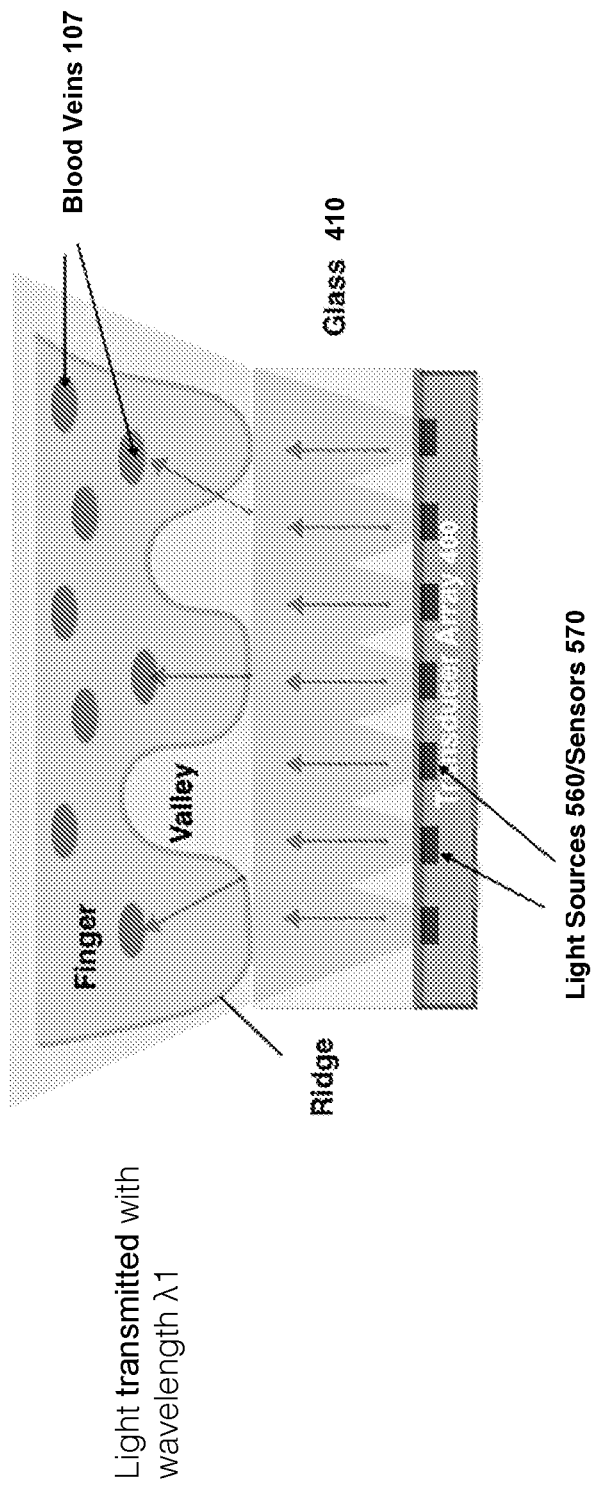

FIG. 58 illustrates a cross sectional view of the integrated optical and ultrasound system of FIG. 57 during transmission of light at a first wavelength $\lambda 1$ from a light source 560 through the glass 410 to a finger on the receiving surface of the glass 410. The transmitted light of the first wavelength $\lambda 1$ can reach the receiving surface of the glass 410, enter the finger, and be transmitted to internal structures of the finger, such as veins 107, that are relatively close to the surface of the finger. Light may be reflected from, for example, the internal structures of finger and from the surface of finger ridges to the optical sensor 570.

Figure 59:
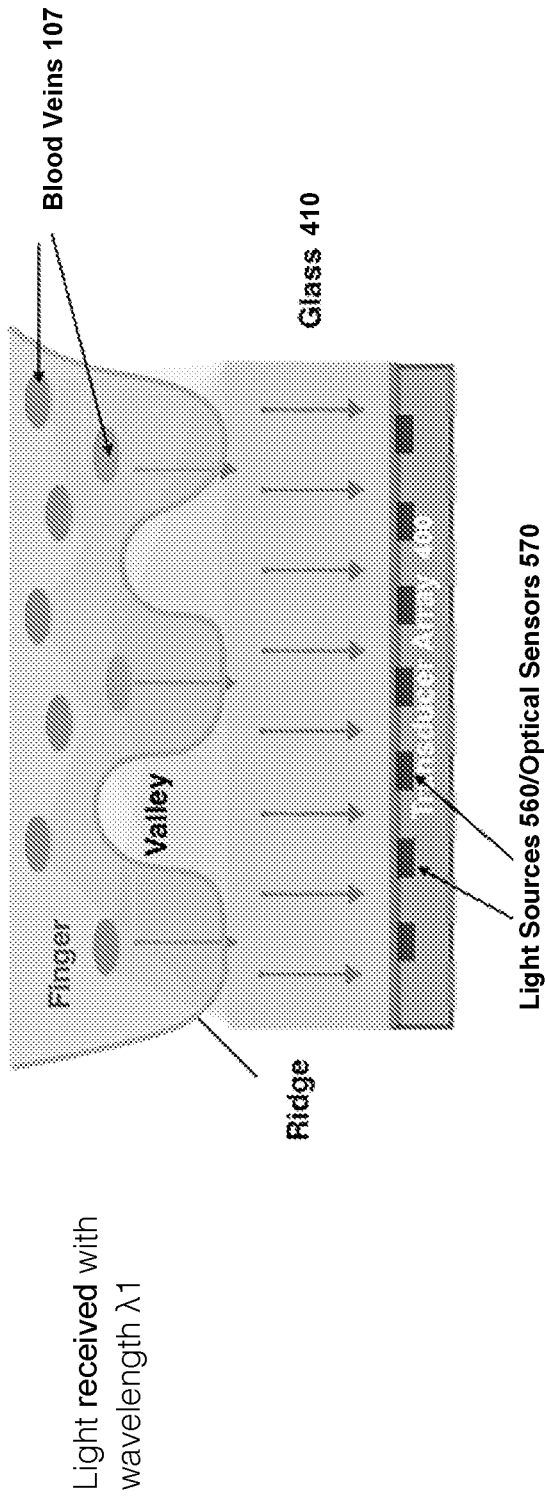

FIG. 59 illustrates a cross sectional view of the integrated optical and ultrasound system of FIG. 57 during reception of reflected light at the first wavelength $\lambda 1$ off of the finger, back through the glass 410 to an optical sensor 570 in the optical system. The sensed reflected light can be associated with recently transmitted light based on the wavelength of the received light, the duration of time since light was transmitted by the light source, and the distance of the path taken by the transmitted and then received reflected light, for example.

Figure 60:
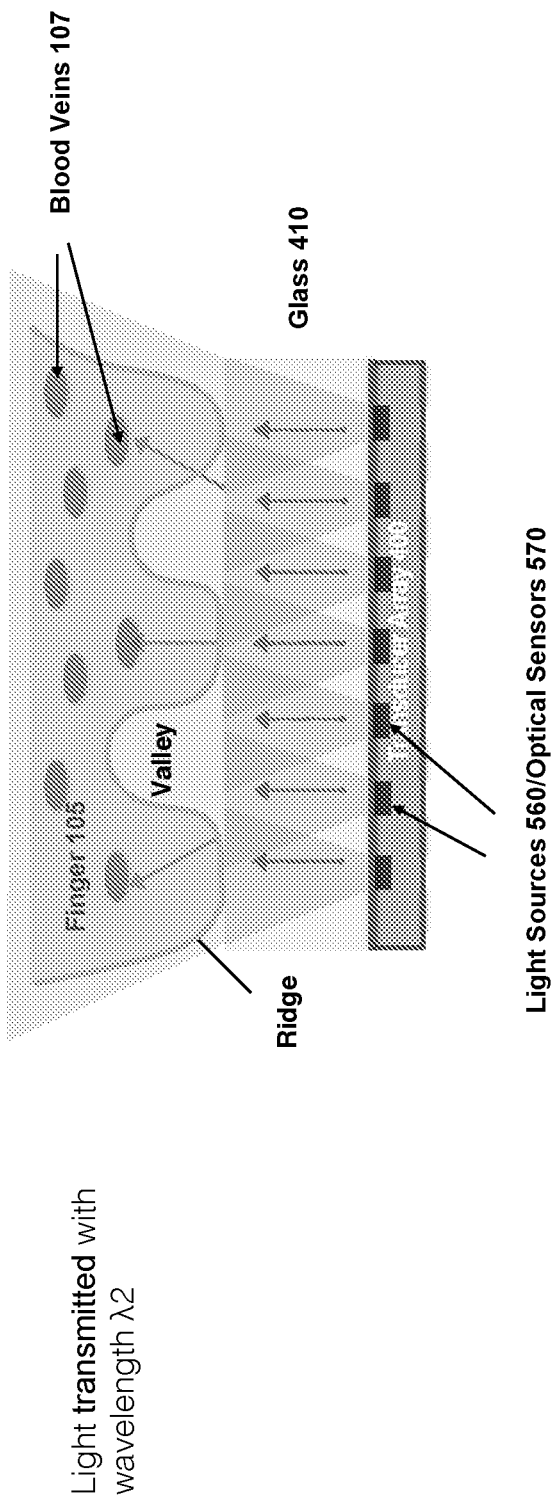

FIG. 60 illustrates a cross sectional view of the integrated optical and ultrasound system of FIG. 57 during transmission of light at a second wavelength $\lambda 2$ from a light source 560 through the glass 410 to a finger on the receiving surface of the glass 410.

Figure 61:
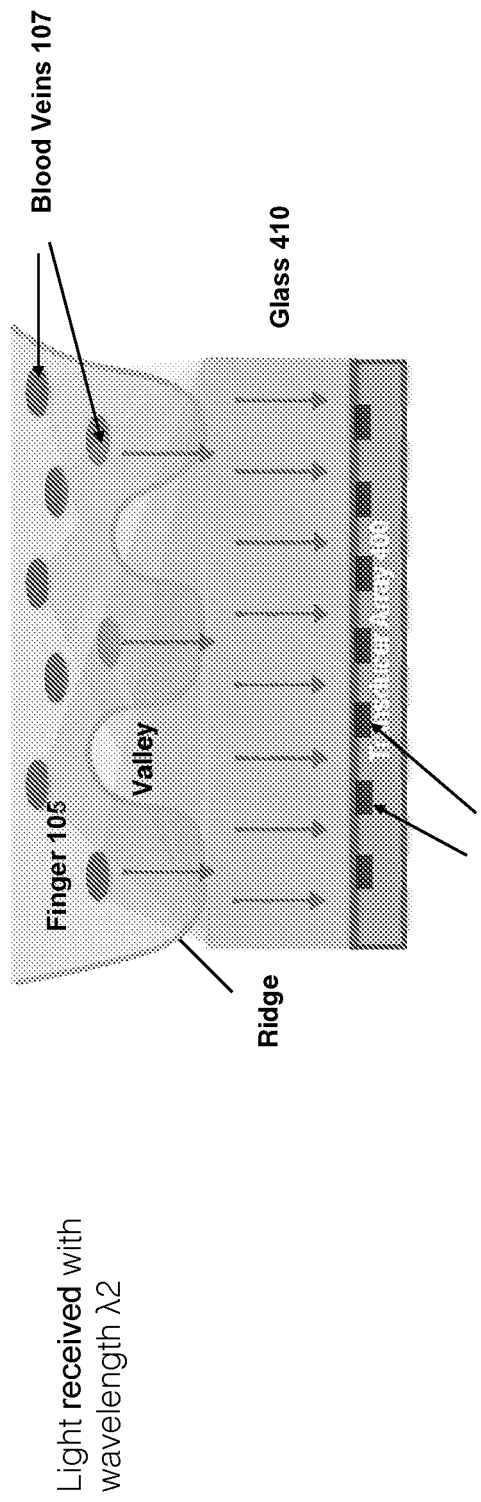

FIG. 61 illustrates a cross sectional view of the integrated optical and ultrasound system of FIG. 57 during reception of reflected light at the second wavelength $\lambda 2$ off of the finger, back through the glass 410 to an optical sensor 570 in the optical system. The sensed reflected light can be associated with recently transmitted light based on the wavelength of the received light, the duration of time since light was transmitted by the light source, and the distance of the path taken by the transmitted and then received reflected light, for example.

Figure 62:
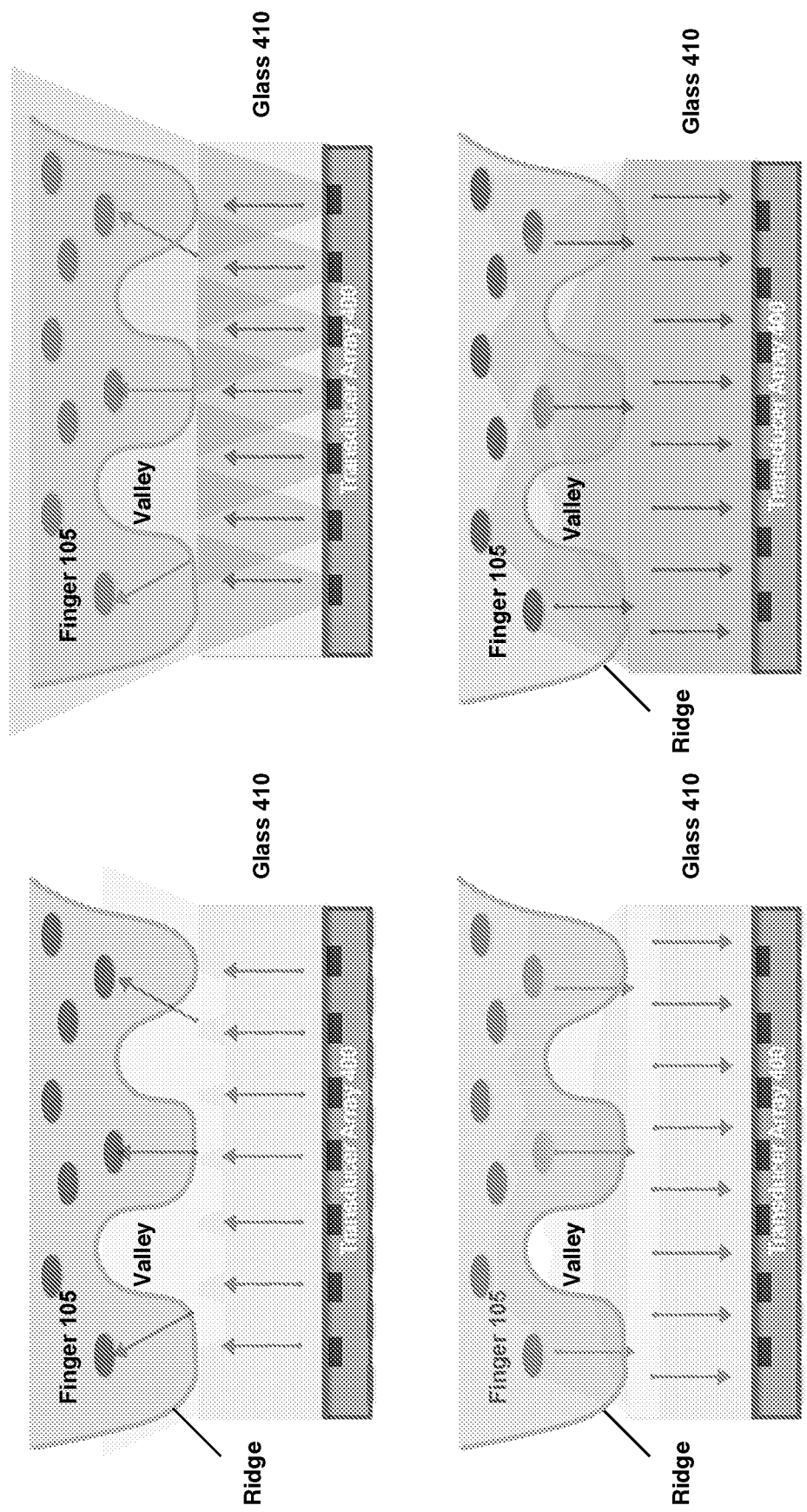

FIG. 62 illustrates the light transmission and reception at the first and second wavelengths, as illustrated in FIGS. 58-61. Comparisons in received light at different wavelengths may be used to, for example, take a reflected pulse oximetry reading of a finger on the receiving surface, as described above with respect to FIG. 42.

Figure 63:
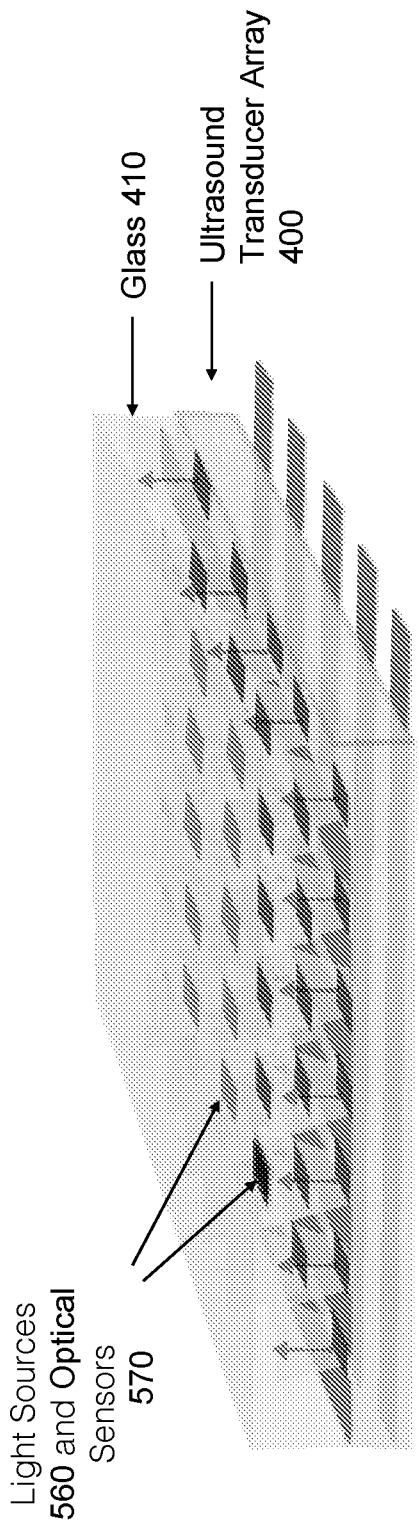

FIG. 63 is a perspective view of the example embodiment of FIG. 57 with an optical system embedded within the ultrasound transducer array 400 with opaque metal electrodes during a transmit phase without a finger on the receiving surface. Light emanates from light sources 560 of the optical system 550 through the glass 410. There is no finger on the receiving surface 125 of the glass 410.

Figure 64:
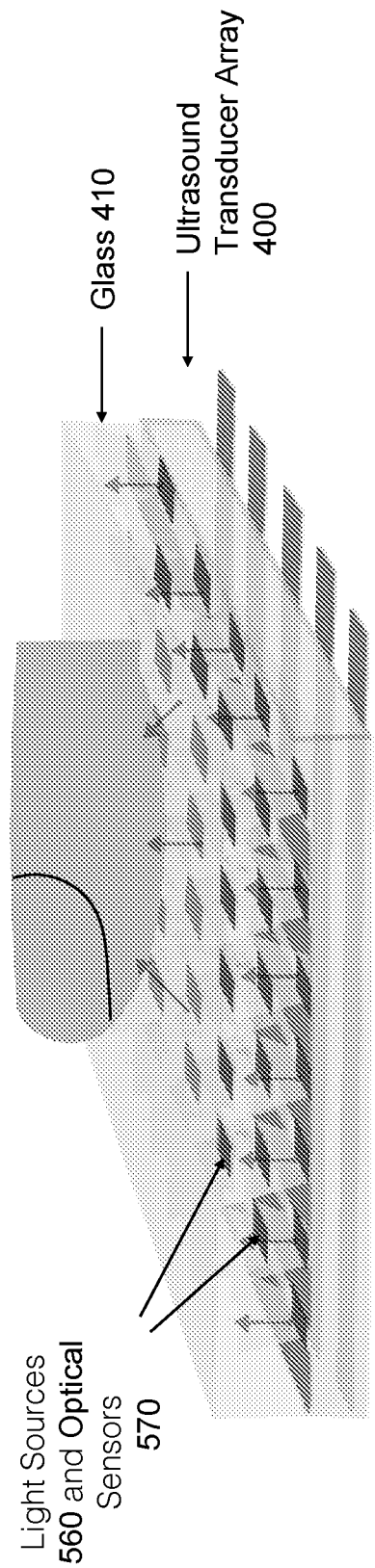

FIG. 64 is a perspective view of the example embodiment of FIG. 57 with an optical system embedded within the ultrasound transducer array 400 with opaque metal electrodes during a transmit phase with a finger on the receiving surface. Light emanates from light sources 560 of the optical system 550 through the glass 410.

Figure 65:
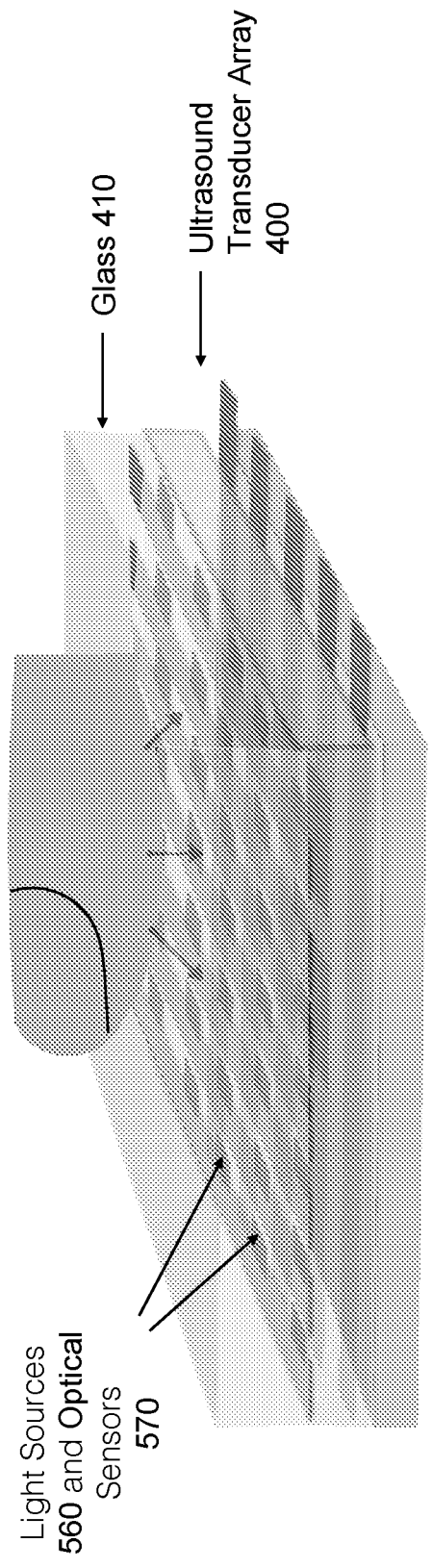

FIG. 65 is a perspective view of the example embodiment of FIG. 47 with an optical system 550 embedded within the ultrasound transducer array 400 with opaque metal electrodes during a receive phase with a finger on the receiving surface.

Figure 66:
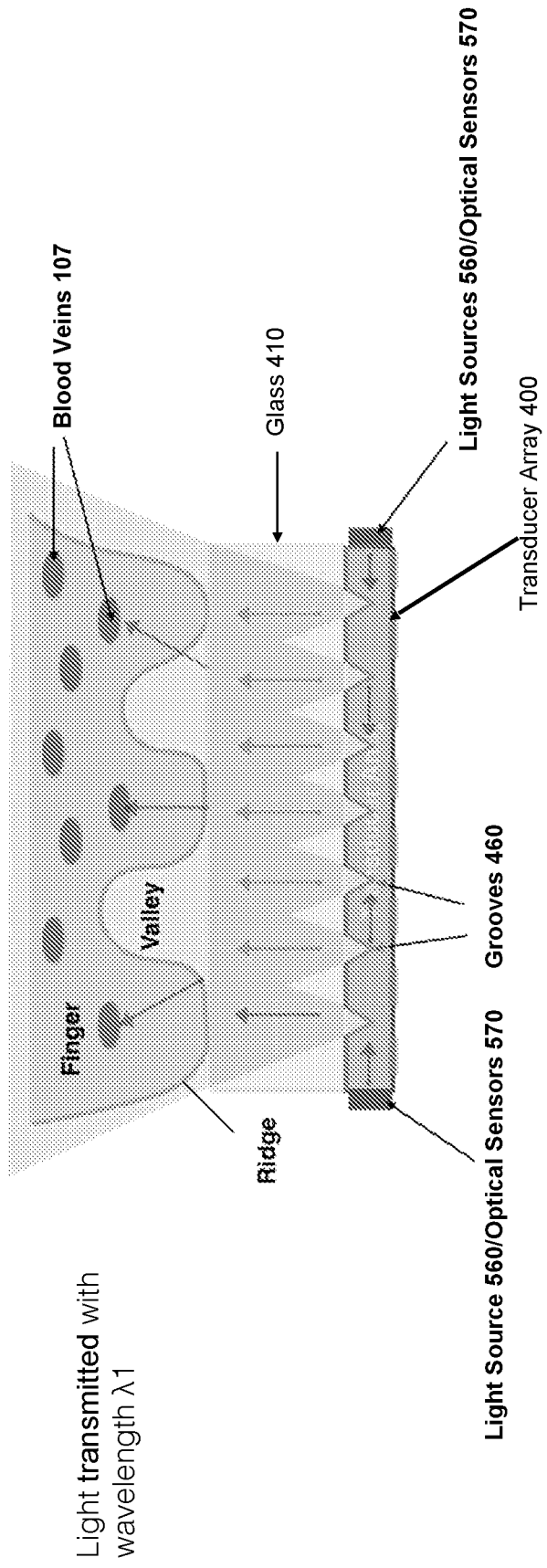

FIG. 66 illustrates a cross sectional view of an example embodiment with light sources 560 and light sensors 570 lateral to and adjoining an ultrasound transducer array 400. In the embodiment of FIG. 66, the light sources 560 can emit light in a direction substantially parallel to the receiving surface. Light emitted by the light sources 560 is transmitted through the transparent transducer material 420 to grooves 460 in the ultrasound transducer array 400, through glass 410 to the receiving surface 125 of glass 410 with a finger. The grooves 460 can turn the light emitted by the light sources 560 toward the receiving surface. The transmitted light can reach the receiving surface of the glass 410, enter finger 105, and be transmitted to internal structures of the finger, such as veins 107, that are relatively close to the surface of the finger. Light may be reflected from, for example, the internal structures of finger and from the surface of finger ridges. Such reflected light may pass through the glass 410 to grooves 460 between the upper metal electrodes and to the light sensors 570 lateral to and adjoining the ultrasound transducer array 400. The grooves 460 can turn the reflected light toward the optical sensors 570.

In addition to the light sources 560 and light sensors 570 lateral to and adjoining the ultrasound transducer array 400, the optical system 550 includes supporting electronics 580 (not shown), which may be to the side of the ultrasound transducer array 400 with the light sources 560 and light sensors 570 and/or below the ultrasound transducer array 400.

FIG. 67 illustrates an example acoustic biometric touch scanner, including an ultrasound system and an optical system 550. The ultrasound system includes an ultrasound transducer array 400, transmit electronics, and receive electronics. The optical system 550 includes a light source 560, an optical sensor 570, and supporting electronics 580.

The illustrated transmit electronics include a transmit switching network 1005, a voltage pulse generator 1010, a transmit beamforming circuit 1015, a transmit control circuit 1020. The illustrated receive electronics include a receive switching network 1025, a low noise amplifier 1030, an analog filter 1035, a time gain compensation circuit 1040, analog to digital converter 1045, a receive beamforming circuit 1050, an envelope detection circuit 1055, a receive control circuit 1060, a processor 1065, and a memory 107. The receive electronics and/or the transmit electronics can be implemented in accordance with any suitable principles and advantages described above with respect to FIG. 10.

The illustrated optical system 550 includes a light source 560, an optical sensor 570, and supporting electronics 580. The illustrated supporting electronics 580 supports the light source 560 with a light source driver 581, a light source current control unit 582, and control circuitry 583. The illustrated supporting electronics 580 supports the optical sensor 570 with control circuitry 583, a trans-impedance amplifier 584, a second stage amplifier 585, an anti-aliasing filter 586, and an analog to digital converter 587. In an embodiment, the optical system 550 corresponds to, and has corresponding components to, a reflectance pulse oximeter.

Control circuitry 583 controls the timing, duration, wavelengths (wavelength ranges), and power of emissions of light from the light sources in the illustrated optical system 550. The control circuitry 583 can also control timing of sensing incident light that may be reflections of previously transmitted light. The control circuitry 583 is shown as a single block in FIG. 67. However, the control circuitry 583 can function to control transmission and reception may be divided, or may be combined with the processor 1065, receive control circuit 1060, and or transmit control circuit 1020 of the ultrasound system. In an embodiment, the control circuitry 583 coordinates with the processor 1065, transmit control circuit 1020 and receive control circuit 1060 to coordinate and control the relative timing of ultrasound transducer array 400 transmissions and light source 560 light emissions. For example, in an embodiment, the ultrasound and light source emissions may be controlled to not overlap. In another embodiment, the ultrasound and light source emissions may be controlled to at least partially overlap.

The light source 560 may include any suitable light source. Example light sources include light emitting diodes, organic light emitting diodes, lasers, and the like. For instance, the light source 560 can include one or more light emitting diodes configured to emit light over a range of frequencies, and of durations and power levels to obtain biometric measurements. Example biometric measurements include a pulse oximetry reading, blood flow measurements, a pulse reading, temperature, glucose detection, blood glucose level, dehydration level, blood alcohol level, and blood pressure. For example, LEDs that emanate light in the visible and infrared portions of the spectrum may be used to obtain biometric measurements. The light source 560 can emit a variety of different wavelengths in certain applications and is not limited to specific wavelengths in such applications. For example a mid-IR laser pulse can be used for glucose detection.

The light source 560 may include multiple light sources arranged in a line, in rows and columns, in a hexagonal tessellation, or other suitable arrangements. An individual light source 560 or multiple light sources may be included in optical system 550. In an embodiment, a single light source 560 may be below the ultrasound transducer array 400, as shown in FIGS. 37 and 47. In an embodiment, individual light sources may be embedded in the ultrasound transducer array 400, in the portions between the top metal electrodes 430 and bottom metal electrodes 440, for example, as shown in FIG. 56. In an embodiment, light sources may be to the sides of the ultrasound transducer array 400, for example, as shown in FIG. 66. In an embodiment, optical fiber(s) or other suitable light turning features can guide light inward.

The light source current control unit 582 controls start time, end time, wavelength and power of pulses of light to be emitted by the light source 560. The light source driver 581 sends the pulses to the light source 560.

Emitted pulses are transmitted by the light source 560 that may be reflected back to the optical sensor 570.

The optical sensor 570 can include any suitable optical sensing elements. For instance, the optical sensor 570 can include one or more photodiodes configured to receive light over a range of frequencies, and of durations and power levels to obtain biometric measurements, such as a pulse oximetry reading and/or blood flow measurements. For example, photodiodes that receive light in the visible and infrared portions of the spectrum may be used to obtain biometric measurements. The optical sensor 570 can sense a variety of different wavelengths in certain applications and is not limited to specific wavelengths in such applications. In an embodiment, the optical sensor 570 can include a multispectral imager capable of sensing light at multiple frequency bands. In an embodiment, the optical sensor 570 can be included in a video camera capable of measuring subtle changes in color in the skin stemming from the flow of blood to detect a pulse.

The optical sensor 570 may include multiple optical sensors arranged in a line, in rows and columns, in a hexagonal tessellation, or other suitable arrangements. An individual optical sensor 570 or multiple optical sensors may be included in optical system 550. In an embodiment, a single optical sensor 570 may be below the ultrasound transducer array 400, for example, as shown in FIGS. 37 and 47. In an embodiment, individual optical sensors 570 may be embedded in the ultrasound transducer array 400, in portions between the top metal electrodes 430 and bottom metal electrodes 440, for example, as shown in FIG. 56. In an embodiment, optical sensors 570 may be to the sides of the ultrasound transducer array 400, for example, as shown in FIG. 66.

In certain embodiments, the optical sensor 570 includes one or more photodiodes that that convert incident photons to a current. The resultant current is converted to a voltage by trans-impedance amplifier 584, and amplified by a second stage amplifier 585. An anti-alias filter low 586 pass filters the amplified voltage from the second stage amplifier to reduce aliasing. The output of the anti-aliasing filter is digitized with an analog to digital converter 587. The analog to digital converter 587 for the optical system 550 can operate at a lower frequency than the ultrasound system analog to digital converter 1045. For example, the optical system 550 analog to digital converter 1045 can operate in, for example, the 2 kHz range, with approximately 22 bit digitization accuracy. Other suitable frequency ranges and/or accuracies can be implemented for particular applications. The analog to digital converter 587 can digitize the analog output of the anti-aliasing filter 586 for subsequent digital processing of the signal. In an embodiment, the analog to digital conversion may occur at a different stage of the receive processing chain.

Figure 68:
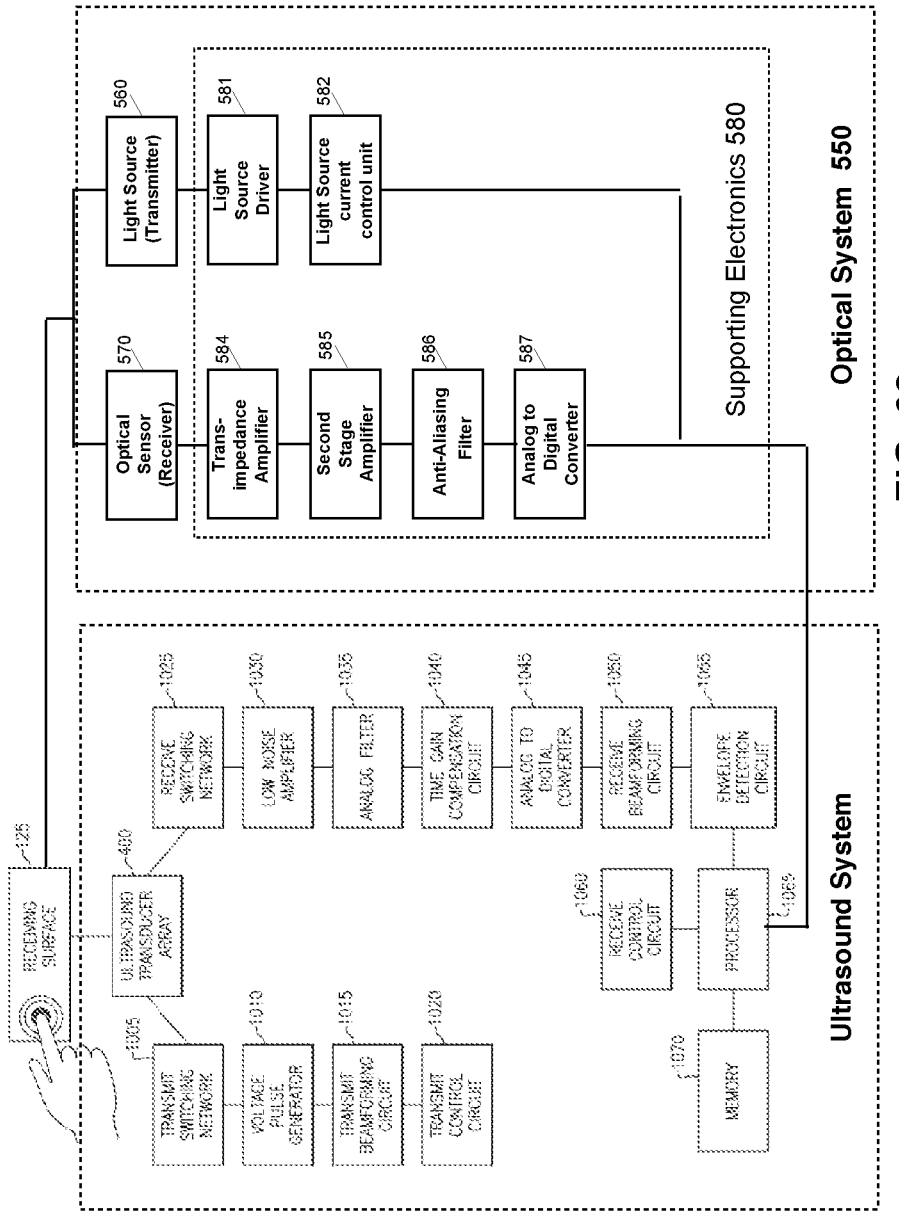
FIG. 68 illustrates an example biometric touch scanner, including an ultrasound system and an optical system. The ultrasound system and optical system share control a processor and control circuitry.

FIG. 68 illustrates an example biometric touch scanner, including an ultrasound system and an optical system. The ultrasound system includes an ultrasound transducer array, transmit electronics, and receive electronics. The optical system includes a light source, an optical sensor, and supporting electronics. The components of FIG. 68 can be implemented as described above with respect to FIG. 10 and FIG. 67. The biometric scanning device of FIG. 67 includes separate components for the ultrasound system and the optical system. In contrast, the biometric scanning device of FIG. 68 includes a shared processing unit for the ultrasound system and optical system. The processor 1065 of FIG. 68 can serve as a processor for the ultrasound system and control circuitry for the optical system.

One aspect of the disclosed technology is a biometric fingerprint sensing device. The device includes an optical emitter configured to transmit light having a frequency in a range from 400 nm to 1000 nm. The device further includes an array of ultrasonic transducers configured to transmit an ultrasound signal having a frequency in a range from 50 megahertz (MHz) to 500 MHz. The ultrasonic transducers include a piezoelectric film. The device further includes first metal electrodes. The device further includes second metal electrodes orthogonal to the first metal electrodes. The first metal electrodes and the second metal electrodes enable addressing of the ultrasonic transducers of the array. The device further includes a surface configured to receive a finger. The device further includes a processor configured to generate an image of at least a portion of a fingerprint of the finger based on a reflection of the visible light and/or the ultrasound signal from the finger. The device further includes an actuator configured to vary the temperature of and/or the pressure on the finger in contact with the receiving surface.

In an embodiment, the optical emitter transmits light through the ultrasonic transducer, the first metal electrodes, and the second metal electrodes. In an embodiment, the ultrasonic transducer is at least partially transparent. In an embodiment, the first and second metal electrodes are at least partially transparent.

In an embodiment, the array of ultrasonic transducers are between the optical emitter and the receiving surface, and the ultrasonic transducers, first metal electrodes, and second metal electrodes are at least partially transparent to the transmitted light.

In an embodiment, the ultrasound transducers transmit the ultrasound signal through the optical emitter.

In an embodiment, the optical emitter comprises an array of optical emitters in squares on a plane, each square bounded by projections of the first metal electrodes and second metal electrodes to the plane.

In an embodiment, the optical emitter adjoins the ultrasound transducer.

Interactive Biometric Scanner

Embodiments of this disclosure relate to a scanner, such as a finger print scanner, with the ability to become an actuator. The actuator can deliver energy to an object, such as a finger. This can establish a two-way communication between the scanner and a user. Such two-way communication can involve real-time interactive authentication process. Authentication with two-way communication can be performed on a timescale of milliseconds for any suitable interactive biometric scanner disclosed herein. For instance, any suitable ultrasonic interactive biometric scanner with ultrasonic sensing and/or actuation disclosed herein can perform two-way authentication on a millisecond timescale. Some other two-way communication techniques disclosed herein can be performed in several seconds. Two-way communication can provide robust authentication. The two-way communication can be referred to as interactivity.

Two-way communication can enable multi-factor authentication that provides real-time interaction aimed at defeating a scammer who might have secretly and/or illegally copied or otherwise obtained data that represents a user's fingerprint scan and/or other biological information (e.g., pulse and temperature from a previous authentication session) from authenticating. Interactions with a finger or other object for authenticating during authentication that are not predictable in advance (e.g., that are random) should be able to prevent scammers from authenticating with prior data. As one example, while having a fingerprint and pulse scanned, a user being authenticated could be prompted to stand while keeping a finger on the scanner. The scanner could then detect a change in pulse associated with standing and the change in pulse could be used to authenticate the user. As another example, haptic energy could be felt by a user and could prompt the user to take action, such as removing a finger from the scanner or changing a force applied to by the finger to the scanner. Such action could be detected by a sensor, such as an ultrasound sensor, by a variety of methods, such as by detecting widening of the ridges (e.g., force detection) and/or capillaries of the finger.

Fingerprint scanners, such as an ultrasound fingerprint scanner, can implement a sensor and also an actuator. As an actuator, the scanner can deliver energy, such as ultrasound in a form that can be felt by the user. This can establish a two-way communication between the scanner and the user. The scanner can detect a response to the delivered energy for use in authentication. As an example, ultrasound energy can be delivered through a focus burst that can be detected by the finger as a pulse of heat, a push, a neuro-modulation such as a tingling sensation in the finger, the like, or any suitable combination thereof. Other energy modalities can alternatively or additionally be used to deliver a signal that can be sensed by the finger. Accordingly, the idea of converting a scanner into a two-way communication device can apply to a variety of forms of scanners. In some instances where the sensor also functions as an actuator, the sensor can detect the response to the delivered energy. For instance, an ultrasound fingerprint sensor can also detect how a variety of liveness parameters (e.g., tissue stiffness and/or temperature) change in response to energy delivered by the ultrasound fingerprint sensor.

The sensor and actuator can be implemented below a surface configured to receive a finger for authentication. The sensor and actuator can be positioned below one or more layers of glass and/or engineered glass. Interactive biometric authentication can be performed while a finger is positioned on a surface of a device that is authenticating the finger.

Certain actuators can deliver energy that is perceptible to a person being authenticated. As one example, an ultrasound fingerprint sensor can provide haptic energy to a finger that a person can perceive to prompt a response from the person (e.g., standing up). Some other actuators can delivery energy that is imperceptible to a person being identified. For instance, an ultrasound fingerprint sensor can generate heat to a degree that a person does not perceive but that can be detected as a response used to authenticate the finger.

Two-way communication can be implemented by one integrated device with different aliveness measurements from the same location as an ultrasound sensor where the finger is being scanned.

Two-way communication can be implemented using different aliveness measurements and interactivity can be performed at the same time that a fingerprint and at the same location. This can ensure that the different aliveness parameters are associated with the same user.

Two way communication can be implemented using different devices to authenticate a person. For example, a person being authenticated can be prompted by one device to interact with a different device. In an embodiment where the two devices are a phone and a tablet, a person can be prompted by the phone to press his finger on the tablet.

With two-way communication, safety and/or security of the scanner can be enhanced. With an interactive authentication session or process, a fake authentication with a scammer using a past sign-in can be prevented. A signal sent by the scanner during authentication can result in the user responding with further action for multi-factor authentication. The signal can be sent at a time that is not easily predictable in advance. The actuator can prompt a variety of responses. Some responses can be involuntary. For instance, a finger can be heated in response to energy being applied to the actuator. Certain responses can involve voluntary user action. For example, the response can be to have another finger scanning as agreed upon by prior agreement, entering a set of numbers, or any other possible actions or many actions all agreed upon earlier when the system was being set up. Other types of excitation could be creating Braille characters under the finger that can be a code eliciting a coded response form the user. These authentication prompts can be generated at random without prior agreement and can be recognized and recorded by a processor, memory, and associated software. Such a processor, memory, or associated software can also embody one or more suitable features of the technology disclosed herein. Detecting any of these types of responses can create a more secure method of authentication relative to just detecting a fingerprint.

Fingerprints do not typically change. Accordingly, if a fingerprint is spoofed, it cannot be easily changed like a password. With two-way communication, aspects of a live finger or live user can be used as an advantage in providing robust authentication. Certain actuation can create involuntary biological responses that can be detected and used in multi-factor authentication that can be difficult to spoof. In some instances, responses to actuation can engage a user's brain such that the user performs a certain action that can be detected and used in multi-factor authentication. Such responses can be particularly challenging to spoof.

The principles and advantages of the two-way communication discussed herein can be implemented in any suitable device, system, or method where authentication is used to access secure data or information. Example applications include secure authentication for electronic devices, guns, and keys for doors in cars or homes. Some other applications include smart cards (e.g., a credit card that includes an integrated chip). Any suitable principles and advantages discussed herein can be implemented in a smart card. A smart card can include a chip that includes a fingerprint scanner, such as an ultrasonic fingerprint sensor. In some instances, a smart card can include a piezoelectric film (e.g., a zinc oxide film) over most or all of a major surface of the card for ultrasonic biometric sensing. Some additional applications include the steering wheel of a car that checks a driver's biometric information (such as heart rate) to determine whether the driver appears to be angry, anxious, intoxicated, the like, or any suitable combination thereof.

Therefore, the "aliveness" measurements enabled by the disclosed technology allow for interactivity. This allows real-time interactions for robust authentication aimed at defeating attempts to gain unauthorized access by a scammer who obtained a digital representation of, for example a user's fingerprint scan or, retinal scan, pulse, temperature, electrocardiogram or other identifiers for a user. Such security systems can be used to control access to a web site database, building, or use of a weapon, for example. If random interactions are required during the authentication process, a copy of an earlier authentication session would not be sufficient to gain access.

The disclosed technology includes systems that can use one more of the following three types of authentication factors: knowledge factors, possession factors, and inherence factors. Knowledge factors include passwords and personal identification numbers (PIN) that are (or should be) known only to an individual user. Possession factors include keys, fobs, smartphones, or a physical cryptographic key like YubiKey. Inherence factors or biometrics include fingerprint, iris, or facial scans, gait, heartbeats, or other biometric indicators. Systems that rely on just one of these three types of factors may be more vulnerable than systems that use two or more of these factors. For example, passwords can be stolen, fobs can be cloned, and biometrics imitated digitally.

Two-factor authentication can involve authentication from two of the three types of authentication factors. For example, a two factor authentication system may involve authentication based on a user entering a knowledge factor, such as a password, and having a possession factor, such as a cell phone, Yubikey, or Duo app. In this example, an attacker with a user's password can be defeated if he does not have the user's cell phone or fob. Similarly, an attacker with the user's cell phone, but without his password, would not be able to authenticate.

Three-factor authentication can involve authentication from all three factors: knowledge, possession, and inherence. Surface-only fingerprints have been used for decades to identify crime suspects. Such fingerprints can be lifted from surfaces, as depicted in Mission Impossible and James Bond movies, or digitally copied to fool authentication systems. Three dimensional fingerprints that capture internal structural features as well as fingerprint surfaces are not as easily lifted from surfaces or digitally copied. An extra level of security is introduced by using inherence or biometric features that change in response to stimuli, as an attacker would not necessarily know in advance which stimuli will be applied during the authentication process.

One concern with introducing fingerprint or iris scan authentication is that an attacker in, for example, a war zone might remove a body part in order to defeat an authentication system. This grisly possibility underscores the importance of testing whether the scanned finger is intact and attached to a live user, as opposed to an amputated finger, a finger of a dead person, a prosthetic finger, or a digital representation of a finger.

The disclosed technology includes methods to measure liveness with actuators that activate neurons via radiation, pressure or heat, causing a change in an inherent feature or biometric. The disclosed technology further includes methods to measure liveness by prompting a user to take an action. This interaction with the user's brain help determine that the finger is a live finger attached to a user, as there is a neurological connection to the brain of the user, to help verify the inherence factor.

For example, a user being scanned by an embodiment of the disclosed technology can have her pulse scanned while the fingerprint is being authenticated, and for two factor authentication the user can be asked to stand while holding on to the scanner. The device would measure a change in heartbeat and/or another parameter that would change a result of standing. Haptic energy could be felt by a user and be a prompt for the user to take an action, such as removing her finger, pushing down on the scanner, which would be registered as a force applied by the finger to the scanner, or typing a letter or word on a screen. The haptic energy can be actuated by a MEMS device and controlled by a controller, such as an ASIC. Involuntary or voluntary finger movement in response to the haptic energy can be detected by a fingerprint sensor.

In certain applications, a user being scanned by an embodiment of the disclosed technology can have her blood oxygen level taken after being prompted to take several deep breaths, which should increase her blood oxygen level. Alternatively, she can be prompted to hold her breath, which should reduce her blood oxygen level. A change in blood oxygen level can be determined based on a comparison of blood oxygen readings before and after a prompt. In an embodiment, the breathing patterns of a user being scanned can be correlated with heart rate, such as an instantaneous heart rate. In an embodiment, changes in the breathing patterns of a user being scanned are analyzed in response to prompts, and correlated with instantaneous heart rates before and after the prompt.

Digital representations of a previous session of an "alive" and authorized user, including her fingerprint, retinal scan, pulse or other measurements, could be used to gain access in some instances in predictable authentication sessions. By randomly or otherwise unpredictably varying, for example, the haptic energy pattern and timing from session to session, the digital representations of prior sessions should not be sufficient to gain unauthorized access.

Some users are reluctant to use their fingerprint to unlock a portable computing device, such as a smart phone, since unlike a password, a fingerprint is not easily changeable. Stolen passwords can easily be replaced, but once someone has stolen the digital likeness of their fingerprint, the fingerprint is not easily changed. The disclosed technology incorporates the uniqueness of a fingerprint from a negative (for those who worry their 'likeness' could be stolen), into a positive with ways to mitigate the issue of someone copying the fingerprint by adding 'aliveness' measurements as well as a random or unpredictable authentication operation that involve a user's unique fingerprint or other characteristics of the finger.

One solution to authenticating that the user is the user, and not a scammer sending the bank the 0s and 1s that represent the user's password or an advanced biometric representation, is to add second factor authentication (2FA) to verify the user. Some current 2FA uses both a password and a second factor for authentication. Examples of a second factor include, for example, a number texted to the user's mobile phone, a code emailed to the user, or correct answers to questions that were previously provided by the user. Some second factor authorizations make use of a second device.

However, existing 2FA methods can be hacked, including random numbers texted to a second device that are then entered by the user, after inputting their password. Furthermore, existing 2FA or multi-factor authentication methods can take time or be difficult for a user, or require a second device, resulting in low usage by users of multi-factor authentication methods.

The disclosed technology includes interactive approaches in which the device can affect a fingerprint, akin to a bright light causing an involuntary muscle contraction in the pupil that is being scanned or a facial recognition system recognizing a closing of an eye following an authentication command to close an eye. The disclosed technology includes an actuator that interacts with the user, causing a detectable response. The interaction can include heating, cooling, vibrating, shining a light, emitting a sound, or any other suitable stimulus that impacts a user. The actuator can be implemented by a fingerprint sensor. In some instances, the actuator can include hardware of a computing device, such as a mobile phone, that is separate from the fingerprint sensor and performs other functionality for the computing device (e.g., vibrating the device). The response can be involuntary or voluntary. Involuntary responses, such as a change in heartbeat or pulse rate may not even be apparent to the user. Other involuntary responses may relate to changes in fingerprint ridges or internal fingerprint structures. Voluntary responses include a directed finger movement, finger pressure, or entering information into a user interface by touch, typing or speech.

As the stimuli can be unpredictable (e.g., random and/or exhibit statistical randomness), can be in multiple steps, and can elicit predictable voluntary or involuntary responses, the disclosed technology enables robust authentication. The stimuli or method sequence can be randomly chosen by, for example, a randomized algorithm and/or using a random number generator. For example, haptic stimuli can be unpredictably varied with respect to interval between vibrations, the number of vibrations, and the duration of vibrations, location of stimuli, or pattern of stimuli. Similarly, different heating stimuli are possible. The user can also be prompted to rapidly rub his finger on the palm of his other hand and then put it back on the fingerprint sensor. The higher temperature could then be measured. This type of interaction would be very difficult to predict. The user can be prompted to reorient the device, move in a particular direction, or squeeze a finger. Each of these actions result in predictable outcomes that can be sensed and analyzed, by, for example, quantifying finger ridge spacing or movement of a point on the finger from frame to frame of an acquired set of ultrasound images of the finger.

In an embodiment, a user can be authenticated using two collocated devices, such as a computer in a bank branch and the user's mobile phone, both of which include biometric touch scanners in accordance with any of the principles and advantages disclosed herein. The user is then authenticated by confirming that the devices are reading fingerprints of the same user with corresponding measure(s), such as temperature of the user, pulse rate, and/or pulse oximetry reading, to authenticate the user.

This approach can be expanded to two users in the same place, in a system analogous to a bank requiring co-signing wires above a certain dollar threshold. Both parties can sign on using an application, indicating one is the account holder and the other a co-signer. Both parties get their fingerprint verified as being their own as well as one or more of their biometric parameters, such as one or more of their pulse, temperature, and oxygen level. The parties switch devices when prompted by the bank or other online site, and fingerprint and one or more biometric parameters are detected for each user after switching. The users are authenticated if the fingerprint and biometric levels match.

An added level of security may be possible by introducing a digital watermark and encryption, in which the biometric data and interactions are combined to form a digital watermark and encrypted within the data stream. For example, such a digital watermark and encryption can be introduced in the data streams of the systems of FIG. 67 and/or FIG. 68. A watermark and encryption can enable the detection of a cut-and-paste action by helping one notice a disruption or pause or break in the data stream. For example, if a bank causes a haptic energy pulse prompt for a user to recognize that they should remove their finger, then the scammer would have to almost instantly send the 0s and 1s equivalent to removing a finger and then also send the requisite 0s and 1s in response to a prompt of standing that would change the pulse—or the 0s and 1s representing the user's fingerprint being pushed down—to be authenticated. A watermark and encryption would be designed to be able to detect splices or interruptions in the flow of data, as the scammer tried to keep up with interactive prompts.

Embodiments of the disclosed technology related to improved devices, systems, and methods for authentication, including authentication to determine aliveness. Such embodiments relate to determining whether a fingertip on a receiving surface of a sensing device is an actual live finger instead of a prosthetic device, non-live finger, or other object that is attempting to authenticate in place of a live finger.

The disclosed technology can address problems related to scammers spoofing remote devices with so-called 'replay' attacks. For example a scammer may try to trick an authentication method by replaying the digital signature used during authentication sessions from the newer biometrics scans. Moreover, certain biometric scans may not stop scammers using a Trojan horse to add a false template (i.e., a template that would be matched with a fingerprint or face algorithm upon authentication) to circumvent the authentication process. With two-way communication between a scanner and a user, it can be significantly more difficult to trick a scanner with a digital signature or a false template or other attempt to trick the scanner.

During transmission a scammer could also attack the transmission between the phone and the bank and tamper with the template stored at a bank or cloud site. Computing devices that include bio-metric scans in addition to a fingerprint scan, such as facial recognition or iris scanning, still can be fooled with false templates or replay attacks.

Therefore, there is a need for simple-to-execute systems of interactivity, with multiple scans happening during an authentication session as a way to overcome these authentication problems. The disclosed technology combines biometric measurements and factors with interactions between different biometric devices for authentication.

Just as Mission Impossible agents and James Bond replicated fingerprints to fool authenticators, it is possible to break into existing systems that lack interactivity with replay attacks, the disclosed technology introduces two way communications, including sensing and effecting, for random, unpredictable interactive sessions for authentication. For example, the disclosed technology can measure a common factor, such as pulse, with a fingerprint device and another separate biometric device. Each measures the pulse during their main authentication process, which is combined with, for example, fingerprint recognition, iris recognition, facial recognition, or retina recognition.

Example embodiments include a fingerprint sensor, an actuator, and a processor configured to authenticate a finger based on an image of the finger generated by the fingerprint sensor and a detected response to the energy delivered by the actuator. The fingerprint sensor can implement the actuator in certain embodiments. Various embodiments will now be described with reference to the drawings.

Figure 69:
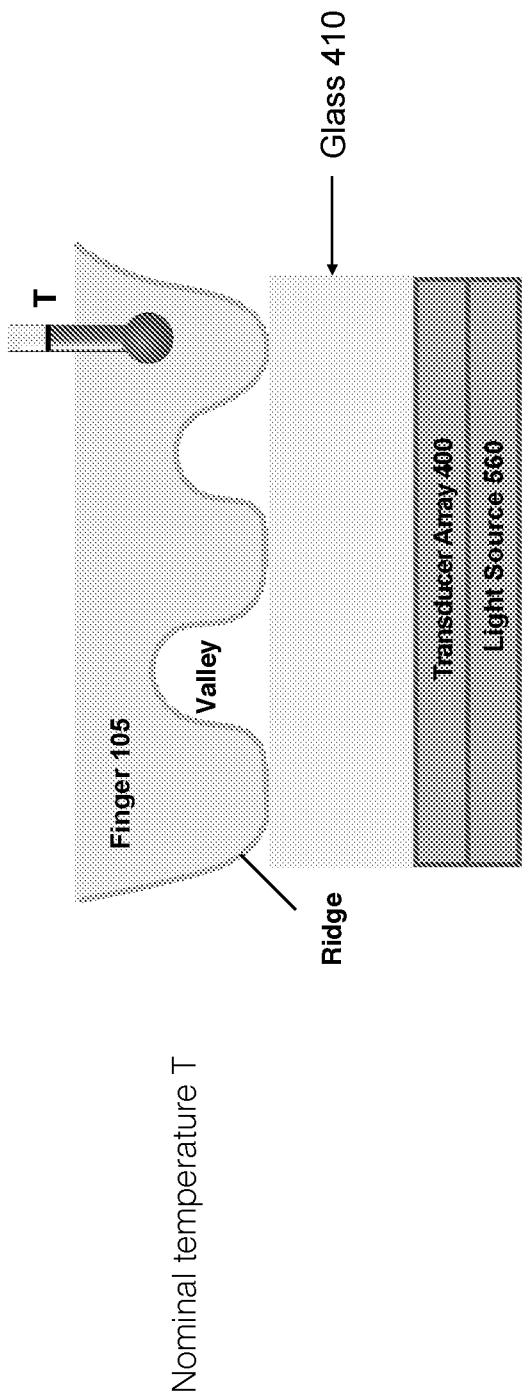
FIG. 69 illustrates an example embodiment of a biometric touch scanner with two way communication, including a light source actuator below an ultrasound transducer array.

FIG. 69 illustrates an example embodiment of a biometric touch scanner with two way communication, including a light source 560 actuator below an ultrasound transducer array 400, which is below glass 410 with a receiving surface upon which a finger can be placed. In an embodiment, the light source 560 is a component of an optical system 550 as described above with respect to FIG. 68.

Figure 70:
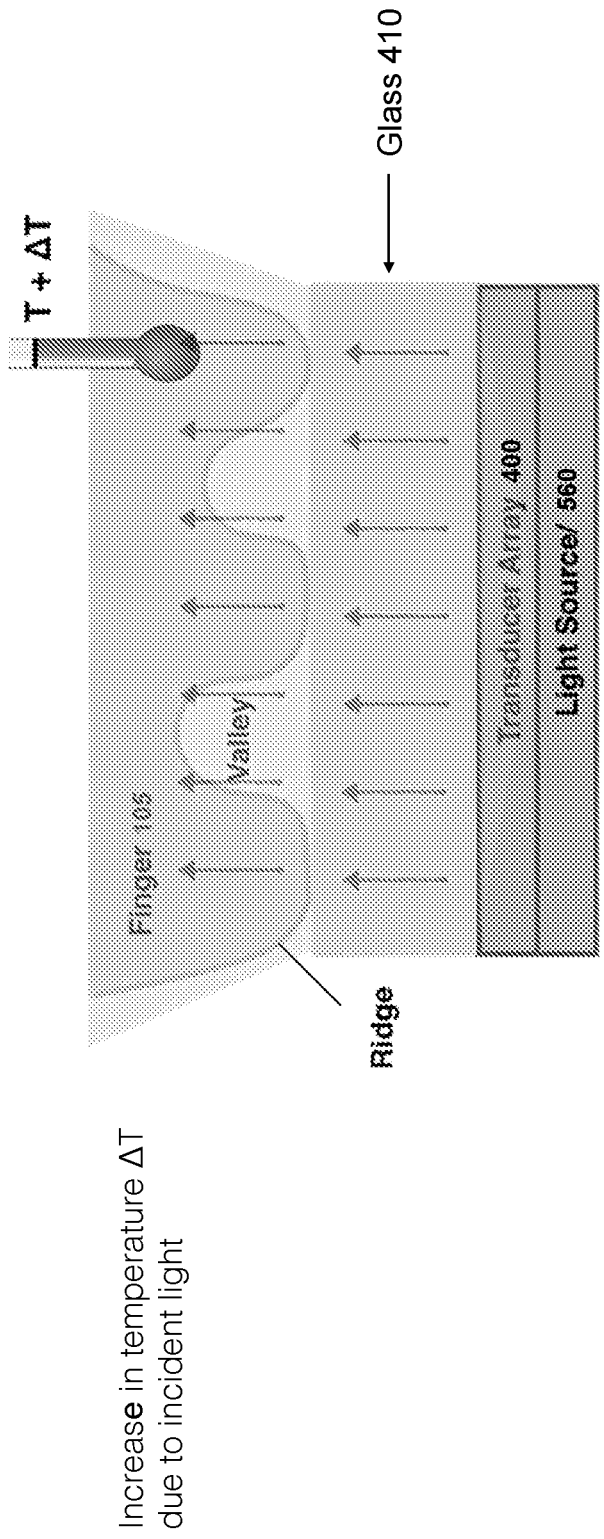
FIG. 70 illustrates the embodiment of FIG. 69, for which the light source actuator shines light through the ultrasound transducer array and glass to a finger on the receiving surface of the glass, such that the light source incrementally heats the finger.

FIG. 70 illustrates the embodiment of FIG. 69, in which the light source 560 actuator transmits light through the ultrasound transducer array 400 and glass 410 to a finger 105 on the receiving surface of the glass 410. The light source 560 emits light at a wavelength, for a duration, and at a power level sufficient to heat at least a portion of the finger 105 on the receiving surface from temperature T to temperature T+ΔT, where T may be close to room temperature and/or finger temperature, and ΔT is sufficient to be detectable by the biometric source scanner. The change in temperature ΔT can be discernable by a person, but not so large as to burn the person's finger. For example, ΔT may vary from a tenth of a degree to several degrees on the Fahrenheit scale. The change in temperature ΔT can be detected by the ultrasound transducer array 400 in certain applications. The change in temperature ΔT can be detected by a light sensor of an optical system that includes the light source 560 in some instances.

From the temperature difference ΔT, a specific heat of the tissue of the finger 105 can be detected. The change in temperature or specific heat can be different for a live finger and from other objects that could be used in place of a live finger, such as a fake finger or non-live finger. A processor can authenticate the finger 105 based on whether the temperature difference ΔT is consistent with an expected temperature difference associated with live tissue. The processor can also use an image of the finger 105 generated using the ultrasound transducer array 400 to authenticate the finger 105.

Figure 71:
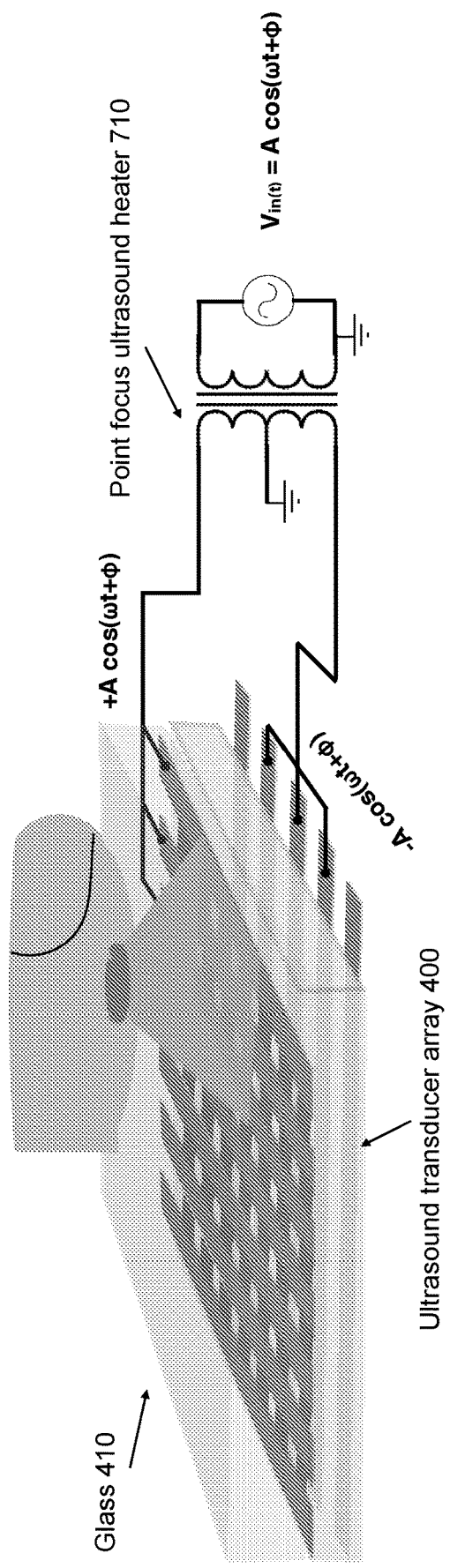
FIG. 71 illustrates an example embodiment of a biometric touch scanner with two way communication, including a point focus ultrasound heater that focuses ultrasound from the ultrasound transducer array through glass to a point (small region) of a finger on the receiving surface of the glass.
Figure 72:
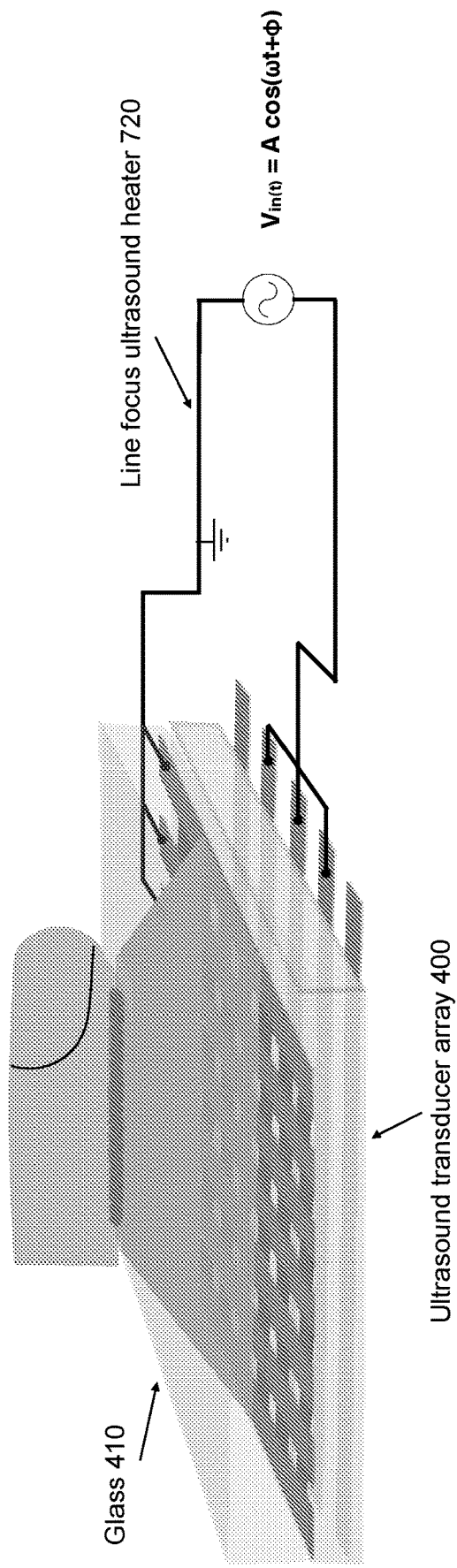
FIG. 72 illustrates an example embodiment of a biometric touch scanner with two way communication, including a line focus ultrasound heater that focuses ultrasound from the ultrasound transducer array through glass to a line (line segment) of a finger on the receiving surface of the glass.

An ultrasound transducer array can be used as an actuator and a sensor. FIGS. 71 and 72 illustrate embodiments in which an ultrasound transducer array is used as a sensor and an actuator. In these embodiments, the ultrasound transducer array can deliver energy to an object and also detect a response to the energy delivered to the object. While the ultrasound transducer array can detect a change in temperature in response to ultrasonic heating in FIGS. 71 and 72, an ultrasonic transducer array can detect a variety of other responses to applied ultrasound energy such as responses to pressure. Moreover, the ultrasound transducer arrays of FIGS. 71 and 72 can also be used in authenticating a fingerprint.

FIG. 71 illustrates an example embodiment of a biometric touch scanner with two way communication, including a point focus ultrasound heater 710 that focuses ultrasound from the ultrasound transducer array 400 through glass 410 to a point (e.g., a relatively small region, dot, or pixel) of a finger on the receiving surface of the glass 410, such that the point focused ultrasound energy incrementally heats the finger. The point focus ultrasound heater 710 can input excitation to opposite electrodes that are 180° out of phase and transmit the focused ultrasound energy on each set of electrodes. A change in temperature of the finger in the area being heated can be detected using the ultrasound transducer array 400 can be used to authenticate the finger.

FIG. 72 illustrates an example embodiment of a biometric touch scanner with two way communication, including a line focus ultrasound heater 720 that focuses ultrasound from the transducer array 400 through glass 410 to a line (linear region) of a finger on the receiving surface of the glass 410, such that the line focused ultrasound energy incrementally heats the finger. The line focus ultrasound heater 720 inputs excitations on one side of the array. A change in temperature of the finger in the linear region being heated can be detected using the ultrasound transducer array 400 can be used to authenticate the finger.

Figure 73:
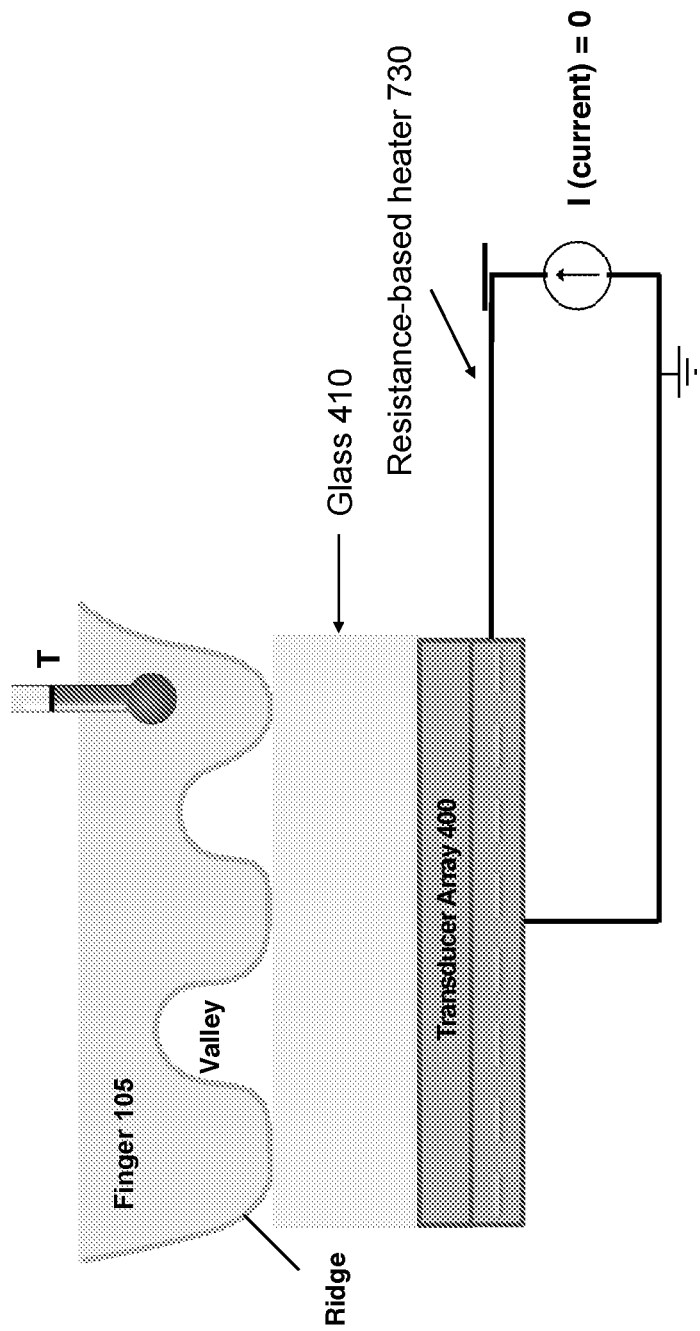
FIG. 73 illustrates an example embodiment of a biometric touch scanner with two way communication, including a resistance based heater capable of sending current through the electrodes (top and bottom metal electrodes) of the ultrasound transducer array.
Figure 74:
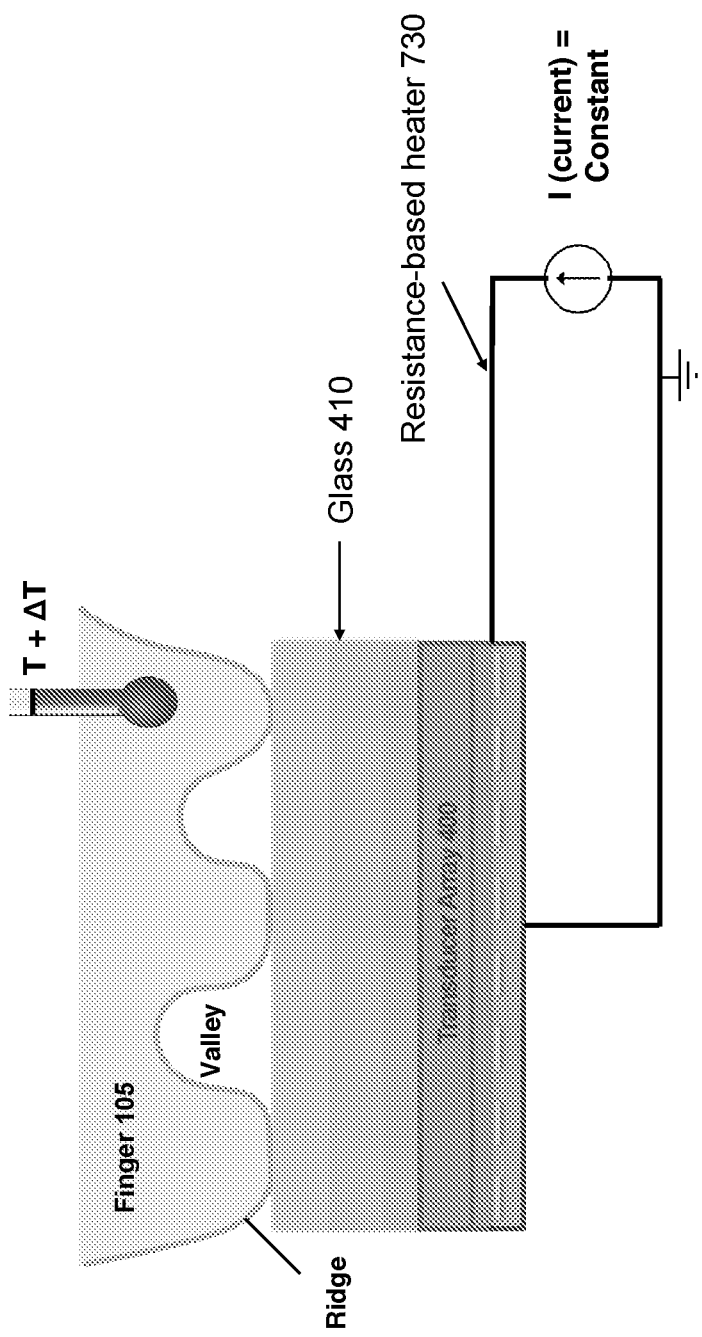
FIG. 74 illustrates an example embodiment of FIG. 73, of a biometric touch scanner with two way communication, including a resistance based heater capable of sending current through the electrodes (top and bottom metal electrodes) of the ultrasound transducer array, emanating heat from the ultrasound transducer array through glass to a finger on the receiving surface of the glass.
Figure 75:
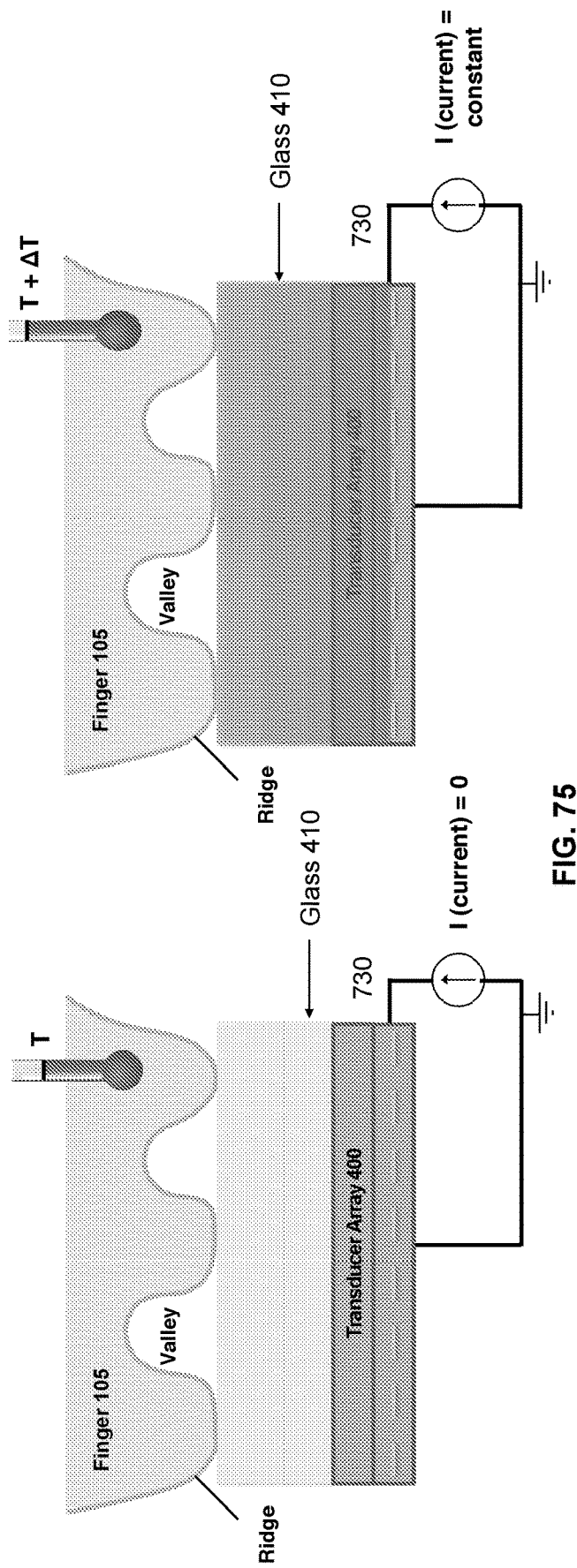
FIG. 75 illustrates operation of the example embodiment of FIGS. 73 and 74, of a biometric touch scanner with two-way communication, including a resistance based heater capable of sending current through the electrodes (top and bottom metal electrodes) of the ultrasound transducer array.

Other actuators can be integrated with a fingerprint sensor, such as an ultrasonic fingerprint sensor. For example, a resistance-based temperature sensor can apply resistance-based heating to a finger and sense the change in temperature. FIGS. 73 to 75 illustrate an example embodiment of an interactive biometric touch scanner with a fingerprint sensor and integrated with an actuator.

FIG. 73 illustrates an example embodiment of a biometric touch scanner with two way communication, including a resistance based heater 730 capable of sending current through the electrodes (top and bottom metal electrodes) of the ultrasound transducer array 400 through glass 410 to a finger on the receiving surface of the glass to create a heating sensation at the user's fingertip.

FIG. 74 illustrates heating a finger 105 with the biometric touch scanner of FIG. 73. The resistance based heater 730 can heat the finger 730 to raise a temperature of some or all of the finger 105 from temperature T to temperature T+ΔT. In some instances, T may be relatively close to room temperature and ΔT is sufficient to be discernable by a person, but not so large as to burn the person's finger. The resistance can alternatively or additionally be implemented using electrodes that are separate from the transducer device electrodes.

FIG. 75 illustrates operation of the embodiment of FIGS. 73 and 74. In the left portion of FIG. 75, no current is flowing and the finger on the receiving surface of the finger on the receiving surface is at a temperature T. The temperature sensor can detect temperature T in this state. In the right portion of FIG. 75, current is flowing through the electrodes, generating resistance-based heating, emitting heat through the glass to a finger on the glass, and raising the heat of the finger on the receiving surface to T+ΔT. The temperature sensor can detect temperature T+ΔT in this state. A processor can use this change in temperature to authentic the finger 105. A processor can also use an image of the finger 105 generated using the transducer array 400 in the authentication.

Interactive biometric authentication can be performed in a wireless communication device, such as a mobile phone. Wireless communication devices include one or more antennas to wirelessly transmit and/or receive signals. Mobile phones typically include a display, such as liquid crystal display (LCD) or an organic light emitting diode (OLED) display. Fingerprint sensors disclosed herein can be positioned below the display of a mobile phone. A mobile phone can also include an engineered glass having surface configured to receive a finger and/or below the surface configured to receive the finger. Fingerprint sensors disclosed herein can be positioned below the engineered glass in a mobile phone. The mobile phones shown in FIGS. 76-81 each include one or more antennas, a display, and a fingerprint sensor. Any of these mobile phones can include a fingerprint sensor integrated with an optical system in accordance with any suitable principles and advantages disclosed herein.

FIGS. 76-81 illustrate representative operations of two way communication scenarios associated with voluntary user response in response to energy delivered by an actuator. In certain instances, authentication that involves voluntary action can engage a brain of the user and provide robust authentication that can be even more difficult to fool than involuntary responses in certain applications. A first example scenario is illustrated in FIGS. 76-79. A second example scenario is illustrated in FIGS. 76, 77, 80 and 81.

Figure 76:
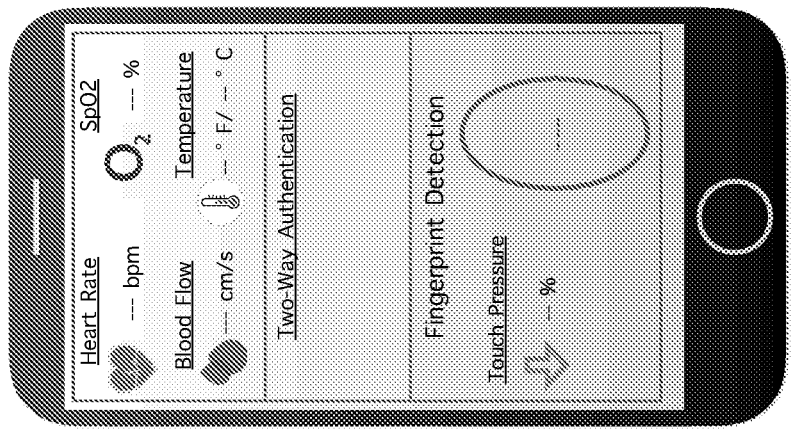

FIG. 76 illustrates the user interface of an example portable communications device including a biometric touch scanner and a display for measurements or indications of heart rate, pulse oxidation levels, blood flow, temperature, two way authentication, and fingerprint detection. In a first operation of the two way communication scenario of FIGS. 76-81, the device prompts the user to scan a finger.

Figure 77:
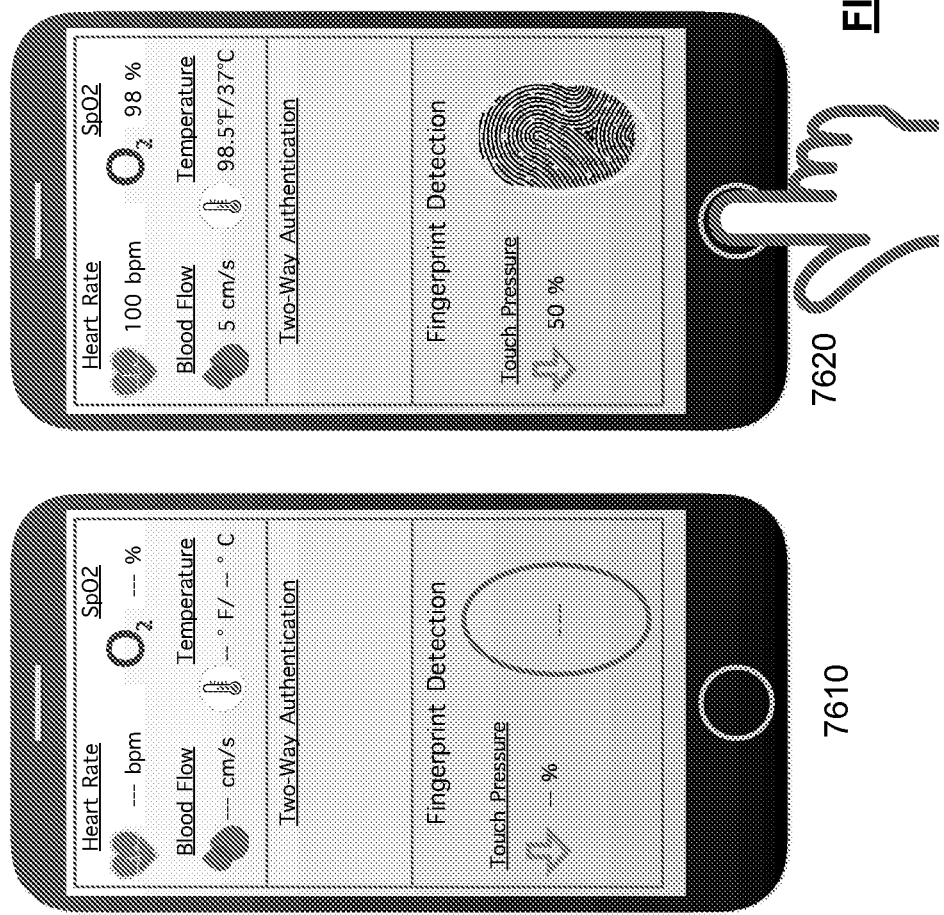

FIG. 77 illustrates an intermediate operation of the two way communication scenarios of FIGS. 76-81, in which the user scans the finger. The biometric touch scanner extracts biometric information and displays biometric information. For example, in FIG. 77 the biometric information includes the fingerprint, a heart rate of 100 bpm, a pulse oxidation measurement of 98%, a blood flow estimate of 5 cm/s, and a temperature of 37° C. Any suitable biometric information can be presented to the user such as any combination of the illustrated biological information and/or other suitable biological information. A placement indictor, such as a green oval, provides feedback if the fingertip is placed properly on the sensor and the biometric information is acquired. A template image of the scanned fingerprint may be displayed within the green oval. This template image signals the user that her finger is properly placed and that a fingerprint was acquired, without necessarily displaying the fingerprint itself.

FIG. 78 illustrates an intermediate operation of the two way communication scenario of FIGS. 76-79. After scanning the biometric information, the device generates a sensation at the user's fingertip with an actuator, by heating, radiation, pressure, neuro-stimulation or any other suitable technique. The user is then prompted to provide an input corresponding to the sensation that is felt. The sensation may correspond to a pulse count, the location at which the sensation is generated, the direction of sensation, the shape of the sensation provided to the finger, the like, or any suitable combination thereof. In FIG. 78, a sensation corresponding to shape A is drawn on the user's fingertip. The display prompts the user to enter the shape corresponding to the sensation felt by the user, as an interactive form of two way authentication. The actuation can be determined such that the two way authentication entry is not predictable in advance.

Figure 79:
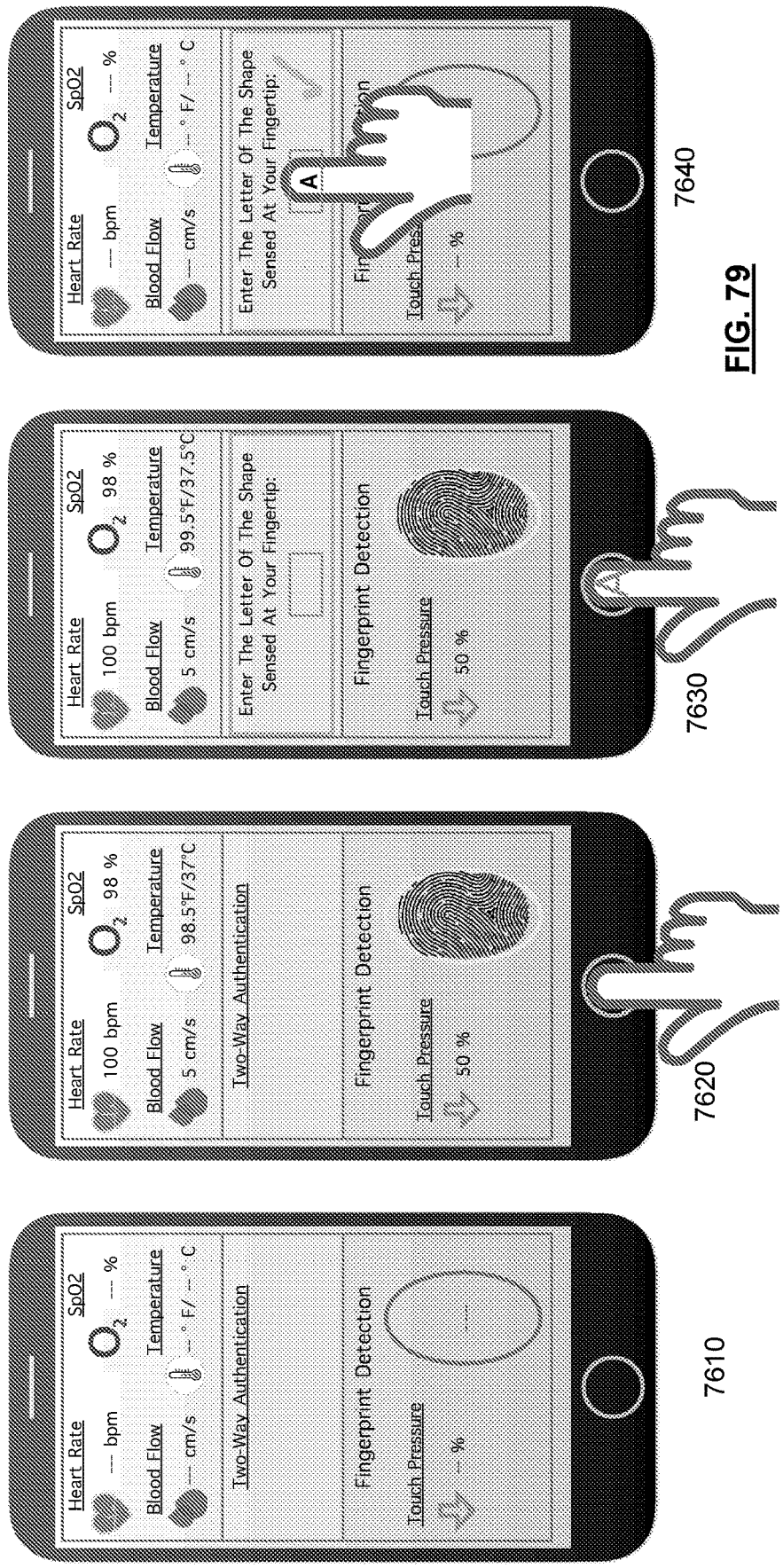

FIG. 79 illustrates another operation of the two way communication scenario of FIGS. 76-79. In response to the prompt of FIG. 78, the user enters the shape sensed at the fingertip, in this example an A. If the user enters a shape that matches the actuated shape that was applied to the finger, the user is authenticated.

Figure 80:
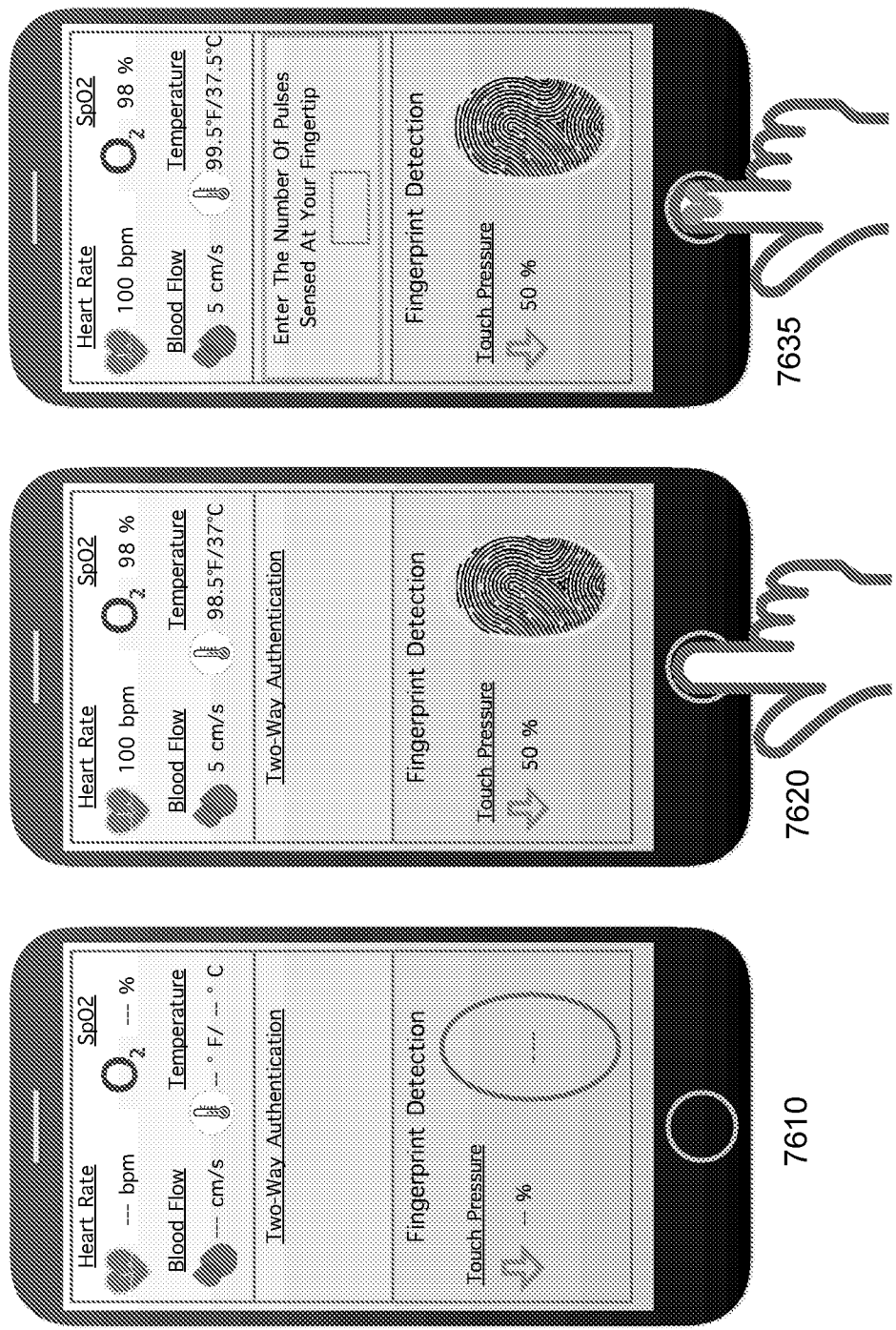

FIG. 80 illustrates an intermediate operation of the two way communication scenario of FIGS. 76, 77, 80 and 81. After scanning the biometric measures, the device generates a sensation at the user's fingertip with an actuator, by heating, radiation, pressure, neuro-stimulation or any other suitable technique. The user is then prompted to input what sensation is felt. The sensation may correspond to a pulse count, the location or corner at which the sensation is generated, the direction of the ultrasound beam (such as top to bottom), or the shape that is drawn on the finger. In FIG. 80, a sensation corresponding to three pulses is applied to the user's fingertip. The display prompts the user to enter the number of sensed pulses. The actuation can be determined such that the two way authentication entry is not predictable in advance.

Figure 81:

FIG. 81 illustrates an operation of the two way communication scenario of FIGS. 76, 77, 80 and 81. In response to the prompt of FIG. 80, the user enters an indication of the number of pulses felt by the user at his fingertip. If the user enters the correct number of pulses (i.e., three, in this example), the user is authenticated.

These two scenarios are representative of two way, three way, or higher levels of multiway authentication. By combining identifying biometric aspects of the user, a fingerprint, and a detected response to actuation, stronger forms of authentication are possible than authentication with system in which biometric measures are not used.

FIG. 82 illustrates two way communication scenarios to determine whether a finger exhibits properties of being attached to a live person. A live finger can provide biometric measurements such as heart rate, blood flow, temperature, peripheral blood oxygen content, etc. A certain number of these biological measurements can be used to authenticate a finger. For instance, it is unlikely that a fake finger can have at least three of the aforementioned biological measurements that mimic a live finger. While it may be possible simulate one or more of these measures with either an artificial finger, digital simulation, or a non-live finger, using a combination of measures for authentication can significantly increase the chances of false identification.

FIG. 82 illustrates the system's ability to determine whether or not a finger is alive. Live finger display 7650 includes biometric measurements of heart rate, pulse oximetry (SpO$_2$), blood flow, and temperature, all of which are within normal ranges. Live finger display 7650 also includes a touch pressure and the user's fingerprint. In comparison, the fake finger display 7660 does not register the biometric features. Attempts to fool a system by using a non-live finger would not be successful because the heart rate and other biometric features are unlikely to be within normal limits, even if the fingerprint appears to be accurate. Artificial fingers that include an expected temperature and valid appearing fingerprint may or may not be able to simulate all of the biometric features. Moreover, they may have particular difficulty responding to prompts regarding, for example a sensed shape or number of pulses, as described in the scenarios of FIGS. 76-81. Responding to prompts that are generated in a manner that exhibits statistical randomness can be particularly difficult for artificial fingers. Such a prompt can be generated randomly by an algorithm.

Figure 83:
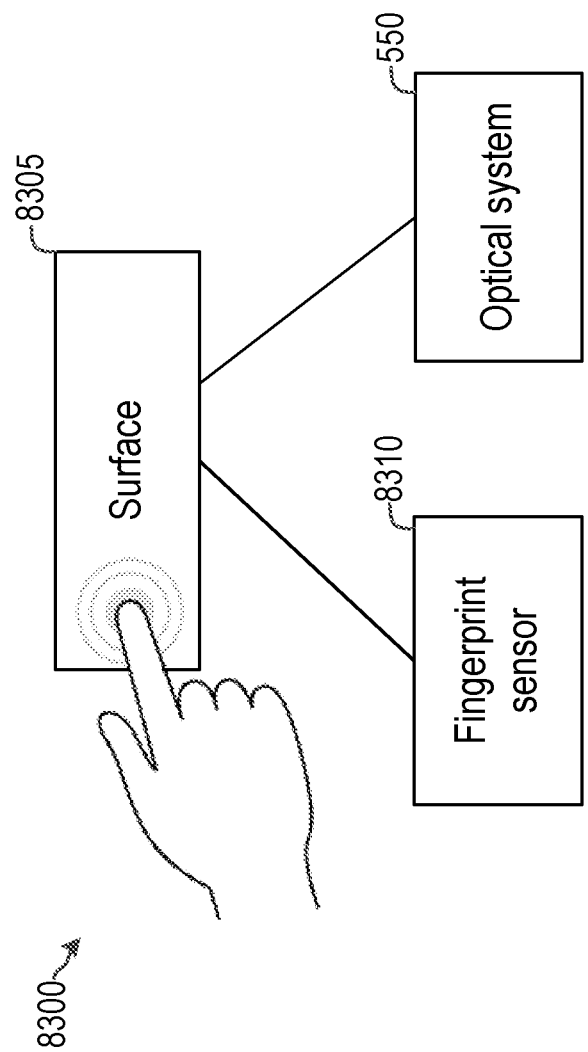
FIG. 83 illustrates an example biometric sensing device, with a surface configured to receive a finger, a fingerprint sensor, and an optical system.

FIG. 83 illustrates an example biometric sensing device 8300, with a surface 8305 configured to receive a finger, a fingerprint sensor 8310, and an optical system 550. The fingerprint sensor 8310 generates data indicative of an image of at least a portion of a fingerprint of the finger in contact with the surface. The optical system 550, integrated with the fingerprint sensor 8310, is configured to transmit light to the surface through the fingerprint sensor. The biometric sensing device 8300 can implement any suitable combination of features of the biometric sensors with integrated optical systems discussed herein. The biometric sensing device 8300 can implement one or more features of interactive biometric scanners discussed herein.

Figure 84:
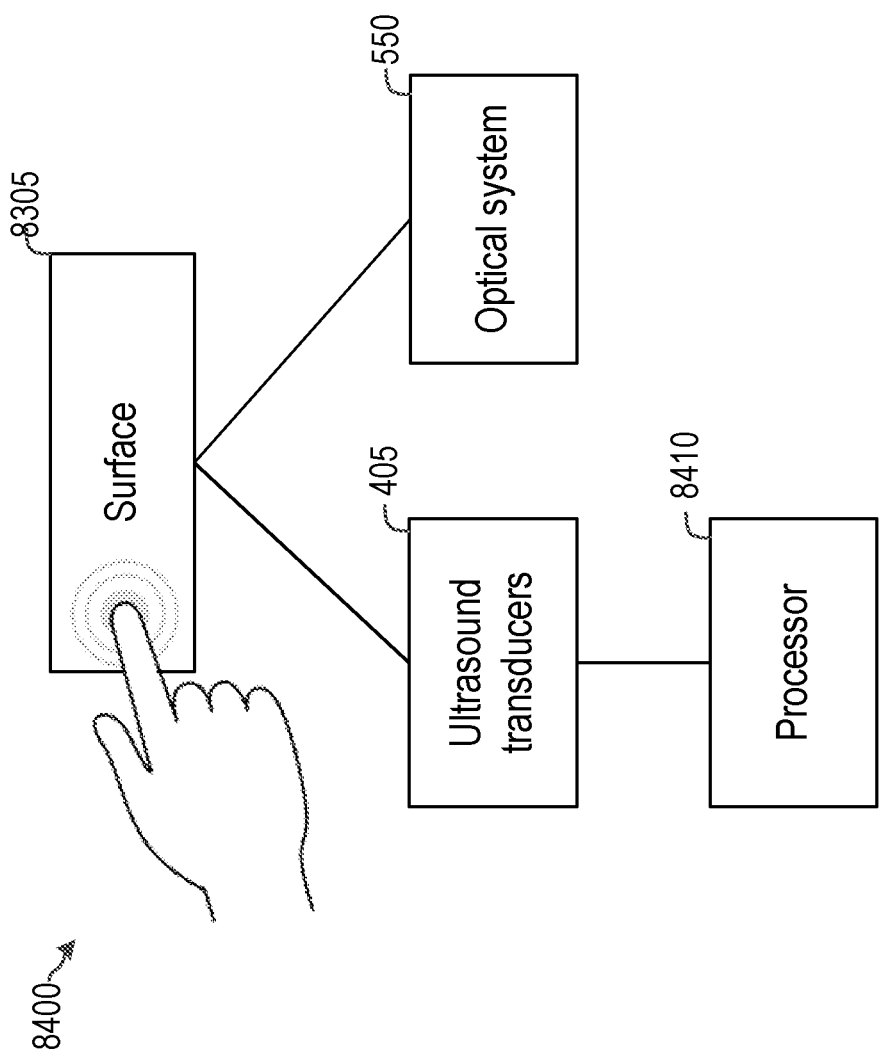
FIG. 84 illustrates an example biometric sensing device, with a surface configured to receive a finger, ultrasound transducers, an optical system and a processor.

FIG. 84 illustrates an example biometric sensing device 8400, with a surface 8305 configured to receive a finger, ultrasound transducers 405, an optical system 550 and one or more processors 8410. The ultrasonic transducers 405 are configured to transmit an ultrasound signal to the surface. The optical system 550 is integrated with the ultrasonic transducers 405. The optical system 550 is configured to transmit light to the surface and receive light reflected from the finger in contact with the surface. One or more processors 8410 are configured to generate an image of at least a portion of a fingerprint based on a reflection of the ultrasound signal from the finger. The one or more processors 8410 are configured to generate a liveness parameter based on the received light. The biometric sensing device 8400 can implement any suitable combination of features of the ultrasound transducers with integrated optical systems discussed herein. The biometric sensing device 8400 can implement one or more features of interactive biometric scanners discussed herein.

Figure 85:
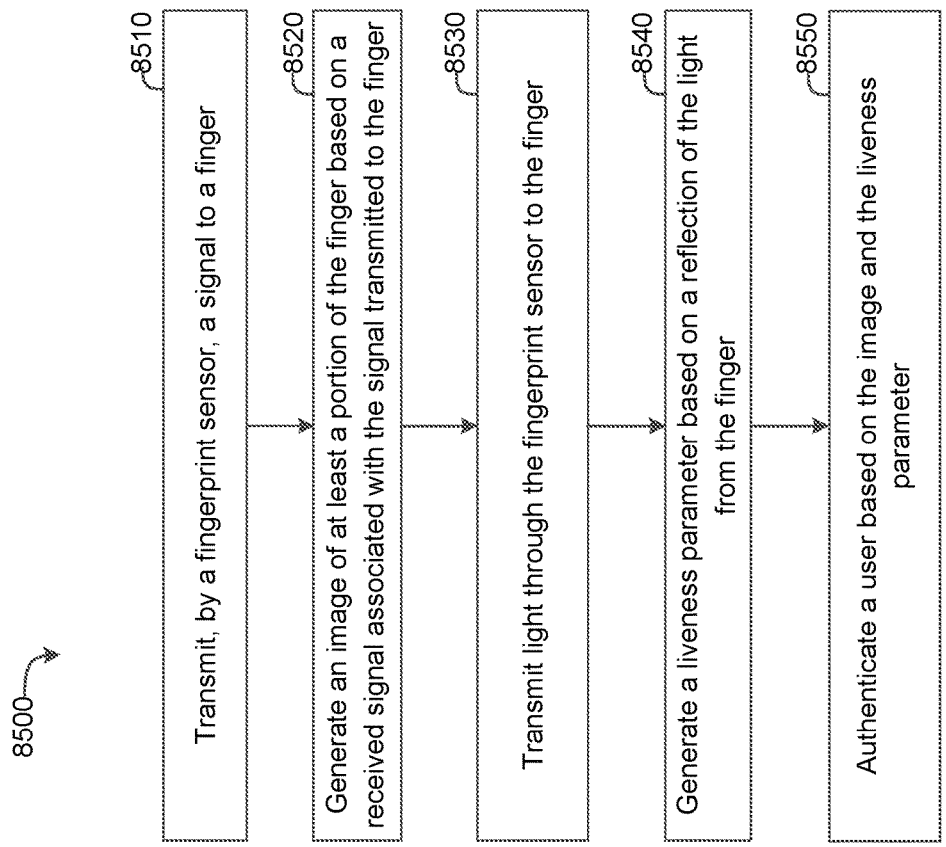
FIG. 85 is a flowchart of a method of authenticating a user.

FIG. 85 is a flowchart of a method 8500 of authenticating a user. In block 8510, method 8500 transmits, by a fingerprint sensor, a signal to the finger. In block 8520, method 8500 generates an image of at least a portion of the finger based on a received signal associated with the signal transmitted to the finger. In block 8530, method 8500 transmits light through the fingerprint sensor to the finger. In block 8540, method 8500 generates a liveness parameter based on a reflection of the light from the finger. In block 8550, method 8500 authenticates a user based on the image and the liveness parameter. The method 8500 can be performed using a system with one or more features of the biometric sensors with integrated optical systems discussed herein. Moreover, any suitable features of the interactive two-way communication discussed herein can be performed with the method 8500.

Figure 86:
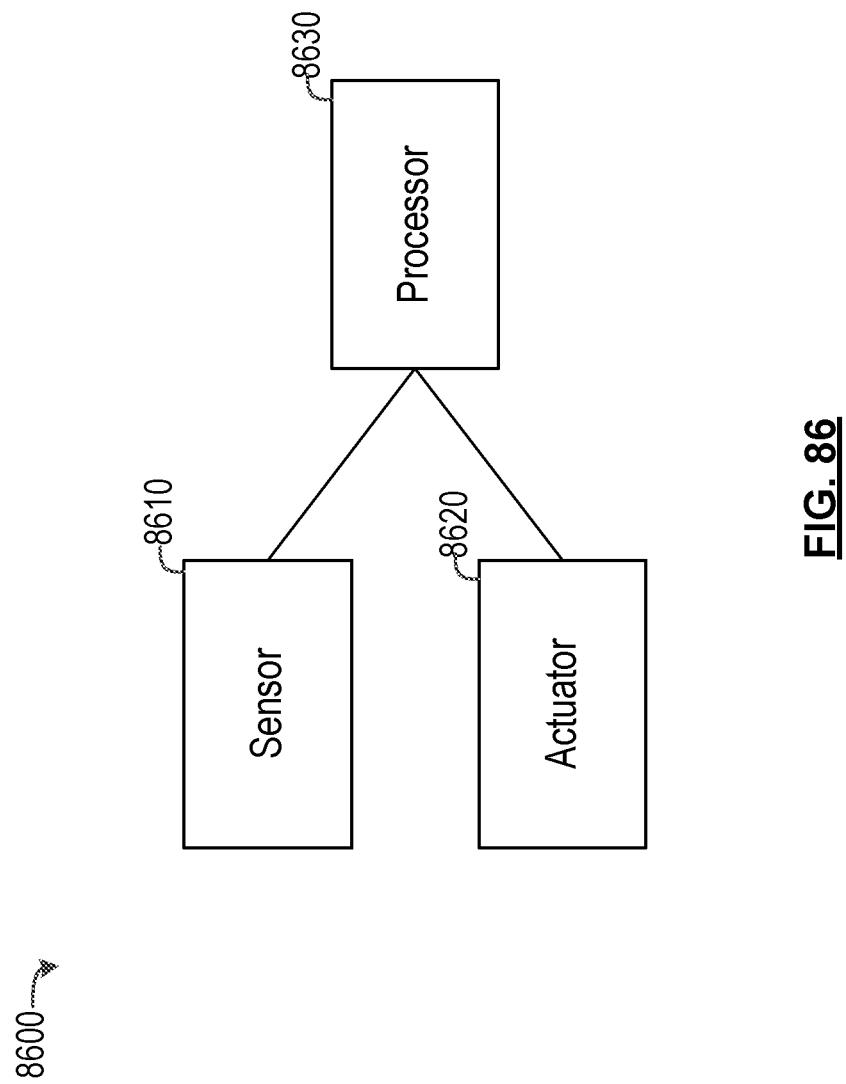
FIG. 86 illustrates an example interactive biometric sensing system, with a sensor, an actuator and a processor.

FIG. 86 illustrates an example interactive biometric sensing system 8600, with a sensor 8610, an actuator 8620 and a processor 8630. Sensor 8610 is configured to generate a biometric image associated with an object. The biometric image can be an image of at least a portion of a finger. Such an image can be of a surface of a finger or an internal structure of the finger. Alternatively, the biometric image can be of at least a portion of a face or an iris. Actuator 8620 is configured to deliver energy to the object. Processor 8630 is configured to authenticate the object based on the biometric image and a response to the energy delivered by the actuator.

Figure 87:
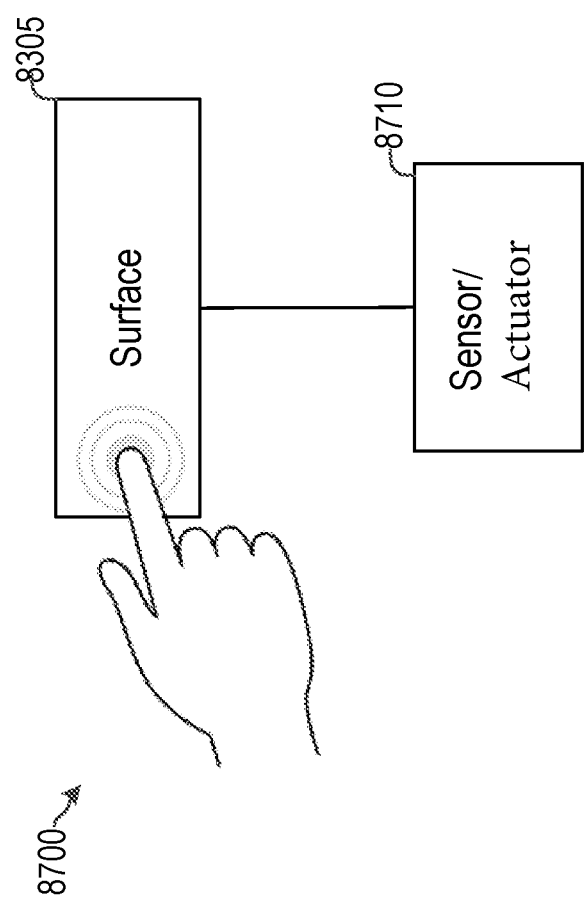
FIG. 87 illustrates an example interactive biometric sensing device, with a surface configured to receive an object, and a sensor that is also configured as an actuator.

FIG. 87 illustrates an example interactive biometric sensing device 8700, with a surface 8305 configured to receive an object, and a sensor 8710. Surface 8305 is configured to receive an object. Sensor 8710 is configured to generate biometric information associated with the object while the object is on the surface, delivery energy to the object, and detect a response to the delivered energy. Accordingly, the sensor 8710 functions as both a sensor and an actuator.

Figure 88:
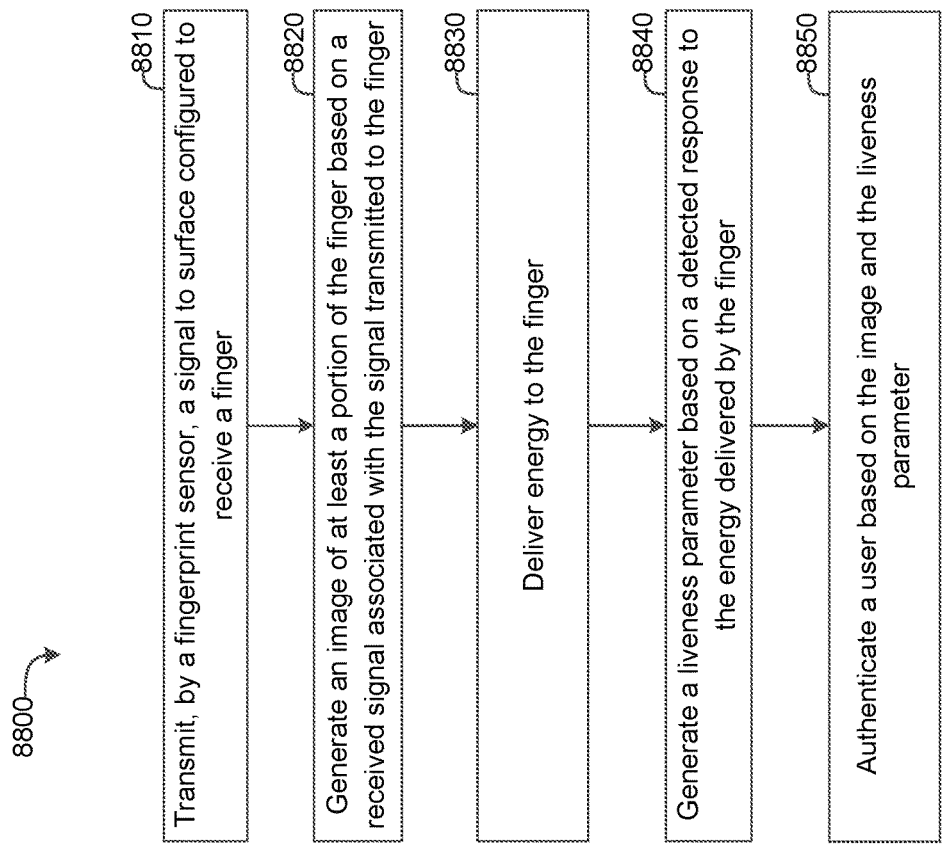
FIG. 88 is a flowchart of a method of authenticating a user.

FIG. 88 is a flowchart of a method 8800 of authenticating a user. In block 8810, method 8800 transmits, by a fingerprint sensor, a signal to a surface configured to receive a finger. In block 8820, method 8800 generates an image of at least a portion of the finger based on a received signal associated with the signal transmitted to the finger. In block 8830, method 8800 delivers energy to the finger. In block 8840, method 8800 generates a liveness parameter based on a detected response to the energy delivered to the finger. In block 8850, method 8800 authenticates a user based on the image and the liveness parameter. Any suitable features of the interactive two-way communication discussed herein can be performed with the method 8800.

Figure 89:
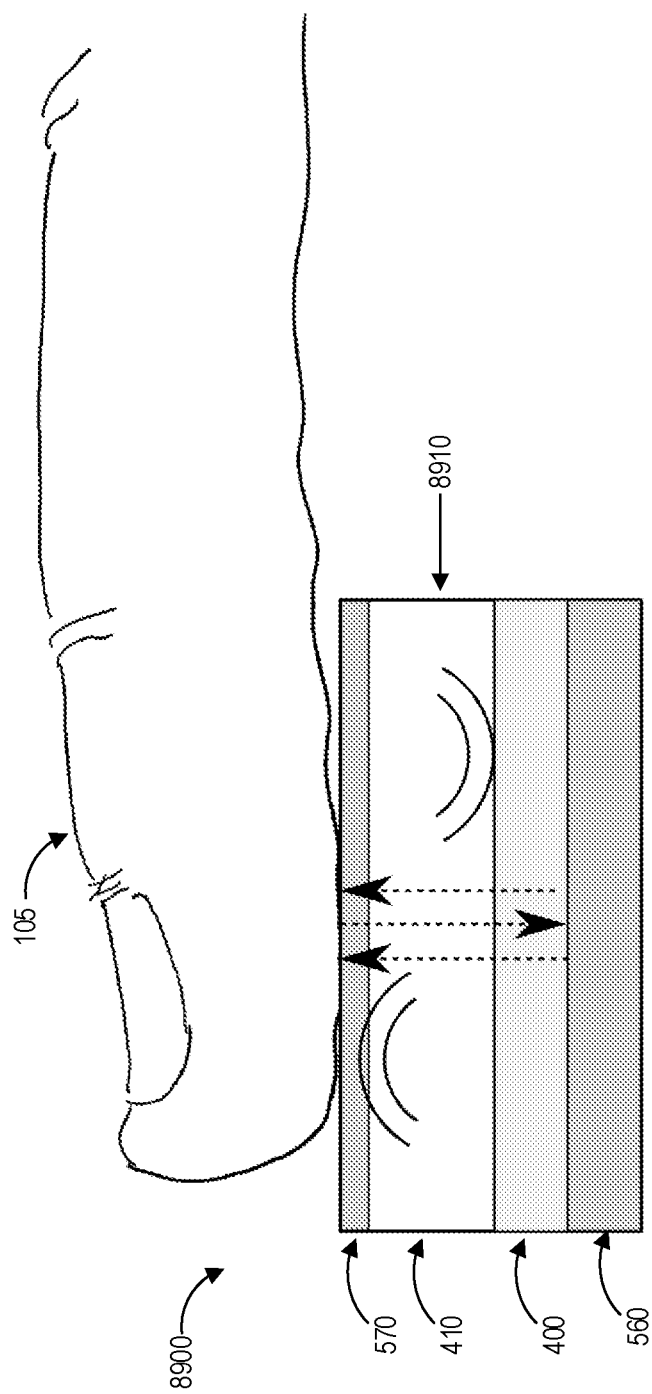
FIG. 89 illustrates a cross sectional view of an example embodiment with a transparent ultrasound transducer array disposed between a light source and an optically transparent light detector.
Figure 90:
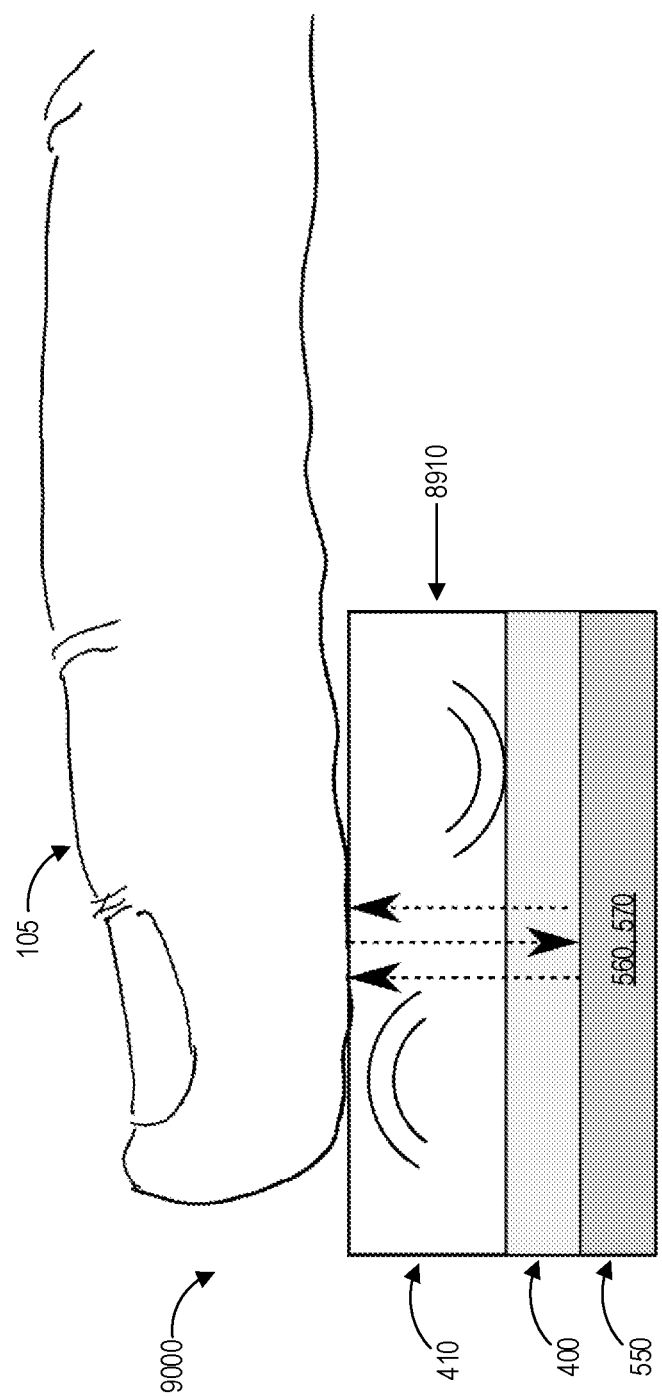
FIG. 90 illustrates a cross sectional view of an example embodiment with an optical system including a light source and a light detector disposed below an optically transparent ultrasound transducer array.

FIGS. 89 and 90 illustrate example embodiments with a fingerprint sensor that is at least partially transparent and that passes light for an optical system. The fingerprint sensor can include an ultrasound transducer array that is at least partially transparent. The ultrasound transducer array may be configured as an optically transparent fingerprint sensor. The ultrasound transducer array may be formed entirely, substantially entirely, or only partially from transparent materials.

Arrangements in which an optical system and an ultrasonic fingerprint scanner are disposed together (e.g., as in the arrangements of FIGS. 81-91) may beneficially prevent spoofing of the authentication process. In particular, such an arrangement may be relatively immune from a high quality dummy fingerprint, as such as dummy fingerprint would not register as a live finger according to readings from the optical system, which may be associated with greater depths of the finger or object being imaged. In such embodiments, the system may be able to identify spoof attempts, even if a fraudster were to place a live finger on some other spot on the device.

FIG. 89 illustrates an example embodiment of a biometric sensing device 8900 in which light source 560 for an optical system (such as optical system 550) is disposed below an ultrasound transducer array 400, while an optical sensor 570 for the optical system is disposed above the ultrasound transducer array 400. The light source 560 may be an infrared and/or a visible light source, such as an LED or an OLED. The light source 560 can be arranged to transmit light at two or more different wavelengths. The ultrasound transducer array 400 may be configured as a fingerprint sensor and may be at least partially transparent to the light from the light source 560. The optical sensor 570 may be a photodetector sensitive to infrared and/or visible light and may also be at least partially acoustically transparent (e.g., so as to enable operation of the fingerprint sensor 400) and at least partially optically transparent (e.g., to as to enable light from light source 560 to pass through sensor 570 on its way from the light source 560 to the finger 105). The photodetector 570 can include a surface to receive the finger 105 in the device 8900.

As illustrated, the device 8900 of FIG. 89 can include a transparent substrate 8910 between the light detector 570 and the ultrasound transducer array 400. The substrate 8910 may be formed from glass 410 or any other suitable transparent material (e.g., any material having suitable optical and acoustic properties to enable operation of the ultrasound transducer array 400 and the optical system including the light source 560).

FIG. 90 illustrates an example embodiment of a biometric sensing device 9000 in which an optical system 550, which can include a light source 560 and an optical sensor 570, is disposed below the ultrasound transducer array 400. In the example of FIG. 90, the optical system 550 need not be acoustically transparent.

Figure 91:
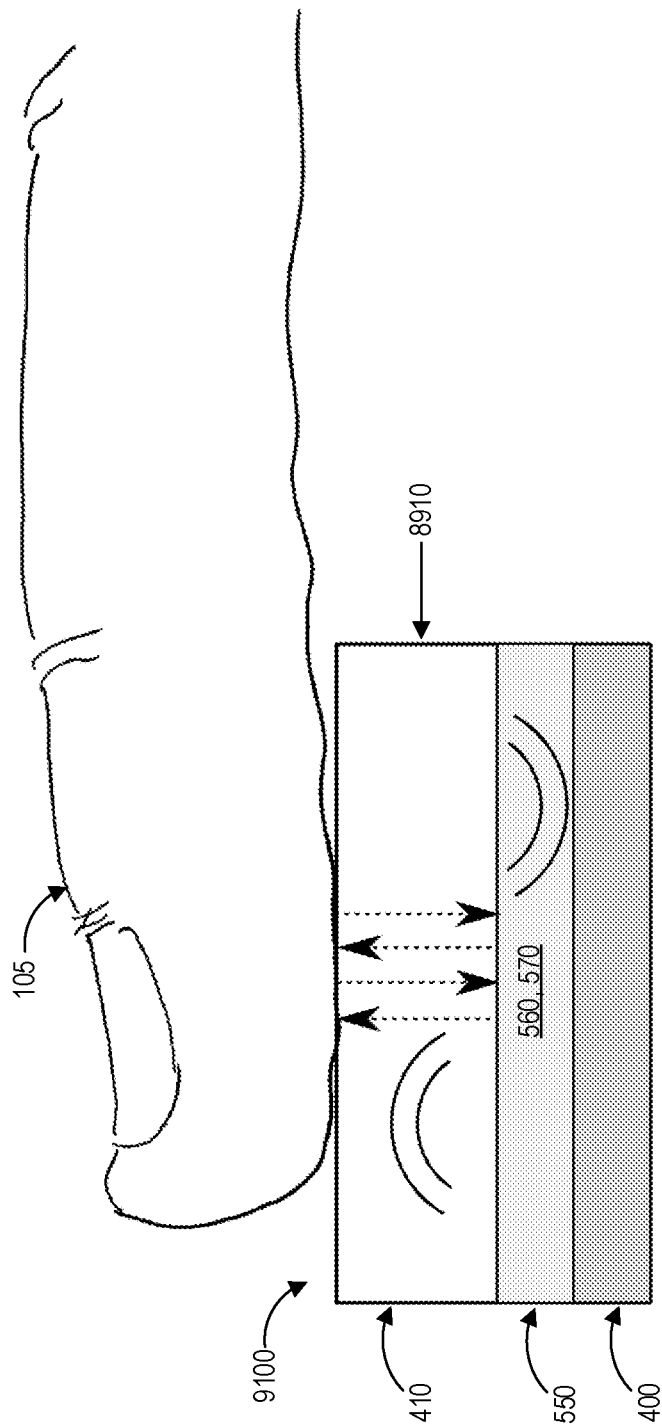
FIG. 91 illustrates a cross sectional view of an example embodiment with an acoustically-transparent optical system including a light source and a light detector disposed above an ultrasound transducer array.

FIG. 91 illustrates an example embodiment of a biometric sensing device 9100 in which optical system 550 is integrated with and disposed above the ultrasound transducer array 400. In the example of FIG. 90, the optical system 550 may be at least partially acoustically transparent, to enable the ultrasound transducer array 400 to image or scan the finger 105 through the optical system 550. In the example of FIG. 91, the ultrasound transducer array 400 need not be optically transparent.

Figure 92:
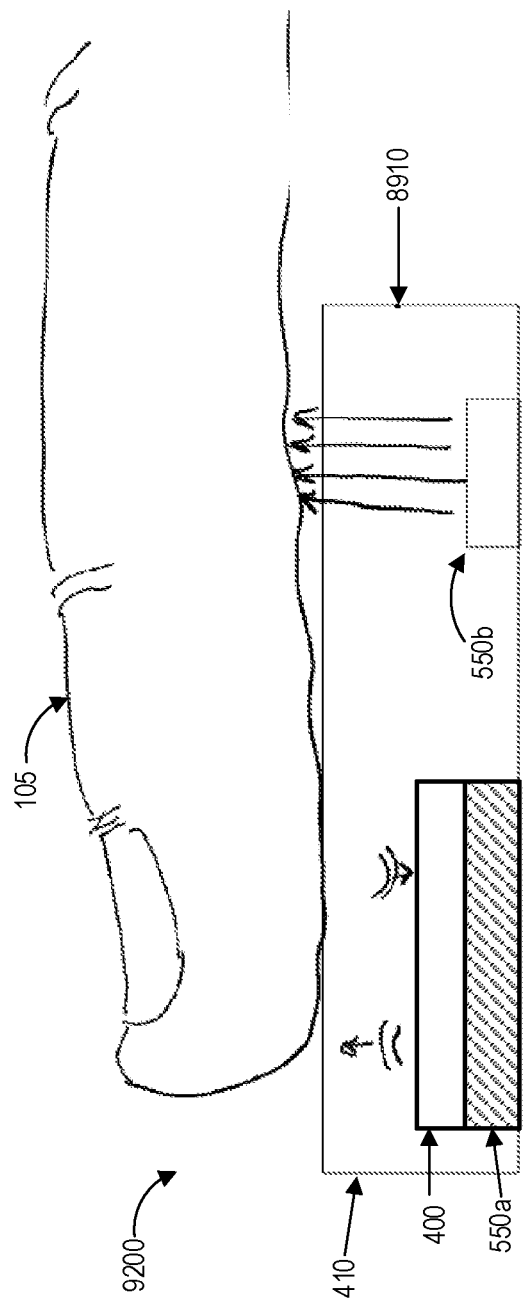
FIG. 92 illustrates a cross section view of an example embodiment with an optical system including a light source and a light detector disposed to a side of an ultrasound transducer array.

FIG. 92 illustrates an example embodiment of a biometric sensing device 9200 including ultrasound transducer array 400 and optical systems 550a and 550b. One optical system 550b is disposed laterally from the transducer array 400 within a device substrate 410. The transducer array 400 is disposed between the other optical system 550a and a surface of the biometric sensing device 9200 configured to receive a finger. The optical system 550b in FIG. 92, which is disposed away from the fingerprint sensor, can scan finger 105 and detect veins within the finger 105 and/or one or more other biometric parameters. The pattern of veins may be used for authenticating and/or identifying the user. The optical system 550b may include components such as an infrared (IR) light source, an LED, and one or more photoreceptors.

Figure 93:
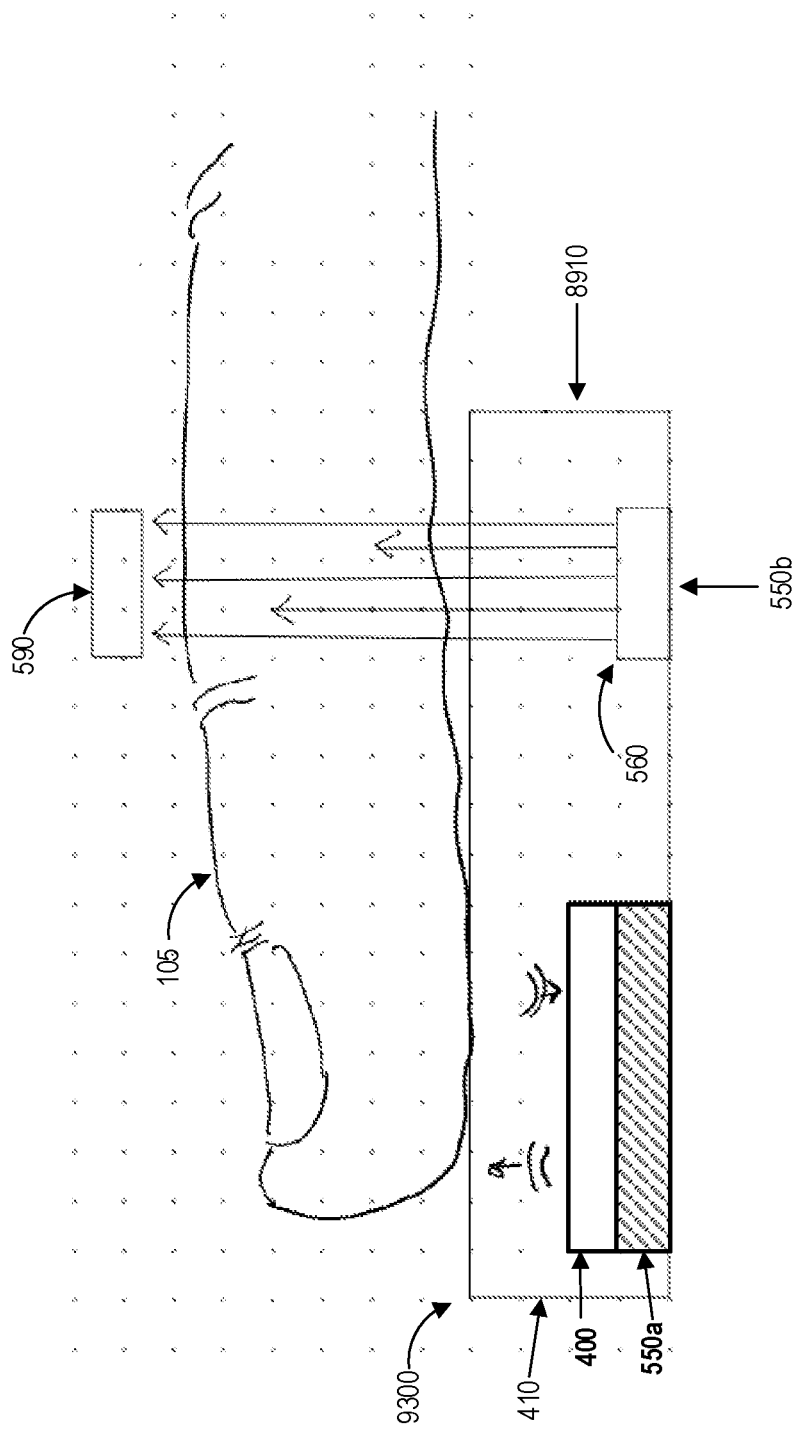
FIG. 93 illustrates a cross section view of an example embodiment with an optical system including a light source disposed to a side of an ultrasound transducer array and utilizing a light detector disposed in a separate device.
Figure 94:
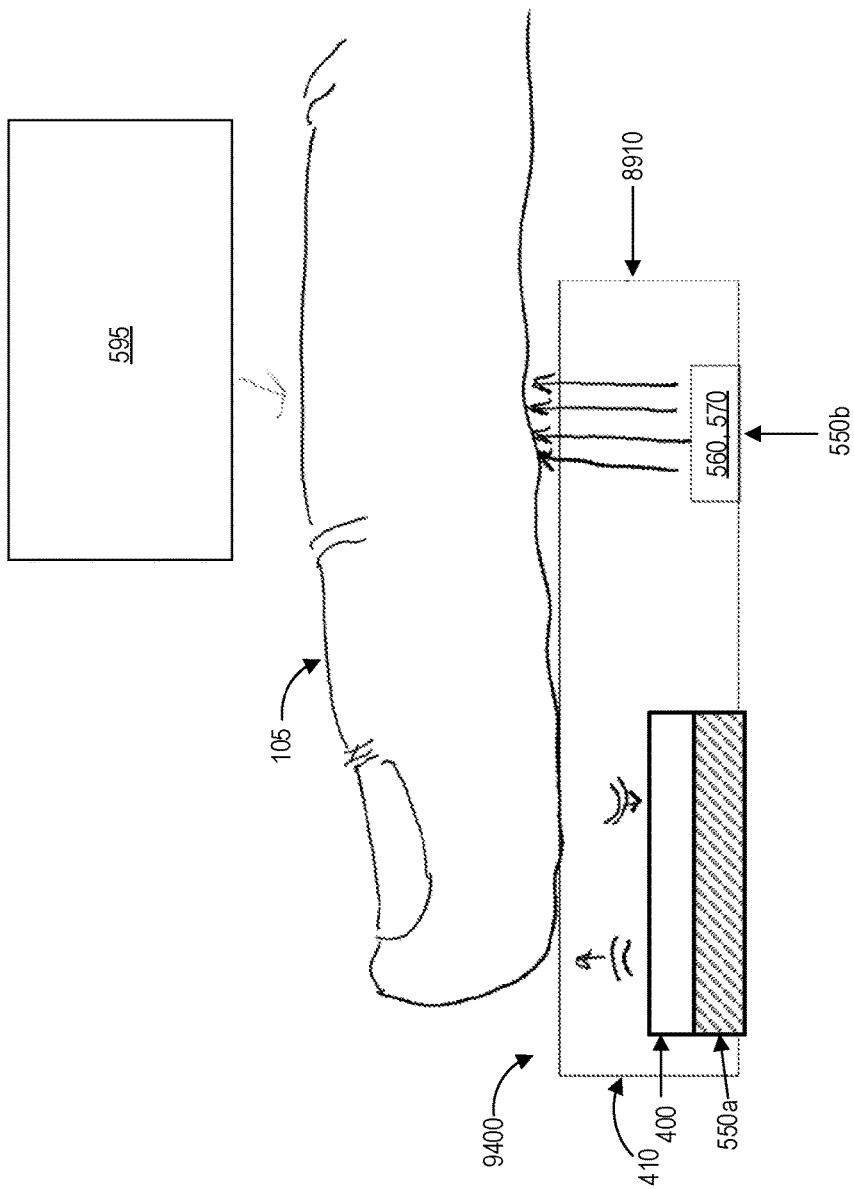
FIG. 94 illustrates a cross section view of an example embodiment with an optical system including a light source disposed to a side of an ultrasound transducer array and utilizing a light detector disposed in a separate device.

FIGS. 93 and 94 illustrate example embodiments including ultrasound transducer array 400 and optical systems 550a and 550b and that includes at least some components located on an external device. Embodiments such as those illustrated in FIGS. 93 and 94 may provide for an additional or alternative means of authentication or liveness verification, without a user's fingerprint being shared and without the user having to expose their fingerprint to another potentially untrusted device. As examples, the external device may identify the user and/or confirm liveness using machine learning-derives identification parameters or using vein or artery patterns in the user's finger or other body part. Additionally, the components on device 9200 and external device 590 (as in FIG. 93) or 595 (as in FIG. 94) may work together to image a pattern of veins within the finger 105, as part of authenticating the finger 105 and associated user.

In the example of FIG. 93, the optical system 550b includes a light source 560 and the external device includes an optical sensor 590. The optical sensor 590 may image or scan the finger 105 using visible and/or infrared light emitted by the light source 560.

In the example of FIG. 94, the optical system 550b may include a light source 560 and may also include an optical sensor 570. The external device may include an external optical system 595 including a light source and/or an optical sensor. With the arrangement of FIG. 94, the finger 105 can be scanned individually by optical sensor 570 and light source 560, scanned individually by external optical system 595, or scanned using a combination of these systems. As a first example, the external optical system 595 may emit light that is received by optical sensor 570 to image the finger 105. As a second example, the light source 560 may emit light that is received by the external optical system 595 to image the finger 105.

The examples of FIGS. 93 and 94 may include an absorptive pulse oximeter or reflective oximeter. In particular, the external device may receive, with sensor 590, visible and/or IR light, emitted by light source 560, and may measure one or more biometric parameters, such as pulse rate and/or blood oxygen content (e.g., $SbO_2$), of the finger 105. In some other embodiments, the external device may emit visible and/or IR light and an optical sensor 570 in the disclosed device may receive the light. In still other embodiments, the external device and/or the disclosed device may operate independently as reflective oximeters.

Smart Cards

Figure 95:
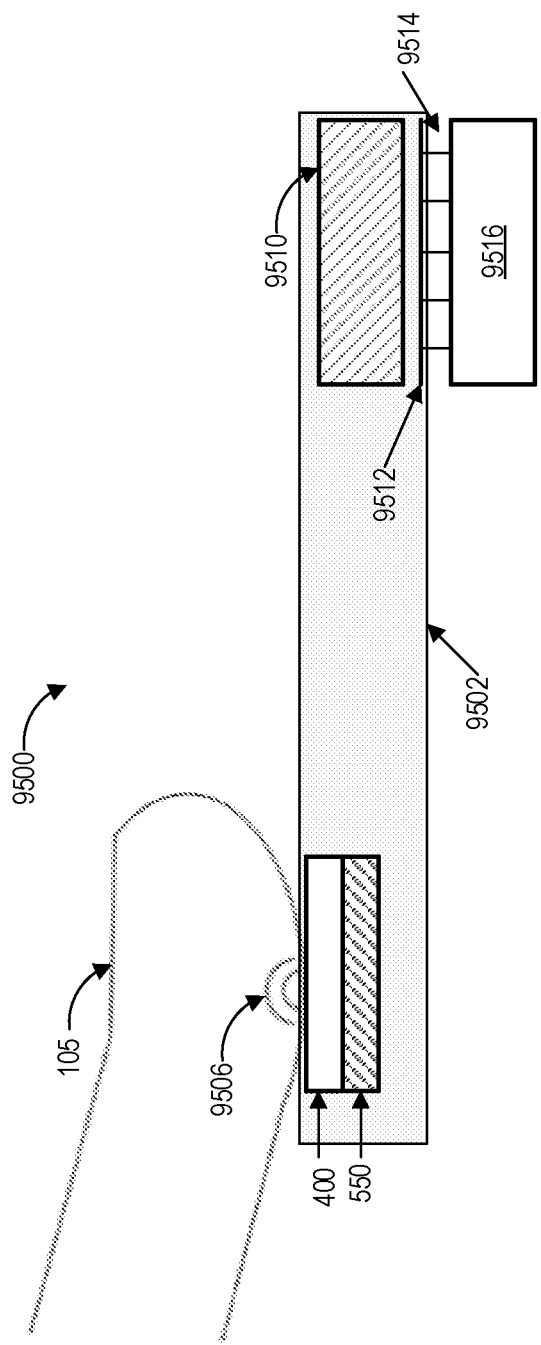
FIG. 95 illustrates a smart card device with a transparent ultrasound transducer array configured as a fingerprint scanner and with an optical system disposed below the transparent transducer array.

As shown in FIG. 95, a smart card 9500 may be provided that includes an optically-transparent ultrasonic fingerprint scanner (such as the ultrasound transducer array 400 described herein) and with an integrated optical system (such as the optical system 550 disclosed herein) that is disposed below the fingerprint scanner. The smart card 9500 can implement any suitable features of interactive biometric authentication disclosed herein by itself and/or in combination with an external device (e.g., a card reader).

The smart card 9500 may be any suitable card, such as a card used for payment purposes and/or for other purposes. As examples, the smart card 9500 may be a credit card, a debit card, a membership card, a rewards card, an identification card, a security card, a clearance card, a security card, an access card, a medical card, an insurance card, etc. Smart card 9500 includes a card body 9502. The card body 9502 can have a size suitable to fit in a wallet. The smart card 9500 can have a thickness in a range from 400 µm to 1000 µm. For example, the smart card 9500 can have a thickness of about 760 µm. The smart card 9500 can be approximately 85.60 mm by 53.98 mm. The smart card 9500 can have rounded corners in certain instances. Additional details and examples of smart cards including ultrasound fingerprint sensors are also described in PCT Patent Application No. PCT/US2018/029309, which is incorporated by reference herein in its entirety.

The ultrasonic fingerprint scanner in the smart card 9500 may be used to authenticate users presenting the smart card 9500 for authentication. The fingerprint scanner 400 may serve to make it less likely that a card could be used by an unauthorized person. As an example, a user may desire to purchase goods using a smart card 9500 and a payment system may be configured to authorize the purchase only upon contemporaneous detection of the user's fingerprint using the fingerprint scanner 400.

In some embodiments, the optical system 550 may also be used in authenticating users presenting the smart card 9500 for authentication. As described in further detail herein, optical systems such as optical system 550 may be used to confirm identity and/or liveness independently or in collaboration with a fingerprint sensor such as ultrasound transducer array 400. The optical system 550 may sense a pulse within finger 105 (thus confirming liveness), may sense an oxygen level of blood in the finger 105 (e.g., using principals similar to those of a reflective oximeter, and potentially confirming liveness), may image a pattern of veins in the finger 105 (thus confirming identity and/or preventing at least some forms of potential deception), etc. These are merely illustrative examples and other examples described herein of how optical systems may work together with ultrasound systems in authenticating a user and preventing fraud may also be applied to applications in smart cards such as the example of FIG. 95.

In certain embodiments, smart card 9500 can include circuitry 9510. The circuitry 9510 can perform one or more of the following functions: assists in the detection of the user's fingerprint, assists with the detection of authentication and/or liveness parameters using the optical system 550, stores the user's fingerprint and/or authentication or liveness information used with the optical system 550 (in a secure manner), or assists in the operation of the smart card 9500 and/or the fingerprint scanners, the optical system 550, the like, or any suitable combination thereof. The circuitry 9510 may include a power source such as a photovoltaic cell, a battery, a capacitor, an RF harvesting circuit, etc. In certain instances, the circuitry 9510 can include one or more of a smartcard chip, a processor, a memory, a power regulator circuit, or the like.

In various embodiments, the smart card 9500 may include one or more contacts 9512 that connect with an external device 9516 over one or more electrical paths 9514. As an example, contacts 9512 may engage with a card reader 9516 when smart card 9500 is inserted into or otherwise in communication with the card reader 9516. In such embodiments, signals may be routed between the card reader 9516 and the fingerprint scanner 400 and/or the circuitry 9510. These signals can include power signals for powering the fingerprint scanner 400 and/or the circuitry 9510 and can include fingerprint scans (e.g., where the user's fingerprint is stored remotely), verification results (e.g., where the user's fingerprint is stored locally on the smart card 9500), the like, or any suitable combination thereof. In some embodiments, some or all of the transmission and readout circuitry for fingerprint scanner 400 may be omitted from the card 9500 and provided within external circuitry of the card reader 9516. This can reduce the cost and complexity of the smart card 9500.

In some other embodiments, the smart card 9500 may include wireless communication circuitry (including an antenna) in the circuitry 9510 and may convey data associated with scans of the user's fingerprint and/or fingerprint verification results wirelessly to external circuitry such as card reader 9516. As examples, the circuits 9510 may transmit signals using near-field frequencies or other radio frequency signals.

As illustrated in FIG. 95, the ultrasound scanner 400 and the optical system 550 can be embedded within a card body 9502 of the smart card 9500. In some embodiments, the ultrasound scanner 400 and the optical system 550 can be embedded flush with a surface that receives the user's finger 105 as shown in FIG. 95. In some other embodiments, the ultrasound scanner 400 and the optical system 550 can be flush with a surface opposite to a surface that receives the user's finger 105 and ultrasonic waves 9506 may be transmitted by scanner 400 through the card body 9502. In other various embodiments, the ultrasound scanner 400 and the optical system 550 can be embedded within the volume of smart card 9500 (e.g., not flush with any surface of the smart card 9500) and can be completely or nearly completely surrounded by the material forming the card body 9502. If desired, the optical system 550 may also be disposed apart from the ultrasound scanner 400, such as in the examples of FIGS. 92-95. In still other embodiments, the ultrasonic fingerprint scanner 400 and/or some or all of the optical system 550 can be provided on a surface of the smart card 9500 (e.g., on an opposite side or the same side as the side that receives the user's finger 105).

The ultrasound transducer array 400 may be formed from a piezoelectric material such as a piezoelectric polymer polyvinylidene fluoride (PVDF), a zinc oxide (ZnO) thin film, or other desired materials. The ultrasound transducer array 400 of the smart card 9500 can be at least partly optically transparent such that light from the optical system can propagate though the transducer array to the finger 105 and light reflected from the finger 105 can propagate through the ultrasound transducer array 400 to the optical system. A ZnO thin film and/or associated metal electrodes can be optically transparent. A PVDF piezoelectric layer can be optically transparent. For instance, a sufficiently thin (e.g., less than 9 microns thick) PVDF layer can be optically transparent. In some embodiments, the card body 9502 may be flexible. In some other embodiments the card body 9502 may be rigid. The ultrasound transducer array 400 can be flexible. For instance, a PVDF based ultrasound transducer array 400 can be flexible.

Accordingly, a flexible ultrasonic fingerprint scanner that is at least partly optically transparent is provided with integrated optics. In this case, the ultrasonic fingerprint scanner can be made sufficiently transparent for light from a light source to propagate therethrough and for reflected light to propagate though to a photoreceptor. This fingerprint scanner with integrated optics can be included in a smart card.

Figure 96:
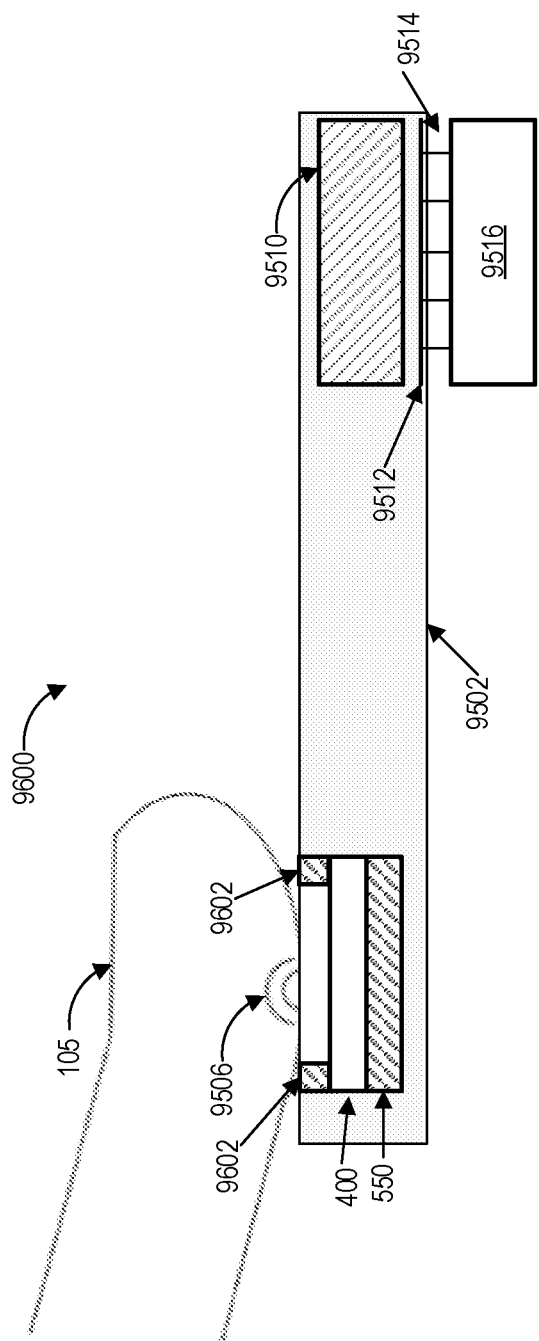
FIG. 96 illustrates a smart card device with an ultrasound transducer array configured as a fingerprint scanner and one or more light sources disposed above the ultrasound transducer array.

As shown in FIG. 96, a smart card 9600 can have one or more light sources such as LEDs 9602 disposed above the ultrasonic fingerprint scanner 400. Such an arrangement can facilitate emitting relatively large amounts of light into the finger 105, as light from the LEDs 9602 need not pass through the ultrasound transducer array 400. The illustrated ultrasound transducer array 400 can be transparent or only be partially optically transparent and thus may absorb at least some light passing through it. Such large amounts of light may be beneficial when detecting vein patterns in the finger 105 and/or or when measuring pulse or blood oxygen levels in the finger 105.

In another embodiment, a card similar to the illustrated smart card 9600 can be implemented without the illustrated optical system 550 disposed below the ultrasonic fingerprint scanner 400. In such an embodiment, the ultrasonic fingerprint scanner 400 can be non-optically transparent or optically transparent.

Mobile Devices

Figure 97:
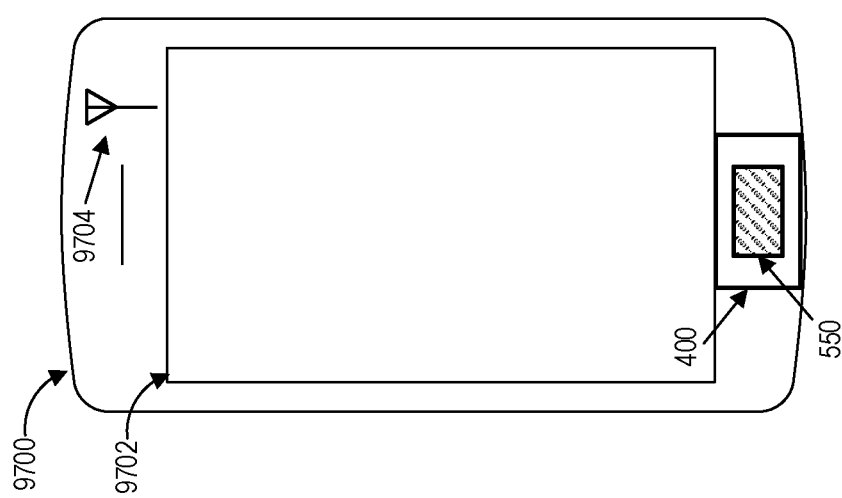
FIG. 97 illustrates a mobile device with a transparent ultrasound transducer array configured as a fingerprint scanner and with an optical system disposed below the transparent transducer array.

As shown in FIG. 97, a mobile device 9700 may be provided that includes an optically-transparent ultrasonic fingerprint scanner (such as the ultrasound transducer array 400 described herein) and with an optical system (such as the optical system 550 disclosed herein) that is disposed below the fingerprint scanner. The mobile device 9700 may be a mobile phone such as a smart phone, a tablet device, a portable device, a handheld device, etc. The mobile device 9700 may also include a display 9702, which may be a touchscreen display, and one or more antennas such as antenna 9704. The antenna 9704 can transmit and/or receive radio frequency signals. The mobile device 9704 can implement any suitable features of interactive biometric authentication disclosed herein.

FIG. 97 illustrates that ultrasound transducer array 400 and optical system 550 may be disposed on a front side of the mobile device 9700. The array 400 and optical system 550 may alternatively or additionally be disposed on a rear side or lateral side face of the mobile device 9700. While FIG. 97 illustrates the array 400 and optical system 550 as being below the display 9702, this is merely illustrative. In general, array 400 and optical system 550 may be disposed to any side of the display 9702 or can be disposed within the display 9702 (e.g., behind the display 9702). Optical system 550 is shown as being smaller than the array 400 in FIG. 97 merely for illustrative purposes. In general, optical system 550 may be smaller, larger, or the same size as the ultrasound transducer array 400.

Multiple Device Authentication

Figure 98:
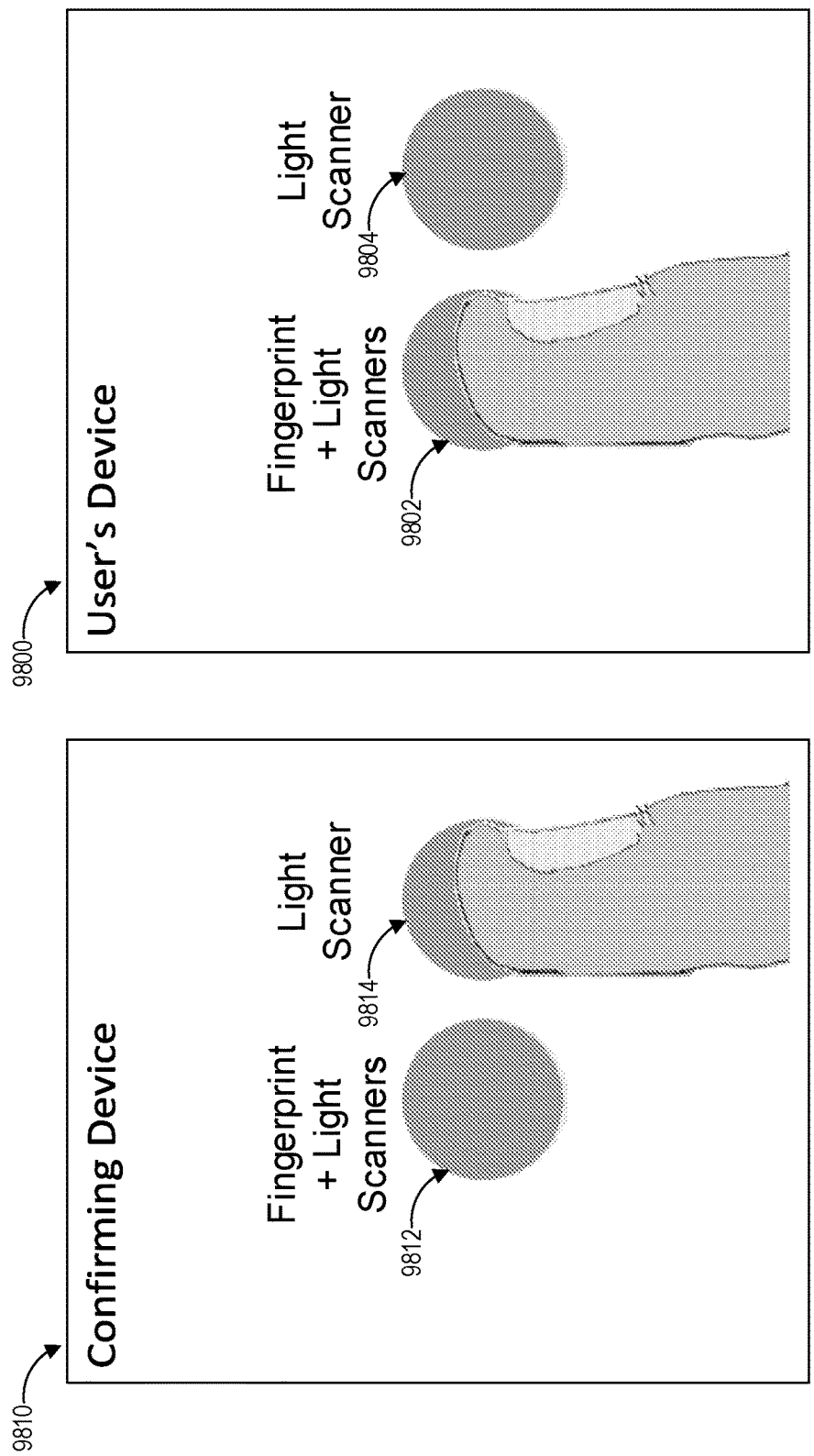
FIG. 98 illustrates a user device and a confirming device that may be used in a multiple device authentication process.

FIG. 98 illustrates multiple device authentication using a user's device 9800 and a confirming device 9810. The user's device 9800 and the confirming device 9810 can be mobile phones, for example. The user's device 9800 includes an integrated fingerprint and light scanner 9802 and a light scanner 9804. The integrated fingerprint and light scanner 9802 can include an ultrasound fingerprint sensor and a light scanner in accordance with any suitable principles and advantages disclosed herein. For example, the ultrasound fingerprint sensor can be at least partially transparent and the light scanner can transmit and receive light through the ultrasound fingerprint sensor. The light scanner 9804 can detect one or more biometric parameters, such as a PPG waveform, a heart rate, a respiration rate, a vein pattern, the like, or any combination thereof. The light scanner 9804 can include a reflexive oximeter. The confirming device 9810 includes an integrated fingerprint and light scanner 9812 and a light scanner 9814.

In some instances, readings of reflective pulse oximeters may be adversely affected by differences in ambient light and/or pressure of tissue on the sensor. Accordingly, it may be beneficial to configure the light scanner 9804 of the user's device 9800 and configure the light scanner 9814 of the confirming device 9810 to reduce and/or minimize differences in ambient light during scanning and/or to reduce and/or minimize any difference in pressures between scanned tissue and the sensors. As an example, the light scanners 9804 and 9814 may be located in similar positions and/or with similar orientations on their respective devices, such that a user holding the devices generally presses a scanned finger onto each of the light scanners 9804 and 9814 with the same finger, at a similar level of pressure, with a similar orientation, the like, or any combination thereof. This can reduce and/or minimize differences in scans obtained by the two light scanners.

A user can be authenticated using his or her fingerprint using the fingerprint sensor of the integrated fingerprint and light scanner 9802. A confirmation of the match can be sent to indicate that the user's fingerprint has been authenticated. This confirmation can be sent to a bank or other interested party. The user, in the same location as the fingerprint sensor, has PPG waveforms read and analyzed. Data, such as a pattern associated with the PPG waveform and/or one or more other biometric parameters can be sent to the interested party. The user, with a second finger on a confirming device, such as another phone or computer, can have a biometric parameter sensed using a light scanner 9814. The light scanner 9814 can have substantially the same or similar equipment and software to determine a biometric parameter (e.g., take a PPG waveform reading). Associated data is sent to the interested party (e.g., a bank) to confirm a match with data from the user's phone.

The interested party through our device's software and machine learning techniques can detect features that relate to age and state of health that correspond to the user over past interactions. For example, parts of a PPG waveform reading can be different, as there is variability hour to hour. This variability can help prevent a replay attack. Since the user has two fingers on both devices, any hour to hour differences in the PPG waves are shown to be the same at the time on both devices.

Accordingly, a biometric parameter or pattern (e.g., a PPG scan) can be used for identification and/or authentication purposes. Substantially the same or similar equipment and software on two different devices can be used in the authentication. The ultrasound fingerprint scan can be done only on one of the devices at the same time and location as the light scan on the other device. The other device does not detect the fingerprint, so the user's fingerprint will not be exposed to the other device or copied.

Machine learning can be used to develop an algorithm to add identifying characteristics available for a second step authentication. Those characteristics can show up on both phones and they could be stored external to the authentication devices, such as at a bank or cloud website for confirmations. The characteristics could relate to, for example, a heart condition or age or more specific readings of heart rate than just the summary pulse number. A scammer using his or her own finger for a PPG scan along with a replay attack of a recorded ultrasound fingerprint authentication of the user they are hacking, assuming they could break into a phone to get the ultrasound fingerprint algorithm, would have to have similar characteristics (e.g., be about the same age and heart condition and breathing condition) as the authentic user to be authenticated with this technology.

Another algorithm could capture some of the relevant PPG waves that are variable hour to hour, so that there would also be an authentication element that picks up the various of the PPG reading, so that each time the variability would make the reading slightly different, though the variability would be recorded as the same for the user's finger on the user device 9800 and the user's finger on the confirming device 9810.

Using a second device for authentication allows for second step authentication by a second device without exposing the user's fingerprint to the second device. This can be useful for a credit card company or merchant authenticating a translation. A driver of a ridesharing service or a hotel manager may already have a known location, and their device can be used for authenticating a user without reading the user's fingerprint. With this technology, the authenticating party, such as a bank, could then know that the user has traveled from Palo Alto to San Diego and their location has been verified by a global positioning system (GPS) on both the smart phones of either a Uber driver or the person at a San Diego hotel front desk. The same live signs from the reflective oximeter appear on the user's phone where his or her fingerprint is authenticated at the same time as the life sign is being read. This can provide robust authentication.

Dynamic Biometrics and Machine Learning

Although some embodiments are discussed with reference to a liveness parameter, any suitable biometric sensing device disclosed herein can be used to detect dynamic biometrics. Dynamic biometrics can represent a pattern of one or more biometric parameters over time. Detecting dynamic biometrics can involve one or more of imaging, measuring, or analyzing real-time physiological responses of living tissue to external and/or internal stimuli. By using dynamic biometrics, a biometric authentication system can be more resistant to presentation attacks. Moreover, dynamic biometrics can be more distinctive than static readings, such as an average pulse or blood oxygen level. In fact, dynamic biometric can be sufficiently distinct to verify a person in combination with a fingerprint. One or more processors (e.g., one or more of the processors 1065, 8410, or 8630) can track a one or more biometric parameters generated using any suitable biometric sensing device disclosed herein over time. As an example, biorhythms related to a reflective oximeter can be used in authentication.

The dynamic biometrics can be detecting during a fingerprint authentication processor. One or more processors can apply machine learning to identify traits of a person responding to prompts from an actuator of any suitable interactive biometric sensing device disclosed herein. Any suitable interactive device or interactive system disclosed herein that is able to actuate (for example, apply haptic energy) can enable measurement of individual characteristics as to how a person responds to our device during an authentication session. The processor(s) can detect patterns when a person responds to a prompt, such as being prompted to stand up while being authenticated by both an ultrasound sensor and our optical system that is generating a photoplethysmogram (PPG).

Dynamic biometrics can be used to generate improved, personalized biometric readings. Machine learning can be used to find patterns in various biometric parameters, such as PPG scans, respiration rate, heart rate, the like, or any combination thereof. Such patterns can be used in biometric authentication. For instance, PPG waves can change hour to hour, based on the activity of a person. If a mismatch from what is expected by machine learning and/or artificial intelligence is detected by PPG readings, this can cause authentication to fail or lead to an authentication system taking additional readings to authenticate a person.

Machine learning and/or other techniques can capture a reasonably distinct signature of a person from one or more biometric parameters (e.g., a PPG) during authentication (e.g., while generating an image of at least a portion of a finger). The reasonably distinct signature can be verified using two different sensing devices, such as sensing devices on different mobile phones. As an example, a first mobile phone can read a biometric parameter using a reflective oximeter of an optical system below an ultrasound fingerprint sensor. On a second device, the person can use a reflective oximeter of the second device to match the biometric parameter without risking exposure of sensitive data, such as a fingerprint. Having the substantially the same reflective oximeter, substantially same frequency, and substantially the same software can aid in verifying the biometric parameter for robust authentication.

A biometric pattern is not permanent and can change hour to hour based on a person's activity, yet still provide distinctive aspects that can appear day to day. Accordingly, a way to duplicate some life pattern, that is not unique but still reasonably distinctive (e.g., about 1 in several thousand) can be implemented on two devices concurrently. Since the readings should be slightly different, the user is not giving away his or her unique fingerprint or facial identification while undergoing an additional measurement for authentication.

Additional Embodiments

Embodiments of the disclosed technology can use an ultrasound transducer array in accordance with any suitable principles and advantages discussed herein as part of an interaction with a user being authenticated by a fingerprint scanner and/or a camera scanner equipped with facial recognition and motion-sensing software at the same time. Having some action(s) by the user triggered and then detected by the two devices can provide increased security. Incorporating several different interactive efforts with two biometric devices create multiple possibilities that would be hard for a scammer to fake and/or anticipate with a 'replay' attack. The disclosed technology can employ two or more modalities in such interactions that authenticate the user, while they are also registering that an action has been taken in response to a trigger by one of the authentication devices.

For example, if the user were triggered by the ultrasound transducer array 400 to make a specific motion, such as tilting his or her face upwards, in response to haptic energy applied to the tip of the finger, or alternatively tilting the face down, in response to haptic energy applied to the bottom of the fingerprint, such a motion could be detected by a portable computing device equipped with a three dimensional motion sensor, that, for example combines a camera and associated infrared beam, at the same time that a facial identification authentication is completed.

In this case, a user's finger, whose fingerprint is being authenticated by the ultrasound system, can detect a signal of haptic energy from the fingerprint device to prompt the user to react. Next, the user's face, authenticated by a separate device such as a phone camera, is detected to have moved. For example, part of the authentication scheme can prompt the user to close an eye or wink. Both the facial authentication and facial movement information are then passed to a system to register and confirm the actions as part of the authentication process. In this case, one would have created cross-talk and work being done, coordinated and confirmed between the two different biometric devices.

An advantage of registering movement by a user's face, instead of his arm, has the advantage that the user's face can be confirmed to be from the same person as the confirmed fingerprint.

In an embodiment, the order can be reversed: A camera/flash/illuminator could also initiate an action, such as a small red light, prompting the user to temporarily remove their fingerprint that is being authenticated from the screen. At the same time, the red light might also signal that the user briefly move their head from side-to-side. In this case, the camera/flash/illuminator can trigger an action that is read as a response by both devices. The camera/flash/illuminator registers the head movement and the fingerprint reader registers the removal of the finger.

With interactivity, multiple scans can occur concurrently during an authentication session. In such scans, several different bio-metric measurements can be combined, with a common measurement/factor and with interactions between different bio-metric devices. A system can include different biometric sensors and a fingerprint sensor/device equipped with multi-mode biometric scanning.

An interactive biometric system can measure a common factor, such as pulse, with a fingerprint device and another separate biometric device, with each measuring the same common factor during their main authentication process while they each are measuring two other factors, such as the fingerprint and face.

The disclosed technology enables confirmation of aliveness of a fingertip or other appendage from another biometric scanning device on the same phone, computer, or other device. Examples of detecting an aliveness parameter include scanning a pulse from minute color changes in the face, from the movement of blood via heart pulses, from the phone's camera as well as from our fingerprint device, using the similar principal of reflective oximeter. Both of these pulse scans can happen while the user's facial identification is confirmed by the phone's camera and the fingerprint scanner is confirming the user's fingerprint. This can create a common denominator of a measurement shared and confirmed by itself and the camera authenticating the face or iris.

If both the camera and our fingerprint scanner are measuring the pulse, then the pulse would increase if a user stood up, and that would be measured by both the camera and the fingerprint scanner—so such an interactive action would be measured by two different biometric sensors on the phone. Furthermore, a camera device with a 3D motion sensor could detect such a motion change from the user standing up while the camera is also reading a change in the pulse.

In order to confirm that the fingerprint scanner heart beat is similar to measurement by the camera's facial identification scanner, the heart rate or timing between beats can be compared to determine that they are the same, even though the beats occur at different times in the finger and in the face due to different distances from the heart.

Combining two or more different biometric scanning devices with multiple variables or measurements (for example, heart rates measured by different sensor modalities) at the same time that the two multi-mode biometric scanning devices are authenticating that the user is the same person with a recognized face and fingerprint, it is harder for a scammer to fool both sensors, as a fake face would have to register the same pulse as that of a fake fingerprint.

Other sensor modalities can be included, such as measuring respiration rates by camera, which can be similar to using an optical system 550 for reflective oximetry. For example, plethysmograms captured by the optical system can be analyzed using image processing and pattern recognition techniques to determine changes in respiration rates.

In some embodiments, multi-factor authentication can be performed on one integrated ultrasound/reflectance pulse oximeter device and some multi-factor authentication can be prompted by the larger device (such as a smart phone). As an example, a smart phone can vibrate as a prompt.

A device, such as a mobile phone, can program at what stage an aliveness reading is involved in authentication and/or at what stage an interactive authentication session is implemented. Users can desire that their mobile phones to turn on reliably and quickly, and therefore a basic ultrasound fingerprint scan can unlock the phone. Such a measurement can reduce the chances of a false rejection. Built into a mobile phone's settings or in an application installed on the phone, a user could configure a setting so that authentication can also include another biometric reading (e.g., pulse, temperature and/or $SpO_2$ reading) for access to certain files and/or a user could add an interactive authentication with random prompts coming from the phone computing unit or an application specific integrated circuit. A user, or a third party wanting to authenticate the user, could program the phone, as to when the device would employ interactive authentication to add security access and identity protection for external connections, such as signing on to the office remotely or the cloud or for shopping or bank sites. Accordingly, a biometric authentication system can operate in different modes with different levels of authentication. Such a system can be configurable such that accessing certain files and/or certain functionalities of a device can involve higher levels of authentication, such as any suitable features of the interactive biometric sensing discussed herein.

To implement interactive authentication in accordance with the principles and advantages discussed herein, an application on a mobile phone or computer can accept input from a third party to initiate an actuator prompting a user. Accordingly, a third party can direct random and/or unpredictable interactive biometric prompts and/or biometric measurements.

An interactive biometric sensing system can include a sensor configured to generate a biometric image associated with an object, a prompting device configured to prompt an action associated with the object, and a processor configured to authenticate the object based on the biometric image and a detected biometric response to the prompt. For instance, the sensor can be a fingerprint sensor. The prompting device can prompt the user to take action, such as by providing text and/or audio to prompt the user to take action (e.g., to stand up, to jump, etc.) that should result in a detection biometric response. Then the biometric response can be detected and the processor can authenticate the used using both the biometric image and the detected response.

One aspect of the disclosed technology is an acoustic fingerprint sensing device. The device includes an array of ultrasonic transducers configured to transmit an ultrasound signal having a frequency in a range from 50 megahertz (MHz) to 500 MHz. The ultrasonic transducers include a piezoelectric film. The device further includes first metal electrodes. The device further includes second metal electrodes that can be orthogonal to the first metal electrodes. The first metal electrodes and the second metal electrodes enable addressing of the ultrasonic transducers of the array. The device further includes a surface configured to receive a finger. The device further includes a processor configured to generate an image of at least a portion of a fingerprint of the finger in contact with the surface based on a reflection of the ultrasound signal from the finger. The device further includes an actuator configured to vary the temperature of and/or the pressure on the finger in contact with the surface.

In an embodiment, the actuator includes the ultrasonic transducers.

In an embodiment the actuator varies the pressure in a series of pulses focused on a configurable region of the receiving surface. In an embodiment, the actuator focuses heat on a configurable region of the receiving surface to increase the temperature at the region by at least 0.1° C.

In an embodiment, the frequency of the ultrasound signal is in a range from 125 MHz to 250 MHz. In an embodiment, the frequency of the ultrasound signal is in a range from 50 MHz to 100 MHz. In an embodiment, the piezoelectric film has a thickness in a range from 3 micrometers (km) to 75 km. In an embodiment, the piezoelectric film has a thickness in a range from 10 micrometers (km) to 20 km.

In an embodiment, the device further includes a receiver circuit configured to process an electronic receive signal generated by the array of ultrasonic transducers in response to the reflection to provide a processed signal to the processor.

In an embodiment, the image has a resolution of at least 500 pixels per inch.

In an embodiment, the first metal electrodes are in physical contact with a plate that includes the surface.

In an embodiment, the piezoelectric film comprises at least one of zinc oxide, aluminum nitride, or lead zirconium titanate. In an embodiment, the surface is a surface of a plate that comprises glass and a matching layer, and the matching layer has a thickness corresponding to a quarter of a wavelength of the ultrasound signal in material of the matching layer.

In an embodiment, the processor is configured to estimate a force at which the finger contacts the receiving surface based on an area of the finger in contact with the receiving surface. In an embodiment, the processor is configured to detect a temperature of the finger based on a sound speed associated with the reflection. In an embodiment, the processor is configured to detect a parameter associated with a liveness of the finger based on the reflection, and to provide an indication of whether the finger is part of a live human based on the liveness parameter.

Another aspect is a method of authenticating a fingerprint. The method includes: addressing ultrasound transducers of an array of ultrasound transducers using first metal electrodes and second metal electrodes, the second metal electrodes orthogonal to the first metal electrodes. The method further includes transmitting, by the array of ultrasonic transducers, a first ultrasound signal in a frequency range from 50 megahertz (MHz) to 500 MHz towards a receiving surface. The method further includes receiving, using the one or more ultrasonic transducers, a reflection of the first ultrasound signal. The method further includes generating a first image of at least a portion of a finger on the receiving surface based on the reflection of the first ultrasound signal. The method further includes varying, by an actuator, the temperature of and/or the pressure on the finger in contact with the receiving surface. The method further includes transmitting, by the array of ultrasound transducers, a second ultrasound signal having a frequency in a range from 50 megahertz (MHz) to 500 MHz. The method further includes generating a second image of at least a second portion of the fingerprint of the finger based on a reflection of the second ultrasound signal. The method further includes authenticating the fingerprint in response to a comparison of the first image and the second image, corresponding to the change in temperature of and/or the pressure on the finger in contact with the receiving surface.

In an embodiment, the method further includes varying, by the actuator, the pressure in a series of pulses focused on a configurable region of the receiving surface. In embodiment, the method further includes heating, by the actuator, a configurable region of the receiving surface to increase the temperature at the region. In some instances, the temperature can be increased by at least 0.1° C.

In an embodiment, the method further includes processing an electronic receive signal generated by the array of ultrasonic transducers in response to the reflection of the first ultrasound signal.

In an embodiment, the first metal electrodes are in physical contact with a plate that includes the receiving surface.

In an embodiment, the method further includes estimating a force at which the finger contacts the receiving surface based on an area of the finger in contact with the receiving surface. In an embodiment, the method further includes detecting a temperature of the finger based on a sound speed associated with the reflection. In an embodiment, the method further includes detecting a parameter associated with a liveness of the finger based on the reflection. In an embodiment, the method further includes providing an indication of whether the finger is part of a live human based on the liveness parameter.

Another aspect is a biometric sensing and actuating device for fingerprint identification. The device includes an array of ultrasonic transducers configured to transmit an ultrasound signal having a frequency in a range from 50 megahertz (MHz) to 500 MHz. The device further includes first metal electrodes. The device further includes second metal electrodes that can be orthogonal to the first metal electrodes. The first metal electrodes and the second metal electrodes enable addressing of the ultrasonic transducers of the array. The device further includes a surface configured to receive a finger. The device further includes a processor configured to generate an image of at least a portion of a fingerprint of the finger based on a reflection of the ultrasound signal from the finger. The device further includes an actuator that varies the temperature of and/or the pressure on the finger in contact with the receiving surface. In an embodiment, the actuator comprises the ultrasonic transducer. In an embodiment, the actuator varies the pressure in a series of pulses focused on a region of the receiving surface. In an embodiment, the actuator focuses heat on a region of the receiving surface. This can increase the temperature at the region by a detectable amount, such as at least 0.1° C.

Another aspect is a method for authenticating a fingerprint using a biometric sensing and actuating device. The method includes addressing ultrasound transducers of an array of ultrasound transducers using first metal electrodes and second metal electrodes, the second metal electrodes that can be orthogonal to the first metal electrodes. The method further includes transmitting, by the array of ultrasonic transducers, a first ultrasound signal having a frequency in a range from 50 megahertz (MHz) to 500 MHz. The method further includes generating a first image of at least a portion of a first fingerprint of a first finger based on a reflection of the first ultrasound signal. The method further includes heating a region of a receiving surface to increase a temperature of the region by least 0.1° C. The method further includes transmitting, by the array of ultrasound transducers, a second ultrasound signal having a frequency in a range from 50 megahertz (MHz) to 500 MHz. The method further includes detecting the increase in temperature based on a reflection of the second ultrasound signal. The method further includes authenticating the first fingerprint based on the first image and the detected increase in temperature.

Another aspect is a method for authenticating a fingerprint using a biometric sensing and actuating device. The method includes addressing ultrasound transducers of an array of ultrasound transducers using first metal electrodes and second metal electrodes, the second metal electrodes that can be orthogonal to the first metal electrodes. The method further includes transmitting, by the array of ultrasonic transducers, a first ultrasound signal having a frequency in a range from 50 megahertz (MHz) to 500 MHz. The method further includes generating a first image of at least a portion of a first fingerprint of a first finger based on a reflection of the first ultrasound signal. The method further includes varying the pressure of a region of a receiving surface on a finger in contact with the receiving surface by xx $N/m^2$ (or yy psi). The method further includes transmitting, by the array of ultrasound transducers, a second ultrasound signal having a frequency in a range from 50 megahertz (MHz) to 500 MHz. The method further includes generating a second image of at least a second portion of a second fingerprint of a second finger based on a reflection of the second ultrasound signal. The method further includes authenticating the first fingerprint in response to a comparison of the first image and the second image, corresponding to the change in pressure of the region of the receiving surface. The discernable pressure change can be set by the mechanical noise floor in the transducer, the transducer sensitivity, the noise figure of the electronics, or any combination thereof.

Another aspect is a biometric sensing device for fingerprint identification using both optical and ultrasonic signals. The device includes a light source configured to transmit light. The light can have a frequency in a range from 400 nm to 1000 nm, for example. The device includes an array of ultrasonic transducers configured to transmit an ultrasound signal having a frequency in a range from 50 megahertz (MHz) to 500 MHz. The device further includes first metal electrodes. The device further includes second metal electrodes that can be orthogonal to the first metal electrodes. The first metal electrodes and the second metal electrodes enable addressing of the ultrasonic transducers of the array. The device further includes a surface configured to receive a finger. The device further includes a processor configured to authenticate the finger based on a reflection of the light and/or the ultrasound image from the finger.

In an embodiment, the light source transmits light through the ultrasonic transducer, the first metal electrodes, and the second metal electrodes, wherein the ultrasonic transducer is at least partially transparent, wherein the first metal electrodes are at least partially transparent, and wherein the second metal electrodes are at least partially transparent. In this embodiment, the array of ultrasonic transducers are between the optical emitter and the receiving surface, and the ultrasonic transducers, first metal electrodes, and second metal electrodes are at least partially transparent to the transmitted light.

In an embodiment, the ultrasound transducers transmit the ultrasound signal through the light source. In this embodiment, the ultrasound signal passes through the light source. This embodiment may include an array of light sources in squares on a plane, each square bounded by projections of the first metal electrodes and second metal electrodes in the plane.

In an embodiment, the light source adjoins the ultrasound transducer. In this embodiment, the light source and the ultrasound transducer are side by side but in close proximity to each other.

Applications and Conclusion

Some of the embodiments described above have provided examples in connection with ultrasound-based fingerprint sensors. However, the principles and advantages of the embodiments can be used for any other suitable devices, systems, apparatuses, and/or methods that could benefit from such principles and advantages. Although described in the context of fingerprints, one or more features described herein can also be utilized in detecting any other suitable part of a human or animal.

The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments. Various embodiments can apply different techniques for fabricating different types of electronic devices.

Aspects of this disclosure can be implemented in various devices. For example, the acoustic biometric sensing devices discussed herein can be implemented in a mobile phone such as a smart phone, a tablet computer, a steering wheel, a gun, a door, a door handle, a wall, an elevator, or any other suitable application that could benefit from any of the principles and advantages discussed herein.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. An interactive biometric authentication system comprising:
   a sensor configured to generate biometric image data associated with a user, the sensor being further configured as an actuator to deliver energy to a body part of the user to enable interactive authentication between the interactive biometric authentication system and the user based on a response of the user to the delivered energy, wherein the response engages a brain of the user; and
   a processor in communication with the sensor, the processor configured to authenticate the user based on the biometric image data and based on the response of the user to the energy delivered to the body part of the user by the sensor.

2. The interactive biometric authentication system of claim 1, wherein the sensor comprises ultrasound transducers.

3. The interactive biometric authentication system of claim 2, wherein the ultrasound transducers are configured to apply pressure to the body part of the user, and the response is to the pressure applied to the body part of the user.

4. The interactive biometric authentication system of claim 1, wherein the sensor is configured to detect the response and provide an indication of the response to the processor.

5. The interactive biometric authentication system of claim 1, wherein the sensor is configured to deliver the energy to the body part of the user as a prompt in a manner that exhibits statistical randomness.

6. The interactive biometric authentication system of claim 1, wherein the interactive biometric authentication system is configured to detect a real-time response to the energy delivered to the body part of the user.

7. The interactive biometric authentication system of claim 1, further comprising a surface configured to receive the body part of the user, wherein the sensor is configured to deliver energy to the body part of the user while the body part of the user is positioned on the surface.

8. The interactive biometric authentication system of claim 7, further comprising engineered glass disposed between the sensor and the surface, wherein the sensor is configured to deliver the energy to the body part of the user through the engineered glass.

9. An interactive biometric authentication system comprising:
   a sensor configured to generate biometric image data associated with an object;
   an actuator configured to deliver energy to the object to enable interactive authentication between the interactive biometric authentication system and the object based on a response of a user to the delivered energy; and
   a processor in communication with the sensor, the processor configured to authenticate the object based on the biometric image data generated by the sensor and based on the response of the user to the energy delivered to the object by the actuator.

10. The interactive biometric authentication system of claim 9, wherein the response is a change in temperature, a movement, a muscle contraction, or a change in pulse rate.

11. The interactive biometric authentication system of claim 9, wherein actuator is configured to deliver energy as a prompt that exhibits statistical randomness.

12. The interactive biometric authentication system of claim 9, wherein the interactive biometric authentication system is configured to detect a real-time response to the energy delivered to the object.

13. The interactive biometric authentication system of claim 9, further comprising a surface configured to receive the object, wherein the actuator is configured to deliver energy to the object while the object is positioned on the surface.

14. The interactive biometric authentication system of claim 9, wherein the actuator comprises a heater.

15. A method of authenticating a user, the method comprising:
   receiving a signal indicating that a fingerprint of the user has been authenticated using fingerprint image data generated by a user device;
   receiving, from a confirming device, data indicative of biometric information associated with the user and a location of the confirming device; and
   authenticating the user based at least in part on (i) the signal indicating that the fingerprint has been authenticated and (ii) the data indicative of the biometric information associated with the user and the location of the confirming device.

16. The method of claim 15, wherein the biometric information associated with the user does not comprise image data associated with a fingerprint of the user.

17. The method of claim 15, further comprising receiving biometric data associated with the user from the user device, and wherein the authenticating is based at least in part on the biometric data.

18. The method of claim 17, wherein the biometric data represents a first PPG reading and wherein the biometric information represents a second PPG reading.

19. The method of claim 17, wherein the biometric data is generated using a light scanner of the user device, and the biometric information is generated using a light scanner of the confirming device.

20. The method of claim 15, wherein a fingerprint sensor of the user device comprises an ultrasound fingerprint sensor.

* * * * *